(12) United States Patent
Boehm et al.

(10) Patent No.: US 8,071,584 B2
(45) Date of Patent: Dec. 6, 2011

(54) INDOLE CARBOXAMIDES AS IKK2 INHIBITORS

(75) Inventors: Jeffrey Charles Boehm, King of Prussia, PA (US); Jakob Busch-Petersen, King of Prussia, PA (US); Wei Fu, King of Prussia, PA (US); Qi Jin, King of Prussia, PA (US); Jeffrey K. Kerns, King of Prussia, PA (US); Huijie Li, King of Prussia, PA (US); Guoliang Lin, King of Prussia, PA (US); Xichen Lin, King of Prussia, PA (US); Christopher E. Neipp, King of Prussia, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 109 days.

(21) Appl. No.: 12/532,773

(22) PCT Filed: Mar. 20, 2008

(86) PCT No.: PCT/US2008/057583
§ 371 (c)(1),
(2), (4) Date: Sep. 23, 2009

(87) PCT Pub. No.: WO2008/118724
PCT Pub. Date: Oct. 2, 2008

(65) Prior Publication Data
US 2010/0130468 A1     May 27, 2010

Related U.S. Application Data

(60) Provisional application No. 60/896,558, filed on Mar. 23, 2007.

(51) Int. Cl.
| | |
|---|---|
| *A61K 31/397* | (2006.01) |
| *A61K 31/55* | (2006.01) |
| *A61K 31/5377* | (2006.01) |
| *A61K 31/4436* | (2006.01) |
| *A61K 31/404* | (2006.01) |
| *C07D 409/14* | (2006.01) |
| *C07D 413/14* | (2006.01) |
| *C07D 209/04* | (2006.01) |

(52) U.S. Cl. ........... 514/210.21; 514/217.08; 514/235.2; 514/339; 514/414; 540/602; 544/143; 546/277.4; 548/466

(58) Field of Classification Search ............ 514/210.21, 514/217.03, 217.08, 235.2, 254.08, 339, 514/414, 415; 540/544, 596, 602; 544/143, 544/373; 546/277.4; 548/466, 490
See application file for complete search history.

(56) References Cited

U.S. PATENT DOCUMENTS

| | | | |
|---|---|---|---|
| 4,775,761 A | 10/1988 | Strupczewski | |
| 5,026,856 A | 6/1991 | Yatsunami et al. | |
| 5,256,673 A | 10/1993 | Böttcher et al. | |
| 6,245,799 B1 | 6/2001 | Asselin et al. | |
| 6,358,944 B1 | 3/2002 | Fritz et al. | |
| 6,589,954 B1 | 7/2003 | Mavunkel et al. | |
| 6,919,335 B2 | 7/2005 | Iwanowicz et al. | |
| 2002/0147189 A1 | 10/2002 | Cai et al. | |
| 2002/0161004 A1 | 10/2002 | Browner et al. | |
| 2003/0022898 A1 | 1/2003 | Burke et al. | |
| 2006/0281836 A1 | 12/2006 | Kerns et al. | |
| 2007/0254873 A1 | 11/2007 | Kerns et al. | |
| 2007/0281933 A1 | 12/2007 | Kerns et al. | |
| 2008/0269291 A1 | 10/2008 | Kerns et al. | |
| 2008/0293802 A1 | 11/2008 | Kerns et al. | |
| 2009/0143372 A1 | 6/2009 | Kerns et al. | |
| 2010/0130468 A1 | 5/2010 | Busch-Petersen et al. | |

FOREIGN PATENT DOCUMENTS

| | | |
|---|---|---|
| DE | 3342632 | 6/1985 |
| DE | 19500689 | 7/1996 |
| DE | 19807993 | 9/1999 |
| DE | 19928424 | 12/2000 |
| DE | 10112151 | 9/2002 |

(Continued)

OTHER PUBLICATIONS

Aupperle et al., "NF-κB Regulation by IκB Kinase in Primary Fibroblast-Like Synoviocytes" *J. Immunology* (1999) 163:427-433.

(Continued)

*Primary Examiner* — Kamal Saeed
*Assistant Examiner* — Kristin Bianchi
(74) *Attorney, Agent, or Firm* — Nora L. Stein; Theodore R. Furman

(57) ABSTRACT

The invention is directed to novel indole carboxamide derivatives. Specifically, the invention is directed to compounds according to formula (I):

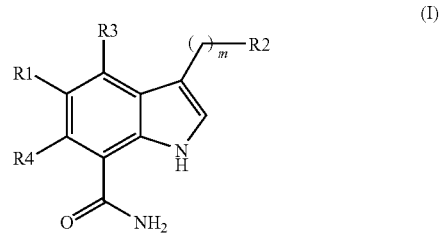

wherein R1, R2, R3, R4, and m are as defined herein.
The compounds of the invention are inhibitors of IKK2 and can be useful in the treatment of disorders associated with inappropriate IKK2 (also known as IKKβ) activity, such as rheumatoid arthritis, asthma, rhinitis, and COPD (chronic obstructive pulmonary disease). Accordingly, the invention is further directed to pharmaceutical compositions comprising a compound of the invention. The invention is still further directed to methods of inhibiting IKK2 activity and treatment of disorders associated therewith using a compound of the invention or a pharmaceutical composition comprising a compound of the invention.

24 Claims, No Drawings

FOREIGN PATENT DOCUMENTS

| | | |
|---|---|---|
| DE | 10259244 | 7/2004 |
| EP | 279263 | 8/1993 |
| EP | 610134 | 8/1994 |
| EP | 416609 | 1/1997 |
| EP | 0812826 | 12/1997 |
| EP | 1077213 | 2/2001 |
| EP | 1134221 | 9/2001 |
| EP | 1209158 | 5/2002 |
| WO | WO94/21627 | 9/1994 |
| WO | WO94/21630 | 9/1994 |
| WO | WO98/06715 | 2/1998 |
| WO | WO98/28292 | 7/1998 |
| WO | WO99/43652 | 2/1999 |
| WO | WO99/17773 | 4/1999 |
| WO | WO0100610 | 1/2001 |
| WO | WO01/34598 | 5/2001 |
| WO | WO0130774 | 5/2001 |
| WO | WO0158890 | 8/2001 |
| WO | WO0168648 | 9/2001 |
| WO | WO01/83472 | 11/2001 |
| WO | WO01/87298 | 11/2001 |
| WO | WO0198290 | 12/2001 |
| WO | WO02/14317 | 2/2002 |
| WO | WO02/16353 | 2/2002 |
| WO | WO02/24693 | 3/2002 |
| WO | WO0224679 | 3/2002 |
| WO | WO0228860 | 3/2002 |
| WO | WO0230353 | 4/2002 |
| WO | WO02230423 | 4/2002 |
| WO | WO0241843 | 5/2002 |
| WO | WO0244153 | 6/2002 |
| WO | WO0246171 | 6/2002 |
| WO | WO02/051837 | 7/2002 |
| WO | WO02060386 | 8/2002 |
| WO | WO02094265 | 11/2002 |
| WO | WO02094322 | 11/2002 |
| WO | WO02094813 | 11/2002 |
| WO | WO03007076 | 1/2003 |
| WO | WO03010158 | 2/2003 |
| WO | WO03010163 | 2/2003 |
| WO | WO03022898 | 3/2003 |
| WO | WO03024935 | 3/2003 |
| WO | WO03024936 | 3/2003 |
| WO | WO03027075 | 4/2003 |
| WO | WO03037886 | 5/2003 |
| WO | WO03065625 | 5/2003 |
| WO | WO03/087087 | 10/2003 |
| WO | WO03084959 | 10/2003 |
| WO | WO03095430 | 11/2003 |
| WO | WO03/101987 | 12/2003 |
| WO | WO03103661 | 12/2003 |
| WO | WO2004/019935 | 3/2004 |
| WO | WO2004/024730 | 3/2004 |
| WO | WO2004/024732 | 3/2004 |
| WO | WO2004/024736 | 3/2004 |
| WO | WO2004022553 | 3/2004 |
| WO | WO2004075846 | 9/2004 |
| WO | WO2004089913 | 10/2004 |
| WO | WO2004106293 | 12/2004 |
| WO | WO2005012283 | 2/2005 |
| WO | WO2005035537 | 4/2005 |
| WO | WO2005067923 | 7/2005 |
| WO | WO2006/002434 | 1/2006 |
| WO | WO 2006/034317 | 3/2006 |
| WO | WO2006/106326 | 10/2006 |
| WO | WO2007/005534 | 1/2007 |

OTHER PUBLICATIONS

Aupperle et al., "Nf-κB Regulation by IκB Kinase-2 in Rheumatoid Arthritis Synoviocytes" *J. Immunology* (2001) 166:31496-31501.

Breton et al., "The Natural Product Hymenialdisine Inhibits Interleukin-8 Production in U937 Cells by Inhibition of Nuclear Factor-κB" *JPET* (1997) 282(1):459-466.

Burke et al., "BMS-345541 Is a Highly Selective Inhibitor of IκB Kinase That Binds at an Allosteric Site of the Enzyme and Blocks NF-κB-dependent Transcription in Mice" *J. Biol Chem.* (2003) 278:1450-1456.

Guttridge et al., "Nκ-B-Induced Loss of *MyoD* Messenger RNA: Possible Role in Muscle Decay and Cachexia " Science (2000) 289:2363-2365.

Murata et al., "Discovery of novel and selective IKK-β serine-threonine protein kinase inhibitors. Part 1." *Bioorg. Med. Chem. Letter* (2003) 13:913-198.

Murata et al., "Synthesis and structure—activity relationships of novel IKK-β inhibitors. Part 2: Improvement of in vitro activity" *Bioorg. Med. Chem. Letter* (2004) 14(15):4013-4017 and "Synthesis and structure—activity relationships of novel IKK-β inhibitors. Part 3: Orally active anti-inflammatory agents," *Bioorg. Med. Chem. Letter* (2004) 14(15):4019-4022.

Peet et al., "IκB Kinases α and β Show a Random Sequential Kinetic Mechanism and Are Inhibited by Staurosporine and Quercetin" *J. Biol. Chem.* (1999) 274:32655-32661.

Pierce, et al., "Novel Inhibitors of Cytokine-induced IκBκ Phosphorylation and Endothelial Cell Adhesion Molecule Expression Show Anti-inflammatory Effects in Vivo" *J. Biol. Chem.* (1997) 272:21096-21103.

Roshak, et al., "Inhibition of NFκB-Mediated Interleukin-1β-Stimulated Prostaglandin $E_2$ Formation by the Marine Natural Product Hymenialdisine" *JPET* (1997) 283(2):955-961.

Roshak, et al., "Manipulation of Distinct NFκB Proteins Alters Interleukin-lβ-induced Human Rheumatoid Synovial Fibroblast Prostaglandin $E_2$ Formation" *J. Biol. Chem.* (1996) 271:31496-31501.

Sullivan et al., "2-Chloro-4-(trifluoromethyl)pyrimidine-5-*N*-(3',5'-bis(trifluoromethyl)phenyl)-carboxamide: A Potent Inhibitor of NF-κB- and AP-1-Mediated Gene Expression Identified Using Solution-Phase Combinatorial Chemistry" *J. Med. Chem.* (1998) 41:413-419.

Tak et al., "Inhibitor of nuclear factor κB kinase β is a key regulator of synovial inflammation" *Arthritis and Rheumatism* (2001) 44(8):1897-1907.

Wahl et al., "Sulfasalazine: a potent and specific inhibitor of nuclear factor kappa B" *J. Clin. Invest.*(1998) 101(5):1163-1174.

Wisniewski et al., "Assay for IκB Kinases Using an in Vivo Biotinylated IκB Protein Substrate" *Analytical Biochem.* (1999) 274:220-228.

U.S. Appl. No. 12/093,750, filed May 15, 2008, Kerns et al.
U.S. Appl. No. 12/096,397, filed Jun. 6, 2008, Kerns et al.
U.S. Appl. No. 12/532,773, filed Sep. 23, 2009, Busch-Petersen et al.
U.S. Appl. No. 10/597,154, filed Jul. 13, 2006, Baldwin et al.
U.S. Appl. No. 11/570,060, filed Dec. 5, 2006, Jeffrey K. Kerns.
U.S. Appl. No. 11/575,416, filed Mar. 16, 2007, Kerns et al.
C. G. Wermuth. *The Practice of Medicinal Chemistry*, Academic Press, pp. 203-214 (1996).
Restriction Requirement dated May 20, 2009 in U.S. Appl. No. 10/597,154.
Official Action dated Oct. 27, 2009 in U.S. Appl. No. 10/597,154.
Final Action dated Jul. 15, 2010 in U.S. Appl. No. 10/597,154.
Restriction Requirement dated Dec. 15, 2009 in U.S. Appl. No. 11/570,060.
Official Action dated May 20, 2010 in U.S. Appl. No. 11/570,060.
Final Action dated May 14, 2009 in U.S. Appl. No. 11/575,416.
Official Action dated Jan. 4, 2010 in U.S. Appl. No. 11/575,416.
Notice of Allowance dated Nov. 12, 2010 in U.S. Appl. No. 11/575,416.
Restriction Requirement dated Aug. 10, 2010 in U.S. Appl. No. 12/093,750.
Abstract No. 98323-88-7 (Sep. 29, 1985).
Notice of Allowance dated Jan. 31, 2011 in U.S. Appl. No. 11/931,189.

INDOLE CARBOXAMIDES AS IKK2 INHIBITORS

This application is a 371 national stage filing of PCT/US2008/057583 filed Mar. 20, 2008, which claims the benefit of U.S. Provisional Application No. 60/896,558, filed Mar. 23, 2007, which is incorporated in its entirety.

FIELD OF THE INVENTION

The invention is directed to certain indole carboxamide compounds, which are inhibitors of kinase activity. More specifically, the compounds are IKK2 inhibitors. These compounds are useful in the treatment of disorders associated with inappropriate IKK2 (also known as IKKβ) activity, in particular in the treatment and prevention of disorders mediated by IKK2 mechanisms including inflammatory and tissue repair disorders. Such disorders include rheumatoid arthritis, asthma, rhinitis, and COPD (chronic obstructive pulmonary disease).

BACKGROUND OF THE INVENTION

An important large family of enzymes is the protein kinase enzyme family. Currently, there are about 500 different known protein kinases. However, because three to four percent of the human genome is a code for the formation of protein kinases, there may be many thousands of distinct and separate kinases in the human body. Protein kinases serve to catalyze the phosphorylation of an amino acid side chain in various proteins by the transfer of the γ-phosphate of the ATP-$Mg^{2+}$ complex to said amino acid side chain. These enzymes control the majority of the signaling processes inside cells, thereby governing cell function, growth, differentiation and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety and ubiquitousness, protein kinases have become one of the most important and widely studied family of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), includes cyclic AMP- and cyclic GMP-dependent protein kinases, calcium and phospholipid dependent protein kinase, calcium- and calmodulin-dependent protein kinases, casein kinases, cell division cycle protein kinases and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor and others. Studies have indicated that many tyrosine kinases are transmembrane proteins with their receptor domains located on the outside of the cell and their kinase domains on the inside. Much work is also under progress to identify modulators of tyrosine kinases as well.

Nuclear factor κB (NF-κB) belongs to a family of closely related dimeric transcription factor complexes composed of various combinations of the Rel/NF-κB family of polypeptides. The family consists of five individual gene products in mammals, RelA (p65), NF-κB1 (p50/p105), NF-κB2 (p49/p100), c-Rel, and RelB, all of which can form hetero- or homodimers. These proteins share a highly homologous 300 amino acid "Rel homology domain" which contains the DNA binding and dimerization domains. At the extreme C-terminus of the Rel homology domain is a nuclear translocation sequence important in the transport of NF-κB from the cytoplasm to the nucleus. In addition, p65 and cRel possess potent transactivation domains at their C-terminal ends.

The activity of NF-κB is regulated by its interaction with a member of the inhibitor IκB family of proteins. This interaction effectively blocks the nuclear localization sequence on the NF-κB proteins, thus preventing migration of the dimer to the nucleus. A wide variety of stimuli activate NF-κB through what are likely to be multiple signal transduction pathways. Included are bacterial products (LPS), some viruses (HIV-1, HTLV-1), inflammatory cytokines (TNFα, IL-1), environmental and oxidative stress and DNA damaging agents. Apparently common to all stimuli however, is the phosphorylation and subsequent degradation of IκB. IκB is phosphorylated on two N-terminal serines by the recently identified IκB kinases (IKK-α and IKK-β). IKK-β is also known as IKK2. Site-directed mutagenesis studies indicate that these phosphorylations are critical for the subsequent activation of NF-κB in that once phosphorylated the protein is flagged for degradation via the ubiquitin-proteasome pathway. Free from IκB, the active NF-κB complexes are able to translocate to the nucleus where they bind in a selective manner to preferred gene-specific enhancer sequences. Included in the genes regulated by NF-κB are a number of cytokines and chemokines, cell adhesion molecules, acute phase proteins, immuno-regulatory proteins, eicosanoid metabolizing enzymes and anti-apoptotic genes.

It is well-known that NF-κB plays a key role in the regulated expression of a large number of pro-inflammatory mediators including cytokines such as TNF, IL-1β, IL-6 and IL-8, cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases.

The importance of NF-κB in inflammatory disorders is further strengthened by studies of airway inflammation including asthma, in which NF-κB has been shown to be activated. This activation may underlie the increased cytokine production and leukocyte infiltration characteristic of these disorders. In addition, inhaled steroids are known to reduce airway hyperresponsiveness and suppress the inflammatory response in asthmatic airways. In light of the recent findings with regard to glucocorticoid inhibition of NF-κB, one may speculate that these effects are mediated through an inhibition of NF-κB.

Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α or IL-1β. Such a distribution may be the underlying mechanism for the increased cytokine and eicosanoid production characteristic of this tissue. See Roshak, A. K., et al., *J. Biol. Chem.,* 271, 31496-31501 (1996). Expression of IKK-β has been shown in synoviocytes of rheumatoid arthritis patients and gene transfer studies have demonstrated the central role of IKK-β in stimulated inflammatory mediator production in these cells. See Aupperele et al. *J. Immunology* 1999. 163:427-433 and Aupperle et al. *J. Immunology* 2001; 166:2705-11. More recently, the intra-articular administration of a wild type IKK-β adenoviral construct was shown to cause paw swelling while intra-articular administration of dominant-negative IKKβ inhibited adjuvant-induced arthritis in rat. See Tak et al. *Arthritis and Rheumatism* 2001, 44:1897-1907.

The NF-κB/Rel and IκB proteins are also likely to play a key role in neoplastic transformation and metastasis. Family members are associated with cell transformation in vitro and in vivo as a result of overexpression, gene amplification, gene rearrangements or translocations. In addition, rearrangement and/or amplification of the genes encoding these proteins are seen in 20-25% of certain human lymphoid tumors. Further, NF-κB is activated by oncogenic ras, the most common defect in human tumors and blockade of NF-κB activation inhibits ras mediated cell transformation. In addition, a role for NF-κB in the regulation of apoptosis has been reported strengthening the role of this transcription factor in the regulation of tumor cell proliferation. TNF, ionizing radiation and DNA damaging agents have all been shown to activate NF-κB which in turn leads to the upregulated expression of several anti-apoptotic proteins. Conversely, inhibition of NF-κB has been shown to enhance apoptotic-killing by these agents in several tumor cell types. As this likely represents a major mechanism of tumor cell resistance to chemotherapy, inhibitors of NF-κB activation may be useful chemotherapeutic agents as either single agents or adjunct therapy. Recent reports have implicated NF-κB as an inhibitor of skeletal cell differentiation as well as a regulator of cytokine-induced muscle wasting (Guttridge et al. Science; 2000; 289: 2363-2365.) further supporting the potential of NFκB inhibitors as novel cancer therapies.

Several NF-κB inhibitors are described in C. Wahl, et al. *J. Clin. Invest.* 101(5), 1163-1174 (1998), R. W. Sullivan, et al. *J. Med. Chem.* 41, 413-419 (1998), J. W. Pierce, et al. *J. Biol. Chem.* 272, 21096-21103 (1997).

The marine natural product hymenialdisine is known to inhibit NF-κB. Roshak, A., et al., *JPET,* 283, 955-961 (1997). Breton, J. J and Chabot-Fletcher, M. C., *JPET,* 282, 459-466 (1997).

Additionally, patent applications have been filed on aminothiophene inhibitors of the IKK2, see Callahan, et al., WO 2002030353; Baxter, et al., WO 2001058890, Faull, et al., WO 2003010158; Griffiths, et al., WO2003010163; Fancelli, et al., WO 200198290; Granetto, et al., WO 2003037886; imidazole inhibitors of IKK2, see Callahan, et al., WO 200230423; anilinophenylpyrimidine inhibitors of IKK2, see Kois, et al., WO 2002046171; β-carboline inhibitors of IKK2, see Ritzeler, et al, WO 2001068648, Ritzeler, et al, EP 1134221; Nielsch, et al. DE 19807993; Ritzeler, et al., EP 1209158; indole inhibitors of IKK2, see Ritzeler, et al., WO 2001030774; benzimidazole inhibitors of the IKK2, see Ritzeler, et al., DE 19928424; Ritzeler et al, WO 2001000610; Ritzeler, et al., WO 2004022553; aminopyridine inhibitors of IKK2, see Lowinger, et al, WO 2002024679; Murata, et al, WO 2002024693; Murata, et al., WO 2002044153; aminopyrimidine inhibitors of IKK2, see Bollbuck, et al., WO 2004089913; pyrazole inhibitors of IKK2, see Bergmanis, et al., WO 2003024935; Metz, et al., WO 2003024936; Geng et al., WO 2003027075; Stealey, et al., WO 2003035625; Xu, et al., WO 200307076; Lennon, et al., WO 2003095430; pyrazinone inhibitors of IKK2, see Boys, et al., WO 2005035527; pyrazolaquinazoline inhibitors of IKK2, see Beaulieu, et al., WO 2002028860; Burke et al, WO 2002060386; Burke, et al. US 20030022898; thiophene tricyclic inhibitors of IKK2, see Belema, et al., WO 2003084959; pyrazolopurine inhibitors of IKK2, see Qiu, et al., WO 2004075846; oxazolo and thiazolo pyridine inhibitors of IKK2, see Pitts, et al., WO 2004106293; quinoline inhibitors of IKK2, Browner, et al., WO2002041843, Browner, et al., US 20020161004 and pyridylcyanoguanidine inhibitors of IKK2, see Bjorkling, et al., WO 2002094813, Binderup et al, WO 2002094322 and Madsen, et al., WO 200294265; thienopyridine inhibitors of IKK2, see Cywin, et al., WO 2003103661; Liu, et al., WO 2005035537; benzothiophene inhibitors of IKK2, see Chen et al., WO 2005012283. The natural products staurosporine, quercetin, K252a and K252b have been shown to be IKK2 inhibitors, see Peet, G. W. and Li, J. J. *Biol. Chem.,* 274, 32655-32661 (1999) and Wisniewski, D., et al., *Analytical Biochem.* 274, 220-228 (1999). Synthetic inhibitors of IKK2 have also been described, see Burke, et al. *J. Biol. Chem.,* 278, 1450-1456 (2003), Murata, et al., *Bioorg. Med. Chem. Lett.,* 13, 913-198 (2003), Murata, et al., *Bioorg. Med. Chem. Lett.,* 14, 4013-4017 (2004), and Murata, et al., *Bioorg. Med. Chem. Lett.,* 14, 4019-4022 (2004) have described IKK2 inhibitors.

Thus, attempts have been made to prepare compounds that inhibit IKK2 activity and a number of such compounds have been disclosed in the art. However, in view of the number of pathological responses that are mediated by IKK2, there remains a continuing need for inhibitors of IKK2 which can be used in the treatment of a variety of conditions.

The present inventors have discovered novel indole carboxamide compounds, which are inhibitors of kinase activity, in particular inappropriate IKK2 activity. Such indole carboxamide derivatives are therefore useful in the treatment of disorders associated with inappropriate kinase, in particular inappropriate IKK2 activity in particular in the treatment and prevention of disease states mediated by IKK2 mechanisms including inflammatory and tissue repair disorders, particularly rheumatoid arthritis, inflammatory bowel disease, asthma, rhinitis, and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus erythematosus, multiple sclerosis, psoriatic arthritis, alkylosing spondylitis, tissue and organ rejection, Alzheimer's disease, stroke, atherosclerosis, restonosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia.

SUMMARY OF THE INVENTION

The invention is directed to novel indole carboxamide compounds. Specifically, the invention is directed to compounds according to formula (I):

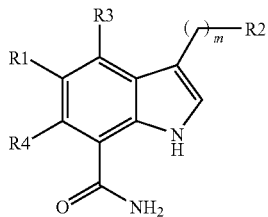

wherein R1, R2, R3, R4, and m are as defined below.

The compounds of the invention are inhibitors of IKK2 and can be useful in the treatment of disorders associated with inappropriate IKK2 (also known as IKKβ) activity, such as rheumatoid arthritis, asthma, rhinitis, and COPD (chronic obstructive pulmonary disease). Accordingly, the invention is further directed to pharmaceutical compositions comprising a compound of the invention. The invention is still further directed to methods of inhibiting IKK2 activity and treatment of disorders associated therewith using a compound of the invention or a pharmaceutical composition comprising a compound of the invention.

DETAILED DESCRIPTION OF THE INVENTION

The invention is directed to compounds according to formula (I):

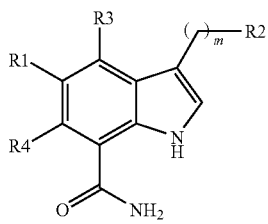

wherein:
R1 is the group —YZ;
Y is a bond, $C_1$-$C_6$ alkylene, $C_2$-$C_6$ alkenylene, or $C_2$-$C_6$ alkynylene;
Z is optionally substituted aryl or optionally substituted heteroaryl,
  where said aryl and heteroaryl are optionally substituted with one to three substituents each independently selected from the group consisting of: halo, —CN, optionally substituted $C_1$-$C_6$ alkyl, optionally substituted $C_1$-$C_6$ haloalkyl, heteroaryl optionally substituted with one to three $C_1$-$C_6$ alkyl groups; —N(Rb)$SO_2$Re, —N(Rb)C(O)Ra, —C(O)NRaRb, —C(O)NRfRg, —C(O)H, —$SO_2$Ri, —NRaRb, —$SO_2$NRaRb, —$SO_2$NRfRg, —ORc, —SRb, —N(Rb)C(O)NRaRb, —N(Rb)C(O)NRfRg, and —N(Rb)C(O)ORd, where said $C_1$-$C_6$ alkyl and $C_1$-$C_6$ haloalkyl are optionally substituted with one to three substituents each independently selected from the group consisting of: —CN, —NRaRb, —N(Rb)$SO_2$Re, —C(O)Ra, —C(O)NRaRb, $SO_2$Ri, —$SO_2$NRaRb, $C_3$-$C_6$ cycloalkyl, —ORc, —SRb, phenyl, and heterocycloalkyl optionally substituted with one or two $C_1$-$C_6$ alkyl groups;
R2 is an optionally substituted 4-10 member heterocycloalkyl containing S, S=O, or $S(O)_2$ as member atom(s) and the remaining member atoms are carbon, said 4-10 member heterocycloalkyl being optionally substituted with one to three substituents each independently selected from the group consisting of OH, $C_1$-$C_6$ alkyl, and phenyl; or
R2 is the bicyclo group of formula (II):

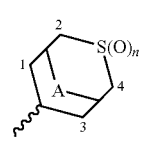

wherein A is a bridging group selected from: —$CH_2$—$CH_2$— or —$CH_2$—X—$CH_2$— and connects carbon atoms 1 or 2 to carbon atoms 3 or 4; X is O, NR5, or $S(O)_n$; R5 is H, $C_1$-$C_6$ alkyl, or —$SO_2$NRaRb; and each n is independently 0, 1, or 2;
R3 and R4 are each independently H or fluoro;
m is 0 or 1;
each Ra is independently selected from the group consisting of: H, $C_2$-$C_6$ alkenyl, $C_1$-$C_6$ alkyl, $C_1$-$C_6$ alkyl substituted with one to three substituents independently selected from the group consisting of: halo, CN, $C(O)NH_2$, $N(CH_3)_2$, $SO_2$Ri, CO(O)Rb, —N(Rb)C(O)Rb, —ORc, —SRc, $C_3$-$C_7$ cycloalkyl, $C_1$-$C_6$ haloalkyl, heterocycloalkyl, phenyl, and heteroaryl; phenyl, phenyl substituted with one to three substituents independently selected from the group consisting of: halo, $C_1$-$C_6$ alkyl, $C_1$-$C_6$ haloalkyl, $NH_2$, heteroaryl, —ORc, and —NRfRg; heteroaryl, heteroaryl substituted with one to three substituents independently selected from the group consisting of: halo, $C_1$-$C_6$ alkyl, $C_1$-$C_6$ haloalkyl, $NH_2$, heteroaryl, —ORc, and —NRfRg; $C_3$-$C_7$ cycloalkyl, $C_3$-$C_7$ cycloalkyl substituted with one to three substituents independently selected from the group consisting of: halo, $C_1$-$C_6$ alkyl, $C_1$-$C_6$ haloalkyl, $NH_2$, heteroaryl, —ORc, and —NRfRg; heterocycloalkyl, and heterocycloalkyl substituted with one to three substituents independently selected from the group consisting of: halo, $C_1$-$C_6$ alkyl, $C_1$-$C_6$ haloalkyl, $NH_2$, heteroaryl, —ORc, and —NRfRg;
each Rb is independently selected from the group consisting of: H, $C_1$-$C_6$ alkyl, and $C_3$-$C_7$ cycloalkyl;
each Rc is independently selected from the group consisting of: H, $C_1$-$C_6$ alkyl, $C_1$-$C_6$ alkyl substituted with one to three substituents independently selected from the group consisting of: OH, $C_3$-$C_6$ cycloalkyl, phenyl, heterocycloalkyl, and heteroaryl; $C_1$-$C_6$ haloalkyl, $C_1$-$C_6$ haloalkyl substituted with one to three substituents independently selected from the group consisting of: OH, $C_3$-$C_6$ cycloalkyl, phenyl, heterocycloalkyl, and heteroaryl; $C_3$-$C_7$ cycloalkyl, $C_3$-$C_7$ cycloalkyl substituted with one to three $C_1$-$C_3$ alkyl groups; heterocycloalkyl, heterocycloalkyl substituted with one to three $C_1$-$C_3$ alkyl groups; aryl, aryl substituted with one to three substituents independently selected from the group consisting of: halo, $C_1$-$C_3$ alkyl, $C_1$-$C_3$ haloalkyl, and OH; heteroaryl, and heteroaryl substituted with one to three substituents independently selected from the group consisting of: halo, $C_1$-$C_3$ alkyl, $C_1$-$C_3$ haloalkyl, and OH;
each Rd is independently an optionally substituted $C_1$-$C_3$ alkyl, where said $C_1$-$C_3$ alkyl is optionally substituted with one to three substituents selected from the group consisting of: $C_3$-$C_6$ cycloalkyl, optionally substituted phenyl, and optionally substituted heteroaryl; and where said phenyl and heteroaryl are optionally substituted with one to three substituents selected from the group consisting of: halo, $C_1$-$C_6$ alkyl, and $C_3$-$C_6$ cycloalkyl;
each Re is independently selected from the group consisting of: $C_1$-$C_6$ alkyl, $C_1$-$C_6$ alkyl substituted with one substituent selected from the group consisting of: phenyl, heteroaryl, heterocycloalkyl, and NRaRb; phenyl, phenyl substituted with one to three substituents selected from the group consisting of: halo, CN, $C_1$-$C_6$ alkyl, $C_1$-$C_6$ haloalkyl, and ORh; heteroaryl, heteroaryl substituted with one to three substituents selected from the group consisting of: halo, CN, $C_1$-$C_6$ alkyl, $C_1$-$C_6$ haloalkyl, and, ORh; $C_5$-$C_7$ cycloalkyl, $C_5$-$C_7$ cycloalkyl substituted with one to three substituents selected from the group consisting of: halo, $C_1$-$C_6$ alkyl, and $C_3$-$C_6$ cycloalkyl; heterocycloalkyl, and heterocycloalkyl substituted with one to three substituents selected from the group consisting of: halo, $C_1$-$C_6$ alkyl, and $C_3$-$C_6$ cycloalkyl;

each Rf and Rg is independently taken together with the nitrogen atom to which they are attached forming a ring having from 4 to 7 member atoms wherein said ring optionally contains one additional heteroatom as a member atom, said ring being saturated or unsaturated but not aromatic, and said ring being optionally substituted with one or two $C_1$-$C_3$ alkyl substituents;

each Rh is independently selected from the group consisting of: H, $C_1$-$C_6$ alkyl, and $C_1$-$C_8$ haloalkyl; and each Ri is independently selected from the group consisting of: $C_3$-$C_7$ cycloalkyl, OH, and $C_1$-$C_3$ alkyl optionally substituted with one OH.

In one embodiment of the present invention Y is a bond.

In another embodiment m is 0. In another embodiment of the invention m is 1.

In another embodiment of the invention one of R3 and R4 is hydrogen and the other is fluoro. In another embodiment both R3 and R4 are hydrogen.

In another embodiment of the present invention Z is optionally substituted heteroaryl. Suitably Z is optionally substituted thienyl, furanyl, thiazolyl, pyrazolyl, isoxazolyl, pyridinyl, indazolyl, 2,3-dihydrobenzofuranyl, or benzothienyl.

In another embodiment Z is heteroaryl, suitably thienyl, furanyl, thiazolyl, pyrazolyl, isoxazolyl, pyridinyl, indazolyl, 2,3-dihydrobenzofuranyl, or benzothienyl each of which is optionally substituted with one to three substituents each independently selected from halo, —CN, optionally substituted $C_1$-$C_6$ alkyl, optionally substituted $C_1$-$C_6$ haloalkyl, —NRaRb, —SO$_2$NRaRb, —SO$_2$NRfRg, —ORc, and heteroaryl optionally substituted with one to three $C_1$-$C_6$ alkyl groups; where said $C_1$-$C_6$ alkyl and $C_1$-$C_6$ haloalkyl are optionally substituted with one to three substituents each independently selected from the group consisting of: —CN, —NRaRb, —SO$_2$Ri, —SO$_2$NRaRb, $C_3$-$C_6$ cycloalkyl, —ORc, —SRb, and heterocycloalkyl optionally substituted with one or two $C_1$-$C_6$ alkyl groups; wherein each Ra is independently selected from the group consisting of $C_1$-$C_6$ alkyl, $C_1$-$C_6$ alkyl substituted with one to three —ORc groups; each Rb and Rc is independently selected from the group consisting of H and $C_1$-$C_6$ alkyl; each Rf and Rg is independently taken together with the nitrogen atom to which they are attached forming a ring having from 4 to 7 member atoms wherein said ring optionally contains one additional heteroatom as a member atom, said ring being saturated or unsaturated but not aromatic, and said ring being optionally substituted with one or two $C_1$-$C_3$ alkyl substituents; and each Ri is independently selected from $C_3$-$C_7$ cycloalkyl and $C_1$-$C_3$ alkyl optionally substituted with one OH.

In another embodiment Z is thienyl optionally substituted with one $C_1$-$C_6$ alkyl group, wherein said $C_1$-$C_6$ alkyl is optionally substituted with one substituent selected from the group consisting of: NRaRb and heterocycloalkyl optionally substituted with one or two $C_1$-$C_6$ alkyl groups.

In another embodiment of the present invention Z is optionally substituted aryl, suitably phenyl. Suitably Z is phenyl optionally substituted with one to three substituents each independently selected from the group consisting of halo, —CN, optionally substituted $C_1$-$C_6$ alkyl, optionally substituted $C_1$-$C_6$ haloalkyl, optionally substituted heteroaryl, —N(Rb)SO$_2$Re, —N(Rb)C(O)Ra, —C(O)NRaRb, —C(O)H, —NRaRb, and —ORc; wherein where said $C_1$-$C_6$ alkyl and $C_1$-$C_6$ haloalkyl are optionally substituted with one to three substituents each independently selected from the group consisting of: —CN, —NRaRb, and —ORc; wherein each Ra, Rb, and Rc is independently selected from the group consisting of H and $C_1$-$C_6$ alkyl; and each Re is independently selected from $C_1$-$C_6$ alkyl.

In a further embodiment R2 is the group of formula (III):

(III)

optionally substituted with one to three substituents each independently selected from the group consisting of OH, $C_1$-$C_6$ alkyl, and phenyl; and wherein p is 0, 1, or 2 and q is 1, 2, or 3.

In a further embodiment of the present invention R2 is an optionally substituted 7-10 member heterocycloalkyl containing S(O)$_2$ as member atoms and the remaining member atoms are carbon, said 7-10 member heterocycloalkyl being optionally substituted with one to three substituents each independently selected from the group consisting of OH, $C_1$-$C_6$ alkyl, and phenyl.

In another embodiment R2 is

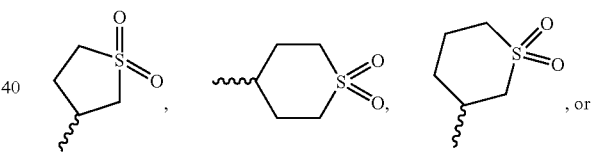

, or

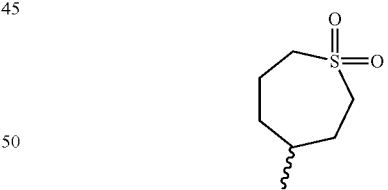

optionally substituted with one to three substituents each independently selected from the group consisting of OH, $C_1$-$C_3$ alkyl, and phenyl; or R2 is the bicyclo group

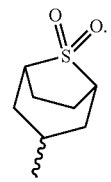

In a further embodiment R2 is

In an further embodiment R2 is

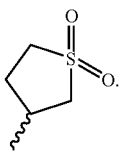

In a further embodiment R2 is

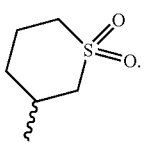

In a further embodiment R2 is

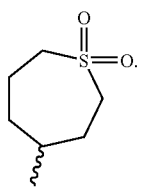

In a further embodiment R2 is

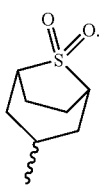

In another embodiment R2 is

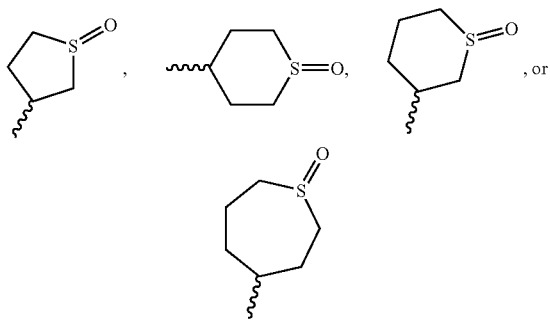

optionally substituted with one to three substituents each independently selected from the group consisting of OH, C$_1$-C$_3$ alkyl, and phenyl;

In a further embodiment R2 is

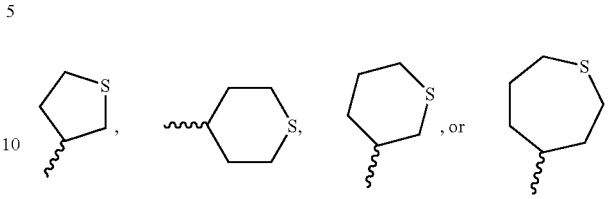

optionally substituted with one to three substituents each independently selected from the group consisting of OH, C$_1$-C$_3$ alkyl, and phenyl.

It is to be understood that the present invention covers all combinations of substituent groups described hereinabove.

Examples of the present invention include, but are not limited to, the following:

3-(1,1-dioxidotetrahydro-2H-thiopyran-4-yl)-5-phenyl-1H-indole-7-carboxamide;
3-(1,1-dioxidotetrahydro-2H-thiopyran-4-yl)-5-(3-thienyl)-1H-indole-7-carboxamide;
5-(2,5-difluorophenyl)-3-(1,1-dioxidotetrahydro-2H-thiopyran-4-yl)-1H-indole-7-carboxamide;
3-(1,1-dioxidotetrahydro-2H-thiopyran-4-yl)-5-(3-methylphenyl)-1H-indole-7-carboxamide;
5-(3-cyanophenyl)-3-(1,1-dioxidotetrahydro-2H-thiopyran-4-yl)-1H-indole-7-carboxamide;
3-(1,1-dioxidotetrahydro-2H-thiopyran-4-yl)-5-(2-fluorophenyl)-1H-indole-7-carboxamide;
5-(2,4-difluorophenyl)-3-(1,1-dioxidotetrahydro-2H-thiopyran-4-yl)-1H-indole-7-carboxamide;
3-(1,1-dioxidotetrahydro-2H-thiopyran-4-yl)-5-(4-fluorophenyl)-1H-indole-7-carboxamide;
3-(1,1-dioxidotetrahydro-2H-thiopyran-4-yl)-5-(2-furanyl)-1H-indole-7-carboxamide;
3-(1,1-dioxidotetrahydro-2H-thiopyran-4-yl)-5-(3-furanyl)-1H-indole-7-carboxamide;
3-(1,1-dioxidotetrahydro-2H-thiopyran-4-yl)-5-(3-pyridinyl)-1H-indole-7-carboxamide;
3-(1,1-dioxidotetrahydro-2H-thiopyran-4-yl)-5-(4-hydroxyphenyl)-1H-indole-7-carboxamide;
3-(1,1-dioxidotetrahydro-2H-thiopyran-4-yl)-5-(3-hydroxyphenyl)-1H-indole-7-carboxamide;
5-(3,5-dimethylphenyl)-3-(1,1-dioxidotetrahydro-2H-thiopyran-4-yl)-1H-indole-7-carboxamide;
3-(1,1-dioxidotetrahydro-2H-thiopyran-4-yl)-5-(4-ethylphenyl)-1H-indole-7-carboxamide;
3-(1,1-dioxidotetrahydro-2H-thiopyran-4-yl)-5-[3-(hydroxymethyl)phenyl]-1H-indole-7-carboxamide;
3-(1,1-dioxidotetrahydro-2H-thiopyran-4-yl)-5-[4-(methyloxy)phenyl]-1H-indole-7-carboxamide;
5-(4-chlorophenyl)-3-(1,1-dioxidotetrahydro-2H-thiopyran-4-yl)-1H-indole-7-carboxamide;
5-(3-chloro-4-fluorophenyl)-3-(1,1-dioxidotetrahydro-2H-thiopyran-4-yl)-1H-indole-7-carboxamide;
3-(1,1-dioxidotetrahydro-2H-thiopyran-4-yl)-5-[3-(trifluoromethyl)phenyl]-1H-indole-7-carboxamide;
5-[4-(1,1-dimethylethyl)phenyl]-3-(1,1-dioxidotetrahydro-2H-thiopyran-4-yl)-1H-indole-7-carboxamide;
5-(4-butylphenyl)-3-(1,1-dioxidotetrahydro-2H-thiopyran-4-yl)-1H-indole-7-carboxamide;
3-(1,1-dioxidotetrahydro-2H-thiopyran-4-yl)-5-(2-thienyl)-1H-indole-7-carboxamide;

3-(1,1-dioxidotetrahydro-2H-thiopyran-4-yl)-5-(3-fluorophenyl)-1H-indole-7-carboxamide;
3-(1,1-dioxidotetrahydro-2H-thiopyran-4-yl)-5-[3-(methyloxy)phenyl]-1H-indole-7-carboxamide;
3-(1,1-dioxidotetrahydro-2H-thiopyran-4-yl)-5-[3-(ethyloxy)phenyl]-1H-indole-7-carboxamide;
5-[3-(acetylamino)phenyl]-3-(1,1-dioxidotetrahydro-2H-thiopyran-4-yl)-1H-indole-7-carboxamide;
5-(3-chlorophenyl)-3-(1,1-dioxidotetrahydro-2H-thiopyran-4-yl)-1H-indole-7-carboxamide;
3-(1,1-dioxidotetrahydro-2H-thiopyran-4-yl)-5-[4-(hydroxymethyl)phenyl]-1H-indole-7-carboxamide;
3-(1,1-dioxidotetrahydro-2H-thiopyran-4-yl)-5-[3-fluoro-4-(methyloxy)phenyl]-1H-indole-7-carboxamide;
3-(1,1-dioxidotetrahydro-2H-thiopyran-4-yl)-5-(4-pyridinyl)-1H-indole-7-carboxamide;
3-(1,1-dioxidotetrahydro-2H-thiopyran-4-yl)-5-(4-fluoro-3-methylphenyl)-1H-indole-7-carboxamide;
5-(4-aminophenyl)-3-(1,1-dioxidotetrahydro-2H-thiopyran-4-yl)-1H-indole-7-carboxamide;
5-(6-chloro-3-pyridinyl)-3-(1,1-dioxidotetrahydro-2H-thiopyran-4-yl)-1H-indole-7-carboxamide;
3-(1,1-dioxidotetrahydro-2H-thiopyran-4-yl)-5-(6-fluoro-3-pyridinyl)-1H-indole-7-carboxamide;
3-(1,1-dioxidotetrahydro-2H-thiopyran-4-yl)-5-(2-hydroxyphenyl)-1H-indole-7-carboxamide;
5-(3,5-dichlorophenyl)-3-(1,1-dioxidotetrahydro-2H-thiopyran-4-yl)-1H-indole-7-carboxamide;
5-(3,4-dichlorophenyl)-3-(1,1-dioxidotetrahydro-2H-thiopyran-4-yl)-1H-indole-7-carboxamide;
5-[4-(butyloxy)phenyl]-3-(1,1-dioxidotetrahydro-2H-thiopyran-4-yl)-1H-indole-7-carboxamide;
5-[4-(dimethylamino)phenyl]-3-(1,1-dioxidotetrahydro-2H-thiopyran-4-yl)-1H-indole-7-carboxamide;
3-(1,1-dioxidotetrahydro-2H-thiopyran-4-yl)-5-(5-methyl-2-furanyl)-1H-indole-7-carboxamide;
5-(3,5-difluorophenyl)-3-(1,1-dioxidotetrahydro-2H-thiopyran-4-yl)-1H-indole-7-carboxamide;
3-(1,1-dioxidotetrahydro-2H-thiopyran-4-yl)-5-(3,4,5-trifluorophenyl)-1H-indole-7-carboxamide;
3-(1,1-dioxidotetrahydro-2H-thiopyran-4-yl)-5-[3-methyl-4-(methyloxy)phenyl]-1H-indole-7-carboxamide;
3-(1,1-dioxidotetrahydro-2H-thiopyran-4-yl)-5-[4-(propyloxy)phenyl]-1H-indole-7-carboxamide;
3-(1,1-dioxidotetrahydro-2H-thiopyran-4-yl)-5-{3-[(1-methylethyl)oxy]phenyl}-1H-indole-7-carboxamide;
3-(1,1-dioxidotetrahydro-2H-thiopyran-4-yl)-5-[6-(methyloxy)-3-pyridinyl]-1H-indole-7-carboxamide;
3-(1,1-dioxidotetrahydro-2H-thiopyran-4-yl)-5-{3-[(methylsulfonyl)amino]phenyl}-1H-indole-7-carboxamide;
3-(1,1-dioxidotetrahydro-2H-thiopyran-4-yl)-5-(4-propylphenyl)-1H-indole-7-carboxamide;
5-[3,5-dimethyl-4-(methyloxy)phenyl]-3-(1,1-dioxidotetrahydro-2H-thiopyran-4-yl)-1H-indole-7-carboxamide;
3-(1,1-dioxidotetrahydro-2H-thiopyran-4-yl)-5-{4-[(1-methylethyl)oxy]phenyl}-1H-indole-7-carboxamide;
3-(1,1-dioxidotetrahydro-2H-thiopyran-4-yl)-5-[3-(propyloxy)phenyl]-1H-indole-7-carboxamide;
3-(1,1-dioxidotetrahydro-2H-thiopyran-4-yl)-5-[4-(trifluoromethyl)phenyl]-1H-indole-7-carboxamide;
3-(1,1-dioxidotetrahydro-2H-thiopyran-4-yl)-5-{3-[(trifluoromethyl)oxy]phenyl}-1H-indole-7-carboxamide;
3-(1,1-dioxidotetrahydro-2H-thiopyran-4-yl)-5-[4-hydroxy-3-(methyloxy)phenyl]-1H-indole-7-carboxamide;
3-(1,1-dioxidotetrahydro-2H-thiopyran-4-yl)-5-{5-[(methyloxy)methyl]-3-thienyl}-1H-indole-7-carboxamide;
5-(5-cyano-3-thienyl)-3-(1,1-dioxidotetrahydro-2H-thiopyran-4-yl)-1H-indole-7-carboxamide;
5-[5-(cyanomethyl)-3-thienyl]-3-(1,1-dioxidotetrahydro-2H-thiopyran-4-yl)-1H-indole-7-carboxamide;
3-(1,1-dioxidotetrahydro-2H-thiopyran-4-yl)-5-(4-methylphenyl)-1H-indole-7-carboxamide;
5-(3,4-difluorophenyl)-3-(1,1-dioxidotetrahydro-2H-thiopyran-4-yl)-1H-indole-7-carboxamide;
5-[4-(acetylamino)phenyl]-3-(1,1-dioxidotetrahydro-2H-thiopyran-4-yl)-1H-indole-7-carboxamide;
3-(1,1-dioxidotetrahydro-2H-thiopyran-4-yl)-5-[4-(ethyloxy)phenyl]-1H-indole-7-carboxamide;
3-(1,1-dioxidotetrahydro-2H-thiopyran-4-yl)-5-[2-(methyloxy)phenyl]-1H-indole-7-carboxamide;
3-(1,1-dioxidotetrahydro-2H-thiopyran-4-yl)-5-(2-methylphenyl)-1H-indole-7-carboxamide;
5-[4-(cyanomethyl)phenyl]-3-(1,1-dioxidotetrahydro-2H-thiopyran-4-yl)-1H-indole-7-carboxamide;
3-(1,1-dioxidotetrahydro-2H-thiopyran-4-yl)-5-[5-(3-hydroxy-3-methylbutyl)-2-thienyl]-1H-indole-7-carboxamide;
5-[6-(dimethylamino)-3-pyridinyl]-3-(1,1-dioxidotetrahydro-2H-thiopyran-4-yl)-1H-indole-7-carboxamide;
5-(2-chloro-4-pyridinyl)-3-(1,1-dioxidotetrahydro-2H-thiopyran-4-yl)-1H-indole-7-carboxamide;
5-(2,3-dihydro-1-benzofuran-5-yl)-3-(1,1-dioxidotetrahydro-2H-thiopyran-4-yl)-1H-indole-7-carboxamide;
5-[5-(1-azetidinylmethyl)-3-thienyl]-3-(1,1-dioxidotetrahydro-2H-thiopyran-4-yl)-1H-indole-7-carboxamide;
3-(1,1-dioxidotetrahydro-2H-thiopyran-4-yl)-5-[5-({methyl[2-(methyloxy)ethyl]amino}methyl)-3-thienyl]-1H-indole-7-carboxamide;
3-(1,1-dioxidotetrahydro-2H-thiopyran-4-yl)-5-[5-(hexahydro-1H-azepin-1-ylmethyl)-3-thienyl]-1H-indole-7-carboxamide;
5-{5-[(dimethylamino)methyl]-3-thienyl}-3-(1,1-dioxidotetrahydro-2H-thiopyran-4-yl)-1H-indole-7-carboxamide;
3-(1,1-dioxidotetrahydro-2H-thiopyran-4-yl)-5-(5-{[methyl(1-methylethyl)amino]methyl}-3-thienyl)-1H-indole-7-carboxamide;
3-(1,1-dioxidotetrahydro-2H-thiopyran-4-yl)-5-(5-{[ethyl(methyl)amino]methyl}-3-thienyl)-1H-indole-7-carboxamide;
5-{5-[(diethylamino)methyl]-3-thienyl}-3-(1,1-dioxidotetrahydro-2H-thiopyran-4-yl)-1H-indole-7-carboxamide;
5-(5-{[{2-[(1,1-dimethylethyl)oxy]ethyl}(methyl)amino]methyl}-3-thienyl)-3-(1,1-dioxidotetrahydro-2H-thiopyran-4-yl)-1H-indole-7-carboxamide;
3-(1,1-dioxidotetrahydro-2H-thiopyran-4-yl)-5-{3-[(methylamino)methyl]phenyl}-1H-indole-7-carboxamide;
5-{3-[(dimethylamino)methyl]phenyl}-3-(1,1-dioxidotetrahydro-2H-thiopyran-4-yl)-1H-indole-7-carboxamide;
5-[3-({[(1S)-1,2-dimethylpropyl]amino}methyl)phenyl]-3-(1,1-dioxidotetrahydro-2H-thiopyran-4-yl)-1H-indole-7-carboxamide;
3-(1,1-dioxidotetrahydro-2H-thiopyran-4-yl)-5-(1H-indazol-5-yl)-1H-indole-7-carboxamide;
5-(4-bromo-1,3-thiazol-2-yl)-3-(1,1-dioxidotetrahydro-2H-thiopyran-4-yl)-1H-indole-7-carboxamide;
3-(1,1-dioxidotetrahydro-2H-thiopyran-4-yl)-5-[5-(3-hydroxypropyl)-3-thienyl]-1H-indole-7-carboxamide;
3-(1,1-dioxidotetrahydro-2H-thiopyran-4-yl)-5-(1,3-thiazol-2-yl)-1H-indole-7-carboxamide;
3-(1,1-dioxidotetrahydro-2H-thiopyran-4-yl)-5-(1,3-thiazol-5-yl)-1H-indole-7-carboxamide;
3-(1,1-dioxidotetrahydro-2H-thiopyran-4-yl)-5-(5-methyl-3-thienyl)-1H-indole-7-carboxamide;

3-(1,1-dioxidotetrahydro-2H-thiopyran-4-yl)-5-(5-methyl-2-thienyl)-1H-indole-7-carboxamide;

3-(1,1-dioxidotetrahydro-2H-thiopyran-4-yl)-5-(4-methyl-3-thienyl)-1H-indole-7-carboxamide;

3-(1,1-dioxidotetrahydro-2H-thiopyran-4-yl)-5-(1,3,5-trimethyl-1H-pyrazol-4-yl)-1H-indole-7-carboxamide;

5-(5-chloro-2-thienyl)-3-(1,1-dioxidotetrahydro-2H-thiopyran-4-yl)-1H-indole-7-carboxamide;

5-(5-cyano-2-thienyl)-3-(1,1-dioxidotetrahydro-2H-thiopyran-4-yl)-1H-indole-7-carboxamide;

3-(1,1-dioxidotetrahydro-2H-thiopyran-4-yl)-5-(3-methyl-2-thienyl)-1H-indole-7-carboxamide;

3-(1,1-dioxidotetrahydro-2H-thiopyran-4-yl)-5-(1,3-thiazol-4-yl)-1H-indole-7-carboxamide;

3-(1,1-dioxidotetrahydro-2H-thiopyran-4-yl)-5-(2-methyl-1,3-thiazol-4-yl)-1H-indole-7-carboxamide;

5-(4-cyano-3-thienyl)-3-(1,1-dioxidotetrahydro-2H-thiopyran-4-yl)-1H-indole-7-carboxamide;

5-[5-(cyclopropylmethyl)-3-thienyl]-3-(1,1-dioxidotetrahydro-2H-thiopyran-4-yl)-1H-indole-7-carboxamide;

3-(1,1-dioxidotetrahydro-2H-thiopyran-4-yl)-5-{5-[(methyloxy)methyl]-2-thienyl}-1H-indole-7-carboxamide;

3-(1,1-dioxidotetrahydro-2H-thiopyran-4-yl)-5-{5-[(ethyloxy)methyl]-2-thienyl}-1H-indole-7-carboxamide;

3-(1,1-dioxidotetrahydro-2H-thiopyran-4-yl)-5-{5-[(ethyloxy)methyl]-3-thienyl}-1H-indole-7-carboxamide;

3-(1,1-dioxidotetrahydro-2H-thiopyran-4-yl)-5-{5-[(propyloxy)methyl]-2-thienyl}-1H-indole-7-carboxamide;

3-(1,1-dioxidotetrahydro-2H-thiopyran-4-yl)-5-{5-[(propyloxy)methyl]-3-thienyl}-1H-indole-7-carboxamide;

3-(1,1-dioxidotetrahydro-2H-thiopyran-4-yl)-5-[5-(4-morpholinylmethyl)-3-thienyl]-1H-indole-7-carboxamide;

3-(1,1-dioxidotetrahydro-2H-thiopyran-4-yl)-5-{5-[2-(methyloxy)ethyl]-2-thienyl}-1H-indole-7-carboxamide;

3-(1,1-dioxidotetrahydro-2H-thiopyran-4-yl)-5-{5-[2-(ethyloxy)ethyl]-2-thienyl}-1H-indole-7-carboxamide;

3-(1,1-dioxidotetrahydro-2H-thiopyran-4-yl)-5-[5-(methyloxy)-2-thienyl]-1H-indole-7-carboxamide;

3-(1,1-dioxidotetrahydro-2H-thiopyran-4-yl)-5-[5-(4-morpholinylmethyl)-2-thienyl]-1H-indole-7-carboxamide;

3-(1,1-dioxidotetrahydro-2H-thiopyran-4-yl)-5-[5-(4-morpholinylmethyl)-2-furanyl]-1H-indole-7-carboxamide;

3-(1,1-dioxidotetrahydro-2H-thiopyran-4-yl)-5-{5-[(ethylthio)methyl]-3-thienyl}-1H-indole-7-carboxamide;

3-(1,1-dioxidotetrahydro-2H-thiopyran-4-yl)-5-(5-{[(1-methylethyl)thio]methyl}-3-thienyl)-1H-indole-7-carboxamide;

3-(1,1-dioxidotetrahydro-2H-thiopyran-4-yl)-5-{5-[(propylthio)methyl]-3-thienyl}-1H-indole-7-carboxamide;

3-(1,1-dioxidotetrahydro-2H-thiopyran-4-yl)-5-(5-{[(1-methylpropyl)thio]methyl}-3-thienyl)-1H-indole-7-carboxamide;

3-(1,1-dioxidotetrahydro-2H-thiopyran-4-yl)-5-{5-[(ethylthio)methyl]-2-thienyl}-1H-indole-7-carboxamide;

3-(1,1-dioxidotetrahydro-2H-thiopyran-4-yl)-5-(5-{[(1-methylethyl)thio]methyl}-2-thienyl)-1H-indole-7-carboxamide;

3-(1,1-dioxidotetrahydro-2H-thiopyran-4-yl)-5-[5-(hexahydro-1H-azepin-1-ylmethyl)-2-furanyl]-1H-indole-7-carboxamide;

3-(1,1-dioxidotetrahydro-2H-thiopyran-4-yl)-5-[5-(hexahydro-1H-azepin-1-ylmethyl)-2-thienyl]-1H-indole-7-carboxamide;

3-(1,1-dioxidotetrahydro-2H-thiopyran-4-yl)-5-[5-(4-morpholinylmethyl)-3-furanyl]-1H-indole-7-carboxamide;

3-(1,1-dioxidotetrahydro-2H-thiopyran-4-yl)-5-[5-(hexahydro-1H-azepin-1-ylmethyl)-3-furanyl]-1H-indole-7-carboxamide;

3-(1,1-dioxidotetrahydro-2H-thiopyran-4-yl)-5-[5-(2-methylpropyl)-3-thienyl]-1H-indole-7-carboxamide;

3-(1,1-dioxidotetrahydro-2H-thiopyran-4-yl)-5-{5-[(ethyloxy)methyl]-2-furanyl}-1H-indole-7-carboxamide;

3-(1,1-dioxidotetrahydro-2H-thiopyran-4-yl)-5-[5-(hydroxymethyl)-3-thienyl]-1H-indole-7-carboxamide;

3-(1,1-dioxidotetrahydro-2H-thiopyran-4-yl)-5-[5-(tetrahydro-1,4-oxazepin-4(5H)-ylmethyl)-3-thienyl]-1H-indole-7-carboxamide;

3-(1,1-dioxidotetrahydro-2H-thiopyran-4-yl)-5-[5-(tetrahydro-1,4-oxazepin-4(5H)-ylmethyl)-2-furanyl]-1H-indole-7-carboxamide;

5-(5-{[(2R,6S)-2,6-dimethyl-4-morpholinyl]methyl}-3-thienyl)-3-(1,1-dioxidotetrahydro-2H-thiopyran-4-yl)-1H-indole-7-carboxamide;

3-(1,1-dioxidotetrahydro-2H-thiopyran-4-yl)-5-{5-[(4-methyl-1-piperazinyl)methyl]-2-furanyl}-1H-indole-7-carboxamide;

3-(1,1-dioxidotetrahydro-2H-thiopyran-4-yl)-5-{5-[(ethylthio)methyl]-2-furanyl}-1H-indole-7-carboxamide;

3-(1,1-dioxidotetrahydro-2H-thiopyran-4-yl)-5-{5-[(methyloxy)methyl]-2-furanyl}-1H-indole-7-carboxamide;

3-(1,1-dioxidotetrahydro-2H-thiopyran-4-yl)-5-[5-(1-pyrrolidinylsulfonyl)-2-thienyl]-1H-indole-7-carboxamide;

5-[5-({[(1S)-1,2-dimethylpropyl]amino}sulfonyl)-2-thienyl]-3-(1,1-dioxidotetrahydro-2H-thiopyran-4-yl)-1H-indole-7-carboxamide;

3-(1,1-dioxidotetrahydro-2H-thiopyran-4-yl)-5-(5-{[(2-hydroxyethyl)sulfonyl]methyl}-2-thienyl)-1H-indole-7-carboxamide;

3-(1,1-dioxidotetrahydro-2H-thiopyran-4-yl)-5-[5-(2-hydroxyethyl)-2-thienyl]-1H-indole-7-carboxamide;

3-(1,1-dioxidotetrahydro-2H-thiopyran-4-yl)-5-[5-(hydroxymethyl)-2-thienyl]-1H-indole-7-carboxamide;

3-(1,1-dioxidotetrahydro-2H-thiopyran-4-yl)-5-(1-methyl-1H-imidazol-2-yl)-1H-indole-7-carboxamide;

3-(1,1-dioxidotetrahydro-2H-thiopyran-4-yl)-5-[5-(1-methyl-1H-imidazol-2-yl)-2-thienyl]-1H-indole-7-carboxamide;

3-(1,1-dioxidotetrahydro-2H-thiopyran-4-yl)-5-[5-(1H-imidazol-2-yl)-3-thienyl]-1H-indole-7-carboxamide;

3-(1,1-dioxidotetrahydro-2H-thiopyran-4-yl)-5-[5-(1-methyl-1H-imidazol-2-yl)-3-thienyl]-1H-indole-7-carboxamide;

3-(1,1-dioxidotetrahydro-2H-thiopyran-4-yl)-5-[3-(1H-pyrazol-1-yl)phenyl]-1H-indole-7-carboxamide;

3-(1,1-dioxidotetrahydro-2H-thiopyran-4-yl)-5-[5-(5-isoxazolyl)-2-thienyl]-1H-indole-7-carboxamide;

3-(1,1-dioxidotetrahydro-2H-thiopyran-4-yl)-5-[5-(2-methyl-1,3-thiazol-4-yl)-2-thienyl]-1H-indole-7-carboxamide;

5-(3,5-dimethyl-1H-pyrazol-4-yl)-3-(1,1-dioxidotetrahydro-2H-thiopyran-4-yl)-1H-indole-7-carboxamide;

5-(3,5-dimethyl-4-isoxazolyl)-3-(1,1-dioxidotetrahydro-2H-thiopyran-4-yl)-1H-indole-7-carboxamide;

5-(2-cyanophenyl)-3-(1,1-dioxidotetrahydro-2H-thiopyran-4-yl)-1H-indole-7-carboxamide;

5-(4-cyanophenyl)-3-(1,1-dioxidotetrahydro-2H-thiopyran-4-yl)-1H-indole-7-carboxamide;

5-[3-(cyanomethyl)phenyl]-3-(1,1-dioxidotetrahydro-2H-thiopyran-4-yl)-1H-indole-7-carboxamide;

3-(1,1-dioxidotetrahydro-2H-thiopyran-4-yl)-2',3'-dihydro-1H,1'H-5,5'-biindole-7-carboxamide;

5-(4-cyano-3-fluorophenyl)-3-(1,1-dioxidotetrahydro-2H-thiopyran-4-yl)-1H-indole-7-carboxamide;
5-[2-(aminocarbonyl)phenyl]-3-(1,1-dioxidotetrahydro-2H-thiopyran-4-yl)-1H-indole-7-carboxamide;
5-[3-(dimethylamino)phenyl]-3-(1,1-dioxidotetrahydro-2H-thiopyran-4-yl)-1H-indole-7-carboxamide;
3-(1,1-dioxidotetrahydro-2H-thiopyran-4-yl)-5-[3-(2-hydroxyethyl)phenyl]-1H-indole-7-carboxamide;
3-(1,1-dioxidotetrahydro-2H-thiopyran-4-yl)-5-[2-(2-hydroxyethyl)phenyl]-1H-indole-7-carboxamide;
3-(1,1-dioxidotetrahydro-2H-thiopyran-4-yl)-5-[5-fluoro-2-(methyloxy)phenyl]-1H-indole-7-carboxamide;
5-(3-chloro-4-methylphenyl)-3-(1,1-dioxidotetrahydro-2H-thiopyran-4-yl)-1H-indole-7-carboxamide;
5-[5-cyano-2-(methyloxy)phenyl]-3-(1,1-dioxidotetrahydro-2H-thiopyran-4-yl)-1H-indole-7-carboxamide;
5-[3-cyano-4-(methyloxy)phenyl]-3-(1,1-dioxidotetrahydro-2H-thiopyran-4-yl)-1H-indole-7-carboxamide;
3-(1,1-dioxidotetrahydro-2H-thiopyran-4-yl)-5-[3-(hydroxymethyl)-4-(methyloxy)phenyl]-1H-indole-7-carboxamide;
3-(1,1-dioxidotetrahydro-2H-thiopyran-4-yl)-5-{4-[(2-hydroxyethyl)oxy]phenyl}-1H-indole-7-carboxamide;
5-[3-(cyanomethyl)-4-(methyloxy)phenyl]-3-(1,1-dioxidotetrahydro-2H-thiopyran-4-yl)-1H-indole-7-carboxamide;
5-[4-(diethylamino)phenyl]-3-(1,1-dioxidotetrahydro-2H-thiopyran-4-yl)-1H-indole-7-carboxamide;
3-(1,1-dioxidotetrahydro-2H-thiopyran-4-yl)-5-[4-(2-oxo-1-pyrrolidinyl)phenyl]-1H-indole-7-carboxamide;
3-(1,1-dioxidotetrahydro-2H-thiopyran-4-yl)-5-{5-[2-({[(1S)-1-(hydroxymethyl)propyl]amino}sulfonyl)ethyl]-2-thienyl}-1H-indole-7-carboxamide;
3-(1,1-dioxidotetrahydro-2H-thiopyran-4-yl)-5-[5-(2-{[(4-hydroxycyclohexyl)amino]sulfonyl}ethyl)-3-thienyl]-1H-indole-7-carboxamide;
3-(1,1-dioxidotetrahydro-2H-thiopyran-4-yl)-5-[5-(2-{[(2-hydroxyethyl)amino]sulfonyl}ethyl)-2-thienyl]-1H-indole-7-carboxamide;
5-[5-(difluoromethyl)-3-thienyl]-3-(1,1-dioxidotetrahydro-2H-thiopyran-4-yl)-1H-indole-7-carboxamide;
5-(2-chloro-3-thienyl)-3-(1,1-dioxidotetrahydro-2H-thiopyran-4-yl)-1H-indole-7-carboxamide;
3-(1,1-dioxidotetrahydro-2H-thiopyran-4-yl)-5-[1-methyl-3-(trifluoromethyl)-1H-pyrazol-4-yl]-1H-indole-7-carboxamide;
5-(2,4-dimethyl-1,3-thiazol-5-yl)-3-(1,1-dioxidotetrahydro-2H-thiopyran-4-yl)-1H-indole-7-carboxamide;
3-(1,1-dioxidotetrahydro-2H-thiopyran-4-yl)-5-(4-methyl-1,3-thiazol-2-yl)-1H-indole-7-carboxamide;
3-(1,1-dioxidotetrahydro-2H-thiopyran-4-yl)-6-fluoro-5-phenyl-1H-indole-7-carboxamide;
3-(1,1-dioxidotetrahydro-2H-thiopyran-4-yl)-4-fluoro-5-phenyl-1H-indole-7-carboxamide;
3-(1,1-dioxidotetrahydro-2H-thiopyran-4-yl)-4-fluoro-5-(3-thienyl)-1H-indole-7-carboxamide;
5-[5-(1-azetidinylsulfonyl)-2-thienyl]-3-(1,1-dioxidotetrahydro-2H-thiopyran-4-yl)-1H-indole-7-carboxamide;
3-(1,1-dioxidotetrahydro-3-thienyl)-5-(4-fluorophenyl)-1H-indole-7-carboxamide;
3-[(3S)-1,1-dioxidotetrahydro-3-thienyl]-5-(4-fluorophenyl)-1H-indole-7-carboxamide;
3-[(3R)-1,1-dioxidotetrahydro-3-thienyl]-5-(4-fluorophenyl)-1H-indole-7-carboxamide;
3-(1,1-dioxidotetrahydro-3-thienyl)-5-phenyl-1H-indole-7-carboxamide;
3-(1,1-dioxidotetrahydro-3-thienyl)-5-(3-thienyl)-1H-indole-7-carboxamide;
5-(4-cyanophenyl)-3-[(3S)-1,1-dioxidotetrahydro-3-thienyl]-1H-indole-7-carboxamide;
3-[(3S)-1,1-dioxidotetrahydro-3-thienyl]-5-(4-fluoro-3-methylphenyl)-1H-indole-7-carboxamide;
5-[3,4-bis(methyloxy)phenyl]-3-[(3S)-1,1-dioxidotetrahydro-3-thienyl]-1H-indole-7-carboxamide;
5-(3,4-difluorophenyl)-3-(1,1-dioxidotetrahydro-3-thienyl)-1H-indole-7-carboxamide;
3-(1,1-dioxidotetrahydro-3-thienyl)-5-{4-[(trifluoromethyl)oxy]phenyl}-1H-indole-7-carboxamide;
5-(3-cyanophenyl)-3-(1,1-dioxidotetrahydro-3-thienyl)-1H-indole-7-carboxamide;
3-(1,1-dioxidotetrahydro-3-thienyl)-5-{3-[(trifluoromethyl)oxy]phenyl}-1H-indole-7-carboxamide;
3-(1,1-dioxidotetrahydro-3-thienyl)-5-(3-methylphenyl)-1H-indole-7-carboxamide;
5-(2,4-difluorophenyl)-3-(1,1-dioxidotetrahydro-3-thienyl)-1H-indole-7-carboxamide;
5-[5-(1-azetidinylmethyl)-3-thienyl]-3-(1,1-dioxidotetrahydro-3-thienyl)-1H-indole-7-carboxamide;
3-(1,1-dioxidotetrahydro-3-thienyl)-5-[5-(hexahydro-1H-azepin-1-ylmethyl)-3-thienyl]-1H-indole-7-carboxamide;
3-(1,1-dioxidotetrahydro-3-thienyl)-5-[5-(1-pyrrolidinylmethyl)-3-thienyl]-1H-indole-7-carboxamide;
3-(1,1-dioxidotetrahydro-3-thienyl)-5-(2-furanyl)-1H-indole-7-carboxamide;
3-(1,1-dioxidotetrahydro-3-thienyl)-5-(3-furanyl)-1H-indole-7-carboxamide;
3-(1,1-dioxidotetrahydro-3-thienyl)-5-(2-thienyl)-1H-indole-7-carboxamide;
5-(1-benzothien-5-yl)-3-(1,1-dioxidotetrahydro-3-thienyl)-1H-indole-7-carboxamide;
3-[(3-endo)-8,8-dioxido-8-thiabicyclo[3.2.1]oct-3-yl]-5-phenyl-1H-indole-7-carboxamide;
3-[(3-endo)-8,8-dioxido-8-thiabicyclo[3.2.1]oct-3-yl]-5-(2-furanyl)-1H-indole-7-carboxamide;
3-[(3-endo)-8,8-dioxido-8-thiabicyclo[3.2.1]oct-3-yl]-5-(3-furanyl)-1H-indole-7-carboxamide;
3-[(3-endo)-8,8-dioxido-8-thiabicyclo[3.2.1]oct-3-yl]-5-(3-thienyl)-1H-indole-7-carboxamide;
3-[(3-endo)-8,8-dioxido-8-thiabicyclo[3.2.1]oct-3-yl]-5-(2-thienyl)-1H-indole-7-carboxamide;
3-[(3-endo)-8,8-dioxido-8-thiabicyclo[3.2.1]oct-3-yl]-5-(4-fluorophenyl)-1H-indole-7-carboxamide;
3-[(3-endo)-8,8-dioxido-8-thiabicyclo[3.2.1]oct-3-yl]-5-phenyl-1H-indole-7-carboxamide;
3-[(3-exo)-8,8-dioxido-8-thiabicyclo[3.2.1]oct-3-yl]-5-(2-furanyl)-1H-indole-7-carboxamide;
3-[(3-endo)-8,8-dioxido-8-thiabicyclo[3.2.1]oct-3-yl]-5-(3-thienyl)-1H-indole-7-carboxamide;
3-[(3-exo)-8,8-dioxido-8-thiabicyclo[3.2.1]oct-3-yl]-5-(2-thienyl)-1H-indole-7-carboxamide;
3-[(3-endo)-8,8-dioxido-8-thiabicyclo[3.2.1]oct-3-yl]-5-(4-fluorophenyl)-1H-indole-7-carboxamide;
3-[(3-endo)-8,8-dioxido-8-thiabicyclo[3.2.1]oct-3-yl]-5-[5-(hexahydro-1H-azepin-1-ylmethyl)-3-thienyl]-1H-indole-7-carboxamide;
5-[5-(1-azetidinylmethyl)-3-thienyl]-3-[(3-endo)-8,8-dioxido-8-thiabicyclo[3.2.1]oct-3-yl]-1H-indole-7-carboxamide;
3-[(3-endo)-8,8-dioxido-8-thiabicyclo[3.2.1]oct-3-yl]-5-[5-(1-pyrrolidinylmethyl)-3-thienyl]-1H-indole-7-carboxamide;
5-{5-[(dimethylamino)methyl]-3-thienyl}-3-[(3-endo)-8,8-dioxido-8-thiabicyclo[3.2.1]oct-3-yl]-1H-indole-7-carboxamide;

5-(5-{[(cyclopropylmethyl)amino]methyl}-3-thienyl)-3-[(3-endo)-8,8-dioxido-8-thiabicyclo[3.2.1]oct-3-yl]-1H-indole-7-carboxamide;

3-[(3-exo)-8,8-dioxido-8-thiabicyclo[3.2.1]oct-3-yl]-5-[5-(hexahydro-1H-azepin-1-ylmethyl)-3-thienyl]-1H-indole-7-carboxamide;

5-{5-[(dimethylamino)methyl]-3-thienyl}-3-[(3-exo)-8,8-dioxido-8-thiabicyclo[3.2.1]oct-3-yl]-1H-indole-7-carboxamide;

3-[(3-exo)-8,8-dioxido-8-thiabicyclo[3.2.1]oct-3-yl]-5-[5-(1-pyrrolidinylmethyl)-3-thienyl]-1H-indole-7-carboxamide;

5-[5-(1-azetidinylmethyl)-3-thienyl]-3-[(3-exo)-8,8-dioxido-8-thiabicyclo[3.2.1]oct-3-yl]-1H-indole-7-carboxamide;

3-(1,1-dioxido-4-thiepanyl)-5-phenyl-1H-indole-7-carboxamide;

3-(1,1-dioxido-4-thiepanyl)-5-(3-fluorophenyl)-1H-indole-7-carboxamide;

3-(1,1-dioxido-4-thiepanyl)-5-[4-(methyloxy)phenyl]-1H-indole-7-carboxamide;

5-(3,4-difluorophenyl)-3-(1,1-dioxido-4-thiepanyl)-1H-indole-7-carboxamide;

5-(3-cyanophenyl)-3-(1,1-dioxido-4-thiepanyl)-1H-indole-7-carboxamide;

3-(1,1-dioxidotetrahydro-2H-thiopyran-3-yl)-5-(3-furanyl)-1H-indole-7-carboxamide;

3-(1,1-dioxidotetrahydro-2H-thiopyran-3-yl)-5-(2-furanyl)-1H-indole-7-carboxamide;

3-(1,1-dioxidotetrahydro-2H-thiopyran-3-yl)-5-(3-thienyl)-1H-indole-7-carboxamide;

3-(1,1-dioxidotetrahydro-2H-thiopyran-3-yl)-5-(4-fluorophenyl)-1H-indole-7-carboxamide;

3-(1,1-dioxidotetrahydro-2H-thiopyran-3-yl)-5-phenyl-1H-indole-7-carboxamide;

3-(1,1-dioxidotetrahydro-2H-thiopyran-3-yl)-5-(2-thienyl)-1H-indole-7-carboxamide;

3-(2,6-dimethyl-1,1-dioxidotetrahydro-2H-thiopyran-4-yl)-5-(3-thienyl)-1H-indole-7-carboxamide;

3-(2,2-dimethyl-1,1-dioxidotetrahydro-2H-thiopyran-4-yl)-5-(4-fluorophenyl)-1H-indole-7-carboxamide;

3-(2,2-dimethyl-1,1-dioxidotetrahydro-2H-thiopyran-4-yl)-5-(4-fluorophenyl)-1H-indole-7-carboxamide;

3-(2,2-dimethyl-1,1-dioxidotetrahydro-2H-thiopyran-4-yl)-5-(4-fluorophenyl)-1H-indole-7-carboxamide;

3-(2,2-dimethyl-1,1-dioxidotetrahydro-2H-thiopyran-4-yl)-5-phenyl-1H-indole-7-carboxamide;

3-(2,2-dimethyl-1,1-dioxidotetrahydro-2H-thiopyran-4-yl)-5-(3-thienyl)-1H-indole-7-carboxamide;

3-(2,2-dimethyl-1,1-dioxidotetrahydro-2H-thiopyran-4-yl)-5-(3-furanyl)-1H-indole-7-carboxamide;

3-(2,2-dimethyl-1,1-dioxidotetrahydro-2H-thiopyran-4-yl)-5-(2-thienyl)-1H-indole-7-carboxamide;

3-(2,2-dimethyl-1,1-dioxidotetrahydro-2H-thiopyran-4-yl)-5-(2-furanyl)-1H-indole-7-carboxamide;

3-(2,2-dimethyl-1,1-dioxidotetrahydro-2H-thiopyran-4-yl)-5-[5-(hexahydro-1H-azepin-1-ylmethyl)-3-thienyl]-1H-indole-7-carboxamide;

5-{5-[(dimethylamino)methyl]-3-thienyl}-3-(2,2-dimethyl-1,1-dioxidotetrahydro-2H-thiopyran-4-yl)-1H-indole-7-carboxamide;

3-(2,2-dimethyl-1,1-dioxidotetrahydro-2H-thiopyran-4-yl)-5-[5-(1-pyrrolidinylmethyl)-3-thienyl]-1H-indole-7-carboxamide;

5-[5-(1-azetidinylmethyl)-3-thienyl]-3-(2,2-dimethyl-1,1-dioxidotetrahydro-2H-thiopyran-4-yl)-1H-indole-7-carboxamide;

3-(2,2-dimethyl-1,1-dioxidotetrahydro-2H-thiopyran-4-yl)-5-[5-(1-pyrrolidinylmethyl)-2-thienyl]-1H-indole-7-carboxamide;

5-{5-[(dimethylamino)methyl]-2-thienyl}-3-(2,2-dimethyl-1,1-dioxidotetrahydro-2H-thiopyran-4-yl)-1H-indole-7-carboxamide;

5-[5-(1-azetidinylmethyl)-2-thienyl]-3-(2,2-dimethyl-1,1-dioxidotetrahydro-2H-thiopyran-4-yl)-1H-indole-7-carboxamide;

3-(2,2-dimethyl-1,1-dioxidotetrahydro-2H-thiopyran-4-yl)-5-[5-(hexahydro-1H-azepin-1-ylmethyl)-2-thienyl]-1H-indole-7-carboxamide;

3-(2,2-dimethyl-1,1-dioxidotetrahydro-2H-thiopyran-4-yl)-5-[5-(1-pyrrolidinylsulfonyl)-2-thienyl]-1H-indole-7-carboxamide;

5-[5-(cyclopentylsulfonyl)-2-thienyl]-3-(2,2-dimethyl-1,1-dioxidotetrahydro-2H-thiopyran-4-yl)-1H-indole-7-carboxamide;

3-[(2R,4R)-2-(1-methylethyl)-1,1-dioxidotetrahydro-2H-thiopyran-4-yl]-5-(3-thienyl)-1H-indole-7-carboxamide;

3-[2-(1-methylethyl)-1,1-dioxidotetrahydro-2H-thiopyran-4-yl]-5-phenyl-1H-indole-7-carboxamide;

5-(3-furanyl)-3-[2-(1-methylethyl)-1,1-dioxidotetrahydro-2H-thiopyran-4-yl]-1H-indole-7-carboxamide;

5-(2-furanyl)-3-[2-(1-methylethyl)-1,1-dioxidotetrahydro-2H-thiopyran-4-yl]-1H-indole-7-carboxamide;

3-[(2R,4R)-2-(1-methylethyl)-1,1-dioxidotetrahydro-2H-thiopyran-4-yl]-5-(2-thienyl)-1H-indole-7-carboxamide;

3-[(2S,4R)-2-(1-methylethyl)-1,1-dioxidotetrahydro-2H-thiopyran-4-yl]-5-(3-thienyl)-1H-indole-7-carboxamide;

3-(1,1-dioxido-2-phenyltetrahydro-2H-thiopyran-4-yl)-5-(3-thienyl)-1H-indole-7-carboxamide;

3-[(2R,4S)-1,1-dioxido-2-phenyltetrahydro-2H-thiopyran-4-yl]-5-(3-thienyl)-1H-indole-7-carboxamide;

3-[(2S,4R)-1,1-dioxido-2-phenyltetrahydro-2H-thiopyran-4-yl]-5-(3-thienyl)-1H-indole-7-carboxamide;

3-[(2R,4S)-1,1-dioxido-2-phenyltetrahydro-2H-thiopyran-4-yl]-5-(2-thienyl)-1H-indole-7-carboxamide;

3-[(2R,4S)-1,1-dioxido-2-phenyltetrahydro-2H-thiopyran-4-yl]-5-(3-furanyl)-1H-indole-7-carboxamide;

3-[(2S,4R)-1,1-dioxido-2-phenyltetrahydro-2H-thiopyran-4-yl]-5-(2-furanyl)-1H-indole-7-carboxamide;

3-[(2R,4S)-1,1-dioxido-2-phenyltetrahydro-2H-thiopyran-4-yl]-5-phenyl-1H-indole-7-carboxamide;

3-[(1,1-dioxidotetrahydro-2H-thiopyran-4-yl)methyl]-5-(3-furanyl)-1H-indole-7-carboxamide;

3-[(1,1-dioxidotetrahydro-2H-thiopyran-4-yl)methyl]-5-phenyl-1H-indole-7-carboxamide;

3-[(1,1-dioxidotetrahydro-2H-thiopyran-4-yl)methyl]-5-(2-thienyl)-1H-indole-7-carboxamide;

3-[(1,1-dioxidotetrahydro-2H-thiopyran-4-yl)methyl]-5-(4-fluorophenyl)-1H-indole-7-carboxamide;

3-[(1,1-dioxidotetrahydro-2H-thiopyran-4-yl)methyl]-5-(3-thienyl)-1H-indole-7-carboxamide;

3-[(1,1-dioxidotetrahydro-2H-thiopyran-4-yl)methyl]-5-[5-(hexahydro-1H-azepin-1-ylmethyl)-3-thienyl]-1H-indole-7-carboxamide;

3-[(1,1-dioxidotetrahydro-3-thienyl)methyl]-5-phenyl-1H-indole-7-carboxamide;

3-[(1,1-dioxidotetrahydro-3-thienyl)methyl]-5-(3-thienyl)-1H-indole-7-carboxamide;

5-{5-[(dimethylamino)methyl]-3-thienyl}-3-[(1,1-dioxidotetrahydro-3-thienyl)methyl]-1H-indole-7-carboxamide;

3-[(1,1-dioxidotetrahydro-2H-thiopyran-3-yl)methyl]-5-(3-thienyl)-1H-indole-7-carboxamide; and 3-[(1,1-dioxidotetrahydro-2H-thiopyran-3-yl)methyl]-5-(4-fluorophenyl)-1H-indole-7-carboxamide The compounds according to formula (I) may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in formula (I), or in any chemical structure illustrated herein, is not specified the structure is intended to encompass any stereoisomer and all mixtures thereof. Thus, compounds according to formula (I) containing one or more chiral center may be used as racemic mixtures, enantiomerically enriched mixtures, or as enantiomerically pure individual stereoisomers.

Individual stereoisomers of a compound according to formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to formula (I) may also contain double bonds or other centers of geometric asymmetry. Where the stereochemistry of a center of geometric asymmetry present in formula (I), or in any chemical structure illustrated herein, is not specified, the structure is intended to encompass the trans (E) geometric isomer, the cis (Z) geometric isomer, and all mixtures thereof. Likewise, all tautomeric forms are also included in formula (I) whether such tautomers exist in equilibrium or predominately in one form.

The skilled artisan will appreciate that pharmaceutically-acceptable salts of the compounds according to formula (I) may be prepared. Indeed, in certain embodiments of the invention, pharmaceutically-acceptable salts of the compounds according to formula (I) may be preferred over the respective free base or free acid because such salts may impart greater stability or solubility to the molecule thereby facilitating formulation into a dosage form. Accordingly, the invention is further directed to pharmaceutically-acceptable salts of the compounds according to formula (I).

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

In certain embodiments, compounds according to formula (I) may contain an acidic functional group. Suitable pharmaceutically-acceptable salts include salts of such acidic functional groups. Representative salts include pharmaceutically-acceptable metal salts such as sodium, potassium, lithium, calcium, magnesium, aluminum, and zinc salts; carbonates and bicarbonates of a pharmaceutically-acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, and cyclohexylamine.

In certain embodiments, compounds according to formula (I) may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

As used herein, the term "compounds of the invention" means both the compounds according to formula (I) and the pharmaceutically-acceptable salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

TERMS AND DEFINITIONS

"Alkyl" refers to a saturated hydrocarbon chain having the specified number of member atoms. For example, $C_1$-$C_6$ alkyl refers to an alkyl group having from 1 to 6 member atoms. Alkyl groups may be optionally substituted with one or more substituents as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Aryl" refers to an aromatic hydrocarbon ring. Aryl groups are monocyclic ring systems or bicyclic ring systems. Monocyclic aryl ring refers to phenyl. Bicyclic aryl rings refer to napthyl and rings wherein phenyl is fused to a cycloalkyl or cycloalkenyl ring having 5, 6, or 7 member atoms. Aryl groups may be optionally substituted with one or more substituents as defined herein.

"Cycloalkyl" refers to a saturated hydrocarbon ring having the specified number of member atoms. Cycloalkyl groups are monocyclic ring systems. For example, $C_3$-$C_6$ cycloalkyl refers to a cycloalkyl group having from 3 to 6 member atoms. Cycloalkyl groups may be optionally substituted with one or more substituents as defined herein. Cycloalkyl includes cyclopropyl, cyclobutyl, cyclopentyl, and cyclohexyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct specie in vitro or in vivo.

"Halo" refers to the halogen radical fluoro, chloro, bromo, or iodo.

"Haloalkyl" refers to an alkyl group wherein at least one hydrogen atom attached to a member atom within the alkyl group is replaced with halo. Haloalkyl includes trifluoromethyl.

"Heteroaryl" refers to an aromatic ring containing from 1 to 4 nitrogen, oxygen or sulfur atoms as member atoms in the ring. Heteroaryl groups containing more than one heteroatom may contain different heteroatoms. Heteroaryl groups may be optionally substituted with one or more substituents as defined herein. Heteroaryl groups are monocyclic ring systems or are fused, spiro, or bridged bicyclic ring systems. Monocyclic heteroaryl rings have 5 or 6 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benzopyranyl, benzoxazolyl, benzofuranyl, isobenzofuranyl, benzothiazolyl, benzothienyl, furopyridinyl, and napthyridinyl.

"Heterocycloalkyl" refers to a saturated or unsaturated ring containing from 1 to 4 nitrogen, oxygen, sulfur, C(O), SO, or $SO_2$ as member atoms. However, heterocycloalkyl rings are not aromatic. Heterocycloalkyl groups containing more than one heteroatom may contain different heteroatoms. Heterocycloalkyl groups may be optionally substituted with one or more substituents as defined herein. Heterocycloalkyl groups are monocyclic ring systems having from 4 to 10 member atoms. In certain embodiments heterocycloalkyl groups are monocyclic ring systems having from 4 to 7 member atoms. In other embodiments heterocycloalkyl is saturated. In other embodiments, heterocycloalkyl is unsaturated but not aromatic. Heterocycloalkyl includes pyrrolidinyl, pyrrolidinonyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, azetidinyl, thiepanyl, dioxidothiepanyl, tetrahydrothiopyranyl, dioxido-tetrahydrothiopyranyl, and dioxido-tetrahydrothienyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted or substituted with one or more substituents as defined herein. "Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| g (grams); | mg (milligrams); |
| L (liters); | mL (milliliters); |
| μL (microliters); | psi (pounds per square inch); |
| M (molar); | mM (millimolar); |
| i. v. (intravenous); | Hz (Hertz); |
| MHz (megahertz); | mol (moles); |
| mmol (millimoles); | rt (room temperature); |
| min (minutes); | h (hours); |
| mp (melting point); | TLC (thin layer chromatography); |
| T$_r$ (retention time); | RP (reverse phase); |
| MeOH (methanol); | i-PrOH (isopropanol); |
| TEA (triethylamine); | TFA (trifluoroacetic acid); |
| TFAA (trifluoroacetic anhydride); | THF (tetrahydrofuran); |
| DMSO (dimethylsulfoxide); | AcOEt (ethyl acetate); |
| DME (1,2-dimethoxyethane); | DCM (dichloromethane); |
| DCE (dichloroethane); | DMF (N,N-dimethylformamide); |
| CDI (1,1-carbonyldiimidazole); | HOAc (acetic acid); |
| HOBt (1-hydroxybenzotriazole); | mCPBA (meta-chloroperbenzoic acid; |
| EDC (1-[3-dimethylamino) propyl]-3-ethylcarbodiimide hydrochloride); | |
| BOC (tert-butyloxycarbonyl); | FMOC (9-fluorenylmethoxycarbonyl); |
| CBZ (benzyloxycarbonyl); | Ac (acetyl); |
| atm (atmosphere); | TMS (trimethylsilyl); |
| BSA (bovine serum albumin); | ATP (adenosine triphosphate); |
| HPLC (high pressure liquid chromatography); | |
| TBAF (tetra-n-butylammonium fluoride); | |
| HEPES (4-(2-hydroxyethyl)-1-piperazine ethane sulfonic acid); | |
| EDTA (ethylenediaminetetraacetic acid); | |
| DDQ (2,3-Dichloro-5,6-dicyano-1,4-benzoquinone); | |
| TBTU (O-Benzotriazol-1-yl-N,N,N',N'-tetramethyluronium tetrafluoroborate); | |
| TMEDA (N,N,N',N'-tetramethy1-1,2-ethanediamine); | |
| TMSOTf (trimethylsilylTriflate); | |
| NBS (N-bromosuccinimide); and | |
| dppf (1,1'-bis(diphenylphosphino)ferrocene); | |

All references to ether are to diethyl ether and brine refers to a saturated aqueous solution of NaCl.

Compound Preparation

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the Examples section.

Compounds of formula I can be prepared, for example, according to Schemes 1-13 depicted below.

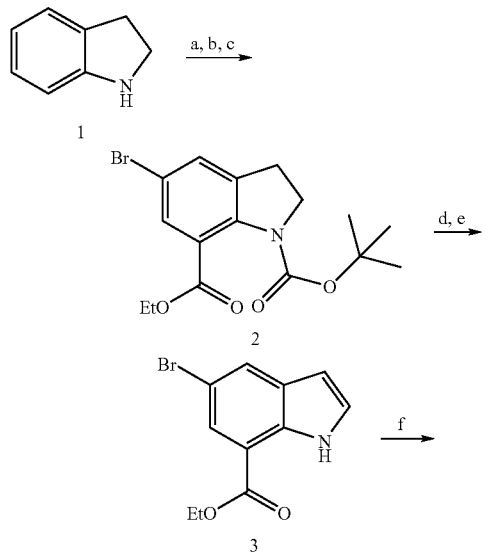

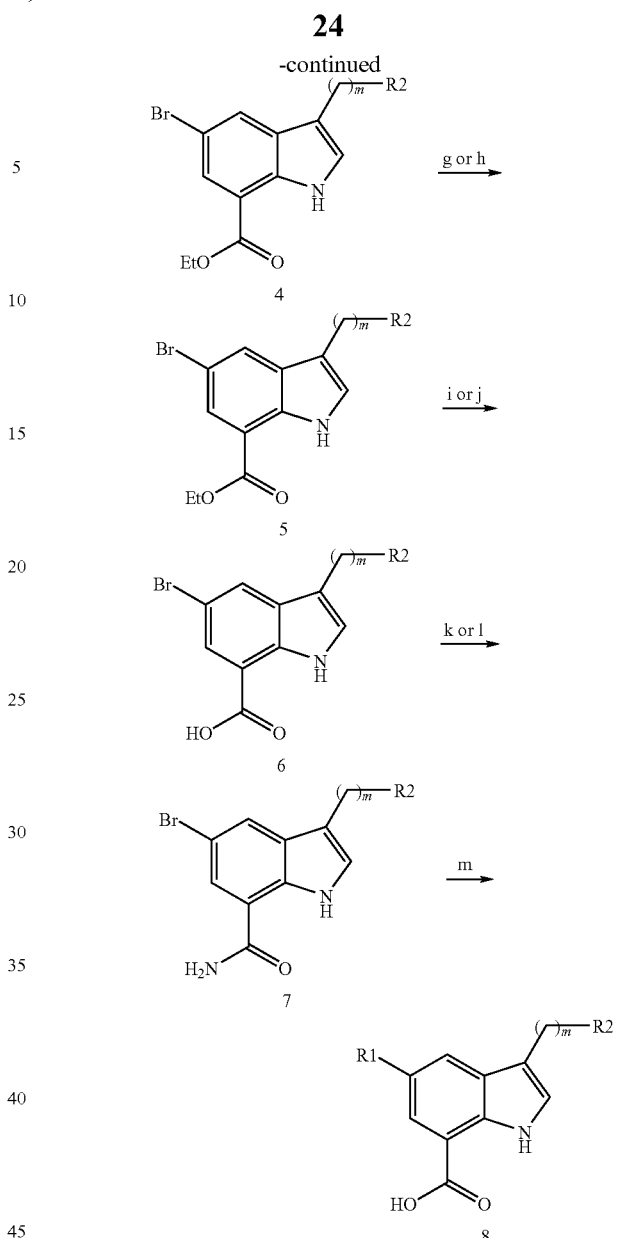

Conditions: a) (BOC)$_2$O, NaOH, THF; b) sec-BuLi, ClCO$_2$Et, TMEDA, Et$_2$O; c) N-bromosuccinimide, DCM; d) TFA; e) DDQ, CHCl$_3$; f) RC(O)R', TMSOTf, Et$_3$SiH, DCM; g) Urea•H$_2$O$_2$, TFAA, CH$_3$CN; h) m-CPBA, DCM; i) aqu. NaOH, MeOH; j) aqu. LiOH, MeOH; k) EDC•HCl, HOBt, NH$_3$/1,4-dioxane, DMF; l) TBTU, Et$_3$N, NH$_3$/MeOH; m) R1B(OR)$_2$, PdCl$_2$(dppf), K$_2$CO$_3$, 1,4-dioxanne/H$_2$O.

Scheme 1 represents a general scheme for the preparation of compounds according to formula I wherein m is 0 or 1 and R1 is a 4-10-membered heterocycloalkyl, each of which contains a sulfide, sulfoxide, or sulfone as member atom(s) within the ring. The indoline 1 depicted as starting material is commercially available. Reaction conditions for both Scheme 1 and the other schemes that follow are as described in their respective schemes; however, the skilled artisan will appreciate that certain modifications in the reaction conditions and/or reagents used are possible.

Treatment of indoline 1 with di-tert-butyl dicarbonate in the presence of a suitable base such as sodium hydroxide, in a suitable solvent such as THF or methylene chloride, produces the desired BOC protected product. Further transformation to the desired bromide 2 can be accomplished via lithiation using sec-butyllithium in the presence of TMEDA and quenching with ethyl chloroformate followed by bromination with N-bromosuccinimide. Treatment of bromide 2 with trifluoroacetic acid followed by oxidation with DDQ provides the indole 3. Incorporating the fully saturated group $(CH_2)_m R2$ is performed via reaction with the appropriate aldehyde or ketone precursor to $(CH_2)_m R2$ with in situ reduction. This transformation can be completed under acidic conditions. As an example of such a transformation, for the case in Scheme 1, condition "f", TMSOTf-promoted condensation with an aldehyde or ketone RC(O)R' and reduction with $Et_3SiH$ provides the sulfide 4. The sulfide is then oxidized to the sulfone 5 with a urea.$H_2O_2$/TFAA mixture in $CH_3CN$. Alternatively, the sulfide may be oxidized with m-CPBA in DCM. Hydrolysis of 5 with aqueous NaOH or LiOH in MeOH and treatment of the resulting carboxylic acid 6 with EDC.HCl, HOBt, and $NH_3$ in 1,4-dioxane and DMF provides the amide 7. Alternatively, the amide 7 may be obtained by treatment of 6 with TBTU, $Et_3N$, and $NH_3$ in MeOH. Installation of the substituent R1 can be accomplished via a transition metal mediated coupling using an appropriate catalyst and coupling partner. As an example of such a transformation, for the case in Scheme 1 condition "m", a Suzuki cross-coupling reaction with the bromide 7 can be accomplished using a boronic ester or acid in the presence of $PdCl_2(dppf)$ and $K_2CO_3$ in 1,4-dioxane and water. In some circumstances, R1 may contain functional group(s) such as aldehydes or sulfonyl halides or sulfonyl esters that may be further elaborated by reaction with an appropriate reagent, such as an amine, under appropriate conditions, such as in the presence of a reducing agent or base. It will be appreciated by the skilled artisan that this may occur prior to or subsequent to the transition metal mediated installation of R1 on the indole template.

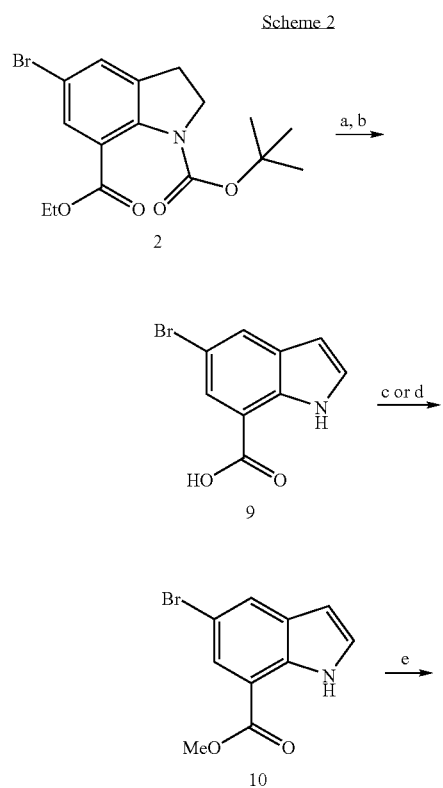

Scheme 2

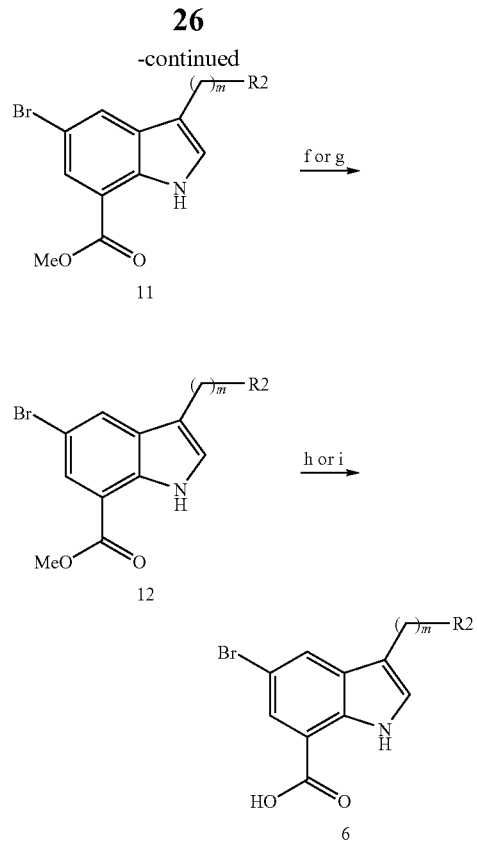

Conditions: a) aqu. NaOH, MeOH; b) DDQ, $CHCl_3$; c) MeI, $Na_2CO_3$, DMF; d) MeOH, HCl; e) RC(O)R', TMSOTf, $Et_3SiH$, DCM; f) Urea•$H_2O_2$, TFAA, $CH_3CN$; g) mCPBA, DCM; h) aqu. NaOH, MeOH; i) aqu. LiOH, MeOH.

Alternatively, the intermediate 6 depicted in Scheme 1 may also be prepared as shown in Scheme 2. Hydrolysis of the BOC-protected indoline 2 with aqueous NaOH in MeOH, followed by oxidation with DDQ in $CHCl_3$, gives the indole carboxylic acid 9. The acid 9 may be esterified either by treatment with MeI and $Na_2CO_3$ in DMF, or with HCl in MeOH to give the ester 10. Incorporating the fully saturated group $(CH_2)_m R2$ is performed via reaction with the appropriate aldehyde or ketone precursor to $(CH_2)_m R2$ with in situ reduction. This transformation can be completed under acidic conditions. As an example of such a transformation, for the case in Scheme 2, condition "e", TMSOTf-promoted condensation with an aldehyde or ketone RC(O)R' and reduction with $Et_3SiH$ provides the sulfide 4. The sulfide is then oxidized to the sulfone 12 with a urea.$H_2O_2$/TFAA mixture in $CH_3CN$. Alternatively, the sulfide may be oxidized with mCPBA in DCM. Hydrolysis of 5 with aqueous NaOH or LiOH in MeOH then gives the carboxylic acid 6.

Scheme 3

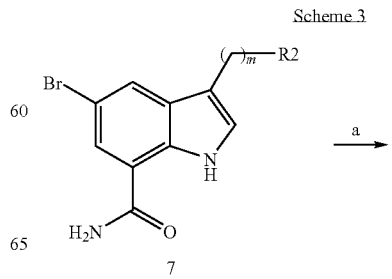

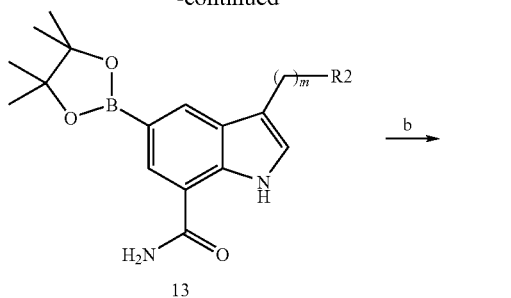

Conditions: a) Bispinacolatodiboron, KOAc, PdCl$_2$(dppf), 1,4-dioxane; b) R1-X, PdCl$_2$(dppf), K$_2$CO$_3$, 1,4-dioxane/water.

Scheme 3 represents an alternative method for the installation of the R1 group. Treatment of the bromide 7 with bispinacolatodiboron in the presence of KOAc and PdCl$_2$(dppf) in 1,4-dioxane gives the boronate ester 13. The boronate 13 may then be reacted with an appropriately functionalized aryl or heteroaryl group R1-X, where X is a bromide, iodide, or triflate in the presence of a base such as K$_2$CO$_3$ and a catalyst such as PdCl$_2$(dppf) to give the desired product 8.

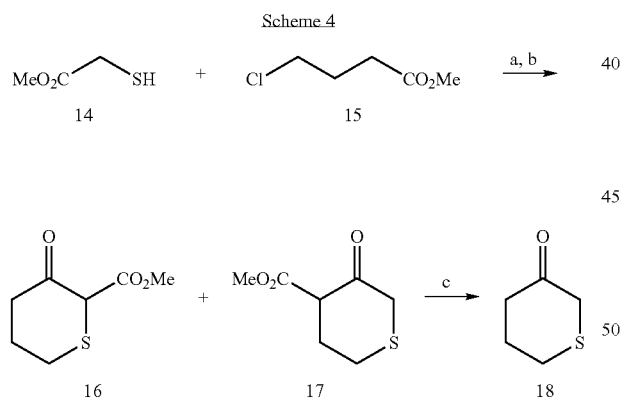

Conditions: a) NaOMe, NaI, MeOH; b) NaOMe, toluene; c) aqueous H$_2$SO$_4$.

The cyclic sulfide RC(O)R' used to make one of the groups (CH$_2$)$_m$R2 on intermediate 4 or 11 wherein R2 is one example of a 7-membered heterocycloalkyl may be prepared as shown in Scheme 4. The commercially available sulfide 14 may be alkylated with the commercially available chloride 15 in the presence of a base such as NaOMe and a catalyst such as NaI in MeOH. The alkylated intermediate may then undergo a Dieckman cyclization in the presence of a base such as NaOMe in toluene. The mixture of cyclized products 16 and 17 then undergo hydrolysis and subsequent decarboxylation when treated with aqueous H$_2$SO$_4$ to give the sulfide 18.

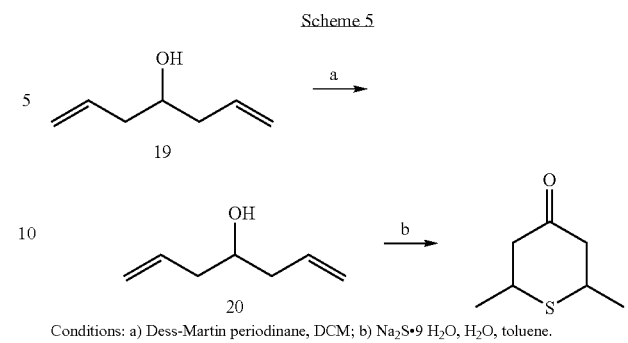

Conditions: a) Dess-Martin periodinane, DCM; b) Na$_2$S•9 H$_2$O, H$_2$O, toluene.

The cyclic sulfide RC(O)R' used to make one of the groups (CH$_2$)$_m$R2 on intermediate 4 or 11 wherein R2 is a 7-membered heterocycloalkyl with alkyl groups flanking the sulfur atom may be prepared as shown in Scheme 5. Oxidation of the commercially available alcohol 19 with Dess-Martin periodinane reagent in DCM gives the ketone 20. Treatment of 20 with Na$_2$S.9H$_2$O in water and toluene first isomerizes the alkenes of 20 into conjugation with the ketone, which then undergoes a double conjugate addition with Na$_2$S.9H$_2$O to provide the cyclic sulfide 21 in racemic form.

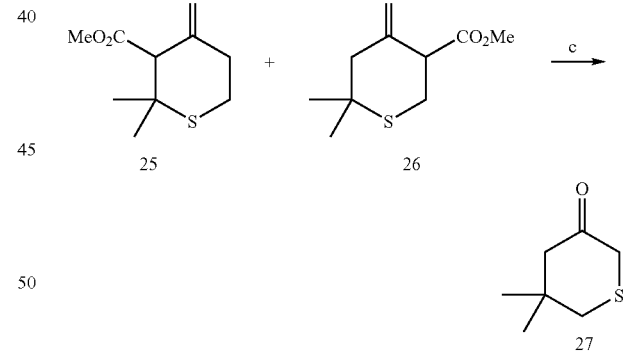

Conditions: a) piperidine, MeOH; b) LDA, THF; c) aqueous H$_2$SO$_4$.

Another method for making a cyclic sulfide RC(O)R' used to prepare one of the groups (CH$_2$)$_m$R2 on intermediate 4 or 11 wherein m is 0 or 1 and R2 is a 7-membered heterocycloalkyl with alkyl groups flanking the sulfur atom is represented in Scheme 6. Conjugate addition of the commercially available thiol 22 with the enoate 23 in the presence of piperidine in MeOH gives the sulfide 24. Treatment of 24 with a base such as LDA in THF gives a mixture of the cyclized products 25 and 26. Hydrolysis and decarboxylation of the mixture of 25 and 26 in aqueous H$_2$SO$_4$ then provides the cyclic sulfide 27.

Scheme 7

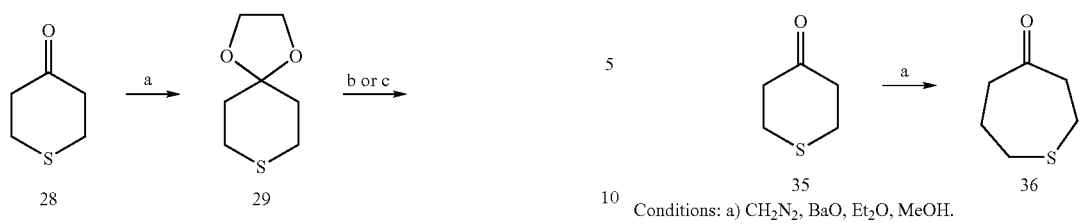

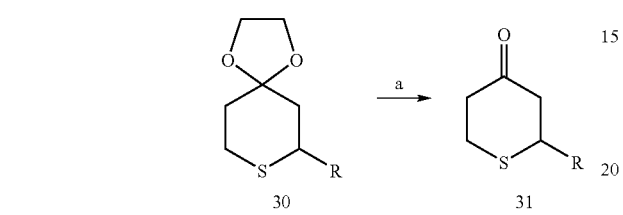

Conditions: a) Ethylene gylcol, p-toluene suflonic acid, toluene; b) NCS, benzene, isopropylmagnesium bromide, CuI; c) NCS, benzene, phenylmagnesium bromide, CuI; d) aqueous HCl, HOAc.

Another method for making a cyclic sulfide RC(O)R' used to prepare one of the groups $(CH_2)_mR2$ on intermediate 4 or 11 wherein m is 0 or 1 and R2 is a 7-membered heterocycloalkyl with alkyl groups flanking the sulfur atom is represented in Scheme 7. The acetonide 29 was prepared by treatment of the commercially available cyclic sulfide 28 with ethylene glycol and p-toluene sulfonic acid in toluene. Treatment of 29 with NCS in benzene followed by reaction with a Grignard reagent such as isopropylmagnesium bromide or phenylmagnesium bromide in the presence of a copper (I) salt such as CuI then gave the sulfide 30. Removal of the acetonide group of 30 with HCl in acetic acid then provided the keto sulfide 31.

Scheme 8

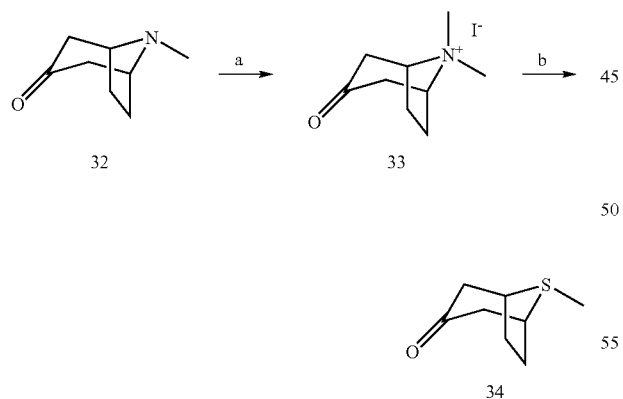

Conditions: a) MeI, Et$_2$O; b) Na$_2$S·9H$_2$O, H$_2$O.

The cyclic sulfide RC(O)R' used to make the bridged bicyclic group $(CH_2)_mR2$ on intermediate 4 or 11 may be prepared as shown in Scheme 8. Treatment of commercially available tropinone 32 with methyliodide in Et$_2$O gave the iodide salt 33. Replacement of the ammonium group of 33 then occurred upon exposure to Na$_2$S.9H$_2$O in H$_2$O, giving the bridged bicyclic keto sulfide 34.

Scheme 9

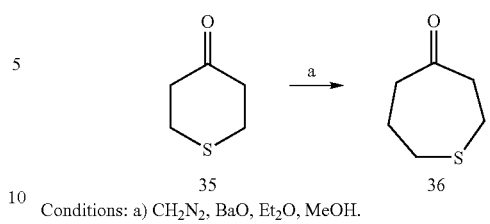

Conditions: a) CH$_2$N$_2$, BaO, Et$_2$O, MeOH.

The cyclic sulfide RC(O)R' used to make the 8-membered group $(CH_2)_mR2$ on intermediate 4 or 11 may be prepared as shown in Scheme 9. Treatment of commercially available sulfide 35 with diazomethane in the presence of BaO in diethyl ether and MeOH gives the ring-expanded product 36.

Scheme 10

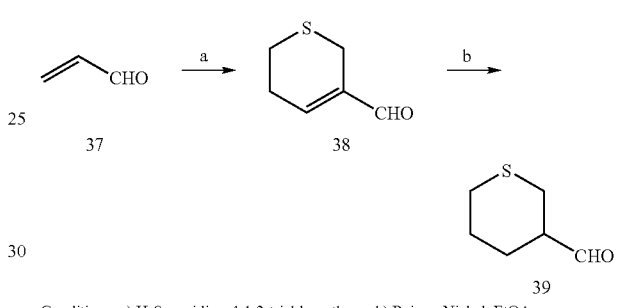

Conditions: a) H$_2$S, pyridine, 1,1,2-trichloroethane; b) Rainey-Nickel, EtOAc.

Another method for making a cyclic sulfide RC(O)R' used to prepare one of the groups $(CH_2)_mR2$ on intermediate 4 or 11 wherein m is 0 or 1 and R2 is a 6-membered heterocycloalkyl containing a sulfur is represented in Scheme 10. Condensation of commercially available acrolein 37 with H$_2$S provides the sulfide 38. Reduction of the double bond of 38 then gives the saturated aldehyde 39.

Scheme 11

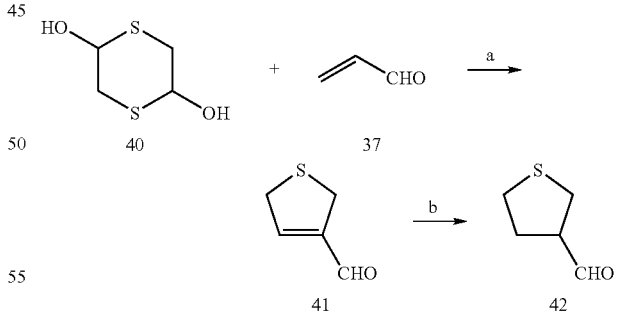

Conditions: a) water; b) Pd/C, H$_2$, EtOAc.

The cyclic sulfide RC(O)R' used to make one of the groups $(CH_2)_mR2$ on intermediate 4 or 11 wherein m is 0 or 1 and R2 is a 5-membered heterocycloalkyl containing a sulfur may be prepared as shown in Scheme 11. Condensation of commercially available 1,4-dithiane-2,5-diol 40 and acrolein 37 in water provides the sulfide 3441 Palladium catalyzed reduction of the double bond of 41 under hydrogen then gives the saturated aldehyde 42.

Scheme 12

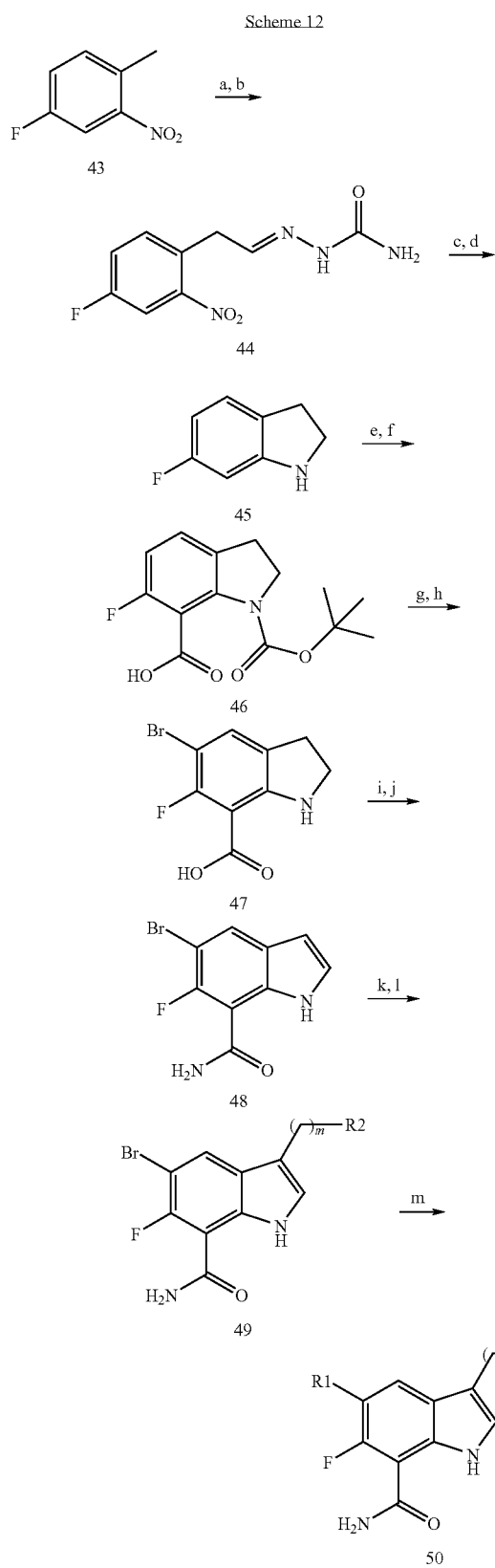

Conditions: a) DMF·DMA, pyrrolidine; b) semicarbazide, H₂O, MeOH; c) Rh/C, Fe(OAc)₂, toluene; d) BH₃·TEA, aqueous HCl, 1,4-dioxane; e) (BOC)₂O, TEA, DCM ; f) sec-BuLi, CO₂, TMEDA, Et₂O; g) NBS, DCM; h) TFA, DCM; i) MnO₂, THF; j) CDI, NH₃, DCM; k) RC(O)R', HOAc, H₃PO₄; l) Na₂EDTA, Oxone, NaHCO₃, DME, H₂O; m) R1B(OR)₂, PdCl₂(dppf), K₂CO₃, 1,4-dioxanne/water.

A method for preparation of compounds of formula I wherein R4=F is illustrated in Scheme 12. Treatment of the commercially available nitro compound 43 with DMF.DMA in the presence of pyrrolidine, followed by condensation with semicarbazide in H₂O and MeOH gives the semicarbazone 44. Reduction of 44 with Fe(OAc)₂ in the presence of catalytic Rh/C in toluene, followed by further reduction of the cyclized intermediate with BH₃.TEA in the presence of aqueous HCl in 1,4-dioxane provides the indoline 45. Further transformation to the acid 46 can be accomplished via treatment of 45 with di-tert-butyl dicarbonate in the presence of TEA in DCM, followed by lithiation of the BOC protected product with sec-BuLi in the presence of TMEDA and quenching with CO₂. Bromination of 46 with NBS in DCM, followed by removal of the BOC group with TFA in DCM gives the indoline 47. The indoline 47 is then oxidized with MnO₂ in THF, and then treated with CDI and NH₃ in DCM to give the amide 48. Incorporating the fully saturated group (CH₂)ₘR2 is performed via reaction with the appropriate aldehyde or ketone precursor to (CH₂)ₘR2 with in situ reduction. This transformation can be completed under acidic conditions. As an example of such a transformation, for the case in Scheme 12, condition "k", acid promoted condensation of 48 with a ketone RC(O)R' in H₃PO₄ and HOAc gives the indole functionalized with the fully saturated group (CH₂)ₘR2. Oxidation of the sulfide of the (CH₂)ₘR2 group with Oxone in the presence of Na₂EDTA and NaHCO₃ in DME and H₂O then gives the sulfone 49. Installation of the substituent R1 can be accomplished via a transition metal mediated coupling using an appropriate catalyst and coupling partner. As an example of such a transformation, for the case in Scheme 12 condition "m", a Suzuki cross-coupling reaction with the bromide 49 can be accomplished using a boronic ester or acid in the presence of a suitable palladium catalyst such as PdCl₂(dppf) and a suitable base such as K₂CO₃ in 1,4-dioxane and water.

Scheme 13

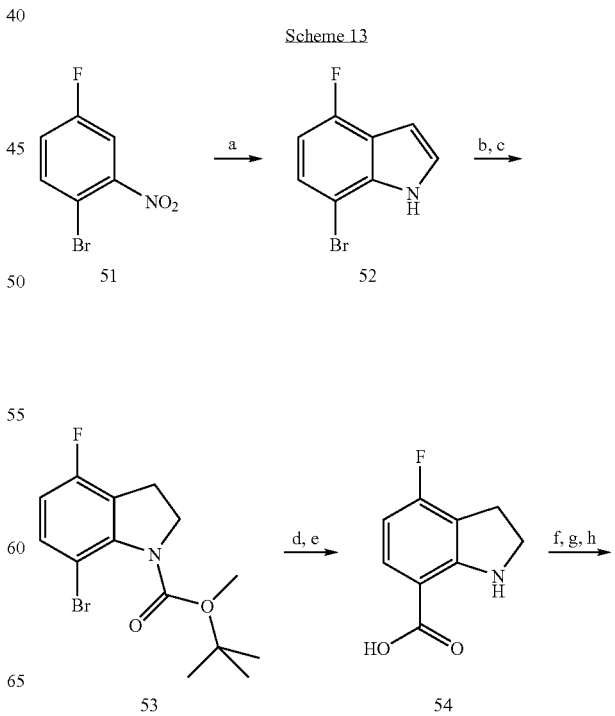

-continued

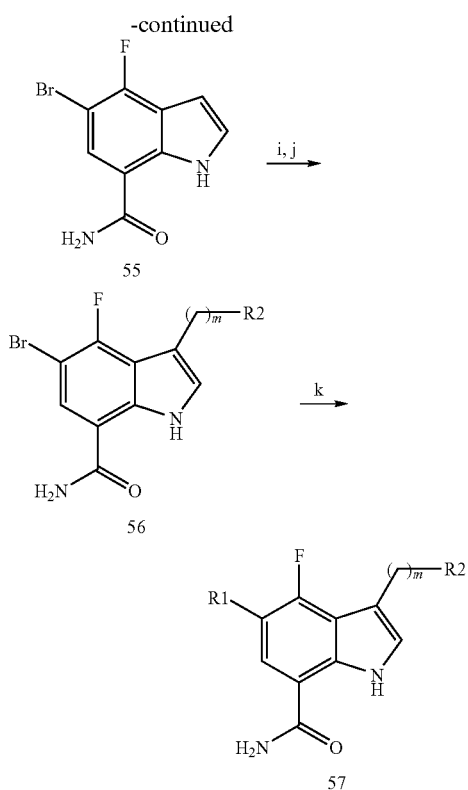

Conditions: a) Vinylmagnesium bromide, THF/DME; b) NaCNBH₃, HOAc; c) (BOC)₂O, DMAP, TEA, DCM; d) tert-BuLi, CO₂, THF; e) aqueous HCl, DCM; f) NBS, DCM/MeOH; g) DDQ, CHCl₃; h) 2M NH₃, MeOH/DCM; i) RC(O)R', HOAC, H₃PO₄; j) NaEDTA, Oxone, NaHCO₃, DME, H₂O; k) R1B(OR)₂, PdCl₂(dppf), K₂CO₃, 1,4-dioxanne/water.

A method for preparation of compounds of formula I wherein R3=F is illustrated in Scheme 11. The indole 52 may be obtained via the Bartoli reaction by treatment of the commercially available nitro compound 51 with vinylmagnesium bromide in THF and DME. Reduction of 52 with NaCNBH₃ in HOAc and subsequent protection with (BOC)₂O in the presence of DMAP and TEA in DCM gives the indoline 53. The acid 54 can be obtained by lithiation of 53 with tert-BuLi in THF, followed by quenching with CO₂, then removal of the BOC group with aqueous HCl in DCM. Bromination of 54 with NBS in DCM and MeOH, followed by oxidation of the indoline with DDQ and subsequent amide formation with NH₃ in MeOH and DCM gives the amide 55. Incorporating the fully saturated group $(CH_2)_mR2$ is performed via reaction with the appropriate aldehyde or ketone precursor to $(CH_2)_m$R2 with in situ reduction. This transformation can be completed under acidic conditions. As an example of such a transformation, for the case in Scheme 13, condition "i", acid promoted condensation of 55 with a ketone RC(O)R' in H₃PO₄ and HOAc gives the indole functionalized with the fully saturated group $(CH_2)_mR2$. Oxidation of the sulfide of the $(CH_2)_mR2$ group with Oxone in the presence of Na₂EDTA and NaHCO₃ in DME and H₂O then gives the sulfone 56. Installation of the substituent R1 can be accomplished via a transition metal mediated coupling using an appropriate catalyst and coupling partner. As an example of such a transformation, for the case in Scheme 13 condition "k", a Suzuki cross-coupling reaction with the bromide 56 can be accomplished using a boronic ester or acid in the presence of PdCl₂ (dppf) and K₂CO₃ in 1,4-dioxane and water.

Methods of Use

The compounds of the invention are inhibitors of IKK2. These compounds can be useful in the treatment of disorders wherein the underlying pathology is (at least in part) attributable to inappropriate IKK2 (also known as IKKβ) activity such as rheumatoid arthritis, inflammatory bowel disease, asthma, rhinitis, and COPD (chronic obstructive pulmonary disease). "Inappropriate IKK2 activity" refers to any IKK2 activity that deviates from the normal IKK2 activity expected in a particular patient. Inappropriate IKK2 activity may take the form of, for instance, an abnormal increase in activity, or an aberration in the timing and or control of IKK2 activity. Such inappropriate activity may result then, for example, from overexpression or mutation of the protein kinase leading to inappropriate or uncontrolled activation. Accordingly, in another aspect the invention is directed to methods of treating such disorders.

Such disorders include inflammatory and tissue repair disorders, particularly rheumatoid arthritis, inflammatory bowel disease, asthma, rhinitis, and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus erythematosus, multiple sclerosis, psoriatic arthritis, alkylosing spondylitis, tissue and organ rejection, Alzheimer's disease, stroke, atherosclerosis, restonosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia. In particular, the compounds of formula (I) can be useful in the treatment of rheumatoid arthritis, asthma, rhinitis, and chronic obstructive pulmonary disease.

The methods of treatment of the invention comprise administering a safe and effective amount of a compound according to formula (I) or a pharmaceutically-acceptable salt thereof to a patient in need thereof. Individual embodiments of the invention include methods of treating any one of the above-mentioned disorders by administering a safe and effective amount of a compound according to formula (I) or a pharmaceutically-acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The invention also provides a compound of the invention for use in medical therapy, and particularly in the treatment of disorders mediated by IKK2 activity. Thus, in a further aspect, the invention is directed to the use of a compound according to formula (I) or a pharmaceutically-acceptable salt thereof in the preparation of a medicament for the treatment of a disorder characterized by inappropriate IKK2 activity.

Particular disorders characterised by inappropriate IKK2 activity include inflammatory and tissue repair disorders, particularly rheumatoid arthritis, inflammatory bowel disease, asthma, rhinitis, and COPD (chronic obstructive pulmonary disease); osteoarthritis, osteoporosis and fibrotic diseases; dermatosis, including psoriasis, atopic dermatitis and ultraviolet radiation (UV)-induced skin damage; autoimmune diseases including systemic lupus erythematosus, multiple sclerosis, psoriatic arthritis, alkylosing spondylitis, tissue and organ rejection, Alzheimer's disease, stroke, atherosclerosis, restenosis, diabetes, glomerulonephritis, cancer, including Hodgkins disease, cachexia, inflammation associated with infection and certain viral infections, including acquired immune deficiency syndrome (AIDS), adult respiratory distress syndrome, and Ataxia Telangiestasia as a result of inhibition of the protein kinase IKK2.

Compositions

The compounds of the invention will normally be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically may contain, for example, from 0.5 mg to 1 g, or from 1 mg to 700 mg, or from 5 mg to 100 mg of a compound of the invention.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds. For example, pharmaceutical compositions of the invention may comprise a compound of the invention in combination with one or more of the following therapeutic agents selected from anti-inflammatory agents, anticholinergic agents (particularly an $M_1/M_2/M_3$ receptor antagonist), $\beta_2$-adrenoreceptor agonists, antiinfective agents, such as antibiotics or antivirals, or antihistamines.

The invention thus provides, in a further aspect, a combination comprising a compound of the invention together with one or more other therapeutically active agents, for example selected from an anti-inflammatory agent, such as a corticosteroid or an NSAID, an anticholinergic agent, a $\beta_2$-adrenoreceptor agonist, an antiinfective agent, such as an antibiotic or an antiviral, or an antihistamine. One embodiment of the invention encompasses combinations comprising a compound of the invention together with a $\beta_2$-adrenoreceptor agonist, and/or an anticholinergic, and/or a PDE-4 inhibitor, and/or an antihistamine.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of the invention together with a $\beta_2$-adrenoreceptor agonist.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting $\beta_2$-adrenoreceptor agonists, for example, compounds which provide effective bronchodilation for about 12 hrs or longer, are preferred.

Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl) amino]-1-hydroxyethyl}-2-(hydroxymethyl)phenol;
4-{(1R)-2-[(6-{-4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;
N-2{2-[4-(3-phenyl-4-methoxyphenyl)aminophenyl]ethyl}-2-hydroxy-2-(8-hydroxy-2(1H)-quinolinon-5-yl)ethylamine; and
5-[(R)-2-(2-{-4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, $6\alpha,9\alpha$-difluoro-11$\beta$-hydroxy-16$\alpha$-methyl-17$\alpha$-[(4-methyl-1,3-thiazole-5-carbonyl)oxy]-3-oxo-androsta-1,4-diene-17$\beta$-carbothioic acid S-fluoromethyl ester, $6\alpha,9\alpha$-difluoro-17$\alpha$-[(2-furanylcarbonyl)oxy]-11$\beta$-hydroxy-16$\alpha$-methyl-3-oxo-androsta-1,4-diene-17$\beta$-carbothioic acid S-fluoromethyl ester (fluticasone furoate), $6\alpha,9\alpha$-difluoro-11$\beta$-hydroxy-16$\alpha$-methyl-3-oxo-17$\alpha$-propionyloxy-androsta-1,4-diene-17$\beta$-carbothioic acid S-(2-oxo-tetrahydrofuran-3S-yl) ester, $6\alpha,9\alpha$-difluoro-11$\beta$-hydroxy-16$\alpha$-methyl-3-oxo-17$\alpha$-(2,2,3,3-tetramethycyclopropylcarbonyl) oxy-androsta-1,4-diene-17$\beta$-carbothioic acid S-cyanomethyl ester and $6\alpha,9\alpha$-difluoro-11$\beta$-hydroxy-16$\alpha$-methyl-17$\alpha$-(1-methycyclopropylcarbonyl)oxy-3-oxo-androsta-1,4-diene-17$\beta$-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16$\alpha$,17-[[(R)-cyclohexylmethylene]bis(oxy)]-11$\beta$,21-dihydroxypregna-1,4-diene-3,20-dione), butixocort propionate, RPR-106541, and ST-126. Preferred corticosteroids include fluticasone propionate, $6\alpha$, 9$\alpha$-difluoro-11$\beta$-hydroxy-16$\alpha$-methyl-17$\alpha$-[(4-methyl-1,3-thiazole-5-carbonyl)oxy]-3-oxo-androsta-1,4-diene-17$\beta$-carbothioic acid S-fluoromethyl ester, $6\alpha,9\alpha$-difluoro-17$\alpha$-[(2-furanylcarbonyl)oxy]-11$\beta$-hydroxy-16$\alpha$-methyl-3-oxo-androsta-1,4-diene-17$\beta$-carbothioic acid S-fluoromethyl ester, $6\alpha,9\alpha$-difluoro-11$\beta$-hydroxy-16$\alpha$-methyl-3-oxo-17$\alpha$-(2,2,3,3-tetramethycyclopropylcarbonyl)oxy-androsta-1,4-diene-17$\beta$-carbothioic acid S-cyanomethyl ester and $6\alpha,9\alpha$-difluoro-11$\beta$-hydroxy-16$\alpha$-methyl-17$\alpha$-(1-methycyclopropylcarbonyl)oxy-3-oxo-androsta-1,4-diene-17$\beta$-carbothioic acid S-fluoromethyl ester. In one embodiment the corticosteroid is $6\alpha,9\alpha$-difluoro-17$\alpha$-[(2-furanylcarbonyl)oxy]-11$\beta$-hydroxy-16$\alpha$-methyl-3-oxo-androsta-1,4-diene-17$\beta$-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment, the invention provides the use of the compounds of the invention in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:
(3-endo)-3-(2,2-di-2-thienylethenyl)-8,8-dimethyl-8-azoniabicyclo[3.2.1]octane iodide;
(3-endo)-3-(2-cyano-2,2-diphenylethyl)-8,8-dimethyl-8-azoniabicyclo[3.2.1]octane bromide;
4-[hydroxy(diphenyl)methyl]-1-{2-[(phenylmethyl)oxy]ethyl}-1-azoniabicyclo[2.2.2]octane bromide; and
(1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;

(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of the invention together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I) or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., *J. Med. Chem.* 46:3957-3960 (2003).

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when comingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution, while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to oral inhalation or intranasal administration. Appropriate dosage forms for such administration, such as an aerosol formulation or a metered dose inhaler, may be prepared by conventional techniques.

For administration by inhalation the compounds may be delivered in the form of an aerosol spray presentation from pressurized packs or a nebulizer, with the use of a suitable propellant, e.g. dichlorodifluoromethane, trichlorofluoromethane, dichlorotetrafluoroethane, a hydrofluoroalkane such as tetrafluoroethane or heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di or poly-saccharides (eg. lactose or starch). Use of lactose is preferred.

Each capsule or cartridge may generally contain between 20 μg-10 mg of the compound of formula (I) optionally in combination with another therapeutically active ingredient. Alternatively, the compound of the invention may be presented without excipients.

Suitably, the packing/medicament dispenser is of a type selected from the group consisting of a reservoir dry powder inhaler (RDPI), a multi-dose dry powder inhaler (MDPI), and a metered dose inhaler (MDI).

By reservoir dry powder inhaler (RDPI) it is meant an inhaler having a reservoir form pack suitable for comprising multiple (un-metered doses) of medicament in dry powder form and including means for metering medicament dose from the reservoir to a delivery position. The metering means may for example comprise a metering cup, which is movable from a first position where the cup may be filled with medicament from the reservoir to a second position where the metered medicament dose is made available to the patient for inhalation.

By multi-dose dry powder inhaler (MDPI) is meant an inhaler suitable for dispensing medicament in dry powder form, wherein the medicament is comprised within a multi-dose pack containing (or otherwise carrying) multiple, define doses (or parts thereof) of medicament. In a preferred aspect, the carrier has a blister pack form, but it could also, for example, comprise a capsule-based pack form or a carrier onto which medicament has been applied by any suitable process including printing, painting and vacuum occlusion.

In the case of multi-dose delivery, the formulation can be pre-metered (eg as in Diskus, see GB 2242134, U.S. Pat. Nos. 6,632,666, 5,860,419, 5,873,360 and 5,590,645 or Diskhaler, see GB 2178965, 2129691 and 2169265, U.S. Pat. Nos. 4,778,054, 4,811,731, 5,035,237, the disclosures of which are hereby incorporated by reference) or metered in use (e.g. as in Turbuhaler, see EP 69715 or in the devices described in U.S. Pat. No. 6,321,747 the disclosures of which are hereby incorporated by reference). An example of a unit-dose device is Rotahaler (see GB 2064336 and U.S. Pat. No. 4,353,656, the disclosures of which are hereby incorporated by reference).

The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

In one aspect, the multi-dose pack is a blister pack comprising multiple blisters for containment of medicament in dry powder form. The blisters are typically arranged in regular fashion for ease of release of medicament there from.

In one aspect, the multi-dose blister pack comprises plural blisters arranged in generally circular fashion on a disc-form blister pack. In another aspect, the multi-dose blister pack is elongate in form, for example comprising a strip or a tape.

Preferably, the multi-dose blister pack is defined between two members peelably secured to one another. U.S. Pat. Nos. 5,860,419, 5,873,360 and 5,590,645 describe medicament packs of this general type. In this aspect, the device is usually provided with an opening station comprising peeling means for peeling the members apart to access each medicament dose. Suitably, the device is adapted for use where the peelable members are elongate sheets which define a plurality of medicament containers spaced along the length thereof, the device being provided with indexing means for indexing each container in turn. More preferably, the device is adapted for use where one of the sheets is a base sheet having a plurality of pockets therein, and the other of the sheets is a lid sheet, each pocket and the adjacent part of the lid sheet defining a respective one of the containers, the device comprising driving means for pulling the lid sheet and base sheet apart at the opening station.

By metered dose inhaler (MDI) it is meant a medicament dispenser suitable for dispensing medicament in aerosol form, wherein the medicament is comprised in an aerosol container suitable for containing a propellant-based aerosol medicament formulation. The aerosol container is typically provided with a metering valve, for example a slide valve, for release of the aerosol form medicament formulation to the patient. The aerosol container is generally designed to deliver a predetermined dose of medicament upon each actuation by means of the valve, which can be opened either by depressing the valve while the container is held stationary or by depressing the container while the valve is held stationary.

Where the medicament container is an aerosol container, the valve typically comprises a valve body having an inlet port through which a medicament aerosol formulation may enter said valve body, an outlet port through which the aerosol may exit the valve body and an open/close mechanism by means of which flow through said outlet port is controllable.

The valve may be a slide valve wherein the open/close mechanism comprises a sealing ring and receivable by the sealing ring a valve stem having a dispensing passage, the valve stem being slidably movable within the ring from a valve-closed to a valve-open position in which the interior of the valve body is in communication with the exterior of the valve body via the dispensing passage.

Typically, the valve is a metering valve. The metering volumes are typically from 10 to 100 µl, such as 25 µl, 50 µl or 63 µl. Suitably, the valve body defines a metering chamber for metering an amount of medicament formulation and an open/close mechanism by means of which the flow through the inlet port to the metering chamber is controllable. Preferably, the valve body has a sampling chamber in communication with the metering chamber via a second inlet port, said inlet port being controllable by means of an open/close mechanism thereby regulating the flow of medicament formulation into the metering chamber.

The valve may also comprise a 'free flow aerosol valve' having a chamber and a valve stem extending into the chamber and movable relative to the chamber between dispensing and non-dispensing positions. The valve stem has a configuration and the chamber has an internal configuration such that a metered volume is defined there between and such that during movement between is non-dispensing and dispensing positions the valve stem sequentially: (i) allows free flow of aerosol formulation into the chamber, (ii) defines a closed metered volume for pressurized aerosol formulation between the external surface of the valve stem and internal surface of the chamber, and (iii) moves with the closed metered volume within the chamber without decreasing the volume of the closed metered volume until the metered volume communicates with an outlet passage thereby allowing dispensing of the metered volume of pressurized aerosol formulation. A valve of this type is described in U.S. Pat. No. 5,772,085. Additionally, intra-nasal delivery of the present compounds is effective.

To formulate an effective pharmaceutical nasal composition, the medicament must be delivered readily to all portions of the nasal cavities (the target tissues) where it performs its pharmacological function. Additionally, the medicament should remain in contact with the target tissues for relatively long periods of time. The longer the medicament remains in contact with the target tissues, the medicament must be capable of resisting those forces in the nasal passages that function to remove particles from the nose. Such forces, referred to as 'mucociliary clearance', are recognised as being extremely effective in removing particles from the nose in a rapid manner, for example, within 10-30 minutes from the time the particles enter the nose.

Other desired characteristics of a nasal composition are that it must not contain ingredients which cause the user discomfort, that it has satisfactory stability and shelf-life properties, and that it does not include constituents that are considered to be detrimental to the environment, for example ozone depletors.

A suitable dosing regime for the formulation of the present invention when administered to the nose would be for the patient to inhale deeply subsequent to the nasal cavity being cleared. During inhalation the formulation would be applied to one nostril while the other is manually compressed. This procedure would then be repeated for the other nostril.

A preferable means for applying the formulation of the present invention to the nasal passages is by use of a pre-compression pump. Most preferably, the pre-compression pump will be a VP7 model manufactured by Valois SA. Such a pump is beneficial as it will ensure that the formulation is not released until a sufficient force has been applied, otherwise smaller doses may be applied. Another advantage of the pre-compression pump is that atomisation of the spray is ensured as it will not release the formulation until the threshold pressure for effectively atomising the spray has been achieved. Typically, the VP7 model may be used with a bottle capable of holding 10-50 ml of a formulation. Each spray will typically deliver 50-100 µl of such a formulation, therefore, the VP7 model is capable of providing at least 100 metered doses.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetrafluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants, e.g., oleic acid or lecithin and cosolvents, e.g. ethanol. Pressurised formulations will generally be retained in a canister (e.g. an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of the active ingredient as produced may be size reduced by conventional means e.g., by micronization. The desired fraction may be separated out by air classification or sieving. Suitably, the particles will be crystalline in form. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 µm and not less than 15% will have a MMD of less than 15 µm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulization may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions may be applied as a topical ointment or cream. When formulated in an ointment, the compound of the invention may be employed with either a paraffinic or a water-miscible ointment base. Alternatively, the compound of the invention may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Unless otherwise noted, all starting materials were obtained from commercial suppliers and used without further purification. Unless otherwise indicated, all temperatures are expressed in ° C. (degrees Centigrade). Unless otherwise indicated, all reactions are conducted under an inert atmosphere at room temperature. For reverse phase HPLC purification, one of the following conditions was used:
TFA Conditions:
Solvent A: 0.1% TFA/$H_2O$
Solvent B: 0.1% TFA/$CH_3CN$
Columns:
YMC C18 S-5 µm/12 nm 50×20 mm preparatory column
YMC C18 S-15 µm/12 nm 75×30 mm preparatory column
Luna 5 µm C18(2) 100 A 50×21.2 mm preparatory column
Luna 5 µm C18(2) 100 A AXIA 50×21.2 mm preparatory column
Waters Sunfire 5 µm C18 OBD 19×100 mm preparatory column
Waters Sunfire Prep C18 OBD 5 µm 30×100 mm preparatory column
Waters XBridge Prep C18 5 µm OBD 30×150 mm preparatory column
Neutral Conditions:
Solvent A: $H_2O$
Solvent B: $CH_3CN$
Columns:
YMC C18 5 µm/12 nm 50×20 mm preparatory column
YMC 75×30 mm S-5 µm/12 nm preparatory column
Basic Conditions:
Solvent A: 0.1% $NH_4OH$/$H_2O$
Solvent B: 0.1% $NH_4OH$/$CH_3CN$ Column:
XBridge C18 5 μm OBD 19×100 mm preparatory column Nuclear magnetic resonance spectra were recorded at 400 MHz using a Bruker AC 400 spectrometer. $CDCl_3$ is deuteriochloroform, $DMSO-d_6$ is hexadeuteriodimethylsulfoxide, and $CD_3OD$ is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Mass spectra were taken on a PE Sciex Single Quadrupole LC/MS API-150 using electrospray (ES) ionization techniques. Elemental analyses were obtained using a Perkin-Elmer 240C elemental analyzer.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel.

LC/MS:
Waters 2795 Separations Module
Waters Micromass ZQ
Waters 996 Photodiode Array Detector
Column: Xterra MS C18 2.1×50 mm 3.5 μm
Flow: 1 mL/min
Column Temperature: 40° C.
Runtime: 5 min
Injection Volume: 5 μl
Detection: UV Total abs 215-280 nm
Gradient:

| Time (min) | % A | % B |
|---|---|---|
| 0 | 95 | 5 |
| 4 | 5 | 95 |
| 4.1 | 95 | 5 |

Acidic Method Conditions
Mobile Phase:
A—Water+0.1% formic acid
B—MeCN+0.1% formic acid
Basic Method Conditions
Mobile Phase:
A—10 mM $NH_4HCO_3$@ pH10 ($NH_4OH$)
B—MeCN Intermediate 1

1,1-Dimethylethyl
2,3-dihydro-1H-indole-1-carboxylate

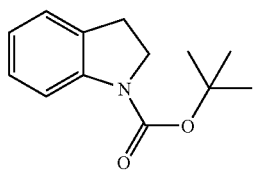

A solution of di-tert-butylcarbonate (427.1 g, 1.96 mol) in $CH_2Cl_2$ (500 mL) was added dropwise at room temperature to a solution of indoline (212 g 1.78 mol) in $CH_2Cl_2$ (1000 mL). A solution of NaOH (85.3 g, 2.13 mol) in water (500 mL) was then added dropwise and the mixture was stirred overnight. The layers were separated and the organic layer was washed with 5% NaOH, brine and dried over $Na_2SO_4$. The organic layer was concentrated under reduced pressure and the crude product was crystallized with petroleum ether, giving 324 g (68%) of the title compound.

Intermediate 2

1-(1,1-Dimethylethyl) 7-ethyl
2,3-dihydro-1H-indole-1,7-dicarboxylate

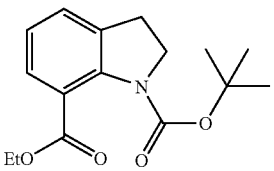

A 1.3 M solution of sec-butyl lithium in cyclohexanes (1642 mL, 2.13 mol) was added dropwise to a solution of 1,1-dimethylethyl 2,3-dihydro-1H-indole-1-carboxylate (300 g, 1.37 mol) and N,N,N',N' tetramethyl-1,2-ethanediamine (248 mL, 1.64 mol) in dry diethyl ether (2.5 L) at −78° C. The reaction mixture was stirred for 2 hours at this temperature and ethyl chloroformate (143.9 mL, 1.50 mol) was added dropwise to the mixture at −78° C. After the addition, the reaction was allowed to warm to room temperature overnight. Water (1 L) was added carefully to the mixture and the organic layer was separated and dried ($Na_2SO_4$). The solution was concentrated and the residue was purified by silica-gel column chromatography (PE:EA=10:1), giving 150 g (38%) of the title compound.

Intermediate 3

Ethyl 5-bromo-2,3-dihydro-1H-indole-7-carboxylate

NBS (51.3 g, 0.29 mol) was added in several portions to a solution of 1-(1,1-dimethylethyl) 7-ethyl 2,3-dihydro-1H-indole-1,7-dicarboxylate (140.3 g, 0.48 mol) in $CH_2Cl_2$ (1200 mL) and the reaction mixture was stirred at room temperature overnight. The reaction solution was washed with 2 M NaOH (500 mL) and water (500 mL), and was then dried ($Na_2SO_4$). The solution was concentrated in vacuo to 500 mL and TFA (130 mL, 1.69 mol) was added. The mixture was stirred at room temperature overnight. A solution of 2 M NaOH was added to bring the reaction mixture to pH>8. The organic layer was separated and the aqueous layer was extracted with CH$_2$Cl$_2$ (3×300 mL). The combined organic layers were dried (Na$_2$SO$_4$) and the solvent was evaporated, giving 129.1 g (99%) of the title compound.

Intermediate 4

Ethyl 5-bromo-1H-indole-7-carboxylate

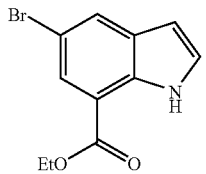

DDQ (119.3 g. 525.7 mmol) was added in several portions to a solution of ethyl 5-bromo-2,3-dihydro-1H-indole-7-carboxylate (129.1 g, 0.48 mmol) in CHCl$_3$ (1500 mL) and the mixture was stirred for 2 h. The reaction was filtered and the solid was washed with CHCl$_3$ (3×500 mL). The filtrate was washed with 5% NaOH (3×500 mL), H$_2$O (500 mL) and brine (500 mL) then dried over Na$_2$SO$_4$. The solution was evaporated and the residue was recrystallized with EtOH, giving 88 g (69%) of the title compound.

LC/MS: m/z 267.6 (M+H), Rt 1.14 min.

Intermediate 5

1-(1,1-Dimethylethyl) 7-methyl-2,3-dihydro-1H-indole-1,7-dicarboxylate

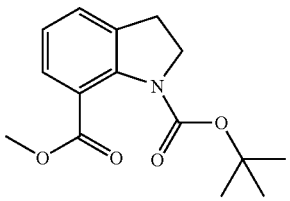

1,1-dimethylethyl 2,3-dihydro-1H-indole-1-carboxylate (5 g, 22.8 mmol) and N,N,N',N'-tetramethyl-1,2-ethanediamine (4.6 mL, 30.5 mmol) was dissolved in dry diethyl ether (300 mL) and cooled to −78° C. in an acetone/dry ice bath. Sec-butyl lithium (1.4 M solution in cyclohexane, 17.6 mL, 24.6 mmol) was added dropwise over 10 minutes and the reaction left stirring for 90 minutes at this temperature. Methyl chloroformate (8.8 mL, 10.8 g, 100 mmol) was added to the mixture and the reaction was allowed to warm to room temperature over 1 hour. Water was added carefully to the mixture and the organic layer separated and washed 3 times with more water. The organic layer was dried over magnesium sulfate, filtered and concentrated in vacuo to give 4.91 g (78%) of the title compound as a gummy yellow solid.

1H NMR (400 MHz, DMSO-d6) δ ppm 1.44 (s, 9H) 3.06 (t, J=8.2 Hz, 2H) 3.69 (s, 3H) 4.02 (t, J=8.3 Hz, 2H) 7.06 (t, J=7.5 Hz, 1H) 7.35 (d, J=7.5 Hz, 1H) 7.39 (dd, J=7.4, 1.1 Hz, 1H) MS m/z 278 (M+1)$^+$ Rt 3.18 min.

Intermediate 6

1-(1,1-Dimethylethyl)7-methyl-5-bromo-2,3-dihydro-1H-indole-1,7-dicarboxylate

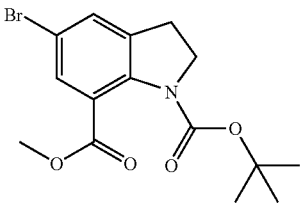

1-(1,1-dimethylethyl) 7-methyl 2,3-dihydro-1H-indole-1,7-dicarboxylate (3.1 g, 11.2 mmol) and N-bromosuccinimide (2.0 g, 11.2 mmol) were dissolved in dry dichloromethane (100 mL) and stirred under a nitrogen atmosphere at room temperature for 16 hours. The reaction was partitioned with sodium hydroxide solution (2 M), separated and washed with more sodium hydroxide solution. The organic layer was dried over magnesium sulfate and concentrated in vacuo to give 3.55 g (89%) of the title compound as a gummy red solid.

1H NMR (400 MHz, DMSO-d6) δ ppm 1.41 (s, 9H) 3.09 (t, J=8.3 Hz, 2H) 3.70 (s, 3H) 4.02 (t, J=8.3 Hz, 2H) 7.46 (s, 1H) 7.60 (s, 1H); MS m/z 356/358 (1:1 ratio) (M+1)$^+$ Rt 3.52 min.

Alternatively, the title compound could be made according to the following procedure:

To a solution of 1-tert-butyl 7-methyl indoline-1,7-dicarboxylate (18 g, 64.9 mmol) in 200 mL of DCM was added NBS (18 g, 71.5 mmol). The mixture was stirred overnight at room temperature. The reaction solution was concentrated and the residue was washed with H$_2$O, extracted with DCM. The combined organic layer was concentrated and the residue was purified by chromatography column on silica gel to get the product as a brown solid (21 g, 91%).

Intermediate 7

Methyl 5-bromo-2,3-dihydro-1H-indole-7-carboxylate

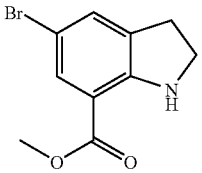

1-(1,1-dimethylethyl) 7-methyl 5-bromo-2,3-dihydro-1H-indole-1,7-dicarboxylate (9 g, 25 mmol) was dissolved in trifluoroacetic acid (6 mL) and stirred at room temperature for 16 hours. Dichloromethane and sodium hydroxide solution (2 M) were added and the organic layer washed twice with sodium hydroxide solution until the aqueous layer pH>7. The organic layer was then concentrated in vacuo to give 6.5 g (100%) of the title compound as a brown solid.

1H NMR (400 MHz, DMSO-d6) δ ppm 2.99 (t, J=8.5 Hz, 2H) 3.61 (t, J=8.4 Hz, 2H) 3.78 (s, 3H) 6.72 (s, 1H) 7.28 (d, J=1 Hz, 1H) 7.46 (d, J=2 Hz, 1H); MS m/z 256/258 (1:1 ratio) (M+1)$^+$ Rt 3.32 min.

Alternatively, the title compound can be made according to the following procedure:

A solution of 5-Bromo-2,3-dihydro-indole-1,7-dicarboxylic acid 1-tert-butyl ester 7-methyl ester (17.2 g, 48.3 mol) in 100 mL of TFA was stirred at room temperature for 18 hours. After checked by TLC, 2 N NaOH solution was added to bring the solution to pH=8-9, then extracted with DCM. The combined organic layer was dried over MgSO$_4$, evaporated to give the product (11.5 g, 93%).

Intermediate 8

Methyl 5-bromo-1H-indole-7-carboxylate

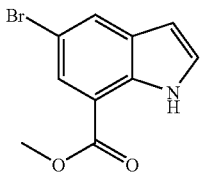

Methyl 5-bromo-2,3-dihydro-1H-indole-7-carboxylate (6.5 g, 25 mmol) was dissolved in tetrahydrofuran (100 mL). Activated manganese dioxide (5 μm particle size, 22 g, 250 mmol) was added and the mixture stirred at room temperature for 16 hours. A further 22 g of activated manganese dioxide was added and the reaction stirred for 96 hours. The reaction was then filtered through celite and concentrated in vacuo to give 5.1 g (80%) of the title compound as a beige solid.

1H NMR (400 MHz, DMSO-d6) δ ppm 3.94 (s, 3H) 6.58 (d, J=3 Hz, 1H) 7.48 (d, J=3 Hz, 1H) 7.8 (d, J=2 Hz, 1H) 8.07 (d, J=1.8 Hz, 1H) 11.39 (bs, 1H); MS m/z 252/254 (1:1 ratio) (M−1) Rt 3.41 min.

Alternatively, the title compound can be prepared as follows:

To a solution of 5-Bromo-2,3-dihydro-1H-indole-7-carboxylic acid methyl ester (11.5 g, 45.1 mmol) in 100 mL THF was added MnO$_2$ (39.2 g, 451 mmol). Then the mixture was stirred overnight at room temperature. The reaction was filtered and the filtrate was concentrated (10 g, 88%).

Alternatively, the title compound can also be prepared as follows:

MeI (7.81 mL, 125 mmol) was added to a mixture of 5-bromo-1H-indole-7-carboxylic acid (10 g, 41.7 mmol) and Na$_2$CO$_3$ (17.66 g, 167 mmol) in DMF (50 mL). The reaction mixture was stirred at room temperature for 2 h and filtered through a pad of silica gel (500 g), eluting with Et$_2$O (600 mL). The eluent was washed with water (1×100 mL) and concentrated under reduced pressure, giving 9.65 g (91%) of the title compound.

LC/MS: m/z 253.8 (M), Rt 2.15 min.

Intermediate 9

5-Bromo-1H-indole-7-carboxylic acid

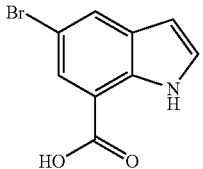

Methyl 5-bromo-1H-indole-7-carboxylate (5 g, 19.7 mmol) was dissolved in methanol (200 mL) and a solution of lithium hydroxide (0.99 g, 41 mmol) in water (10 mL) was added. The mixture was heated at reflux for 50 hours. The methanol was removed in vacuo and the residue diluted with aqueous hydrochloric acid (2 M). The resulting precipitate was filtered off and dried in a heated vacuum pistol to give 4.7 g (99%) of the title compound as a beige solid.

1H NMR (400 MHz, DMSO-d6) δ ppm 6.54 (dd, J=2.0, 3.2 Hz, 1H) 7.42 (t, J=2.8 Hz, 1H) 7.77 (d, J=2 Hz, 1H) 8.03 (d, J=1.8 Hz, 1H) 11.27 (s, 1H) 13.1-13.7 (bs, 1H) MS m/z 238/240 (1:1 ratio) (M−1) Rt 3.41 min.

Intermediate 10

5-Bromo-1H-indole-7-carboxamide

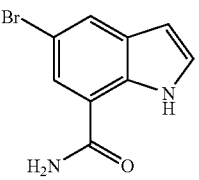

To a solution of 5-bromo-1H-indole-7-carboxylic acid (10.0 g, 42 mmol) in CH$_2$Cl$_2$ (100 mL) at room temperature, EDC (9.66 g, 50.4 mmol), HOBt (6.81 g, 50.4 mmol) and NH$_3$ (2.0 M in MeOH, 84 mL, 168 mmol) were added. The reaction mixture was stirred at room temperature for 16 hours. The solvent was evaporated and the residue partitioned between ethyl acetate (100 mL) and water (100 mL). The water layer was extracted with ethyl acetate (2×100 mL) and the combined organic phase was dried over MgSO$_4$ and concentrated to give 10 g (98%) of the title compound as a crude product.

LC/MS: m/z 240.0 (M+H) Rt 1.95 min.

Intermediate 11

Ethyl 5-bromo-3-(tetrahydro-2H-thiopyran-4-yl)-1H-indole-7-carboxylate

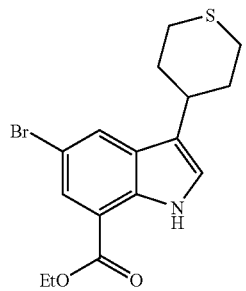

TMSOTf (3.38 mL, 18.7 mmol) was added dropwise to a solution of tetrahydro-4H-thiopyran-4-one (2.17 g, 18.7 mmol) in DCM (100 mL) at 0° C. (bath temp) under nitrogen. A solution of ethyl 5-bromo-1H-indole-7-carboxylate (5 g, 18.7 mmol) in DCM (30 mL) was then added and the reaction was stirred for 30 min. Triethylsilane (4.47 mL, 28.1 mmol) was added and the reaction was allowed to warm to room temperature overnight. The reaction mixture was washed with saturated aqueous Na$_2$CO$_3$ (1×100 mL, and the organic layer was dried (Na$_2$SO$_4$) and concentrated under reduced pressure. The residue was washed with MeOH, giving 4.92 g (72%) of the title compound.

LC/MS: m/z 367.9 (M+H), Rt 2.79 min.

The title compound can also be prepared according to the following procedure:

TMSOTf (1.4 mL, 7.7 mmol) was added dropwise to a solution of tetrahydro-4H-thiopyran-4-one (0.88 g, 7.6 mmol) in DCM (80 mL) in the presence of molecular sieves at 0° C. (bath temp). A solution of ethyl 5-bromo-1H-indole-7-carboxylate (2 g, 7.4 mmol). in DCM (20 mL) was added and the reaction was stirred for 15 min. Triethylsilane (2 mL, 12.5 mmol) was added and the reaction was allowed to warm to room temperature overnight. Saturated aqueous Na$_2$CO$_3$ was added, the layers separated and the aqueous layer extracted with DCM. The combined organic layers were dried (Na$_2$SO$_4$) and concentrated under reduced pressure. The residue was washed with MeOH and dried in a vacuum oven, giving 2.07 g (76%) of the title compound.

Intermediate 12

1-(1,1-Dimethylethyl) 7-ethyl 5-bromo-3-(tetrahydro-2H-thiopyran-4-yl)-1H-indole-1,7-dicarboxylate

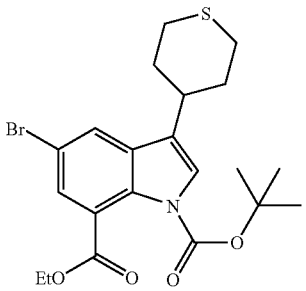

The title compound was prepared in two batches. The first batch was prepared as follows: (Boc)$_2$O (1.77 g, 8.1 mmol) and DMAP (0.33 g, 2.7 mmol) were added to a solution of ethyl 5-bromo-3-(tetrahydro-2H-thiopyran-4-yl)-1H-indole-7-carboxylate (1.99 g, 5.4 mmol) in THF (4 mL) and CH$_3$CN (40 mL). The reaction was stirred at room temperature for 20 h. Additional (Boc)$_2$O (0.6 g, 2.8 mmol) was added and the reaction was stirred for 1 h. The reaction was concentrated under reduced pressure. The crude product was purified by a plug of silica with DCM, giving 2.36 g (93%) of the title compound.

LC/MS: m/z 468.3 (M+H), Rt 3.01 min.

The second batch was prepared as follows:

(Boc)$_2$O (5.84 g, 26.8 mmol) and DMAP (0.819 g, 6.7 mmol) were added to a solution of ethyl 5-bromo-3-(tetrahydro-2H-thiopyran-4-yl)-1H-indole-7-carboxylate (4.92 g, 13.4 mmol) in THF (10 mL) and CH$_3$CN (80 mL). The reaction was stirred at room temperature for 2.5 h and was concentrated under reduced pressure. The crude product was purified by flash chromotography with DCM, giving 5.61 g (90%) of the title compound.

Intermediate 13

1-(1,1-Dimethylethyl) 7-ethyl 5-bromo-3-(1,1-dioxidotetrahydro-2H-thiopyran-4-yl)-1H-indole-1,7-dicarboxylate

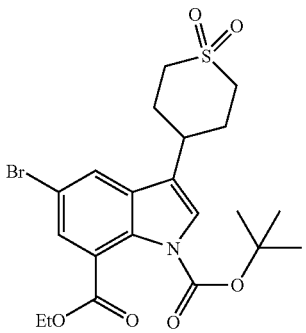

The title compound was prepared in 3 batches. The first batch was prepared as follows:

Urea hydroperoxide (0.37 g, 3.95 mmol) was added in one portion to a mixture of TFAA (0.445 mL, 3.2 mmol) in CH$_3$CN (30 mL). The reaction was stirred for 30 min and was cooled to 0° C. (bath temp). 1-(1,1-Dimethylethyl) 7-ethyl 5-bromo-3-(tetrahydro-2H-thiopyran-4-yl)-1H-indole-1,7-dicarboxylate (0.5 g, 1.07 mmol) was taken up in CH$_3$CN (20 mL), cooled to 0° C. (bath temp) and transferred slowly via cannula to the urea hydroperoxide/TFAA mixture. The ice bath was removed, the reaction was allowed to warm to room temperature, and EtOAc (100 mL) and water (40 mL) were added. The organic layer was washed with water (2×20 mL) and saturated aqueous NaCl (1×20 mL) and was dried (Na$_2$SO$_4$). The solution was concentrated under reduced pressure, the residue was dissolved in DCM (5 mL) and filtered through a plug of silica, eluting with EtOAc. The eluent was concentrated under reduced pressure, giving 0.664 g (>95%) of the title compound.

LC/MS: m/z 500.4 (M), Rt 2.31 min.

The second batch was prepared as follows:

Urea hydroperoxide (0.74 g, 7.9 mmol) was added in one portion to a mixture of TFAA (0.89 mL, 6.4 mmol) in CH$_3$CN (60 mL). The reaction was stirred for 30 min and was cooled to 0° C. (bath temp). 1-(1,1-Dimethylethyl) 7-ethyl 5-bromo-3-(tetrahydro-2H-thiopyran-4-yl)-1H-indole-1,7-dicarboxylate (1 g, 2.14 mmol) was taken up in CH$_3$CN (40 mL), cooled to 0° C. (bath temp) and transferred slowly via cannula to the urea hydroperoxide/TFAA mixture. The ice bath was removed and EtOAc (100 mL) and water (40 mL) were added. The organic layer was washed with water (2×40 mL) and saturated aqueous NaCl (1×40 mL) then dried (Na$_2$SO$_4$). The solution was partly concentrated under reduced pressure and filtered through a plug of silica, eluting with EtOAc. The eluent was concentrated under reduced pressure, giving 1.2 g (>95%) of the title compound.

The third batch was prepared as follows:

Urea hydroperoxide (1.48 g, 15.7 mmol) was added in one portion to a mixture of TFAA (1.78 mL, 12.8 mmol) in CH$_3$CN (120 mL). The reaction was stirred for 30 min and was cooled to 0° C. (bath temp). 1-(1,1-Dimethylethyl) 7-ethyl 5-bromo-3-(tetrahydro-2H-thiopyran-4-yl)-1H-indole-1,7-dicarboxylate (2 g, 4.27 mmol) was taken up in CH₃CN (80 mL), cooled to 0° C. (bath temp) and transferred slowly via cannula to the urea hydroperoxide/TFAA mixture. The ice bath was removed and EtOAc (200 mL) and water (80 mL) were added. The organic layer was washed with water (2×80 mL) and saturated aqueous NaCl (1×80 mL) then dried (Na₂SO₄). The solution was concentrated under reduced pressure, giving 2.76 g (>95%) of the title compound. The three batches were combined.

Intermediate 14

Methyl 5-bromo-3-(tetrahydro-2H-thiopyran-4-yl)-1H-indole-7-carboxylate

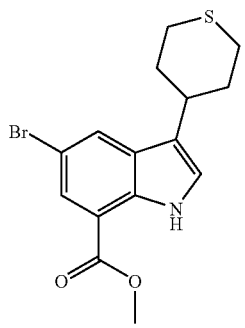

The title compound was prepared in three batches according to the following procedure:

TMSOTf (2.1 mL, 11.8 mmol) was added dropwise over 2.25 min to a solution of tetrahydro-4H-thiopyran-4-one (0.686 g, 5.9 mmol) in DCM (75 mL) at 0° C. (bath temp). A solution of ethyl 5-bromo-1H-indole-7-carboxylate (1.5 g, 5.9 mmol) in DCM (25 mL) was added dropwise via addition funnel over 20 min. Triethylsilane (3.76 mL, 23.6 mmol) was added in one portion and the reaction was allowed to warm to room temperature over 15 h. Saturated aqueous Na₂CO₃ (35 mL) was added, the layers were separated and the aqueous layer was extracted with DCM (1×75 mL). The combined organic layers were concentrated under reduced pressure, the crude product was washed with MeOH (2×8 mL) and dried under high vacuum, giving 1.59 g (76%) of the title compound.

LC/MS: m/z 353.9 (M), Rt 2.59 min.

Intermediate 15

1-(1,1-Dimethylethyl) 7-methyl 5-bromo-3-(tetrahydro-2H-thiopyran-4-yl)-1H-indole-1,7-dicarboxylate

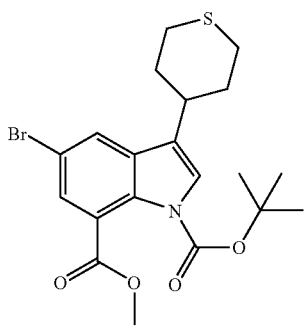

Boc₂O (2.14 mL, 9.23 mmol) and DMAP (0.226 g, 1.9 mmol) were added to a solution of methyl 5-bromo-3-(tet-rahydro-2H-thiopyran-4-yl)-1H-indole-7-carboxylate (2.18 g, 6.2 mmol) in THF (3.5 mL) and MeCN (35 mL). The reaction mixture was stirred at room temperature for 4.5 h and filtered through a pad of silica gel (35 g). The silica pad was washed with DCM (100 mL) and the filtrate was concentrated under reduced pressure, giving 2.64 g of crude product. The crude product was taken up in DCM (10 mL) and purified on a silica cartridge (120 g; Combiflash Companion), eluting at 60 mL/min with a gradient running from 100% hexanes to 10% EtOAc/hexanes over 45 min. The desired fractions were concentrated under reduced pressure and dried under high vacuum.

LC/MS: m/z 353.8 (M−100 (Boc)), Rt 2.88 min.

Intermediate 16

1-(1,1-Dimethylethyl) 7-methyl 5-bromo-3-(1,1-dioxidotetrahydro-2H-thiopyran-4-yl)-1H-indole-1,7-dicarboxylate

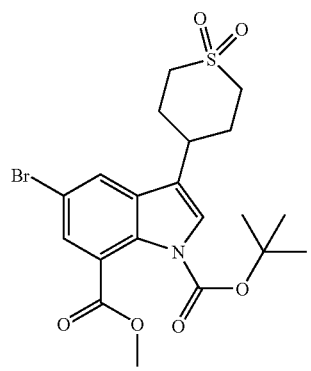

Urea hydroperoxide (1.1 g, 11.6 mmol) was added to a solution of TFAA (1.33 mL, 9.4 mmol) in CH₃CN (17.5 mL). The reaction was stirred for 30 min, cooled to 0° C. (bath temp), and added dropwise via cannula to a cold (0° C.) slurry of 1-(1,1-dimethylethyl) 7-methyl 5-bromo-3-(tetrahydro-2H-thiopyran-4-yl)-1H-indole-1,7-dicarboxylate (1.43 g, 3.2 mmol) in CH₃CN (3.5 mL). The ice bath was removed, the reaction was stirred for 40 min. EtOAc (30 mL) and water (10 mL) were added, the layers were separated and the aqueous layer was extracted with DCM (2×15 mL). The combined organic layers were concentrated under reduced pressure, taken up in DCM (15 mL) and filtered through a pad of silica gel (35 g). The silica pad was washed with EtOAc (150 mL) and the eluent was concentrated under reduced pressure. The residue was taken up in EtOAc (50 mL) and was washed with water (2×10 mL) and saturated aqueous NaCl (1×10 mL). The organic layer was dried (Na₂SO₄), concentrated under reduced pressure and dried under high vacuum, giving 1.03 g (67%) of the title compound.

LC/MS: m/z 485.9 (M), Rt 2.24 min.

Intermediate 17

5-Bromo-3-(1,1-dioxidotetrahydro-2H-thiopyran-4-yl)-1H-indole-7-carboxylic acid

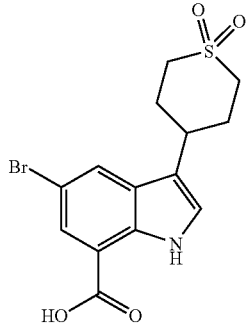

A solution of 6 M NaOH (12 mL, 72.0 mmol) was added to a suspension of 1-(1,1-dimethylethyl) 7-methyl 5-bromo-3-(1,1-dioxidotetrahydro-2H-thiopyran-4-yl)-1H-indole-1,7-dicarboxylate (0.93 g, 1.912 mmol) and 1-(1,1-dimethylethyl) 7-ethyl 5-bromo-3-(1,1-dioxidotetrahydro-2H-thiopyran-4-yl)-1H-indole-1,7-dicarboxylate (3.08 g, 6.16 mmol) in MeOH (50 mL) and water (25 mL) in a 250 mL round bottomed flask fitted with a reflux condenser. The reaction was heated at 85° C. (bath temp) for 1.5 h. The MeOH was removed by rotovap, and a solution of 6 M HCl was added until the mixture had attained a pH of ~1 by pH paper. The yellow solid was filtered off, and the filtrate was extracted with EtOAc (3×10 mL). The combined organic layers were dried ($Na_2SO_4$) and concentrated under reduced pressure, and the residue was combined with the precipitate from the filtration and dried under house vacuum at 45° C. overnight. Recovered 2.98 g (86%) of the title compound.

LC/MS: m/z 371.7 (M), Rt 1.62 min.

Intermediate 18

5-Bromo-3-(1,1-dioxidotetrahydro-2H-thiopyran-4-yl)-1H-indole-7-carboxamide

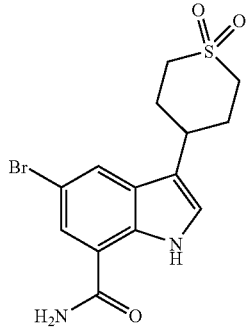

A solution of 0.5 M $NH_3$ in dioxane (12 mL, 6 mmol) was added to a mixture of 5-bromo-3-(1,1-dioxidotetrahydro-2H-thiopyran-4-yl)-1H-indole-7-carboxylic acid (1.1 g, 2.96 mmol), HOBt (0.455 g, 2.96 mmol), and EDC.HCl (1.54 g, 8.02 mmol) in DMF (4 mL) in a Biotage microwave vial. The vial was sealed, and the reaction was heated at 100° C. for 20 min on regular absorbance in a Biotage Initiator microwave. EtOAc (75 mL) and $H_2O$ (75 mL) were added, the layers were separated, and the aqueous layer was extracted with EtOAc (4×100 mL). The combined organic layers were dried ($Na_2SO_4$) and concentrated under reduced pressure to give a light yellow solid. The solid was washed with DCM (1×25 mL) to and aspirated dry to give 2.05 g (96%) of the title compound.

LC/MS: m/z 372.8 (M+H), Rt 1.54 min.

Intermediate 19

3-(1,1-Dioxidotetrahydro-2H-thiopyran-4-yl)-5-(4,4,5,5-tetramethyl-1,3,2-dioxaborolan-2-yl)-1H-indole-7-carboxamide

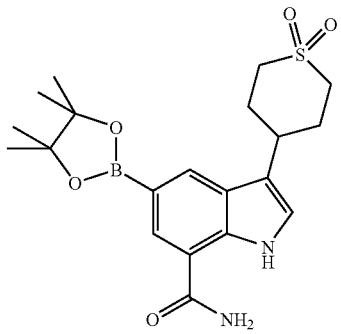

A mixture of 5-bromo-3-(1,1-dioxidotetrahydro-2H-thiopyran-4-yl)-1H-indole-7-carboxamide (40 mg, 0.108 mmol), bis(pinacolato)diboron (82 mg, 0.323 mmol), and KOAc (63.4 mg, 0.646 mmol) was taken up in 1,4-dioxane (1.8 mL) in a 50 mL round-bottomed flask. The mixture was degassed with argon for 10 min, and $PdCl_2$(dppf) (7.88 mg, 10.77 μmol) was added. The reaction was heated at 100° C. (bath temp) for 16 h. The reaction mixture was concentrated under a stream of nitrogen at 50° C. and taken up in water (5 mL) and EtOAc (10 mL). The mixture was filtered through Celite 521, and the Celite pad was rinsed with EtOAc (5 mL). The layers of the filtrate were separated, and the aqueous layer was extracted with EtOAc (1×5 mL). The combined organic layers were dried ($Na_2SO_4$) and filtered. Isolute was added, and the mixture was concentrated under reduced pressure. The Isolute-adsorbed crude product was then purified on a silica cartridge (12 g) with a Combiflash Companion, eluting at 20 mL/min with a gradient running from 30% EtOAc/hexanes to 100% EtOAc over 35 min. The desired fractions were concentrated under reduced pressure, giving 21 mg (45%) of the title compound.

LC/MS: m/z 419.4 (M+H), Rt 0.81 min.

The title compound can also be prepared according to the following procedure:

5-Bromo-3-(1,1-dioxidotetrahydro-2H-thiopyran-4-yl)-1H-indole-7-carboxamide (1.43 g, 3.85 mmol), bispinacolatodiboron (3.25 g, 12.8 mmol, 3.3 eq), potassium acetate (2.29 g, 23.33 mmol, 6.1 eq), and PdCl2(dppf)-CH2Cl2 adduct (394 mg, 0.48 mmol, 0.13 eq) were diluted in dry 1,4-dioxane (70 mL). The mixture was degassed twice by evacuating the flask and backfilling with argon, then was heated at 10° C. overnight. The reaction was cooled to room temperature, then was filtered through celite washing well with dichloromethane, and the solvent was removed in vacuo. The residue was diluted in dichloromethane (100 mL) and water (100 mL), the layers separated, and the aqueous layer was extracted with dichloromethane. The combined organics were dried over sodium sulfate, filtered, and concentrated to afford the crude product as brown oil. This material was dissolved in dichloromethane (~10-15 mL), and hexanes were added slowly with stirring to precipitate the desired. This process was repeated twice. The title compound was isolated by vacuum filtration as a light brown solid (1.31 g, 81%).

LC/MS: m/z 419.4 (M+H), Rt 0.80 min.

Intermediate 20

Methyl 5-bromo-3-(tetrahydro-3-thienyl)-1H-indole-7-carboxylate

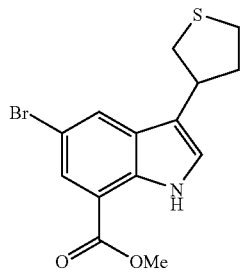

To the stirred mixture of dihydro-3(2H)-thiophenone (0.167 mL, 1.97 mmol) in DCM (25 mL) under N2 was added TMS-OTf (0.71 mL, 3.9 mmol) slowly over about 5 minutes at 0° C. (ice-bath). A solution of ethyl 5-bromo-1H-indole-7-carboxylate (0.50 g, 1.97 mmol) in DCM (5 mL) was added dropwise over 60 min, then triethylsilane (1.26 mL, 9.8 mmol) was added in one portion, and the reaction was allowed to warm slowly to room temperature. Then saturated NaHCO₃ and DCM were added, the layers were separated and the aqueous layer was extracted with DCM twice. The combined organic layers were dried (MgSO₄) and concentrated. The residue was purified using Companion, giving 312 mg (46%) of the title compound.

LC/MS: m/z 341.8 (M+H), Rt 2.45 min.

Intermediate 21

1-(1,1-dimethylethyl) 7-methyl 5-bromo-3-(tetrahydro-3-thienyl)-1H-indole-1,7-dicarboxylate

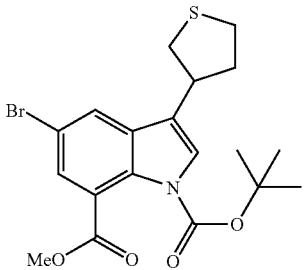

Boc₂O (398 mg, 1.8 mmol) and DMAP (56 mg, 0.46 mmol) were added to a solution of methyl 5-bromo-3-(tetrahydro-3-thienyl)-1H-indole-7-carboxylate (312 mg, 0.91 mmol) in CH₃CN (6.5 mL) and DCM (3.5 mL) at RT. The reaction was stirred at room temperature overnight and filtered through a silica gel pad, eluting with DCM. The filtrate was concentrated to give 430 mg crude product.

LC/MS: m/z 441.8 (M+H), Rt 2.81 min.

Intermediate 22

1-(1,1-dimethylethyl) 7-methyl 5-bromo-3-(1,1-dioxidotetrahydro-3-thienyl)-1H-indole-1,7-dicarboxylate

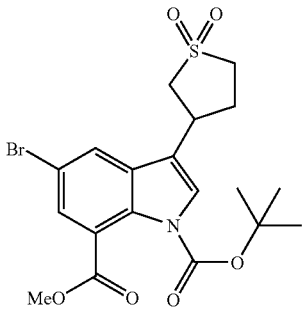

Urea.H₂O₂ (2.83 g, 30.1 mmol) was added in a single portion to a solution of TFAA (3.41 mL, 24.5 mmol) in CH₃CN (30 mL). The reaction was stirred at room temperature for 30 min and then cooled to 0° C. (bath temp). To this cold solution was added dropwise a suspension of 1-(1,1-dimethylethyl) 7-methyl 5-bromo-3-(tetrahydro-3-thienyl)-1H-indole-1,7-dicarboxylate (3.618 g, 8.18 mmol) in CH₃CN (30 mL) at 0° C. (bath temp). The reaction was stirred at room temperature for 40 min. EtOAc and water were added, the layers were separated, and the aqueous layer was extracted with DCM three times. The combined organic layers were filtered through a pad of silica gel and concentrated. The residue was redissolved in ethyl acetate and washed with aq. NaHCO₃, filter and concentrated to give a 4.18 g of product.

LC/MS: m/z 473.8 (M+H), Rt 2.19 min.

Intermediate 23

5-bromo-3-(1,1-dioxidotetrahydro-3-thienyl)-1H-indole-7-carboxylic acid

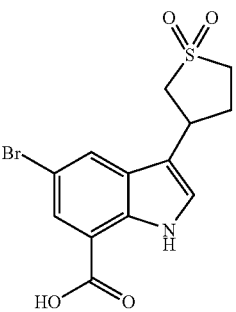

To a microwave vial was added 1-(1,1-dimethylethyl) 7-methyl 5-bromo-3-(1,1-dioxidotetrahydro-3-thienyl)-1H-indole-1,7-dicarboxylate (432 mg, 0.91 mmol), LiOH (109 mg, 4.5 mmol), MeOH (6 mL) and H₂O (3 mL). The mixture was heated to 80° C. for 30 min in the microwave. The reaction mixture was then purified via Gilson HPLC (TFA buffer) to give 99 mg of the title compound.

LC/MS: m/z 357.8 (M+H), Rt 1.40 min.

Intermediate 24

5-bromo-3-(1,1-dioxidotetrahydro-3-thienyl)-1H-indole-7-carboxamide

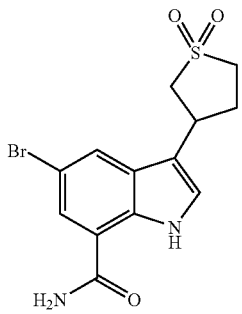

To a solution of 5-bromo-3-(1,1-dioxidotetrahydro-3-thienyl)-1H-indole-7-carboxylic acid (36 mg, 0.1 mmol) in DCM (5 mL) was added HOBt (16 mg, 0.12 mmol), and EDC.HCl (23 mg, 0.12 mmol) and 2 M $NH_3$ in methanol (0.2 mL, 0.4 mmol). The mixture was kept overnight at RT. The mixture was concentrated, and EtOAc and aq. $NaHCO_3$ were added. The aqueous layer was extracted with ethyl acetate once. The combined organic layers were dried ($MgSO_4$) and concentrated to give 36 mg of the title compound.

LC/MS: m/z 356.7 (M+H), Rt 1.37 min.

Alternatively, 5-bromo-3-(1,1-dioxidotetrahydro-3-thienyl)-1H-indole-7-carboxamide can be made from a sequence starting with the ethyl ester:

Intermediate 25

Ethyl 5-bromo-3-(tetrahydro-3-thienyl)-1H-indole-7-carboxylate

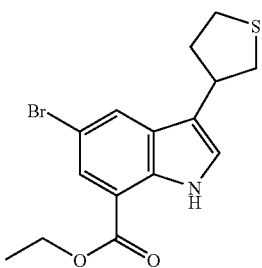

Dihydro-3(2H)-thiophenone (0.381 g, 3.73 mmol) was dissolved in dichloromethane (50 ml) in an oven dried flask containing 3 Å molecular sieves and stirred under Argon at 0° C. TMS-OTf (0.826 g, 3.73 mmol, 0.67 mL) was added slowly to the mixture over 10 min. Ethyl 5-bromo-1H-indole-7-carboxylate (1 g, 3.73 mmol) was dissolved in DCM (6 mL) and added to the reaction via syringe pump over 2 hours, after which it was stirred for 30 min at 0° C. Triethylsilane (0.651 g, 0.89 ml, 5.59 mmol) was then added all at once and the reaction was stirred at room temperature for 18 hours. The reaction was then quenched with a saturated sodium bicarbonate solution (35 mL) and extracted with DCM (2×50 mL). The combined organics were washed with water (2×100 mL), brine, dried with $MgSO_4$, and concentrated. The crude compound was purified on Combiflash silica column with 10% EA/Hexane to give 0.620 g (47%) of the title compound.

LCMS m/z=355 (M+H), RT=1.34 min.

Intermediate 26

Ethyl 5-bromo-3-(1,1-dioxidotetrahydro-3-thienyl)-1H-indole-7-carboxylate

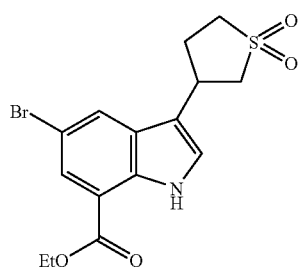

Ethyl 5-bromo-3-(tetrahydro-3-thienyl)-1H-indole-7-carboxylate (0.670 g, 1.82 mmol) was dissolved in 1,2-dimethoxyethane (50 mL). A solution of 0.0004 M EDTA (10 mL) was added followed by the portion-wise addition of a suspension of Oxone (3.49 g, 5.67 mmol) and Sodium bicarbonate (1.59 g, 18.9 mmol), in water (15 mL). The reaction was stirred for 18 hours at room temperature. Afterwards, the reaction was diluted with water (50 mL) and extracted with dichloromethane (2×50 mL). The combined organics were washed with water (2×100 mL). The combined aqueous layers were backwashed with dichloromethane (100 mL). The combined organics were washed with brine, dried with $MgSO_4$, concentrated. The crude compound was purified by Combiflash silica column chromatography using 10% ethyl acetate/dichloromethane on silica to give 0.596 g (82%) of the title compound.

LCMS m/z=388 (M+H), RT=1.02 min.

Intermediate 27

5-Bromo-3-(1,1-dioxidotetrahydro-3-thienyl)-1H-indole-7-carboxylic acid

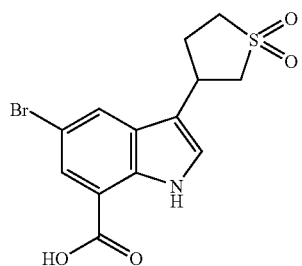

Ethyl 5-bromo-3-(1,1-dioxidotetrahydro-3-thienyl)-1H-indole-7-carboxylate (0.596 g, 1.54 mmol) was dissolved in water (8.2 mL) and methanol (13.8 mL). A 6M NaOH solution (2.55 mL) was added and heated to 85° C. for 1.5 hours. The methanol was then concentrated and the solution was acidified with 6M HCl. The resulting white solid was filtered and dried to give 0.503 g (91%) of product.

LCMS m/z=358 (M+H), RT=0.79 min.

Intermediate 28

5-Bromo-3-(1,1-dioxidotetrahydro-3-thienyl)-1H-indole-7-carboxamide

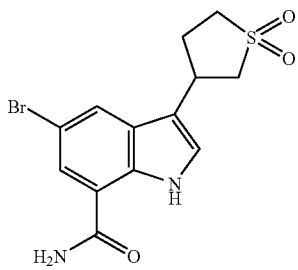

A 20 mL microwave reaction vessel was charged with 5-bromo-3-(1,1-dioxidotetrahydro-3-thienyl)-1H-indole-7-carboxylic acid (0.50 g, 1.40 mmol) EDC (0.81 g, 4.22 mmol), HOBT (0.22 g, 1.40 mmol), and dissolved in DMF (4.65 mL). A 0.5 M solution of ammonia in 1,4 dioxane (5.6 mL, 2.81 mmol) was then added and the reaction was heated in a microwave for 20 minutes, at 100° C. The solution was then dissolved in ethyl acetate and washed with water (3×'s). The aqueous layers were backwashed with ethyl acetate. The organic layers were combined and washed with 6 M sodium hydroxide, brine, dried with magnesium sulfate, and concentrated to give 0.484 g (96%) of the title compound.

LCMS m/z=358 (M+H), RT=0.69 min

Intermediate 29

8,8-Dimethyl-3-oxo-8-azoniabicyclo[3.2.1]octane iodide.

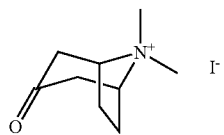

To a stirred solution of N-methylpiperidone (20.0 g, 143.7 mmol) in 150 mL of ether was added dropwise methyliodide (22.4 g, 158.1 mmol) in 100 mL of ether. The exothermic reaction was controlled by the rate of addition of methyl iodide and the mixture was stirred overnight after the addition. The white solid was filtered off by suction and dried in an oven, giving 35.0 g (86.6%) of the title compound.

Intermediate 30

8-Thiabicyclo[3.2.1]octan-3-one.

A mixture of 8,8-dimethyl-3-oxo-8-azoniabicyclo[3.2.1]octane iodide (20.0 g, 71.1 mmol) and Na$_2$S.9H$_2$O (18.8 g, 78.3 mmol) in H$_2$O (225 mL) was stirred at 85° C. under N$_2$ for 2 h. The reaction was allowed to cool, and the mixture was extracted with Et$_2$O (100 mL×3). The combined organic layers were washed with 0.1 M HCl and then washed with brine to neutrality. The organic layer was dried and evaporated, and the resulting yellow solid was decolourized by passing in Et$_2$O through a short column of basic alumina. The eluent was concentrated with a rotary evaporator, giving 4.6 g (45.5%) of the title compound.

$^1$H NMR (400 MHz, CDCl$_3$): δ 1.96-2.19 (m, 4H), 2.62-2.80 (m, 4H), 3.79-3.84 (m, 2H).

Intermediate 31

Ethyl 5-bromo-3-(8-thiabicyclo[3.2.1]oct-3-yl)-1H-indole-7-carboxylate.

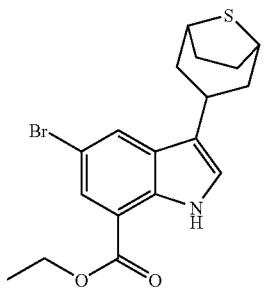

To a solution of 8-thiabicyclo[3.2.1]octan-3-one (1.33 g, 9.32 mmol, 1 eq) in dry dichloromethane (50 mL) was added a spatula tip full of activated 4 A molecular sieves (beads). The ketone solution was cooled to 0° C., and trimethylsilyl triflate (1.7 mL, 9.41 mmol, 1 eq) was added dropwise followed by a solution of ethyl 5-bromo-1H-indole-7-carboxylate (2.5 g, 9.32 mmol, 1 eq) in dichloromethane (25 mL). The mixture was stirred at 23° C. overnight, then was cooled to 23° C. and triethylsilane (2.3 mL, 14.4 mmol, 1.5 eq) was added in a single portion. The reaction was stirred at 23° C. for 1.5 h, then quenched by the addition of saturated aqueous sodium bicarbonate. The mixture was extracted with dichloromethane, and the combined organic extracts were dried over sodium sulfate, filtered, and concentrated. The crude product was purified by Isco Combiflash, 120 gram column, eluting with 0-30% ethyl acetate in hexanes. The ethyl 5-bromo-3-(8-thiabicyclo[3.2.1]oct-3-yl)-1H-indole-7-carboxylate was obtained as a mixture of isomers (2.38 g, 65%).

Intermediate 32

1-(1,1-dimethylethyl) 7-ethyl 5-bromo-3-(8-thiabicyclo[3.2.1]oct-3-yl)-1H-indole-1,7-dicarboxylate

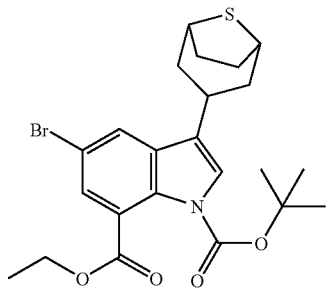

To a solution of ethyl 5-bromo-3-(8-thiabicyclo[3.2.1]oct-3-yl)-1H-indole-7-carboxylate (2.38 g, 6.0 mmol, mixture of isomers) in acetonitrile (30 mL) and tetrahydrofuran (4 mL) was added di-tert-butyl dicarbonate (2.23 g, 10.2 mmol, 1.7 eq) and 4-dimethylaminopyridine (245 mg, 2 mmol, 0.33 eq). The reaction mixture was stirred at 23° C. overnight, after which time a clear yellow solution was obtained. The mixture was filtered through a thin pad of silica gel, eluting with dichloromethane followed by 50% ethyl acetate in hexanes. After removal of the solvent in vacuo, the mixture of isomers of 1-(1,1-dimethylethyl) 7-ethyl 5-bromo-3-(8-thiabicyclo[3.2.1]oct-3-yl)-1H-indole-1,7-dicarboxylate was obtained as a yellow residue (3.06 g, 103%).

LC/MS: m/z 394.0 (M−100), Rt 1.57 min.

Intermediate 33 and 34

1-(1,1-Dimethylethyl) 7-ethyl 5-bromo-3-[(3-endo)-8,8-dioxido-8-thiabicyclo[3.2.1]oct-3-yl]-1H-indole-1,7-dicarboxylate and 1-(1,1-dimethylethyl) 7-ethyl 5-bromo-3-[(3-exo)-8,8-dioxido-8-thiabicyclo[3.2.1]oct-3-yl]-1H-indole-1,7-dicarboxylate.

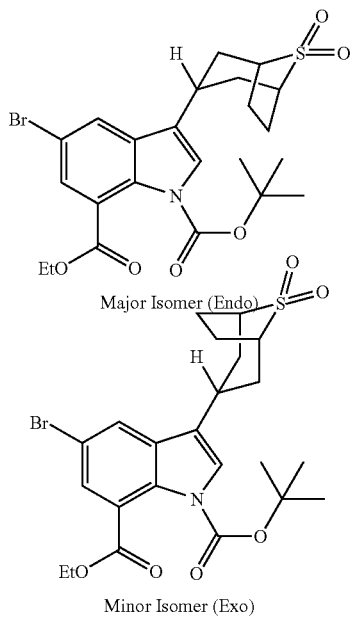

Major Isomer (Endo)

Minor Isomer (Exo)

Triflic anhydride (1.62 mL, 2.71 g, 9.59 mmol) was added to acetonitrile (35 mL) at 23° C. Urea hydrogen peroxide (1.34 g, 14.24 mmol) was subsequently added, and the mixture was stirred at 23° C. for 30 minutes behind a blast shield. (Flask was open to the atmosphere). The peroxide solution was cooled to 0° C. 1-(1,1-dimethylethyl) 7-ethyl 5-bromo-3-(8-thiabicyclo[3.2.1]oct-3-yl)-1H-indole-1,7-dicarboxylate (1.89 g, 3.82 mmol) was dissolved in acetonitrile (50 mL) and cooled to 0° C. The ice cold peroxide solution prepared above was added dropwise to the indole solution, and the mixture was warmed to 23° C. After stirring at 23° C. for 45 minutes, water was added and the mixture was extracted with ethyl acetate. The combined organics were dried (Na₂SO₄), concentrated, and purified by Isco Combiflash (120 gram column, 0-40% EtOAc/hexanes gradient), giving 805 mg of 1-(1,1-dimethylethyl) 7-ethyl 5-bromo-3-[(3-endo)-8,8-dioxido-8-thiabicyclo[3.2.1]oct-3-yl]-1H-indole-1,7-dicarboxylate (endo isomer) and 338 mg of 1-(1,1-dimethylethyl) 7-ethyl 5-bromo-3-[(3-exo)-8,8-dioxido-8-thiabicyclo[3.2.1]oct-3-yl]-1H-indole-1,7-dicarboxylate (exo isomer). Determination of endo/exo geometry was based upon small molecule crystallography of the major isomer, which was shown to be endo.

LC/MS: m/z 425.9 (M−100), Rt 1.27 min.

Intermediate 35

5-bromo-3-[(3-endo)-8,8-dioxido-8-thiabicyclo[3.2.1]oct-3-yl]-1H-indole-7-carboxylic acid

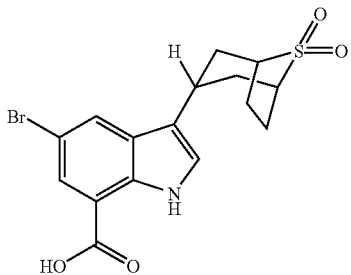

5-bromo-3-[(3-endo)-8,8-dioxido-8-thiabicyclo[3.2.1]oct-3-yl]-1H-indole-7-carboxylic acid (major isomer) (805 mg, 1.53 mmol) was diluted in methanol (10 mL) and water (5 mL). Then 6N NaOH (aq, 3.5 mL, 21 mmol) was added and the whole was heated at 85° C. for 45 minutes. The reaction was cooled to 23° C., concentrated, and acidified with 6N aq HCl to pH=1 by pH paper. The resultant light yellow solid was isolated by vacuum filtration and washed with water. The solid 5-bromo-3-[(3-endo)-8,8-dioxido-8-thiabicyclo[3.2.1]oct-3-yl]-1H-indole-7-carboxylic acid, was dried in the vacuum oven for 2 h with ~45° C. heating to afford 480 mg (79%) of the crude title compound.

LC/MS: m/z 399.9 (M+H), Rt 0.85 min.

Intermediate 36

5-bromo-3-[(3-exo)-8,8-dioxido-8-thiabicyclo[3.2.1]oct-3-yl]-1H-indole-7-carboxylic acid

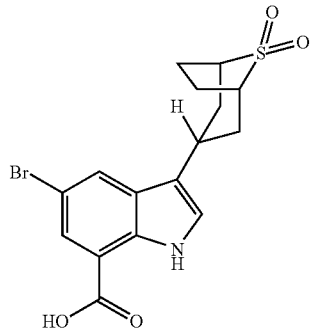

5-bromo-3-[(3-exo)-8,8-dioxido-8-thiabicyclo[3.2.1]oct-3-yl]-1H-indole-7-carboxylic acid (minor isomer) (338 mg, 0.642 mmol) was diluted in methanol (4 mL) and water (2 mL). Then 6N NaOH (aq, 1.75 mL, 10.5 mmol) was added, and the whole was heated at 85° C. Hydrolysis was much slower than the other isomer. An additional portion of 6N NaOH (5 mL, 30 mmol)) was added and the heat was continued at 90° C. for 6 h. The reaction was cooled to 23° C. and concentrated. A solution of 6N aq HCl was added to adjust the pH to a pH=1 by pH paper. The resultant light yellow solid was isolated by vacuum filtration, washing with water. The solid 5-bromo-3-[(3-exo)-8,8-dioxido-8-thiabicyclo[3.2.1]oct-3-yl]-1H-indole-7-carboxylic acid was dried in the vacuum oven for 2 h with ~45° C. heating to afford 153 mg (60%) of the crude title compound LC/MS: m/z 399.9 (M+H), Rt 0.86 min. .

Intermediate 37

5-Bromo-3-[(3-endo)-8,8-dioxido-8-thiabicyclo[3.2.1]oct-3-yl]-1H-indole-7-carboxamide

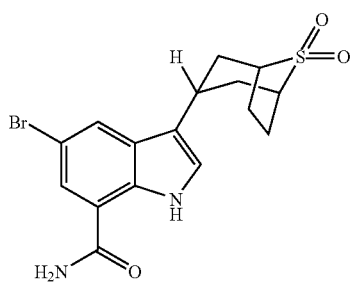

5-bromo-3-[(3-endo)-8,8-dioxido-8-thiabicyclo[3.2.1]oct-3-yl]-1H-indole-7-carboxylic acid (major isomer) (480 mg, 1.21 mmol) (major isomer), HOBt hydrate (185 mg, 1.21 mmol), and EDCl hydrochloride (530 mg, 2.76 mmol) were combined and diluted with 0.5M ammonia in dioxane (10 mL, 5 mmol) and DMF (3 mL). The mixture was heated in a microwave oven under regular absorption at 100° C. for 20 min. The reaction was diluted in ethyl acetate and washed with water. The organic layers were dried (Na$_2$SO$_4$), filtered, and concentrated. The residue was triturated from dichloromethane to afford 0.328 g (69%) of the title compound.

LC/MS: m/z 399.0 (M+H), Rt 0.85 min.

Intermediate 38

5-bromo-3-[(3-exo)-8,8-dioxido-8-thiabicyclo[3.2.1]oct-3-yl]-1H-indole-7-carboxamide

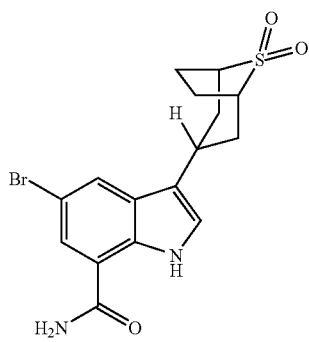

5-Bromo-3-[(3-exo)-8,8-dioxido-8-thiabicyclo[3.2.1]oct-3-yl]-1H-indole-7-carboxylic acid (minor isomer) (153 mg, 0.38 mmol), HOBt hydrate (59 mg, 0.38 mmol), and EDCl hydrochloride (530 mg, 2.76 mmol) were diluted in 0.5M ammonia in dioxane (3 mL, 1.5 mmol) and DMF (1 mL). The reaction mixture was heated in a microwave oven under regular absorption at 100° C. for 20 min, diluted in ethyl acetate and washed with water.

The organic layers were dried (Na$_2$SO$_4$), filtered, and concentrated. The crude product was triturated from dichloromethane/hexanes mixture to afford 124 mg (81%) of the title compound.

LC/MS: m/z 399.0 (M+H), Rt 0.77 min.

Intermediate 39

3-[(3-endo)-8,8-dioxido-8-thiabicyclo[3.2.1]oct-3-yl]-5-(5-formyl-3-thienyl)-1H-indole-7-carboxamide

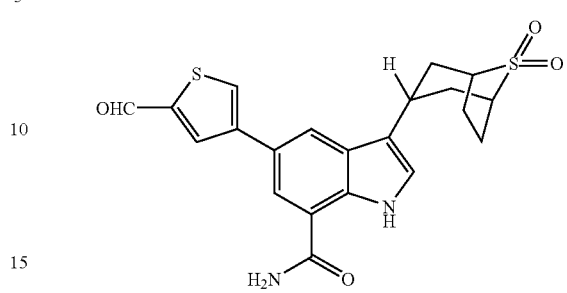

5-Bromo-3-[(3-endo)-8,8-dioxido-8-thiabicyclo[3.2.1]oct-3-yl]-1H-indole-7-carboxamide (150 mg, 0.378 mmol), 4-(4,4,5,5-tetramethyl-1,3,2-dioxaborolan-2-yl)-2-thiophenecarbaldehyde (108 mg, 0.454 mmol), PdCl2(dppf)-CH2Cl2Adduct (28 mg, 0.034 mmol), potassium carbonate (160 mg, 1.16 mmol), 1,4-dioxane (2 mL), and water (1 mL) were combined and the mixture was degassed by bubbling argon through it for 5 minutes. The reaction was heated in a microwave oven (normal setting) at 100° C. for 5 min and filtered through a thiol SPE cartridge. The Thiol SPE cartridge was washed with acetone (3×10 mL) and the eluent was concentrated under reduced pressure, giving a solid that was triturated with diethylether to afford 155 mg (96%) of the title compound.

LC/MS: m/z 428.9 (M+H), Rt 0.78 min.

Intermediate 40

3-[(3-exo)-8,8-dioxido-8-thiabicyclo[3.2.1]oct-3-yl]-5-(5-formyl-3-thienyl)-1H-indole-7-carboxamide

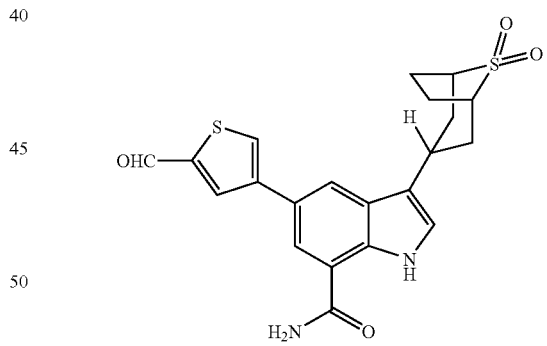

5-bromo-3-[(3-exo)-8,8-dioxido-8-thiabicyclo[3.2.1]oct-3-yl]-1H-indole-7-carboxamide (200 mg, 0.503 mmol) 4-(4,4,5,5-tetramethyl-1,3,2-dioxaborolan-2-yl)-2-thiophenecarbaldehyde (144 mg, 0.605 mmol), PdCl2(dppf)-CH2Cl2Adduct (35 mg, 0.043 mmol), potassium carbonate (215 mg, 1.16 mmol), 1,4-dioxane (2 mL), and water (1 mL) were combined and the mixture was degassed by bubbling argon through it for 5 minutes. The reaction mixture was heated by microwave oven (normal setting) at 100° C. for 5 min and filtered through a thiol SPE cartridge. The thiol cartridge was washed with acetone and the eluant was concentrated and triturated from diethylether.

LC/MS: m/z 428.9 (M+H), Rt 0.80 min.

Intermediate 41

4-Thiepanone

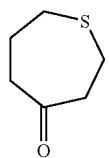

A diazomethane kit was used to make CH$_2$N$_2$:KOH (12.07 g, 215 mmol) was added in the flask with 12 mL EtOH and 8 mL of H$_2$O, the mixture was heated to 65° C. A solution of Diazald (11.53 g, 53.8 mmol) in 120 mL ether was added dropwise, meanwhile collecting the CH$_2$N$_2$ generated, which was dried with KOH. In a separated flask, BaO (6.6 g, 43.0 mmol) was added to a solution of 4H-thiopyran-4-one (5 g, 43.0 mmol) and in MeOH (10 mL). To this solution was added to the CH2N2 in ether slowly and the reaction was stirred overnight at room temperature. The mixture was filtered and the solid was washed with water/EtOAc. The organic was washed with water and brine then concentrated to give the crude product. The crude product was purified by flash chromatography, giving 1.16 g of the title compound.

4-Thiapenone could also be made according to the following procedure:

To a solution of tetrahydro-4H-thiopyran-4-one (Aldrich, 3.0 g, 26 mmol) in dichloromethane (240 mL) at −40° C. (dry ice/acetonitrile bath) was added boron trifluoride diethyl etherate (5 mL, 40 mmol). TMS diazomethane (2M solution in diethyl ether (20 mL, 40 mmol) was then added to the mixture dropwise over approximately 10 minutes. Gas evolution was noted upon addition of the TMS diazomethane and the colorless solution turned yellow. The mixture was stirred at low temperature for 2 h, allowing the dry ice to slowly sublime from the cold bath without replacement. Water (100 mL) was added to the reaction mixture and the mixture was warmed to room temperature and washed with DCM (2×50 mL). The combined organic extracts were dried over sodium sulfate, filtered, and concentrated to afford the crude product as a mixture of an oil and solid. The solid was removed by filtration and the oil purified by Biotage, 40M+ column, eluting with 25% ethyl acetate in hexanes. The title compound was isolated as clear, slightly yellow oil (980 mg, 29%).

Intermediate 42 methyl 5-bromo-3-(4-thiepanyl)-1H-indole-7-carboxylate

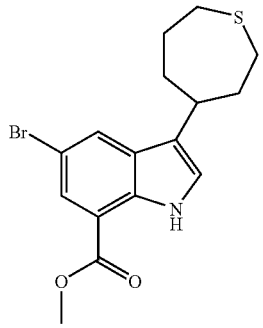

To a flask under argon in an ice-bath, the 4-thiepanone (200 mg, 1.536 mmol) in 6 mL of dried CH$_2$Cl$_2$ was first dried w/4 A sieves and then transferred via a double needle tubing (cannula). TMS-OTf (278 uL, 1.536 mmol) was added dropwise and the reaction was stirred for 10 min. A solution of methyl 5-bromo-1H-indole-7-carboxylate (390 mg, 1.536 mmol) in 7 mL of CH$_2$Cl$_2$ was dried with 4 A sieves and then added into above solution dropwise. Stirring continued for 4 hours and the reaction was warmed to room temperature. The mixture was cooled to 0° C. and triethylsilane (245 uL, 1.536 mmol) was added as one portion. The mixture was stirred overnight then warmed to room temperature. The mixture was quenched water and sat. NaHCO$_3$, then diluted water/AcOEt and washed with H$_2$O and brine. 194 mg of crude product was obtained.

LC/MS: m/z 371.8 (M+H), Rt 2.67 min.

Intermediate 43

1-(1,1-dimethylethyl) 7-methyl 5-bromo-3-(4-thiepanyl)-1H-indole-1,7-dicarboxylate

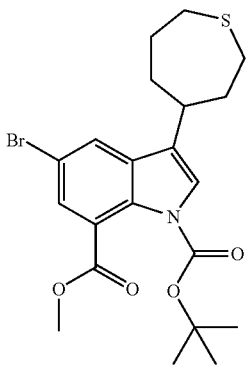

The intermediate methyl 5-bromo-3-(4-thiepanyl)-1H-indole-7-carboxylate, indole (629 mg, 2.115 mmol), DMAP (129 mg, 1.058 mmol) and Boc$_2$O (737 ul, 3.17 mmol) were suspended in 20 mL of CH$_2$Cl$_2$. The resulting mixture was stirred overnight. The mixture was diluted with water/AcOEt, washed with H$_2$O and brine; dried over MgSO$_4$, and concentrated, giving 784 mg of the title compound.

LC/MS: m/z 470.2 (M+H), Rt 3.07 min.

Intermediate 44

1-(1,1-dimethylethyl) 7-methyl 5-bromo-3-(1,1-dioxido-4-thiepanyl)-1H-indole-1,7-dicarboxylate

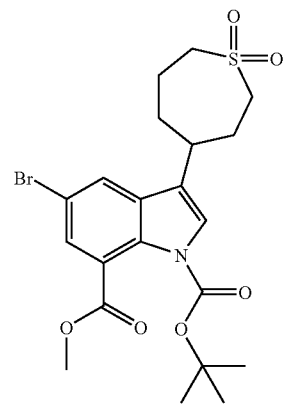

TFAA (521 uL, 3.1 mmol) and urea hydrogen peroxide (411 mg, 4.37 mmol) were dissolved in CH$_3$CN (30 mL) and stirred at room temperature for 30 minutes. The intermediate 1-(1,1-dimethylethyl) 7-methyl 5-bromo-3-(4-thiepanyl)-1H-indole-1,7-dicarboxylate (584 mg, 1.25 mmol) was added at 0° C. in 20 mL CH$_3$CN. The mixture was stirred for 1 hour. The mixture was diluted with AcOEt and washed with water and brine. Upon purifying by Combiflash and eluting with AcOEt and hexanes, 487 mg of the title compound was obtained.

LC/MS: m/z 500.3 (M+H), Rt 3.06 min.

Intermediate 45

3-(1,1-dioxido-4-thiepanyl)-5-phenyl-1H-indole-7-carboxylic acid

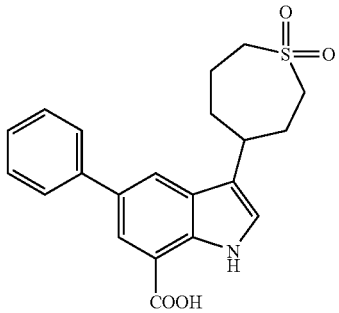

The intermediate 1-(1,1-dimethylethyl) 7-methyl 5-bromo-3-(1,1-dioxido-4-thiepanyl)-1H-indole-1,7-dicarboxylate (88 mg, 0.18 mmol), PdCl2(dppf) (13 mg, 0.109 mmol), K$_2$CO$_3$ (75 mg, 0.54 mmol), and PhB(OH)$_2$ (33 mg, 0.27 mmol) were mixed together and the taken up in dioxane/H$_2$O (3/1, 2 mL). The reaction was heated in a microwave oven at 120° C. for 10 minutes. The mixture was diluted with AcOEt, washed with 1N HCl, H$_2$O and brine, dried over MgSO$_4$, and concentrated. The residue was dissolved in MeOH (5 mL). 6N NaOH (1 mL) was added and the mixture was stirred at room temperature overnight. The reaction was diluted with AcOEt, washed with 1N HCl, H$_2$O, dried over MgSO$_4$, and then concentrated, giving the title compound.

LC/MS: m/z 384.1 (M+H), Rt 1.87 min.

Intermediate 46

Ethyl 5-bromo-3-(4-thiepanyl)-1H-indole-7-carboxylate

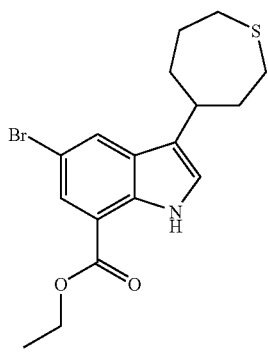

To a solution of 4-thiepanone (900 mg, 6.9 mmol, 1.1 eq) in dry dichloromethane (30 mL) was added activated molecular sieves (4 Å, beads, spatula tip full) and the solution was cooled to 0° C. using an ice water bath. Trimethylsilyl trifluoromethanesulfonate (1.25 mL, 6.9 mmol, 1.1 eq) was added dropwise to the ketone solution, followed by the dropwise addition of ethyl 5-bromo-1H-indole-7-carboxylate (1.69 g, 6.3 mmol, 1 eq) as a solution in dichloromethane (10 mL). The reaction mixture was stirred at rt for 2 h, then warmed to 35° C. for 45 minutes. The deep red reaction mixture was cooled to 0° C. and triethylsilane (2 mL, 12.6 mmol, 2 eq) was added. The mixture was warmed to rt for 30 minutes, then was quenched by the addition of saturated aq. sodium bicarbonate. The aqueous layer was extracted with dichloromethane (2×50 mL), and the combined organic extracts were dried over sodium sulfate, filtered through a thin pad of silica gel (to remove baseline impurities), eluting with 50% ethyl acetate in hexanes, and concentrated to afford the crude product as a yellow residue. The crude material was purified by Isco Combiflash, eluting with 0-30% ethyl acetate in hexanes (120 gram column). The title compound was obtained as a yellow residue (540 mg, 24%).

Intermediate 47

1-(1,1-Dimethylethyl) 7-ethyl 5-bromo-3-(4-thiepanyl)-1H-indole-1,7-dicarboxylate

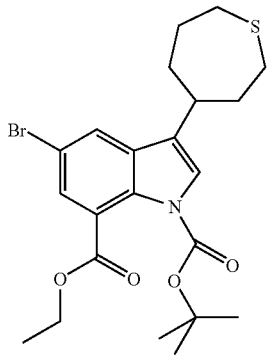

To a solution of ethyl 5-bromo-3-(4-thiepanyl)-1H-indole-7-carboxylate (580 mg, 1.5 mmol) in acetonitrile (5 mL) and tetrahydrofuran (0.5 mL) was added di-tert-butyl dicarbonate (530 mg, 2.43 mmol, 1.6 eq) and 4-dimethylaminopyridine (63 mg, 0.52 mmol, 0.34 eq). The mixture was stirred at rt overnight. Additional di-tert-butyl dicarbonate (300 mg, 1.4 mmol) was added and the mixture was stirred at rt for an additional 1 hour. The crude reaction mixture was filtered through a thin pad of silica gel, eluting with dichloromethane followed by 50% ethyl acetate in hexanes. The combined organic extracts were concentrated to afford the crude product as orange oil, which was subsequently purified by Isco Combiflash, eluting with 0-20% ethyl acetate in hexanes (120 gram column). The title compound (536 mg, 73%) was obtained as a light yellow tarry residue.

Intermediate 48

1-(1,1-Dimethylethyl) 7-ethyl 5-bromo-3-(1,1-dioxido-4-thiepanyl)-1H-indole-1,7-dicarboxylate

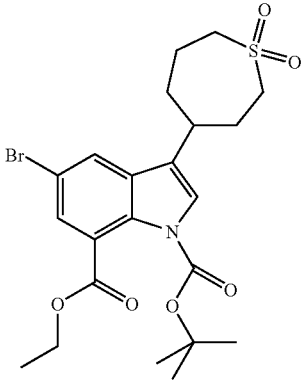

Reaction performed behind a blast shield. Triflic anhydride (0.47 mL, 3.3 mmol, 3 eq) was diluted in acetonitrile (10 mL), and urea hydrogen peroxide (387 mg, 4.1 mmol, 3.7 eq) was added. The mixture was stirred at rt for 30 minutes, then cooled to 0° C. 1-(1,1-dimethylethyl) 7-ethyl 5-bromo-3-(4-thiepanyl)-1H-indole-1,7-dicarboxylate (536 mg, 1.1 mmol, 1 eq) was diluted in acetonitrile (15 mL) and cooled to 0° C. The oxidant solution was added to the indole solution dropwise and the reaction mixture was warmed to rt after addition was complete. After stirring at rt for 45 minutes, water (20 mL) was added and the reaction mixture was extracted twice with ethyl acetate (20 mL). The combined organics were dried over sodium sulfate, filtered, and concentrated. The crude residue was purified by Isco Combiflash, eluting with 0-50% ethyl acetate in hexanes. The product fractions were combined and concentrated to afford a yellow oil, which was subsequently evaporated from dichlormethane/hexanes to afford the title compound as a white solid (273 mg, 48%).

Intermediate 49

5-Bromo-3-(1,1-dioxido-4-thiepanyl)-1H-indole-7-carboxamide

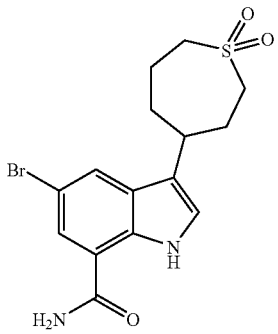

To a solution of 1-(1,1-dimethylethyl) 7-ethyl 5-bromo-3-(1,1-dioxido-4-thiepanyl)-1H-indole-1,7-dicarboxylate (273 mg, 0.53 mmol) in methanol (3 mL) and water (1.6 mL) was added 6 M aqueous sodium hydroxide (1 mL). The mixture was heated to 85° C. for 2 h, after which time a clear yellow solution was obtained. The mixture was cooled to rt, concentrated to remove most of the methanol, and acidified with 6M aqueous hydrochloric acid until a pH=1 was obtained (pH paper). The product formed a gummy solid. The mixture was then concentrated to dryness. A light yellow gummy residue was obtained, which was used in the amide formation step as is. 5-bromo-3-(1,1-dioxido-4-thiepanyl)-1H-indole-7-carboxylic acid (prepared above) was diluted in N,N-dimethylformamide (1 mL) in a 20 mL microwave vial. EDCl hydrochloride (275 mg, 275 mg, 1.43 mmol, 2.7 eq), HOBt hydrate (81 mg, 0.6 mmol, 1.1 eq), and NH$_3$ (0.5 M in dioxane, Aldrich, 8 mL) were added. The mixture was heated in a Biotage microwave oven at 10° C. for 20 minutes under regular absorption. The crude reaction mixture was diluted in ethyl acetate and washed with water. The aqueous layer was washed three times with ethyl acetate (30 mL). The combined organics were dried over sodium sulfate, filtered, and concentrated in vacuum oven. The crude brown oil was purified by Isco Combiflash, 40 gram column, eluting with 0-20% methanol in dichloromethane. The title compound was obtained as a yellow tarry residue (198 mg, 97% combined yield for both steps).

Intermediate 50

Methyl 4-{[2-(methyloxy)-2-oxoethyl]thio}butanoate

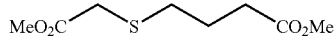

Sodium (3.5 g, 0.15 mol) was added to methanol (150 mL) carefully. After cooling to room temperature, methyl 2-mercaptoacetate (15.6 g, 0.13 mol) was added. The mixture was stirred for 30 mins at room temperature and a little of NaI and methyl 4-chlorobutanoate (20.0 g, 0.15 mol) were added. The reaction mixture was refluxed over night. After cooling to room temperature, the solvent was removed under reduced pressure, then the residue was dissolved in CH$_2$Cl$_2$ (100 mL). The solution was washed with H$_2$O (30 mL), brine (30 mL), and dried with Na$_2$SO$_4$. After removing the solvent, 28.3 g of the crude product was obtained (Yield: 94%).

Intermediate 51

Methyl 3-oxotetrahydro-2H-thiopyran-2-carboxylate

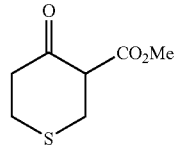

To a suspension of sodium (3.5 g, 0.15 mol) in dry toluene (300 mL) was added an excess of methanol (30 mL). After sodium was disappeared, the excess methanol was removed as the methanol-toluene azeotrope. When the distillation temperature had reached 105° C., Methyl 4-{[2-(methyloxy)-2-oxoethyl]thio}butanoate (28.3 g, 0.14 mol) in toluene (90 mL) was added over a period of ten mins. The methanol-toluene azeotrope was removed by distillation, after the distillation temperature rose to 106° C., the reaction mixture was cooled to room temperature. The reaction mixture was poured into a mixture of ice (100 g) and 12N HCl (20 mL). The organic layer was removed and the aqueous layer was extracted with three 60 mL portions of ether and the combined organic layers were dried over Na$_2$SO$_4$. After removing the solvent, 23.4 g of crude product was obtained (Yield: 96%).

Intermediate 52

Dihydro-2H-thiopyran-3(4H)-one

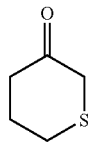

The mixture of S-2 (23.4 g, 0.13 mol) and 2NH$_2$SO$_4$ (100 mL) was refluxed over night and then allowed to cool to room temperature. The mixture was extracted with three 30 mL portions of CH$_2$Cl$_2$. After the solvent was removed, the residue was fractionated in vacuo, giving 5.7 g of the title compound (obtained at 59-60° C./1 mmHg) (Yield: 36.6%).

$^1$H NMR (400 MHz, CHCl$_3$): δ 2.42-2.44 (m, 4H), 2.77-2.79 (m, 2H), 3.20 (s, 2H);

$^{13}$C NMR (100 MHz, CHCl$_3$): δ 28.4, 33.4, 38.5, 41.7, 203.8.

Intermediate 53

Ethyl 5-bromo-3-(tetrahydro-2H-thiopyran-3-yl)-1H-indole-7-carboxylate

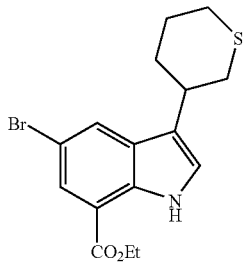

Dihydro-2H-thiopyran-3(4H)-one (0.217 g, 1.86 mmol) was dissolved in dichloromethane (23 mL) in an oven dried flask containing 3 Å molecular sieves and stirred under argon at 0° C. TMS-OTf (0.414 g, 1.86 mmol, 0.33 mL) was added slowly to the mixture over 10 min. Ethyl 5-bromo-1H-indole-7-carboxylate (0.5 g, 1.86 mmol) was dissolved in DCM (7 mL) and added to the reaction via syringe pump over 2 hours, after which it was stirred for 3 hours between 0 and 10° C. The reaction was cooled to 0° C. and triethylsilane (0.325 g, 0.44 mL, 2.8 mmol) was added all at once and the reaction was stirred at room temperature for 18 hours. The reaction was then quenched with a saturated sodium bicarbonate solution and extracted with DCM. The combined organics were washed with water. The combined aqueous layers were back-extracted with DCM. The combined organics were washed with brine, dried with MgSO$_4$, and concentrated. The crude compound was purified on a Combiflash silica column with 5-25% EA/Hexane to give 0.279 g (40%) of the title compound.

LC/MS: m/z 369 (M+H), Rt 2.74 min.

Intermediate 54

Ethyl 5-bromo-3-(1,1-dioxidotetrahydro-2H-thiopyran-3-yl)-1H-indole-7-carboxylate

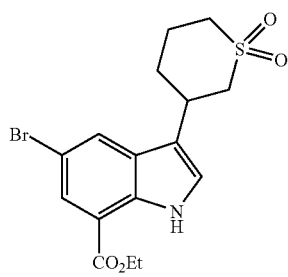

Ethyl 5-bromo-3-(tetrahydro-2H-thiopyran-3-yl)-1H-indole-7-carboxylate (0.375 g, 1.02 mmol) was dissolved in 1,2-Dimethoxyethane (DME) (25 mL). A solution of 0.0004M EDTA (7 mL) was added followed by the portionwise addition of a suspension of oxone (1.88 g, 3.05 mmol) and sodium bicarbonate (0.855 g, 10.18 mmol) in 7 mL water. The reaction was stirred for 3 hours at room temperature. The reaction was diluted with water and extracted with dichloromethane. The combined organics were washed with water 2×. The combined aqueous layers were backwashed with dichloromethane. The combined organics were washed with water, brine, dried with MgSO$_4$ and concentrated. The crude compound was purified by Combiflash silica column chromatography using 0-10% ethylacetate/dichloromethane on silica to give 0.290 g (71%) of the title compound.

LC/MS: m/z 401 (M+H), Rt 1.05 min.

Intermediate 55

5-Bromo-3-(1,1-dioxidotetrahydro-2H-thiopyran-3-yl)-1H-indole-7-carboxylic acid

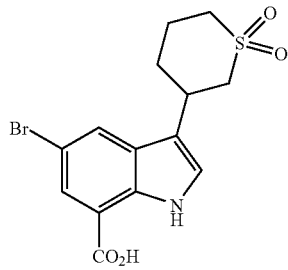

Ethyl 5-bromo-3-(1,1-dioxidotetrahydro-2H-thiopyran-3-yl)-1H-indole-7-carboxylate (0.380 g, 0.949 mmol), was stirred in a methanol (5 mL)/water (3 mL) solution. 6M NaOH (1.5 mL, 0.900 mol, 10 eq) was added and the reaction was heated to 85° C. for 1.5 hours. The methanol was concentrated and the aqueous solution was acidified with 6M HCl. The resulting white solid was filtered and dried under vacuum to give 0.325 g (92%) of the title compound.

LC/MS m/z=373 (M+H), RT=0.81 min.

Intermediate 56

5-Bromo-3-(1,1-dioxidotetrahydro-2H-thiopyran-3-yl)-1H-indole-7-carboxamide

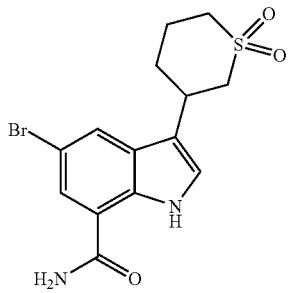

5-bromo-3-(1,1-dioxidotetrahydro-2H-thiopyran-3-yl)-1H-indole-7-carboxylic acid (0.185 g, 0.497 mmol) was suspended in DMF (2 mL) with EDC (0.286 g, 1.49 mmol, 3 eq) and HOBt (0.076, 0.497 mmol) in a 10 mL microwave reaction vessel. 0.5M ammonia in 1,4-dioxane (1.9 mL, 0.9945 mmol, 2 eq) was added and heated on the microwave at 100° C. for 20 minutes. Reaction was diluted with water and extracted with ethyl acetate. The combined organics were washed with 1N NaOH, water, and brine then dried with magnesium sulfate, to give 0.161 g (87%) of the title compound.

LC/MS: m/z 372 (M+H), Rt 0.74 min.

Intermediate 57

1,6-Heptadien-4-one

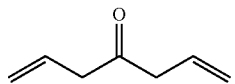

1,6 Heptadiene-4-ol (1.0 g, 8.92 mol) was dissolved in DCM (5 mL). Dess-Martin Periodinane (4.16 g, 9.81 mmol, 1.1 eq) was added and the reaction was cooled in an ice bath. The reaction was then stirred at room temperature for 3 hours. The reaction was diluted with diethyl ether (30 mL) and filtered through Celite. The filtrate was washed with sat. NaHCO$_3$, dried with sodium sulfate and concentrated, giving the title compound.

$^1$H NMR δ=5.9 (m, 2H), 5.2 (m, 4H), 3.25 (d, 4H).

Intermediate 58

2,6-Dimethyltetrahydro-4H-thiopyran-4-one

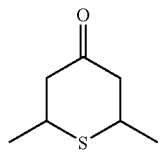

1,6-Heptadien-4-one (0.50 g, 4.54 mmol) was dissolved in toluene (8 mL) and water (4 mL). Sodium sulfide nonahydrate (1.09 g, 4.54 mmol) was dissolved in water (4 mL) and added to the solution above and stirred at room temp. After 5 h, the aqueous layer was saturated with potassium carbonate and extracted with diethyl ether. The combined organics were washed with brine, dried MgSO$_4$, and concentrated. The crude compound was purified on a Combiflash silica column with 0-10% EtOAc/hexanes to give 0.193 g (29%) of the title compound.

Intermediate 59

Ethyl 5-bromo-3-(2,6-dimethyltetrahydro-2H-thiopyran-4-yl)-1H-indole-7-carboxylate

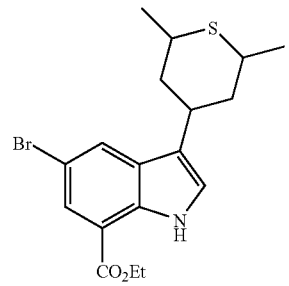

2,6-Dimethyltetrahydro-4H-thiopyran-4-one (0.293 g, 2.03 mmol) was dissolved in dichloromethane (35 mL) in an oven dried flask containing 3 Å molecular sieves and stirred under argon at 0° C. TMS-OTf (0.451 g, 2.03 mmol, 0.36 mL) was added slowly to the mixture over 10 min. Ethyl 5-bromo-1H-indole-7-carboxylate (0.293 g, 2.031 mmol) was dissolved in DCM (10 mL) and added to the reaction via syringe pump over 2 hours, after which it was stirred for 3 hours between 0 and 10° C. The reaction was cooled to 0° C. and triethylsilane (0.353 g, 0.485 mL, 3.04 mmol) was then added all at once and the reaction was stirred at room temperature overnight. The reaction was then quenched with a saturated sodium bicarbonate solution, filtered, then extracted with DCM. The combined organics were washed with water. The combined aqueous layers were back-extracted with DCM. The combined organics were washed with brine, dried with MgSO$_4$, and concentrated. The crude compound was purified on Combiflash silica column with 0-30% EA/DCM to give 0.212 g (26%) of the title compound.

LC/MS: m/z 397 (M+H), Rt 1.51 min.

Intermediate 60

Ethyl 5-bromo-3-(2,6-dimethyl-1,1-dioxidotetrahydro-2H-thiopyran-4-yl)-1H-indole-7-carboxylate

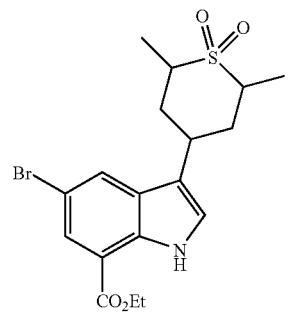

Ethyl 5-bromo-3-(2,6-dimethyltetrahydro-2H-thiopyran-4-yl)-1H-indole-7-carboxylate (0.212 g, 0.535 mmol) was dissolved in 1,2-Dimethoxyethane (DME) (13 mL). A solution of 0.0004M EDTA (3.61 mL, 0.0014 mmol) was added followed by the portion-wise addition of a suspension of Oxone (0.986 g, 1.60 mmol) and Sodium bicarbonate (0.449 g, 5.35 mmol), in 3 mL water. The reaction was stirred overnight at room temperature. An Oxone/sodium bicarbonate solution in the same amounts as above was added to the reaction and stirred for 3 hours. The reaction was diluted with water and dichloromethane. The organic layer was washed 2× water. The combined aqueous layers were backextracted with dichloromethane. The combined organics were washed with water, brine, dried with MgSO$_4$, concentrated. The crude compound was purified by Combiflash silica column chromatography using 0-5% Ethylacetate/dichloromethane on silica to give 0.189 g (82%) of the title compound.

LC/MS: m/z 429 (M+H), Rt 1.14 min.

Intermediate 61

5-Bromo-3-(2,6-dimethyl-1,1-dioxidotetrahydro-2H-thiopyran-4-yl)-1H-indole-7-carboxylic acid

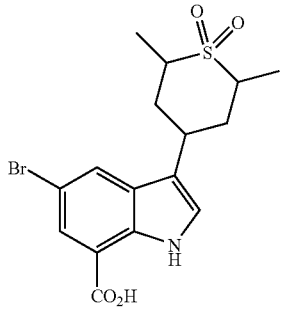

Ethyl 5-bromo-3-(2,6-dimethyl-1,1-dioxidotetrahydro-2H-thiopyran-4-yl)-1H-indole-7-carboxylate (0.189 g, 0.441 mmol), was stirred in a methanol (5 mL)/water (3 mL) solution. 6M NaOH (0.735 mL, 4.41 mol, 10 eq) was added and the reaction was heated to 85° C. for 1.5 hours. LCMS analysis indicated the reaction was completed. The methanol was concentrated and the aqueous solution was acidified with 6M HCl. The resulting white solid was filtered and dried under vacuum to give 0.187 g (92%) of the title compound.

LC/MS: m/z 401 (M+H), Rt 0.89 min.

Intermediate 62

5-Bromo-3-(2,6-dimethyl-1,1-dioxidotetrahydro-2H-thiopyran-4-yl)-1H-indole-7-carboxamide

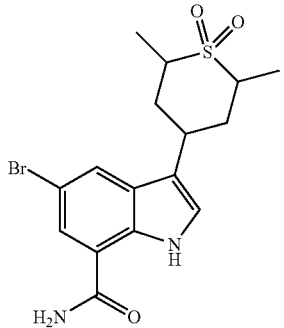

5-bromo-3-(2,6-dimethyl-1,1-dioxidotetrahydro-2H-thiopyran-4-yl)-1H-indole-7-carboxylic acid (0.187 g, 0.467 mmol) was suspended in DMF (3 mL) with EDC (0.269 g, 1.40 mmol, 3 eq) and HOBt (0.072, 0.467 mmol) in a 10 mL microwave reaction vessel. 0.5M Ammonia in 1,4-dioxane (0.93 mL, 0.467 mmol) was added and heated on the microwave at 100° C. for 20 minutes. The reaction was diluted with water and extracted with Ethyl acetate. The combined organics were washed with 2× water, 2×1N NaOH, brine then dried with magnesium sulfate, to give 0.150 g (80%) of the title compound.

LC/MS: m/z 400 (M+H), Rt 0.83 and 0.88 min.

Intermediate 63

3-(2-Methoxycarbonyl-ethylsulfanyl)-3-methyl-butyric acid methyl ester

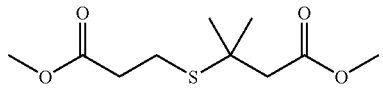

To a well-stirred mixture of methyl 3-methylbut-2-enoate (50.0 g, 438 mmol), 40% Triton B in MeOH (5 mL) and piperidine (4 mL) were added dropwise at 0° C., then methyl 3-mercaptopropanoate (50 g, 396 mmol) was added. After stirring for 24 h at 60° C., Et$_2$O (500 mL) was added, and the organic phase washed thoroughly with 10% H$_2$SO$_4$ (150 mL), sat. NaHCO$_3$ (150 mL), and brine (200 mL) successively, dried over Na$_2$SO$_4$ and evaporated under vacuum to give the title compound as a colorless oil (90.1 g, 97.23%).

$^1$H NMR (400 MHz, CDCl$_3$): δ 2.55-2.59 (m, 4H), 2.79-2.83 (m, 2H), 3.67 (s, 3H), 3.70 (s, 3H).

Intermediate 64 and 65

6,6-Dimethyl-4-oxo-tetrahydro-thiopyran-3-carboxylic acid methyl ester, and 2,2-Dimethyl-4-oxo-tetrahydro-thiopyran-3-carboxylic acid methyl ester

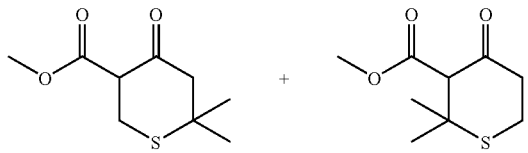

To a freshly prepared LDA solution (89 mL of iPr$_2$NH, 175 mL of 2.5 M BuLi in hexane) in THF (600 mL) was added dropwise a solution of 3-(2-Methoxycarbonyl-ethylsulfanyl)-3-methyl-butyric acid methyl ester (50.0 g, 0.21 mol) in THF (1200 mL) at −78° C. After the reaction mixture was stirred overnight at the room temperature, 10% aq. H$_2$SO$_4$ solution. (2.0 L) was added, and the mixture was extracted with Et$_2$O (3×600 mL). The combined organic layer was dried over Na$_2$SO$_4$ and evaporated under vacuum to give the title compound as yellow oil (42 g).

Intermediate 66

2,2-Dimethyl-tetrahydro-thiopyran-4-one

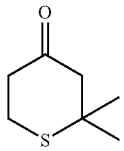

The mixture of 6,6-Dimethyl-4-oxo-tetrahydro-thiopyran-3-carboxylic acid methyl ester and 2,2-Dimethyl-4-oxo-tetrahydro-thiopyran-3-carboxylic acid methyl ester (42 g) in 10% aq. H$_2$SO$_4$ solution (1000 mL) was heated at reflux for 70 h. Then the mixture was extracted with Et$_2$O (3×300 mL), the combined organic layer was washed with sat. NaHCO$_3$ (120 mL) and brine (120 mL), dried over Na$_2$SO$_4$ and evaporated under vacuum to give the title compound as a white solid (5.3 g, 17.7%, two steps).

$^1$H NMR (400 MHz, CDCl$_3$): δ 1.36 (s, 6H), 2.55 (s, 2H), 2.59-2.62 (m, 2H), 2.97-3.00 (m, 2H).

Intermediate 67

5-Bromo-3-(2,2-dimethyl-tetrahydro-thiopyran-4-yl)-1H-indole-7-carboxylic acid methyl ester

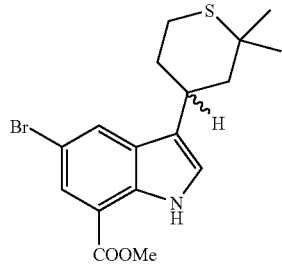

To a solution of 2,2-Dimethyl-tetrahydro-thiopyran-4-one (7.9 g, 55.1 mmol) in DCM (100 mL) was added TMSOTf (10 mL, 55.1 mmol) and 5-Bromo-1H-indole-7-carboxylic acid methyl ester (7.0 g, 27.6 mmol) at 0° C. After 2 hours, Et$_3$SiH (15 mL, 110 mmol) was added at 0° C., then the mixture was stirred for 18 hours. The reaction mixture was quenched with sat. Sodium bicarbonate solution, extracted with DCM (3×100 mL). The combined organic layer was dried over MgSO$_4$ and concentrated under vacuum. The residue was purified by column chromatography on silica gel (PE:EA=50:1 to 30:1) to give the title compound as a light yellow solid (5.5 g, 52%).

$^1$H-NMR δ 1.25 (s, 3H), 1.47 (s, 3H), 1.66 (q, 1H), 1.78 (t, 1H), 1.92 (dd, 1H), 2.25 (dd, 1H), 2.56 (d, 1H), 2.54~2.59 (m, 2H), 3.91 (s, 3H), 7.01 (d, 1H), 7.84 (s, 1H), 7.89 (s, 1H), 9.57 (s, 1H).

Intermediate 68

5-Bromo-3-(2,2-dimethyl-1,1-dioxo-hexahydro-1l6-thiopyran-4-yl)-1H-indole-7-carboxylic acid methyl ester

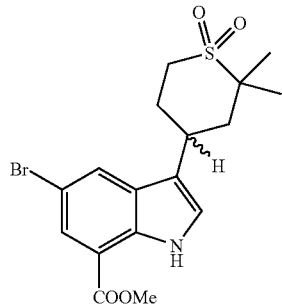

To a solution of 5-bromo-3-(2,2-dimethyl-tetrahydro-thiopyran-4-yl)-1H-indole-7-carboxylic acid methyl ester (5.5 g, 14.4 mmol) in 100 mL DCM was added m-CPBA (7.4 g, 43.3 mmol). The mixture was stirred for 1 hour at room temperature. The reaction was quenched with saturated sodium sulfite solution, extracted with DCM (3×50 mL). The combined organic layer was dried over MgSO$_4$ and concentrated under vacuum, the residue was purified by column chromatography on silica gel (PE:EA=30:1→10:1) to give the title compound as a light yellow solid (5.5 g, 89%).

$^1$H-NMR δ 1.39 (s, 3H), 1.64 (s, 3H), 2.02 (d, 1H), 2.33-2.49 (m, 3H), 3.02 (d, 1H). 3.2710~3.41 (m, 2H), 3.96 (s, 3H), 7.14 (s, 1H), 7.86 (s, 1H), 17.96 (s, 1H), 9.72 (s, 1H).

Intermediate 69

5-Bromo-3-(2,2-dimethyl-1,1-dioxo-hexahydro-1l6-thiopyran-4-yl)-1H-indole-7-carboxylic acid

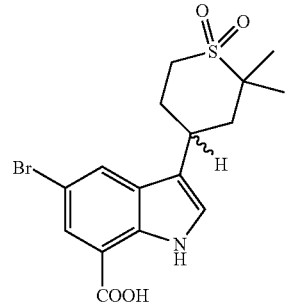

To a solution of 5-bromo-3-(2,2-dimethyl-1,1-dioxo-hexahydro-1l6-thiopyran-4-yl)-1-oxy-1H-indole-7-carboxylic acid methyl ester (5.5 g, 13.3 mmol) in 100 mL MeOH was added 3 N LiOH (22 mL, 66.6 mmol). Then the mixture was heated at reflux for 2 hours. The reaction was concentrated and the residue was dissolved in 1N HCl, extracted with DCM (3×50 mL). The combined organic layer was dried over MgSO$_4$, concentrated under vacuum to give the title compound as a light yellow solid (4.8 g, 94%).

Intermediate 70 and 71

5-Bromo-7-carbamoyl-3-(2,2-dimethyl-1,1-dioxo-hexahydro-1l6-thiopyran-4-yl)-indole-1-carboxylic acid tert-butyl ester

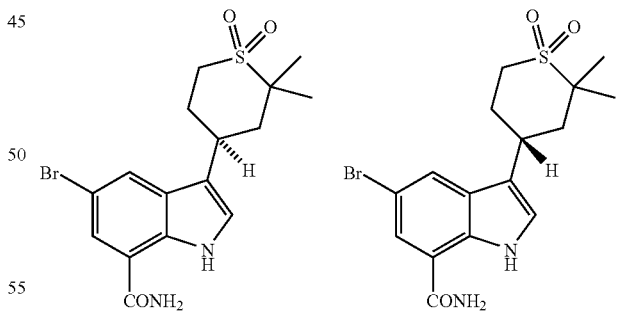

To a solution of 5-Bromo-3-(2,2-dimethyl-1,1-dioxo-hexahydro-1l6-thiopyran-4-yl)-1H-indole-7-carboxylic acid (4.8 g, 12 mmol) in CH$_2$Cl$_2$ (100 mL) was added Et$_3$N (2.4 g, 24 mmol), TBTU (7.7 g, 24 mmol), NH$_3$/MeOH (10 mL). The mixture was stirred for 2 hours at room temperature. The reaction solution was washed with water. The organic phase was dried over MgSO$_4$, concentrated under vacuum and purified by column chromatography on silica gel (PE:EA=10:1→5:1) to give the racemic product as a yellow solid (3.1 g, 64%), which was resolved by chiral SFC HPLC to get 5-bromo-3-[(4S)-2,2-dimethyl-1,1-dioxidotetrahydro-2H-thiopyran-4-yl]-1H-indole-7-carboxamide (1.19 g) and 5-bromo-3-[(4R)-2,2-dimethyl-1,1-dioxidotetrahydro-2H-thiopyran-4-yl]-1H-indole-7-carboxamide (1.36 g).

¹H NMR δ 1.21 (s, 3H), 1.53 (s, 3H), 1.91-1.99 (m, 2H), 2.09-2.20 (m, 2H), 2.96 (d, 1H), 3.32 (s, 3H), 3.37 (t, 1H), 3.55 (t, 1H), 7.17 (s, 1H), 7.45 (s, 1H) 7.81 (s, 1H), 8.11 (s, 1H), 11.03 (s, 1H).

Chiral SFC Separation Conditions

Sample I.D.: 208937-176A1

Instrument and Condition

Instrument: Berger MultiGram™ SFC, Mettler Toledo Co, Ltd

Column: Chiralpak AD, 20 µm, Daicel Chemical Industries, Ltd 300×50 mml.D.

Mobile phase: A: Supercritical $CO_2$, B:MeOH, A:B=45:55 at 200 mL/min

Column Temp: 35° C.

Nozzle Pressure: 100 Bar

Nozzle Temp: 60° C.

Evaporator Temp: 20° C.

Trimmer Temp: 25° C.

Wavelength: 220 nm

Intermediate 72

(racemic)-Ethyl 5-bromo-3-(2,2-dimethyltetrahydro-2H-thiopyran-4-yl)-1H-indole-7-carboxylate

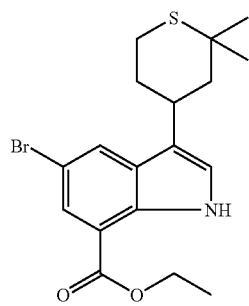

2,2-Dimethyltetrahydro-4H-thiopyran-4-one (0.675 g, 4.68 mmol) was placed in a dried flask fitted up with an addition funnel, a septum and an argon inlet, and dissolved in dry DCM (15 mL), cooled to 0° C., stirred, and then trimethylsilyl trifluoromethanesulfonate (1.692 mL, 9.36 mmol) was added dropwise through the addition funnel over 10 minutes. DCM (5 mL) was used to wash the addition funnel walls. To this mixture was added dropwise ethyl 5-bromo-1H-indole-7-carboxylate (1.341 g, 5 mmol) in DCM (15 mL) over 2 hours. Then triethylsilane (2.98 mL, 18.73 mmol) was added in one portion. The mixture was stirred 2 h at 0° C., and left stirring at 23° C. overnight. The reaction was quenched with a saturated aqueous solution of sodium bicarbonate, and the resulting biphasic mixture extracted with DCM to give 2.115 g of the title compound.

LC/MS: m/z 398.0 (M+H), Rt 1.49 min.

Intermediate 73

(racemic)-1-(1,1-Dimethylethyl) 7-ethyl 5-bromo-3-(2,2-dimethyltetrahydro-2H-thiopyran-4-yl)-1H-indole-1,7-dicarboxylate

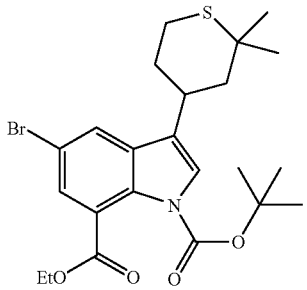

Ethyl 5-bromo-3-(2,2-dimethyltetrahydro-2H-thiopyran-4-yl)-1H-indole-7-carboxylate, (1.585 g, 4 mmol) was placed in a flask and dissolved in Acetonitrile (20 mL). Di-tert-butyl dicarbonate, (2.79 mL, 12.00 mmol) was added and the mixture stirred at 23° C. Neat DMAP (0.489 g, 4.00 mmol) was slowly added over 2 h. The mixture was left stirring at 23° C. overnight. The reaction was quenched with a saturated aqueous solution of sodium bicarbonate (100 mL), and the resulting mixture was evaporated under vacuum to remove most of the acetonitrile and extracted with ethyl acetate. The organic layer was dried ($MgSO_4$) and solvent was removed under vacuum to give 2.6 g of the title compound.

LC/MS: m/z 498.5 (M+H), Rt 1.59 min.

Intermediate 74

(racemic)-1-(1,1-Dimethylethyl) 7-ethyl 5-bromo-3-(2,2-dimethyl-1,1-dioxidotetrahydro-2H-thiopyran-4-yl)-1H-indole-1,7-dicarboxylate

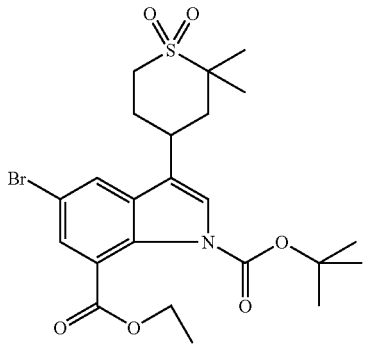

Trifluoroacetic anhydride (1.878 mL, 13.29 mmol) was dissolved in acetonitrile (8 mL) in an open flask. The mixture was cooled to 0° C. and urea hydrogen peroxide (1.534 g, 16.31 mmol) was added in one portion. The mixture was left stirring for 30 mins before adding dropwise a solution of 1-(1,1-dimethylethyl) 7-ethyl 5-bromo-3-(2,2-dimethyltetrahydro-2H-thiopyran-4-yl)-1H-indole-1,7-dicarboxylate, (2.2 g, 4.43 mmol) in acetonitrile (7 mL). The resulting mixture was stirred for 40 minutes at 23° C. The reaction was diluted with water (100 mL). The product was recovered extracting the solution with ethyl acetate (3×20 mL), the organic layers were combined and washed once with water (30 mL). The organic layer was dried ($MgSO_4$) and the solvent was evaporated. The residue was dissolved in DCM/EtOAc 7:3 and injected in a 120 g Companion Flash Chromatography column eluting with hexane/EtOAc to afford 685 mg of the title compound as a yellow powder.

LC/MS: m/z 531.4 (M+H), Rt 1.29 min.

Intermediate 75

(racemic)-5-Bromo-3-(2,2-dimethyl-1,1-dioxidotetrahydro-2H-thiopyran-4-yl)-1H-indole-7-carboxylic acid

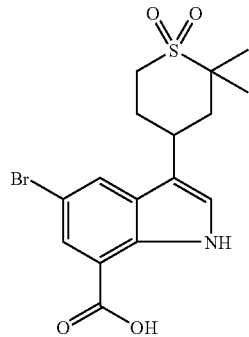

1-(1,1-dimethylethyl) 7-ethyl 5-bromo-3-(2,2-dimethyl-1,1-dioxidotetrahydro-2H-thiopyran-4-yl)-1H-indole-1,7-dicarboxylate (685 mg, 1.296 mmol) was placed in a flask and dissolved in methanol (6 mL) and water (3 mL). An aqueous solution of sodium hydroxide 6N in water (3.24 mL, 19.44 mmol) was added. The mixture was heated in a microwave for 30 mins at 80° C. The mixture was acidified with aqueous HCl 1N until pH=1, and the resulting mixture was extracted with ethyl acetate. The organic layer was dried (MgSO$_4$) and the solvent removed under vacuum to afford 490 mg of the title compound as a yellow powder.

LC/MS: m/z 401.8 (M+H), Rt 0.87 min.

Intermediate 76

(racemic)-5-Bromo-3-(2,2-dimethyl-1,1-dioxidotetrahydro-2H-thiopyran-4-yl)-1H-indole-7-carboxamide

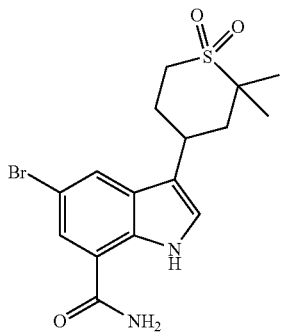

(racemic)-5-bromo-3-(1,1-dioxido-2,2-dimethylthian-4-yl)-1H-indole-7-carboxylic acid (490 mg, 1.224 mmol), was placed in a microwave flask and dissolved with DMF (2 mL) and 1,4-Dioxane (8 mL). HOBt (1-hydroxybenzotriazole) (165 mg, 1.224 mmol) and EDC (1-Ethyl-3-(3-dimethylaminopropyl)carbodiimide) (657 mg, 3.43 mmol) was added. 0.5N NH$_3$ in dioxane (7.34 mL, 3.67 mmol) was added. The reaction mixture was heated under microwave at 10° C. for 20 minutes. The reaction was diluted with saturated aqueous solution of sodium bicarbonate (20 mL) and extracted with ethyl acetate (2×). The organic layers were combined and washed with water, dried (MgSO$_4$) and the solvent was removed under vacuum. The residue was dissolved in the minimum amount of EtOAc (around 2 mL, sonicating and heating when necessary), precipitated by adding hexane, and then filtering off the solid. This operation was repeated on the filtrate to increase the recovery affording a total of 332 mg of the title compound as a pale yellow powder.

LC/MS: m/z 400.9 (M+H), Rt 0.79 min.

Intermediate 77

8-Thiabicyclo[3.2.1]octan-3-one.

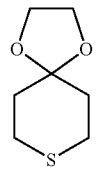

Tetrahydrothiopyran-4-one (19.1 g, 150 mmol), ethylene-1,2-diol (11.2 g, 180 mmol), toluene-p-sulfonic acid (0.5 g), and toluene (500 mL) was heated under reflux in a Dean-Stark apparatus for 1.5 h. The toluene was then removed by rotary evaporation, and the residue dissolved in ether and washed, first with 10% aqueous sodium hydroxide and then with water. The organic layer was dried (Na$_2$SO$_4$) and evaporated, and allowed to crystallize by standing in Et$_2$O overnight, giving 24.4 g (93%) of the title compound.

Intermediate 78

7-(1-Methylethyl)-1,4-dioxa-8-thiaspiro[4.5]decane

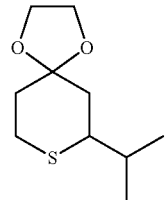

N-Chlorosuccinimide (14.0 g, 104.9 mmol) was added in three portions with stirring over 15 min to a cooled (0° C.) solution of 8-thiabicyclo[3.2.1]octan-3-one (16.0 g, 99.9 mmol) in dry benzene (400 mL) under nitrogen. The mixture was stirred for a further 2.5 h and was then filtered. The filtrate was added dropwise with stirring under nitrogen to a cooled (0° C.) solution of isopropylmagnesium bromide (from isopropyl bromide (28.3 g, 229.7 mmol), magnesium (5.7 g, 234.7 mmol) and CuI (1.52 g, 7.9 mmol)) in dry ether (300 mL). The mixture was stirred for a further 15 h and cold (0° C.), dilute hydrochloric acid was added cautiously. The organic layer was separated and washed successively with water, saturated aqueous sodium bicarbonate, and finally with water again. The dried (Na$_2$SO$_4$) ether-benzene solution was evaporated, giving 13.2 g of the title compound.

Intermediate 79

2-(1-Methylethyl)tetrahydro-4H-thiopyran-4-one

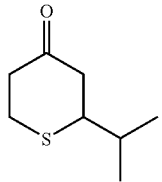

7-(1-Methylethyl)-1,4-dioxa-8-thiaspiro[4.5]decane was dissolved in acetic acid (50 mL) and 2 N aqueous hydrochloric acid (70 mL). After being stirred at room temperature for 15 h, the mixture was extracted with ether (300 mL), and the ether extract washed with water (2×50 mL), 10% aqueous sodium hydroxide (3×50 mL), and finally with water (2×50 mL). The dried (Na$_2$SO$_4$) solution was evaporated, and the residue purified by column chromatography on silica, giving 3.6 (22% over two steps) of the title compound.

$^1$H NMR (400 MHz, CDCl$_3$: δ 1.01 (d, J=5.2 Hz, 6H), 1.625-1.87 (m, 1H), 2.49-2.99 (m, 7H).

Intermediate 80

Ethyl 5-Bromo-3-[2-(1-methylethyl)tetrahydro-2H-thiopyran-4-yl]-1H-indole-7-carboxylate

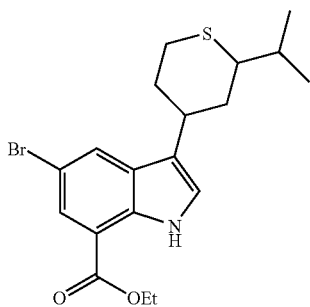

2-(1-methylethyl)tetrahydro-2H-thiopyran-4-one (1.185 g, 7.49 mmol) was dissolved in dry dichloromethane (DCM) (20 mL), cooled in an ice bath to ca 0° C., and stirred under argon. Trimethylsilyl trifluoromethanesulfonate (2.71 mL, 14.98 mmol) was added dropwise over 10 minutes, and dry DCM (5 mL) was used to wash in the last of the trimethylsilyltrifluoromethanesulfonate. To this mixture was added dropwise, a solution of ethyl 5-bromo-1H-indole-7-carboxylate (2.145 g, 8 mmol) in dry DCM (20 mL), and then an additional portion of dry DCM (5 mL) was used to wash the last of ethyl 5-bromo-1H-indole-7-carboxylate into the reaction. Triethylsilane (4.77 mL, 30.0 mmol) was added to the reaction in one portion. The resulting mixture was stirred 2 h at 0° C., and left stirring at 23° C. overnight. The reaction was diluted with saturated aqueous sodium bicarbonate, and the resulting biphasic mixture was extracted with DCM, dried (MgSO$_4$) and the DCM was removed in vacuo to give the title compound as a dark yellow oil.

LC/MS: m/z 414.3 (M+H), Rt 1.58 min.

Intermediate 81

1-(1,1-Dimethylethyl) 7-ethyl 5-bromo-3-[2-(1-methylethyl)tetrahydro-2H-thiopyran-4-yl]-1H-indole-1,7-dicarboxylate

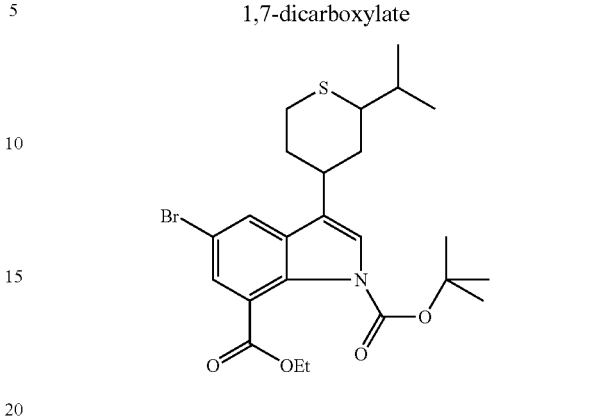

Ethyl 5-bromo-3-[2-(1-methylethyl)tetrahydro-2H-thiopyran-4-yl]-1H-indole-7-carboxylate (2.5 g, 6.09 mmol) was dissolved in acetonitrile (20 mL). Di-tert-butyl dicarbonate (4.24 mL, 18.28 mmol) was added and the mixture stirred at 23° C. Dimethylamino pyridine (0.744 g, 6.09 mmol) was added in small portions over 2 h and the mixture was left stirring at 23° C. overnight. The reaction was diluted with saturated aqueous sodium bicarbonate (100 mL), the resulting mixture was concentrated in vacuo to remove most of the acetonitrile. The resulting aqueous mixture was extracted with ethyl acetate (75 mL). The organic layer was dried (MgSO$_4$) and solvent was removed in vacuo to afford 2.6 g of the title compound as a gummy brown oil.

LC/MS: m/z 512.4 (M+H), Rt 1.67 min.

Intermediate 82

1-(1,1-Dimethylethyl) 7-ethyl 5-bromo-3-[2-(1-methylethyl)-1,1-dioxidotetrahydro-2H-thiopyran-4-yl]-1H-indole-1,7-dicarboxylate

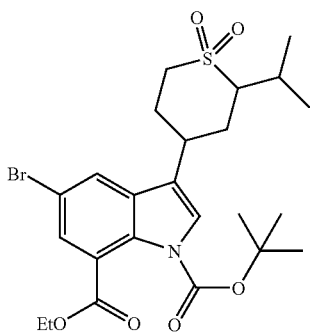

Trifluoroacetic anhydride (0.913 mL, 6.46 mmol) was dissolved in acetonitrile (10 mL). The mixture was cooled with an ice bath to ca 0° C. and urea hydrogen peroxide (0.746 g, 7.93 mmol) was added in several small portions, to avoid a large temperature increase. The mixture was left stirring 30 min before adding dropwise 1-(1,1-dimethylethyl) 7-ethyl 5-bromo-3-[2-(1-methylethyl)tetrahydro-2H-thiopyran-4-yl]-1H-indole-1,7-dicarboxylate (1.1 g, 2.155 mmol) dissolved in acetonitrile (10 mL). The resulting mixture was stirred 40 minutes at 23° C. and then the reaction was diluted with water (100 mL). The aqueous phase was extracted with ethyl acetate (3×20 mL) and the combined organic layers were washed with water (30 mL), dried (MgSO$_4$) and the solvent was evaporated to give a brown gummy solid. The solid was dissolved in DCM and EtOAc and purified by flash chromatography (Combiflash), on a 120 g column with hexane/EtOAc (5 minutes of hexane; 25 minutes to hexane [75%]/ethyl acetate[25%]; 10 minutes of hexane[75%]/ethyl acetate[25%]; 10 minutes to hexane[30%]/ethyl acetate [70%]) to afford 740 mg of the title compound.

LC/MS: m/z 542.3 (M+H), Rt 1.37 min.

Intermediate 83

5-Bromo-3-[2-(1-methylethyl)-1,1-dioxidotetrahydro-2H-thiopyran-4-yl]-1H-indole-7-carboxylic acid

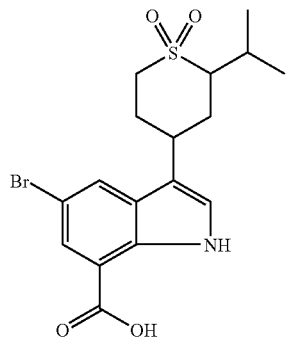

1-(1,1-dimethylethyl) 7-ethyl 5-bromo-3-[2-(1-methylethyl)-1,1-dioxidotetrahydro-2H-thiopyran-4-yl]-1H-indole-1,7-dicarboxylate (1.46 g, 2.69 mmol) was dissolved in methanol (12 mL) and then water (6.00 mL) was added and then 6 N aqueous NaOH (6.73 mL, 40.4 mmol was added and the mixture was heated in a microwave 30 mins at 80° C. The mixture was neutralized with 1 N aqueous HCl until pH=1 and a small amount of yellow solid precipitated which was set aside. The aqueous solution was extracted with ethyl acetate, the organic layers were combined, dried (MgSO$_4$) and solvent was removed under vacuum to afford the title compound.

LC/MS: m/z 416.1 (M+H), Rt 0.98 min.

Intermediate 84

5-Bromo-3-[2-(1-methylethyl)-1,1-dioxidotetrahydro-2H-thiopyran-4-yl]-1H-indole-7-carboxamide

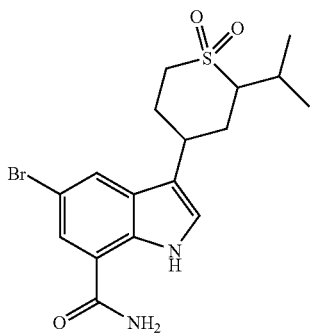

5-Bromo-3-[2-(1-methylethyl)-1,1-dioxidotetrahydro-2H-thiopyran-4-yl]-1H-indole-7-carboxylic acid (1.12 g, 2.69 mmol) was dissolved in N,N-Dimethylformamide (DMF) (4 mL). HOBt (1-hydroxybenzotriazole) (0.364 g, 2.69 mmol) and EDC (1-Ethyl-3-(3-dimethylaminopropyl) carbodiimide) (1.445 g, 7.54 mmol) were added. The mixture was stirred and a solution of 0.5 N ammonia in dioxane (16.15 mL, 8.07 mmol) was added. The reaction mixture was heated under microwave at 100° C. for 20 minutes. The reaction was diluted with saturated aqueous sodium bicarbonate (30 mL) and extracted with ethyl acetate (3×50 mL). The organic layers were combined, washed with water, dried (MgSO$_4$) and the solvent was removed in vacuo to afford 1.5 g of brown oil. The oil was purified by Flash Chromatography (hexanes/ethyl acetate) to afford a pure fraction of a yellow pure solid (190 mg). The remaining product was recovered from the column as a mixture and was purified by dissolution in ethyl acetate, and sonicating to precipitate 420 mg of white crystals. Both the 190 mg from chromatography and 420 mg from the crystallization are combined to afford 610 mg of the title compound, which was >90% of a single isomer based on LC/MS and $^1$H NMR. The stereochemistry of the major isomer was assigned as trans based on a series of NOE experiments. The filtrate from the crystallization step above was concentrated to afford 37 mg of mostly the minor (cis) isomer, (racemic)-5-bromo-3-[cis-2-(1-methylethyl)-1,1-dioxidotetrahydro-2H-thiopyran-4-yl]-1H-indole-7-carboxamide.

LC/MS: m/z 415.1 (M+H), Rt 0.89 min.

Intermediate 85

7-Phenyl-1,4-dioxa-8-thiaspiro[4.5]decane

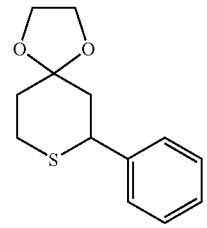

N-Chlorosuccinimide (12.7 g, 94.7 mmol) was added in three portions with stirring during 15 min to a cooled (0° C.) solution of the ethylene ketal (13.8 g, 86.1 mmol) in dry benzene (400 mL) under nitrogen. The mixture was stirred for a further 2.5 h and was filtered. The filtrate was added dropwise with stirring under nitrogen to a cooled (0° C.) solution of phenyl magnesium bromide (from phenyl magnesium bromide (54.1 g, 344.5 mmol), magnesium (8.37 g, 344.5 mmol) and CuI (1.31 g, 6.9 mmol)) in dry ether (300 mL). The mixture was stirred for a further 15 h, and cold (0° C.), dilute hydrochloric acid was added cautiously. The organic layer was separated and washed successively with water, saturated aqueous sodium bicarbonate, and finally with water again. The dried (Na$_2$SO$_4$) ether-benzene solution was evaporated, giving 11.2 g of the title compound.

Intermediate 86

2-Phenyltetrahydro-4H-thiopyran-4-one

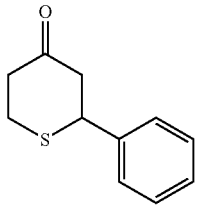

7-Phenyl-1,4-dioxa-8-thiaspiro[4.5]decane was dissolved in acetic acid (50 mL) and 2 N aqueous hydrochloric acid (70 mL). After being stirred at room temperature for 15 h, the mixture was extracted with ether (300 mL), and the ether extract washed with water (2×50 mL), 10% aqueous sodium hydroxide (3×50 mL), and finally with water (2×50 mL). The dried (Na₂SO₄) solution was evaporated, and the residue was crystallized upon standing overnight in ether, giving 3.5 g (21.1% over two steps) of the title compound.

¹H NMR (400 MHz, CDCl₃) δ 2.72-3.06 (m, 6H), 4.23 (dd, J=3.6 Hz, J=7.6 Hz, 1H), 7.28-7.36 (m, 5H).

Intermediate 87

Ethyl 5-bromo-3-(2-phenyltetrahydro-2H-thiopyran-4-yl)-1H-indole-7-carboxylate

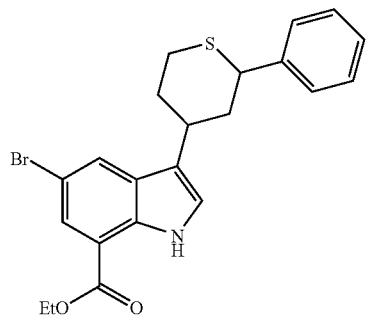

To a solution of 2-phenylthian-4-one (SJTU) (0.900 g, 4.68 mmol) in dichloromethane (DCM) (15 mL), cooled on an ice bath to 0° C., under argon, was added dropwise trimethylsilyl trifluoromethanesulfonate (1.807 mL, 10 mmol) over 10 minutes, an additional portion of dry DCM (5 mL) was used to wash the addition funnel walls. To this mixture ethyl 5-bromo-1H-indole-7-carboxylate (1.340 g, 5.00 mmol) was added dropwise, in solution with of dry DCM, over 2 hours. Finally, triethylsilane (3.19 mL, 20 mmol) was added in one portion and the mixture was stirred 2 h at ca 0° C., and left stirring at 23° C. 16 h. The reaction was quenched with a saturated aqueous solution of sodium bicarbonate, and the resulting biphasic mixture partitioned with DCM to afford 2.21 g of brow gummy oil. LCMS of product may indicate an overlapping mixture of ca 5:2 major to minor isomers (cis/trans).

LC/MS: m/z 448.1 (M+H), Rt 3.23 min.

Intermediate 88

1-(1,1-Dimethylethyl) 7-ethyl 5-bromo-3-(2-phenyltetrahydro-2H-thiopyran-4-yl)-1H-indole-1,7-dicarboxylate

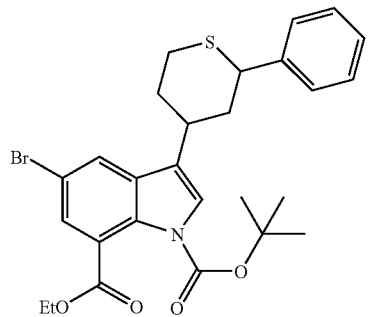

Ethyl 5-bromo-3-(2-phenylthian-4-yl)-1H-indole-7-carboxylate (2.210 g, 4.97 mmol) was placed in a flask and dissolved with acetonitrile (20 mL). di-tert-butyl-dicarbonate (3.46 mL, 14.92 mmol) was added and the mixture stirred at 23° C. Dimethylaminopyridine (0.608 g, 4.97 mmol) was slowly added in small portions over 2 h. The mixture was left stirring at 23° C. 16 h. The reaction was quenched with a saturated aqueous solution of sodium bicarbonate (100 mL), the resulting mixture was evaporated under vacuum to remove most of the acetonitrile and then extracted with ethyl acetate. The organic layer was dried over magnesium sulfate and solvent was removed under vacuum to afford 2.6 g of a gummy brown oil. Again, a possible mixture of major and minor isomers in a 5:2 ratio appears to be present based on LCMS.

LC/MS: m/z 546.2 (M+H), Rt 3.44 min.

Intermediate 89

1-(1,1-Dimethylethyl) 7-ethyl 5-bromo-3-(1,1-dioxido-2-phenyltetrahydro-2H-thiopyran-4-yl)-1H-indole-1,7-dicarboxylate

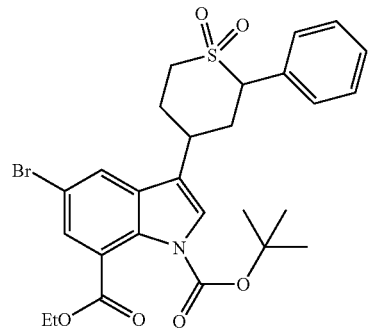

Trifluoroacetic anhydride (2.023 mL, 14.33 mmol) was placed in a flask and diluted with acetonitrile (25 mL). The mixture was cooled with an ice bath to ca 0° C. Urea hydrogen peroxide (1.653 g, 17.57 mmol) was added in several small portions, and the mixture was left stirring 30 min before adding dropwise 1-(1,1-dimethylethyl) 7-ethyl 5-bromo-3-(2-phenylthian-4-yl)-1H-indole-1,7-dicarboxylate (2.6 g, 4.78 mmol) dissolved in acetonitrile (15 mL). The resulting mixture was stirred 2 h at 23° C. Water (100 mL) was added and the resulting mixture was extracted with ethyl acetate (3×20 mL), the organic layers were combined and washed once with water (30 mL). The organic layer was dried (MgSO₄), and the solvent was evaporated to afford a brown gummy solid, which was dissolved in the minimum amount of DCM and run through a pad of silica, to afford 2.8 g of the title compound as a brown gummy solid.

LC/MS: m/z 476 (M−57), Rt 2.71 min.

Intermediate 90

5-Bromo-3-(1,1-dioxido-2-phenyltetrahydro-2H-thiopyran-4-yl)-1H-indole-7-carboxylic acid

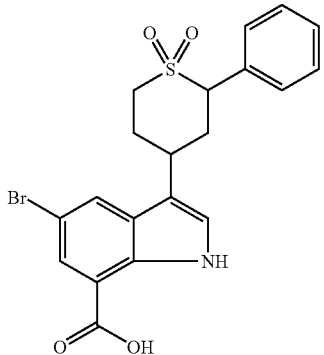

Methyl 1-(1,1-dimethylethyl) 5-bromo-3-(1,1-dioxido-2-phenylthian-4-yl)-1H-indole-1,7-dicarboxylate (170 mg, 0.302 mmol) was placed in a flask and dissolved with Methanol (1 mL) and Water (0.500 mL). An aqueous solution of sodium hydroxide 6N in water (0.5 mL, 3 mmol) was added. The mixture was heated in a microwave 30 mins at 80° C. This procedure was repeated exactly 2 more times. A fourth reaction was run by a similar microwave reaction using methyl 1-(1,1-dimethylethyl) 5-bromo-3-(1,1-dioxido-2-phenylthian-4-yl)-1H-indole-1,7-dicarboxylate (170 mg, 0.302 mmol) and LiOH ((72 mg, 3.00 mmol) in 50% aq methanol (2 mL). These 4 reaction mixtures were combined, acidified with HCl 2M in water (100 mL) and the resulting mixture extracted with DCM (1×), and ethyl acetate (4×). The organic layers were combined, washed once with HCl 1N (30 mL) and dried over magnesium sulfate before removing the solvent in vacuo, giving the title compound as a possible isomeric mixture of major and minor isomer based on LCMS was afforded.

LC/MS: m/z 452.2 (M+H), Rt 0.98 min.

Intermediate 91

5-Bromo-3-(1,1-dioxido-2-phenyltetrahydro-2H-thiopyran-4-yl)-1H-indole-7-carboxamide

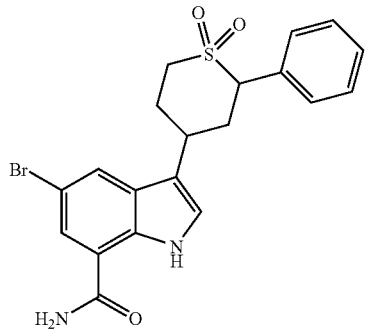

5-bromo-3-(1,1-dioxido-2-phenyltetrahydro-2H-thiopyran-4-yl)-1H-indole-7-carboxylic acid (0.9 g, 2.007 mmol) was put in a flask and dissolved in N,N-Dimethylformamide (DMF) (2 mL). HOBt (1-hydroxybenzotriazole) (0.271 g, 2.007 mmol) and EDC (1-Ethyl-3-(3-dimethylaminopropyl) carbodiimide) (1.078 g, 5.62 mmol) were added. The mixture was stirred and 0.5N NH₃ in dioxane was added (12.04 mL, 6.02 mmol). The reaction mixture was heated under microwave at 100° C. for 20 minutes. The reaction was quenched with a saturated aqueous solution of sodium bicarbonate (50 mL) and extracted with ethyl acetate (3×25 mL). Organic layers were combined and washed with a saturated aqueous solution of sodium bicarbonate, dried (MgSO₄) and concentrated in vacuo. The mixture was dissolved in the minimum amount of DCM and precipitated in hexane, giving 0.575 g of the title compound as a pale brown powder.

LC/MS: m/z 449.1 (M+H), Rt 0.88 min.

Intermediate 92

Methyl 5-bromo-3-(tetrahydro-2H-thiopyran-4-ylmethyl)-1H-indole-7-carboxylate

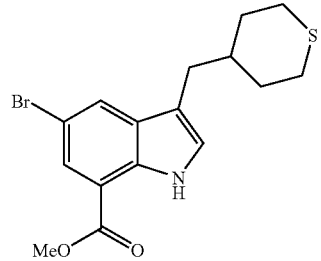

To a solution of tetrahydro-thiopyran-4-carbaldehyde (1.3 g, 9.84 mmol) in DCM (20 mL) was added TMSOTf (3.5 mL, 19.7 mmol) at 0° C. To this mixture 5-Bromo-1H-indole-7-carboxylic acid methyl ester (2.5 g, 9.84 mmol) was added. After 2 hours, Et₃SiH (6.2 mL, 39.4 mmol) was added at 0° C., and stirring continued for 18 hours. The reaction mixture was quenched with sodium bicarbone solution and extracted with DCM. The combined organic layers were dried (MgSO₄), concentrated, and purified by column chromatography on silica gel, giving 1.6 g (44%) of the title compound.

$^1$H-NMR δ 1.31-1.38 (m, 2H), 1.55 (t, 1H), 1.95 (dd, 2H), 2.49-2.57 (m, 6H), 3.90 (m, 6H), 7.00 (d, 1H), 7.80 (dd, 1H), 7.89 (d, 2H), 9.55 (s, 1H).

Intermediate 93

Methyl 5-bromo-3-[(1,1-dioxidotetrahydro-2H-thiopyran-4-yl)methyl]-1H-indole-7-carboxylate

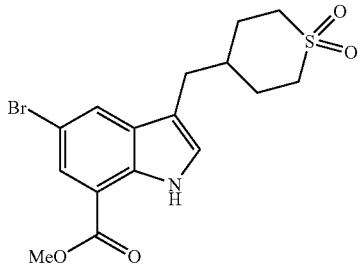

To a solution of methyl 5-bromo-3-(tetrahydro-2H-thiopyran-4-ylmethyl)-1H-indole-7-carboxylate (1.6 g, 4.63 mmol) in DCM (50 mL) was added m-CPBA (2.4 g, 13.9 mmol). The mixture was stirred for 1 hour at room temperature. The reaction was quenched with saturated sodium sulfite solution and extracted with DCM. The combined organic layers were dried (MgSO₄), concentrated, and purified by column chromatography on silica gel, giving 1.3 g (75%) of the title compound.

¹H-NMR δ 1.79-1.87 (m, 3H), 2.05 (dd, 2H), 2.68 (d, 2H), 22.86 (t, 2H), 2.90-2.99 (m, 2H), 3.92 (s, 3H), 7.04 (d, 1H), 7.79 (dd, 1H), 7.92 (d, 1H), 9.64 (s, 1H)

Intermediate 94

5-Bromo-3-[(1,1-dioxidotetrahydro-2H-thiopyran-4-yl)methyl]-1H-indole-7-carboxylic acid

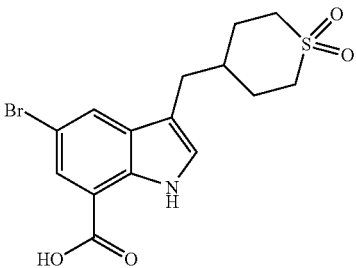

To a solution of methyl 5-bromo-3-[(1,1-dioxidotetrahydro-2H-thiopyran-4-yl)methyl]-1H-indole-7-carboxylate (1.3 g, 3.26 mmol) in MeOH (50 mL) was added a solution of 3 N LiOH (3.5 mL, 9.77 mmol). The mixture was stirred for 2 hours at reflux. The reaction was concentrated, and the residue was dissolved in 1N NaOH and extracted with DCM. The combined organic layers were dried (MgSO₄) and concentrated, giving 1.2 g (96%) of the title compound.

¹H-NMR δ 1.72 (t, 2H), 1.96 (d, 1H), 2.05 (dd, 2H), 2.76 (d, 2H) 3.04 (d, 2H), 3.15 (t, 2H), 7.30 (d, 1H), 7.82 (d, 1H), 8.11 (d, 1H) 11.12 (s, 1H).

Intermediate 95

5-Bromo-3-[(1,1-dioxidotetrahydro-2H-thiopyran-4-yl)methyl]-1H-indole-7-carboxamide

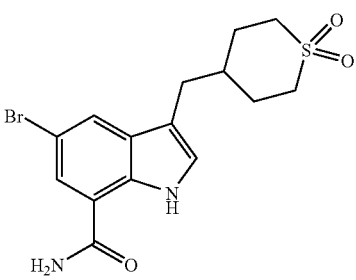

To a solution of 5-bromo-3-[(1,1-dioxidotetrahydro-2H-thiopyran-4-yl)methyl]-1H-indole-7-carboxylic acid (1.2 g, 3.22 mmol) in CH₂Cl₂ (100 mL) was added Et₃N (650 mg, 6.44 mmol), TBTU (2.1 g, 6.44 mmol), and NH₃/MeOH (10 mL). The mixture was stirred for 2 hours at room temperature. The reaction solution was washed with water, and the organic phase was dried (MgSO₄), concentrated, and purified by column chromatography on silica gel, giving 770 mg (65%) of the title compound.

¹H NMR δ 1.56~1.69 (m, 2H), 1.88 (s, 1H), 1.98 (d, 2H), 2.66 (d, 2H), 2.98 (d, 2H), 3.06 (d, 2H), 7.18 (s, 1H), 7.47 (s, 1H), 7.82 (s, 1H), 7.93 (s, 1H) 8.13 (s, 1H), 11.07 (s, 1H).

Intermediate 96

5,6-Dihydro-2H-thiopyran-3-carbaldehyde

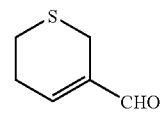

Hydrogen sulfide continued passing into a mixture of 1,1,2-trichloroethane and pyridine for about 0.5 h at 21° C. Acrolein (20.00 g, 0.35 mol) was added dropwise via syringe to the mixture while hydrogen sulfide was passing in simultaneously, maintaining the inner temperature at 35° C. After the addition was complete, the resulting mixture was saturated with hydrogen sulfide. Overall a total of about 14.40 g hydrogen sulfide was taken up. Another portion of acrolein (20 g, 0.35 mol) was added dropwise to the mixture at 32° C. without the introduction of hydrogen sulfide. Stirring continued at room temperature for 7 h, and a solution of 37% phosphoric acid (31 mL) was added. The reaction was then heated at 85° C. for 12 h and then cooled down to room temperature and extracted with DCM (3×150 mL). The combined organic layers were dried (Na₂SO₄), concentrated under reduced pressure, and then purified by chromatography on silica gel, eluting with a mixture of 30-37% EtOAc in PE. This gave 14.2 g (31.2%) of the title compound.

¹H NMR (CDCl₃) δ 2.12-2.19 (m, 2H), 2.28-2.35 (m, 2H), 2.45-2.51 (m, 2H), 2.82-2.88 (m, 2H), 4.23-4.28 (m, 1H), 9.30 (s, 1H).

Intermediate 97

Tetrahydro-2H-thiopyran-3-carbaldehyde

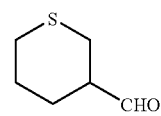

A mixture of 5,6-dihydro-2H-thiopyran-3-carbaldehyde (7.00 g, 0.055 mol) and Raney Ni (1.00 g) in Et₂OAc was stirred at 60° C. under H₂ (50 psi) for 12 h. The catalyst was filtered off, and the filtrate was purified by chromatography eluting with a mixture of PE:EA (30:1), giving 2.50 g (35%) of the title compound.

¹H NMR (CDCl₃) δ 1.40-1.55 (m, 1H), 1.70-1.73 (m, 1H), 1.94-2.02 (m, 2H), 2.50-2.54 (m, 3H), 2.55-2.65 (m, 1H), 2.78-2.82 (m, 1H), 9.57 (s, 1H).

Intermediate 98

Ethyl 5-bromo-3-(tetrahydro-2H-thiopyran-3-ylmethyl)-1H-indole-7-carboxylate

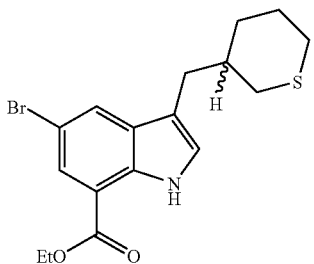

To a 100 mL three-necked flask equipped with an addition funnel was added tetrahydro-2H-thiopyran-3-carbaldehyde (2.50 g, 0.019 mol) and dry DCM (30 mL). Trimethylsilyl trifluoromethanesulfonate was put in the addition funnel. The mixture was cooled down to 0° C. with an ice bath and put under nitrogen atmosphere. Trimethylsilyl trifluoromethanesulfonate was added over 15 min, and 10 mL of dry DCM were used to wash the addition funnel walls. A solution of ethyl 5-bromo-1H-indole-7-carboxylate in 30 mL dry DCM was added to the mixture for 2 h at 0° C., and the mixture was then stirred at room temperature overnight. An aqueous solution of sodium bicarbonate was added, the layers were separated, and the mixture was extracted with DCM (3×100 mL). The combined organic layers were dried (Na₂SO₄), filtered, and purified by chromatography, eluting with a mixture of PE:EA (50:1-30:1) to afford 4.82 g (66.0%) of the title compound.

¹H NMR (CDCl₃) δ 1.11-1.15 (m, 1H), 1.43 (t, 3H), 1.65-1.71 (m, 2H), 1.83-1.87 (m, 1H), 1.96-2.03 (m, 2H), 2.32-2.38 (m, 1H), 2.51-2.59 (m, 2H), 2.66-2.68 (m, 2H), 4.40-4.45 (q, 2H), 7.07 (d, 1H), 7.77 (d, 1H), 7.95 (d, 1H), 9.64 (s, 1H).

Intermediate 99

Ethyl 5-bromo-3-[(1,1-dioxidotetrahydro-2H-thiopyran-3-yl)methyl]-1H-indole-7-carboxylate

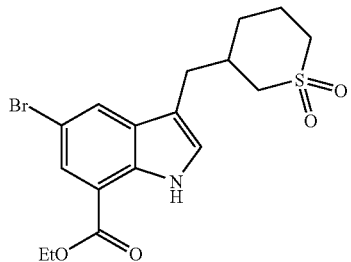

m-CPBA (8.71 g, 0.051 mol) was added to a solution of ethyl 5-bromo-3-(tetrahydro-2H-thiopyran-3-ylmethyl)-1H-indole-7-carboxylate (4.82 g, 0.13 mol) in DCM (150 mL) at room temperature. The reaction mixture was stirred for 2 h and was washed with an aqueous solution of sodium sulphite until KI/faecula showed that no excess m-CPBA remained. The mixture was extracted with DCM, and the combined organic layers were dried (Na₂SO₄), filtered, and purified by chromatography eluting with a mixture of 10-50% EA in PE, giving 1.42 g (27.2%) of the title compound.

¹H NMR (CDCl₃) δ 1.18-1.28 (m, 1H), 1.43 (t, 3H), 1.90-2.15 (m, 3H), 2.46 (m, 1H), 2.62-2.87 (m, 4H), 3.00-3.07 (m, 2H), 4.44 (q, 2H), 7.11 (d, 1H), 7.83 (d, 1H), 7.98 (d, 1H), 9.74 (s, 1H).

Intermediate 100

5-Bromo-3-[(1,1-dioxidotetrahydro-2H-thiopyran-3-yl)methyl]-1H-indole-7-carboxylic acid

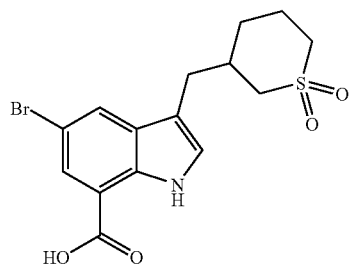

A mixture of ethyl 5-bromo-3-((1,1-dioxo-tetrahydro-2H-thiopyran-3-yl)methyl)-1H-indole-7-carboxylate (1.42 g, 0.034 mol) and LiOH (3.4 mL, 3 M) in MeOH (50 mL) was heated at reflux for one hour. The solvent was evaporated, and the mixture was acidified with 1N HCl and extracted with EtOAc (3×100 mL). The organic layer was dried, filtered and concentrated under reduced pressure, 1.30 (98.5%) of the title compound, which was carried on as is for the next step without further purification.

Intermediate 101

5-Bromo-3-[(1,1-dioxidotetrahydro-2H-thiopyran-3-yl)methyl]-1H-indole-7-carboxamide

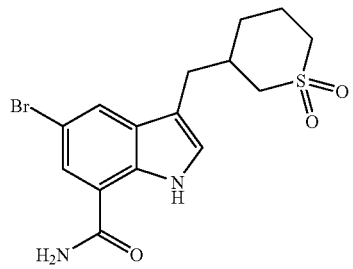

A solution of NH₃/MeOH (40 mL) was added to a mixture of 5-bromo-3-((1,1-dioxo-tetrahydro-2H-thiopyran-3-yl)methyl)-1H-indole-7-carboxylic acid (1.30 g, 0.0034 mol), TEA (0.68 g, 0.0067 mol), and TBTU (2.16 g, 0.067 mol) in DCM (30 mL). The resulting mixture was stirred at room temperature overnight. The solvent was evaporated, and the residue was washed with water and extracted with DCM (2×100 mL). The organic layers were dried, filtered, concentrated under reduced pressure, and purified by chromatography eluting with a mixture of DCM:MeOH (60:1), giving 0.94 g (72.5%) of the title compound.

¹H NMR (CDCl₃) δ 1.15-1.28 (m, 1H), 1.71-1.77 (m, 2H), 2.00-2.02 (m, 1H), 2.13-2.15 (m, 1H), 2.66-2.77 (m, 2H), 2.82-2.88 (m, 2H), 2.90-2.96 (m, 2H), 7.20 (d, 1H), 7.47 (s, 1H), 7.83 (d, 1H), 7.94 (s, 1H), 8.14 (s, 1H), 11.10 (s, 1H).

Intermediate 102

2,5-Dihydro-3-thiophenecarbaldehyde

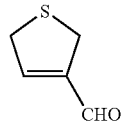

To a solution of 1,4-dithiane-2,5-diol (20.0 g, 131.6 mmol) in water (150 mL) was added acrolein (16.9 g, 302.6 mmol) over a period of 30 min while maintaining a temperature of about 70° C. The resulting solution was heated for 1 h at 70-80° C., and the reaction mixture was steam distilled, giving 6.0 g (40.0%) of the title compound.

$^1$H NMR (CDCl$_3$) δ 3.85 (d, 2H), 3.97 (s, 2H), 6.88 (s, 1H), 9.78 (s, 1H).

Intermediate 103

Tetrahydro-3-thiophenecarbaldehyde

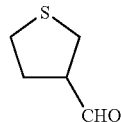

A mixture of 2,5-dihydro-3-thiophenecarbaldehyde (4.0 g, 35.09 mmol) and Pd/C in EtOAc (100 mL) under H$_2$ (40 psi) was stirred for 16 h. The Pd/C was removed by filtration, and the filtrate was concentrated, giving 3.4 g (83.5%) of the title compound.

$^1$H NMR (CDCl$_3$) δ 2.14 (m, 1H), 2.39 (m, 1H), 2.84 (m, 1H), 2.87 (m, 1H), 2.96 (m, 1H), 3.07 (m, 1H), 3.16 (m, 1H), 9.12 (s, 1H).

Intermediate 104

Ethyl 5-bromo-3-(tetrahydro-3-thienylmethyl)-1H-indole-7-carboxylate

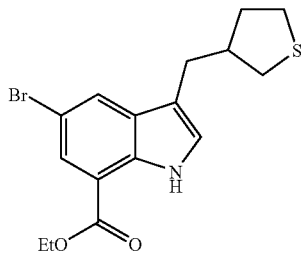

To a solution of tetrahydro-3-thiophenecarbaldehyde (5.0 g, 43.10 mmol) in dichloromethane (200 mL) was added TMS-OTf (15.4 mL, 86.26 mmol) and ethyl 5-bromo-1H-indole-7-carboxylate (11.5 g, 43.10 mmol) dropwise at 0° C. The mixture was stirred at 0° C. for 2 h, and then triethylsilane was added at the same temperature, which was maintained for 2 h. The reaction was warmed to 20° C. and stirred for 16 h. Water was added, the layers were separated, and the organic layer was (Na$_2$SO$_4$), concentrated, and purified on silica gel (PE:EA=50:1), giving 9 g (56.4) of the title compound.

$^1$H NMR (CDCl$_3$): δ 1.43 (t, 3H), 2.08 (m, 1H), 2.58 (m, 2H), 2.88 (m, 6H), 4.44 (q, 2H), 7.09 (s, 1H), 7.89 (s, 1H), 7.95 (s, 1H), 9.65 (s, 1H).

Intermediate 105

Ethyl 5-bromo-3-[(1,1-dioxidotetrahydro-3-thienyl)methyl]-1H-indole-7-carboxylate

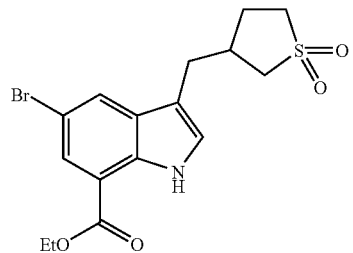

To a solution of ethyl 5-bromo-3-(tetrahydro-3-thienylmethyl)-1H-indole-7-carboxylate (7.61 g, 20.73 mmol) in dichloromethane (150 mL) was added portionwise 3-chlorobenzoperoxoic acid (10.69 g, 62.19 mmol) at room temperature. The resulting solution was stirred for 5 h. Sodium sulfite was added, and the mixture was washed with water, extracted with DCM (3×100 mL), dried (Na$_2$SO$_4$) and concentrated under reduced pressure. The crude product was purified by column on sillal gel (petroleum:ethyl acetate=10:1 to 5:1 to 2:1), giving 3.52 g (42.56%) of the title compound.

$^1$H NMR (CDCl$_3$): δ 1.45 (t, 3H), 1.93 (m, 1H), 2.33 (m, 1H), 2.78 (m, 2H), 2.93 (m, 2H), 3.02 (m, 1H), 3.20 (m, 2H), 4.44 (q, 2H), 7.12 (s, 1H), 7.84 (s, 1H), 7.98 (s, 1H), 9.74 (s, 1H).

Intermediate 106

5-bromo-3-[(1,1-dioxidotetrahydro-3-thienyl)methyl]-1H-indole-7-carboxylic acid

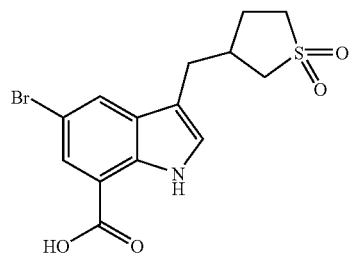

An aqueous solution of lithium hydroxide (0.64 g, 26.49 mmol) was added to a solution of ethyl 5-bromo-3-[(1,1-dioxidotetrahydro-3-thienyl)methyl]-1H-indole-7-carboxylate (3.52 g, 8.83 mmol) in methanol (100 mL) at room temperature. The mixture was heated at reflux for 1 h and then concentrated. The residue was washed with water, acidified with 1N HCl (pH ~3), and filtered, giving the title compound.

$^1$H NMR (DMSO): δ 1.75 (m, 1H), 2.15 (m, 1H), 2.65 (m, 1H), 2.80 (m, 2H), 2.86 (m, 2H), 3.00 (m, 1H), 3.13 (m, 2H), 7.25 (s, 1H), 7.72 (s, 1H), 8.05 (s, 1H), 11.04 (s, 1H).

Intermediate 107

5-Bromo-3-[(1,1-dioxidotetrahydro-3-thienyl)methyl]-1H-indole-7-carboxamide

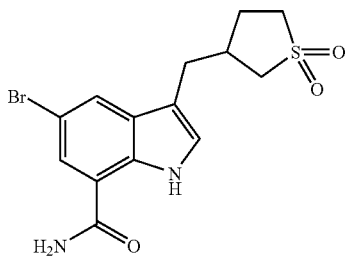

TBTU (5.68 g, 17.68 mmol) and triethylamine (1.79 g, 17.68 mmol) were added to a solution of 5-bromo-3-[(1,1-dioxidotetrahydro-3-thienyl)methyl]-1H-indole-7-carboxylic acid (3.28 g, 8.84 mmol) in dichloromethane (100 mL). After the mixture was stirred for 0.5 h at 20° C., $NH_3$/MeOH was added into the solution, and stirring continued for 2 h. The mixture was washed with water and extracted with EtOAc. The organic phase was dried ($Na_2SO_4$) and concentrated under reduced pressure. The crude product was purified by column chromatography on silica gel (petroleum:ethyl acetate=10:1 to 5:1 to 2:1), giving 1.1 g (33.6%) of the title compound.

$^1$H NMR (DMSO): δ 1.88 (m, 1H), 2.25 (m, 1H), 2.75 (m, 1H), 2.86 (m, 1H), 2.95 (m, 2H), 3.09 (m, 1H), 3.30 (m, 2H), 7.32 (s, 1H), 7.54 (s, 1H), 7.90 (s, 1H), 8.05 (s, 1H), 8.21 (s, 1H), 11.16 (s, 1H).

Intermediate 108

1-[(E)-2-(4-Fluoro-2-nitrophenyl)ethenyl]pyrrolidine

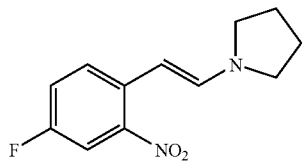

To a stirred solution of 4-fluoro-2-nitrotoluene (50.0 g, 0.327 mol) in DMF (100 mL) was added DMF-DMA (52 mL, 0.392 mol) and pyrrolidine (33 ml, 0.392 mol) in DMF (100 mL). The reaction mixture was stirred at reflux overnight and then concentrated under reduced pressure, giving 84 g of the title compound.

$^1$H NMR: (300 MHz; DMSO-$d_6$) δ 7.70-7.62 (2H, m), 7.56 (1H, d, J=13.6), 7.34-7.27 (1H, m), 5.56 (1H, d, J=13.6), 3.25-3.18 (4H, m) and 1.86-1.82 (4H, m).

Intermediate 109

(1E)-(4-Fluoro-2-nitrophenyl)ethanal semicarbazone

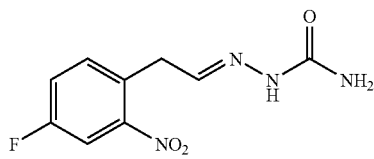

To a stirred solution of 1-[(E)-2-(4-fluoro-2-nitrophenyl)ethenyl]pyrrolidine (77.25 g, 0.327 mol) in warm MeOH (500 mL) was added a solution of semicarbazide HCl (38.3 g, 0.343 mol) in warm water (200 mL). The reaction mixture was stirred at room temperature for 1 h and was then cooled in ice and filtered. The solid was washed with cold 1:1 MeOH/water (2×30 mL) and dried to give 71 g (90% over two steps) of the title compound.

$^1$H NMR: (300 MHz; DMSO-$d_6$) δ 9.94 (1H, s), 7.91 (1H, dd, J=8.9 & 2.4), 7.62-7.51 (2H, m), 7.25 (1H, t, J=4.5), 5.99 (2H, s) and 3.75 (2H, d, J=4.5).

Intermediate 110

6-Fluoro-1H-indole

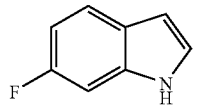

To a stirred suspension of (1E)-(4-fluoro-2-nitrophenyl)ethanal semicarbazone (27.0 g, 0.110 mol) in THF (750 mL) in a 1 L bomb was added Rh/C (5%; 3.5 g, 0.002 mol Rh) slurried in toluene and Fe(OAc)$_2$ (2.9 g, 0.017 mol). The bomb was charged with H$_2$ to 50 atm and stirred at room temperature for 2 days. The reaction mixture was filtered through celite, washing with MeOH (150 mL). The filtrate was concentrated to give a black oil that was partitioned between DCM (500 mL) and water (300 mL). The layers were separated and the aqueous fraction was extracted with DCM (2×200 mL). The combined organic extracts were washed with brine (200 mL), dried (Na$_2$SO$_4$), and concentrated under reduced pressure. The residue was dissolved in DCM (100 mL) and treated with flash silica to decolourise the solution. The mixture was filtered concentrated under reduced pressure, giving 12.9 g (87%) of the title compound.

$^1$H NMR: (300 MHz; DMSO-$d_6$) δ 11.11 (1H, s), 7.49 (1H, dd, J=8.6 & 5.5), 7.30 (1H, t, J=2.4), 7.13 (1H, dd, J=10.3 & 2.4), 6.81 (1H, ddd, J=11.0, 7.6 & 2.4) and 6.40-6.38 (1H, m).

Intermediate 111

6-Fluoro-2,3-dihydro-1H-indole

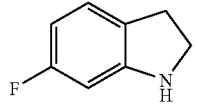

To a stirred solution of 6-fluoro-1H-indole (21.0 g, 0.155 mol) in dioxane (210 mL) was added BH$_3$-NEt$_3$ (92 mL, 0.620 mol) and a 12 M solution of HCl (27 mL, 0.326 mol) dropwise. The reaction mixture was stirred at room temperature for 10 min then at reflux for 2.5 h. The mixture was cooled to room temperature, and 6 M HCl (210 mL) was added. The mixture stirred at room temperature for 10 min and then at reflux for 1.5 h. The dioxane was removed under reduced pressure, and the residue diluted with water (500 mL) and washed with diethyl ether (1×250 mL). The aqueous fraction was basified with 10% NaOH and extracted with diethyl ether (3×250 mL). The combined organic layers were washed with water (2×100 mL) and brine (100 mL), dried (Na$_2$SO$_4$) and concentrated under reduced pressure, giving 22.3 g of the title compound.

$^1$H NMR: (300 MHz; DMSO-d$_6$) δ 6.94-6.89 (1H, m), 6.22-6.16 (2H, m), 5.27 (1H, s), 3.41 (2H, t, J=8.6) and 2.81 (2H, t, J=8.6).

Intermediate 112

1,1-Dimethylethyl 6-fluoro-2,3-dihydro-1H-indole-1-carboxylate

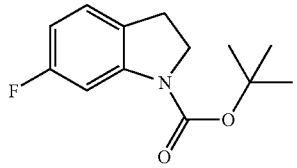

To a stirred solution of 6-fluoro-2,3-dihydro-1H-indole (21.2 g, 0.155 mol) in DCM (250 mL) was added Et$_3$N (54 mL, 0.388 mol) and Boc$_2$O (39.3 g, 0.171 mol). The reaction mixture was stirred at room temperature overnight and then diluted with water (200 mL). The layers were separated, and the aqueous fraction extracted with DCM (3×50 mL). The combined organic extracts were washed with water (2×100 mL), 20% citric acid (2×100 mL) and brine (1×100 mL). The organic layer was then dried (Na$_2$SO$_4$) and concentrated. The resulting crude product was taken up in toluene and hexanes, and silica gel was added. The mixture was filtered and concentrated. The residue was taken up in DCM, and imidazole (13.5 g, 0.198 mol) was added. The mixture was then washed with water (100 ml), HCl (0.5%; 2×100 ml) and brine (50 ml), dried (Na$_2$SO$_4$) and concentrated, giving 8.6 g (23%) of the title compound.

$^1$H NMR: (300 MHz; DMSO-d$_6$) δ 7.17-7.13 (1H, m), 6.72-6.65 (1H, m), 3.91 (2H, t, J=8.8), 2.99 (2H, t, J=8.8) and 1.47 (9H, s).

Intermediate 113

1-{[(1,1-Dimethylethyl)oxy]carbonyl}-6-fluoro-2,3-dihydro-1H-indole-7-carboxylic acid

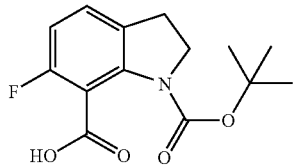

To a stirred solution of 1,1-dimethylethyl 6-fluoro-2,3-dihydro-1H-indole-1-carboxylate (8.7 g, 0.037 mol) in Et$_2$O (150 mL) at −78° C. was added TMEDA (7.2 mL, 0.048 mol) and a solution of 1M sec-BuLi (44 mL, 0.044 mol) dropwise. The reaction mixture was stirred for 1 h at −78° C. and then poured onto crushed CO$_2$ (250 mL). The mixture was allowed to warm to room temperature overnight. The suspension was diluted with water (200 mL) and diethyl ether (50 mL), and the layers were separated. The aqueous fraction was acidified with 1M HCl and extracted with diethyl ether (3×100 mL). The combined organic layers were washed with brine (1×50 mL), dried (Na$_2$SO$_4$), and concentrated under reduced pressure giving 8.0 g (77%) of the title compound.

$^1$H NMR: (300 MHz; DMSO-d$_6$) δ 7.26 (1H, dd, J=8.3 & 5.5), 7.82 (1H, dd, J=10.5 & 8.3), 3.99 (2H, t, J=8.3), 2.99 (2H, t, J=8.3) and 1.42 (9H, s).

Intermediate 114

5-Bromo-1-{[(1,1-dimethylethyl)oxy]carbonyl}-6-fluoro-2,3-dihydro-1H-indole-7-carboxylic acid

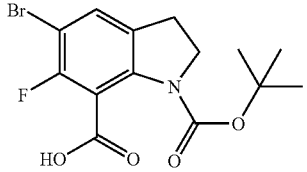

To a stirred solution of 1-{[(1,1-dimethylethyl)oxy]carbonyl}-6-fluoro-2,3-dihydro-1H-indole-7-carboxylic acid (6.9 g, 0.025 mol) in DCM (140 mL) was added NBS (4.8 g, 0.027 mol). The reaction mixture was stirred at room temperature for 3 h. The reaction mixture was washed with water (3×75 mL) and brine (1×75 mL), dried (Na$_2$SO$_4$) and concentrated under reduced pressure, giving 8.3 g (92%) of the title compound.

$^1$H NMR: (300 MHz; DMSO-d$_6$) δ 7.58 (1H, d, J=6.9), 3.99 (2H, t, J=8.1), 3.00 (2H, t, J=8.1) and 1.42 (9H, s).

Intermediate 115

5-Bromo-6-fluoro-2,3-dihydro-1H-indole-7-carboxylic acid

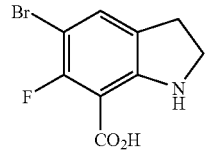

To a stirred solution of 5-bromo-1-{[(1,1-dimethylethyl)oxy]carbonyl}-6-fluoro-2,3-dihydro-1H-indole-7-carboxylic acid (8.3 g, 0.023 mol) in DCM (90 mL) was added TFA (90 mL). The reaction mixture was stirred at room temperature for 3 h and then concentrated. The residue was partitioned between EtOAc (100 mL) and water (100 mL), and the aqueous fraction was extracted with EtOAc (2×50 mL). The combined organic layers were washed with water (1×50 mL) and brine (1×50 mL). dried (Na$_2$SO$_4$) and concentrated under reduced pressure, giving 5.9 g (99%) of the title compound.

$^1$H NMR: (300 MHz; DMSO-d$_6$) δ 7.24 (1H, d, J=6.5), 3.59 (2H, t, J=8.6) and 2.91 (2H, t, J=8.6).

Intermediate 116

5-Bromo-6-fluoro-1H-indole-7-carboxylic acid

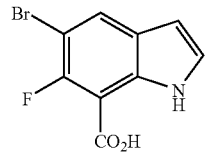

To a stirred solution of 5-bromo-6-fluoro-2,3-dihydro-1H-indole-7-carboxylic acid (5.8 g, 0.022 mol) in THF (120 mL) was added MnO$_2$ (11.6 g, 0.134 mol). The reaction mixture was stirred at reflux overnight and then filtered (hot) through celite, washing with hot THF (2×75 mL). The filtrate was concentrated, giving a brown solid, which was suspended in 1M HCl (150 mL). The mixture stirred at reflux overnight to remove traces of Mn and then cooled to room temperature. The solid was filtered off, dried, and recrystallised from IPA, giving 3.5 g (61%) of the title compound.

$^1$H NMR: (300 MHz; DMSO-$d_6$) δ 11.26 (1H, s), 8.09 (1H, d, J=6.5), 7.37 (1H, s) and 6.49 (1H, s).

Intermediate 117

5-Bromo-6-fluoro-1H-indole-7-carboxamide

CDI (0.7 g, 4.3 mmol) was added in portions to a stirred solution/suspension of 5-bromo-6-fluoro-1H-indole-7-carboxylic acid (1.0 g, 3.9 mmol) in DCM (20 mL). The mixture was stirred at room temperature for 1 hour and then heated at reflux for 30 min. The mixture was cooled in ice, and NH$_3$ gas was bubbled through the solution for 30 min. The reaction mixture stirred at room temperature overnight. The resulting solid was filtered off and triturated sequentially with water, ether and IPA giving 260 mg (26%) of the title compound as a brown solid.

$^1$H NMR: (300 MHz; DMSO-$d_6$) δ 11.29 (1H, br s, NH), 7.95 (1H, d, J 6.5, Ar), 7.85 (1H, br s, NH$_A$H$_B$), 7.82 (1H, br s, NH$_A$H$_B$), 7.35-7.33 (1H, m, Ar) and 6.44-6.43 (1H, m, Ar).

Intermediate 118

5-Bromo-6-fluoro-3-(tetrahydro-2H-thiopyran-4-yl)-1H-indole-7-carboxamide

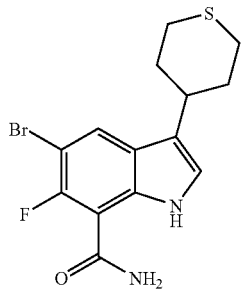

Tetrahydro-4H-thiopyran-4-one (285 mg, 2.451 mmol) was added to a 2 dram vial containing H$_3$PO$_4$ (2 g, 20.41 mmol) and AcOH (3 mL, 52.5 mmol). The reaction was heated to 90° C. (bath temp), and 5-Bromo-6-fluoro-1H-indole-7-carboxamide (210 mg, 0.817 mmol) was added in 3 portions over 3 min. The reaction was heated at 90° C. for 17. The reaction mixture was cooled to room temperature and was then added slowly to a mixture of ice and saturated NH$_4$OH (10 mL) with stirring. EtOAc (10 mL) was then added, the mixture was filtered, and the precipitate was washed with EtOAc (3×10 mL). The layers of the filtrate were separated, and the aqueous layer was extracted with EtOAc (4×10 mL). The combined organic layers were dried (Na$_2$SO$_4$), filtered, and concentrated under a stream of nitrogen at 50° C., giving 281 mg of crude product. The crude product was dissolved in 1:1 MeOH/DCM, and Isolute was added. The mixture was concentrated under reduced pressure, loaded onto a silica cartridge (12 g), and purified on a Combiflash Companion, eluting at 20 mL/min with a gradient running from 20% EtOAc/hexanes to 70% EtOAc/hexanes over 45 min. The desired fractions were concentrated under reduced pressure and dried under high vacuum, giving 53 mg (17%) of the title compound.

LC/MS: m/z 356.9 (M), Rt 1.07 min.

Intermediate 119

5-Bromo-3-(1,1-dioxidotetrahydro-2H-thiopyran-4-yl)-6-fluoro-1H-indole-7-carboxamide

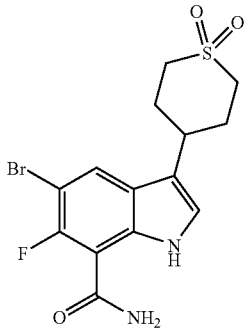

An aqueous solution of 0.0004 M Na$_2$EDTA (0.882 mL, 0.353 μmol) was added to a solution of 5-Bromo-6-fluoro-3-(tetrahydro-2H-thiopyran-4-yl)-1H-indole-7-carboxamide (45 mg, 0.126 mmol) in DME (3 mL). In a separate flask, NaHCO$_3$ (106 mg, 1.260 mmol) was added to a solution of Oxone (232 mg, 0.378 mmol) in water (1 mL). This mixture was then added in 3 portions over 3 min to the DME solution of 5-Bromo-6-fluoro-3-(tetrahydro-2H-thiopyran-4-yl)-1H-indole-7-carboxamide. The reaction was stirred at room temperature for 17 h. Water (2 mL) and DCM (3 mL) were added, the layers were separated, and the aqueous layer was extracted with DCM (3×2 mL). The combined organic layers were washed with saturated NaCl (1×2 mL), dried (Na$_2$SO$_4$), filtered, and concentrated under a stream of nitrogen at 50° C. The residue was dried under high vacuum, giving 9.2 mg (19%) of the title compound.

LC/MS: m/z 388.9 (M), Rt 1.51 min.

Intermediate 120

7-Bromo-4-fluoro-1H-indole

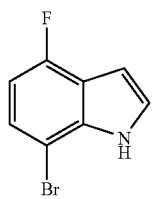

A solution of 1-bromo-4-fluoro-2-nitrobenzene (3.6 g, 16.4 mmol) in THF (100 mL) was added to a solution of 1 M vinylmagnesium bromide in THF (100 mL, 100 mmol) and DME (100 mL) at −78° C. (bath temp). The reaction was stirred at −78° C. for 4 h, and saturated aqueous NH$_4$Cl was added. The layers were separated, and the organic layer was evaporated. The crude product was purified flash chromatography, giving 2 g (57%) of the title compound.

Intermediate 121

7-Bromo-4-fluoro-2,3-dihydro-1H-indole

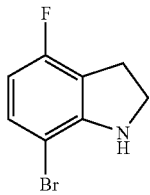

NaCNBH$_3$ (2.4 g, 38.2 mmol) was added portionwise to a solution of 7-bromo-4-fluoro-1H-indole (1 g, 4.7 mmol) in acetic acid at −10° C. (bath temp). The reaction was stirred overnight, cooled to 0° C. (bath temp), and solid KOH was added. Saturated NaHCO$_3$ and EtOAc were added, the layers were separated, and the organic layer evaporated. The crude product was purified by flash chromatography, giving the title compound.

Intermediate 122

1,1-Dimethylethyl 7-bromo-4-fluoro-2,3-dihydro-1H-indole-1-carboxylate

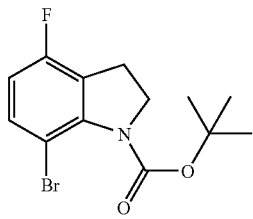

Et$_3$N (0.14 mL, 1 mmol), DMAP (0.2 g, 1.6 mmol), and Boc$_2$(O) (0.7 g, 3.2 mmol) were added to a solution of 7-bromo-4-fluoro-2,3-dihydro-1H-indole (0.23 g, 1.06 mmol) in DCM (10 mL) at room temperature. The reaction was stirred for 4 h and purified by flash chromatography, giving 320 mg (95%) of the title compound.

Intermediate 123

1-{[(1,1-Dimethylethyl)oxy]carbonyl}-4-fluoro-2,3-dihydro-1H-indole-7-carboxylic acid

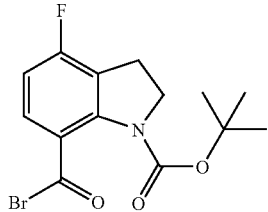

A solution of 1.6 M tert-BuLi (1.2 mL, 1.92 mmol) was added to a solution of 1,1-dimethylethyl 7-bromo-4-fluoro-2,3-dihydro-1H-indole-1-carboxylate (260 mg, 0.92 mmol) in THF (52 mL) at −78 (bath temp). The reaction was stirred for 5 min, and dry ice (CO$_2$) powder was added. The reaction was stirred for 10 min, and was allowed to warm slowly to room temperature. The reaction mixture was washed with EtOAc, and the organic layer was evaporated. The crude product was purified by flash chromatography, giving the title compound.

Intermediate 124

4-Fluoro-2,3-dihydro-1H-indole-7-carboxylic acid

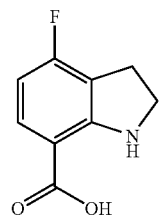

A solution of 1 M HCl (1 mL, 1 mmol) was added to a solution of 1-{[(1,1-Dimethylethyl)oxy]carbonyl}-4-fluoro-2,3-dihydro-1H-indole-7-carboxylic acid (50 mg, x mmol) in DCM at room temperature. The reaction was stirred for 2 h, and additional 1 M HCl (1 mL, 1 mmol) was added. The reaction was stirred overnight, and the mixture was evaporated and dried under high vacuum, giving the title compound.

Intermediate 125

5-Bromo-4-fluoro-2,3-dihydro-1H-indole-7-carboxylic acid

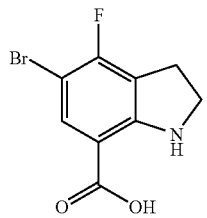

NBS (40 mg, 0.23 mmol) was added to a solution of 4-fluoro-2,3-dihydro-1H-indole-7-carboxylic acid (36 mg, 0.14 mmol) in DCM (3 mL) and MeOH (1 mL). The reaction was stirred at room temperature overnight and filtered. The filtrate was evaporated, and the residue was purified by flash chromatography, giving the title compound.

Intermediate 126

5-Bromo-4-fluoro-1H-indole-7-carboxylic acid

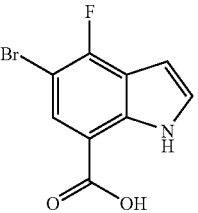

DDQ (17 mg, 0.075 mmol) was added to a solution of 5-bromo-4-fluoro-2,3-dihydro-1H-indole-7-carboxylic acid (17 mg, 0.066 mmol) in CHCl$_3$ (2 mL) at room temperature.

The reaction was stirred for 5 h and filtered. The precipitate was washed with CHCl₃, and the filtrate was evaporated, giving the title compound.

Intermediate 127

5-Bromo-4-fluoro-1H-indole-7-carboxamide

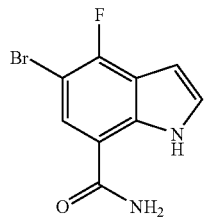

A solution of 2 M NH3/MeOH (0.6 mL, 1.2 mmol) was added to a solution of 5-bromo-4-fluoro-1H-indole-7-carboxylic acid (20 mg, 0.078 mmol) in DCM. The reaction was stirred at room temperature overnight. The mixture was washed with water, and the organic layer was concentrated. The residue was purified by flash chromatography, giving 4 mg (20%) of the title compound.

Intermediate 128

5-Bromo-4-fluoro-3-(tetrahydro-2H-thiopyran-4-yl)-1H-indole-7-carboxamide

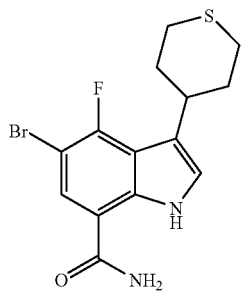

Tetrahydro-4H-thiopyran-4-one (610 mg, 5.25 mmol) was added to a 2 dram vial containing H₃PO₄ (4.3 g, 43.9 mmol) and AcOH (6.5 mL, 114 mmol). The reaction was heated to 90° C. (bath temp), and 5-bromo-4-fluoro-1H-indole-7-carboxamide (450 mg, 1.751 mmol) was added in 5 portions over 5 min. The reaction was heated at 90° C. overnight. After 17 h, the reaction mixture was cooled to room temperature and was then added slowly to a mixture of ice and saturated NH₄OH (15 mL) with stirring. EtOAc (10 mL) was then added, the mixture was filtered, and the precipitate was washed with EtOAc (3×10 mL). The layers of the filtrate were separated, and the aqueous layer was extracted with EtOAc (4×10 mL). The combined organic layers were dried (Na₂SO₄), filtered, and concentrated under a stream of nitrogen at 50° C., giving 837 mg of crude product. The crude product was dissolved in 1:1 MeOH/DCM, and Isolute was added. The mixture was concentrated under reduced pressure, loaded onto a silica cartridge (12 g), and purified on a Combiflash Companion, eluting at 20 mL/min with a gradient running from 20% EtOAc/hexanes to 60% EtOAc/hexanes over 35 min. The desired fractions were concentrated under reduced pressure and dried under high vacuum, giving 160 mg of material. This mixture was resubjected to the reaction conditions shown above for another 17 h. The reaction mixture was cooled to room temperature and was then added slowly to a mixture of ice and saturated NH₄OH (15 mL) with stirring. EtOAc (10 mL) was added, and the layers were separated. The aqueous layer was extracted with EtOAc (2×10 mL), and the combined organic layers were dried (Na₂SO₄) and concentrated under reduced pressure. The crude product was then purified as shown above, giving 100 mg (15%) of the title compound.

LC/MS: m/z 357.8 (M), Rt 1.06 min.

Intermediate 129

5-Bromo-3-(1,1-dioxidotetrahydro-2H-thiopyran-4-yl)-4-fluoro-1H-indole-7-carboxamide

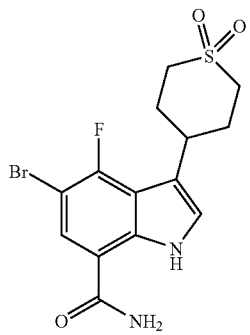

An aqueous solution of 0.0004 M Na₂EDTA (2.06 mL, 0.824 μmol) was added to a solution of 5-bromo-3-(1,1-dioxidotetrahydro-2H-thiopyran-4-yl)-4-fluoro-1H-indole-7-carboxamide (105 mg, 0.294 mmol) in DME (7 mL). In a separate flask, NaHCO₃ (247 mg, 2.94 mmol) was added to a solution of Oxone (542 mg, 0.882 mmol) in water (2 mL). This mixture was then added in 3 portions over 3 min to the DME solution of 5-bromo-3-(1,1-dioxidotetrahydro-2H-thiopyran-4-yl)-4-fluoro-1H-indole-7-carboxamide. The reaction was stirred at room temperature for. After 24 h, water (10 mL) and DCM (15 mL) were added, the layers were separated, and the aqueous layer was extracted with DCM (4×5 mL). The combined organic layers were washed with saturated NaCl (1×5 mL), dried (Na₂SO₄), and filtered. The solution was then concentrated under reduced pressure and dried under high vacuum, giving 93 mg of the title compound.

LC/MS: m/z 388.9 (M), Rt 1.51 min.

Example 1

3-(1,1-Dioxidotetrahydro-2H-thiopyran-4-yl)-5-phenyl-1H-indole-7-carboxamide

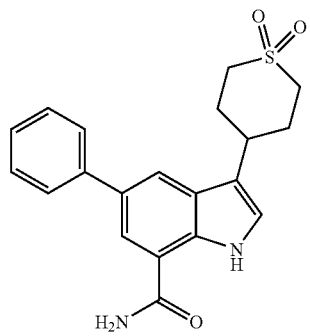

To 5-bromo-3-(1,1-dioxidotetrahydro-2H-thiopyran-4-yl)-1H-indole-7-carboxamide (80 mg, 0.216 mmol) in dioxane and water (4 mL/1 mL) was added phenylboronic acid (36 mg), Pd(PPh₃)₄ (25 mg) and K₂CO₃ (104 mg). The reaction mixture was heated to 150° C. for 20 minutes by microwave irradiation. The organic phase was separated, concentrated, and purified by HPLC to afford the title compound (23 mg).

LC/MS: m/z 368.9 (M+H), Rt 1.73 min

Using the procedure described above for 3-(1,1-Dioxidotetrahydro-2H-thiopyran-4-yl)-5-phenyl-1H-indole-7-carboxamide, 5-bromo-3-(1,1-dioxidotetrahydro-2H-thiopyran-4-yl)-1H-indole-7-carboxamide was reacted with an appropriate aromatic or heteroaromatic bromide to give the compounds listed in Table 1.

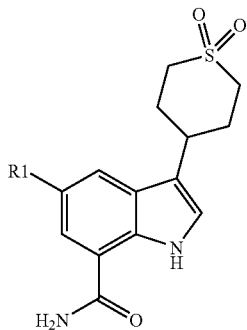

TABLE 1

| Example | R | MS [M]⁺/RT (min) or NMR |
|---------|---|------------------------|
| 2 | (thiophene) | 374.7/1.67 |
| 3 | (2,5-difluorophenyl) | 405.1/1.76 |
| 4 | (3-methylphenyl) | 385.0/1.83 |
| 5 | (3-cyanophenyl) | 394.1/1.70 |
| 6 | (2-fluorophenyl) | 389.1/1.68 |
| 7 | (2,4-difluorophenyl) | 406.2/1.76 |
| 8 | (4-fluorophenyl) | 387.0/1.77 |

Following a similar procedure, 5-bromo-3-(1,1-dioxidotetrahydro-2H-thiopyran-4-yl)-1H-indole-7-carboxamide (25.0 mg, 0.07 mmol) in dioxane:H₂O (2.0 mL, 3:1) was suspended into a microwave tube with fitted magnetic stir bar containing K₂CO₃ (50 mg), boronic acid (0.2 mmol), and Pd(PPh₃)₄ (5.0 mg). The reaction mixture was heated by microwave irradiation at either 120° C. for 5 min or 130° C. for 5, 10, or 20 min (see the Table below). The reaction mixture was concentrated and purified with HPLC to give the compounds listed in Table 2.

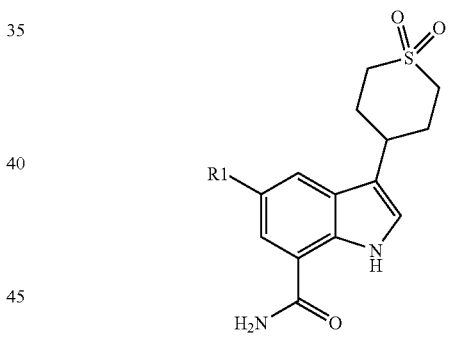

TABLE 2

| Example | R | MS [M]⁺/RT (min) or NMR |
|---------|---|------------------------|
| 9 | (furan-2-yl) (a) | 359/1.51 min |
| 10 | (furan-3-yl) (a) | 359/1.53 min |

TABLE 2-continued
| Example | R | MS [M]⁺/RT (min) or NMR |
|---|---|---|
| 11 | 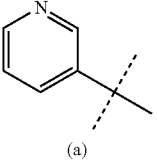 (a) | 370/0.98 min |
| 12 | 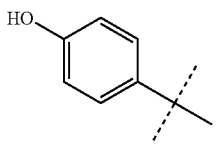 (a) | 385/1.41 min |
| 13 | 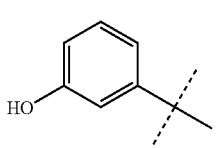 (a) | 385/1.43 min |
| 14 | 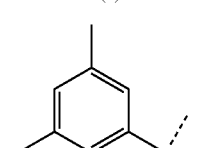 (a) | 397/1.88 min |
| 15 | 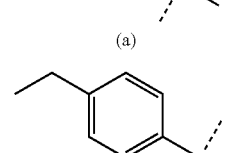 (a) | 397/1.94 min |
| 16 | 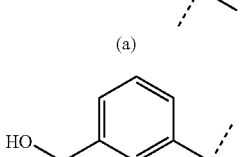 (a) | 397/1.94 min |
| 17 | 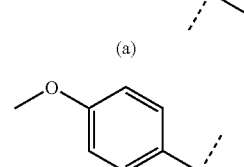 (a) | 399/1.69 min |
| 18 | 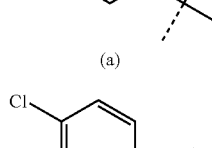 (a) | 403/1.89 min |
| 19 | 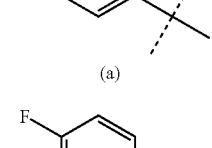 (a) | 421/1.93 min |
| 20 | 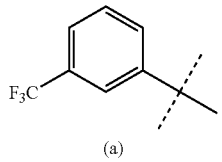 (a) | 437/1.95 min |
| 21 | 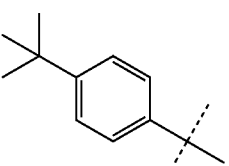 (a) | 425/2.13 min |
| 22 | 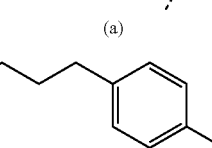 (a) | 425/2.22 min |
| 23 | 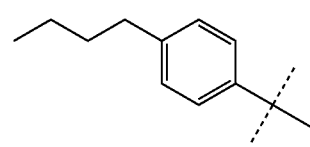 (a) | 375/1.60 min |
| 24 | 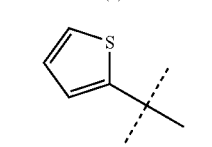 (a) | 387/1.76 min |
| 25 | 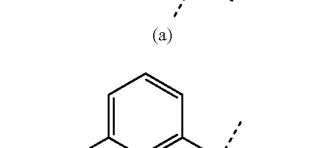 (b) | 399/1.71 min |
| 26 | 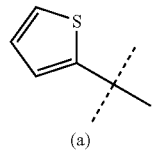 (b) | 413/1.79 min |
| 27 | 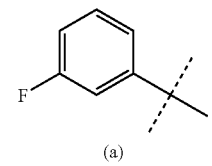 (b) | 426/1.51 min |
| 28 | 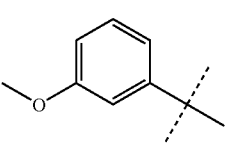 (b) | 403/1.91 min |

TABLE 2-continued

| Example | R | MS [M]+/RT (min) or NMR |
|---|---|---|
| 29 | 4-(hydroxymethyl)phenyl, tert-butyl-like attachment (b) | 399/1.36 min |
| 30 | 2-methoxy-5-(attachment)-fluorophenyl (b) | 417/1.73 min |
| 31 | pyridin-4-yl (b) | 370/0.93 min |
| 32 | 4-fluoro-3-methylphenyl (b) | 401/1.85 min |
| 33 | 4-aminophenyl (b) | 384/1.02 min |
| 34 | 6-chloropyridin-3-yl (b) | 404/1.57 min |
| 35 | 6-fluoropyridin-3-yl (b) | 388/1.48 min |
| 36 | 2-hydroxyphenyl (b) | 385/1.45 |
| 37 | 3,5-dichlorophenyl (b) | 437/2.09 |
| 38 | 3,4-dichlorophenyl (b) | 438/2.05 |
| 39 | 4-butoxyphenyl (b) | 441/2.12 |
| 40 | 4-(dimethylamino)phenyl (b) | 411/1.15 min |
| 41 | 5-methylfuran-2-yl (b) | 373/1.54 min |
| 42 | 3,5-difluorophenyl (b) | 405/1.90 min |
| 43 | 3,4,5-trifluorophenyl (b) | 423/1.89 min |
| 44 | 4-methoxy-3-methylphenyl (b) | 413/1.87 min |
| 45 | 4-propoxyphenyl (b) | 427/1.96 min |

TABLE 2-continued

| Example | R | MS [M]+/RT (min) or NMR |
|---|---|---|
| 46 | 3-isopropoxyphenyl (b) | 427/1.90 min |
| 47 | 6-methoxypyridin-3-yl (b) | 400/1.54 min |
| 48 | 3-(methylsulfonylamino)phenyl (b) | 462/1.54 min |
| 49 | 4-propylphenyl (b) | 411/2.12 min |
| 50 | 4-methoxy-3,5-dimethylphenyl (b) | 427/1.88 min |
| 51 | 4-isopropoxyphenyl (b) | 427/1.95 min |
| 52 | 3-propoxyphenyl (b) | 427/2.01 min |
| 53 | 4-(trifluoromethyl)phenyl (b) | 437/1.95 min |
| 54 | 3-(trifluoromethoxy)phenyl (b) | 453/1.99 min |
| 55 | 4-hydroxy-3-methoxyphenyl (b) | 415/1.50 min |
| 56 | 5-(methoxymethyl)thiophen-3-yl (b) | 419/1.65 min |
| 57 | 5-cyanothiophen-3-yl (b) | 400/1.67 min |
| 58 | 5-(cyanomethyl)thiophen-3-yl (b) | 414/1.67 min | a) Heated at 120° C. for 5 min or 130° C. for 20 min
b) Heated at 120° C. for 10 min Following a similar procedure, 5-bromo-3-(1,1-dioxidotetrahydro-2H-thiopyran-4-yl)-1H-indole-7-carboxamide (30.0 mg, 0.08 mmol) in dioxane/H$_2$O (2.0 mL, 3:1) was suspended into a microwave tube with fitted magnetic stir bar containing K$_2$CO$_3$ (50 mg), boronic acid (0.3 mmol), and palladium catalyst (see the table below). The reaction mixture was heated by microwave irradiation at either 130° C. or 140° C. (see table below) for 10 min. The reaction mixture was concentrated and purified with HPLC to give the compounds listed in Table 3.

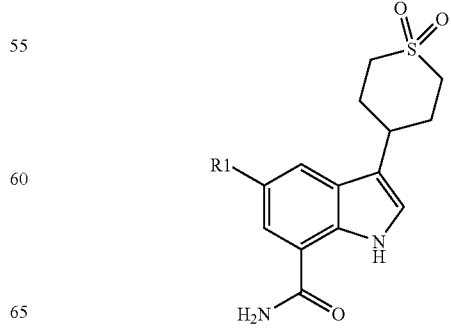

TABLE 3

| Example | R (reaction conditions-see below) | MS [M]⁺/RT |
|---|---|---|
| 59 | 4-tert-butyl-methylphenyl (a, c) | 383/1.85 min |
| 60 | 3,4-difluoro-tert-butylphenyl (a, d) | 405/1.83 min |
| 61 | 4-acetamido-tert-butylphenyl (a, c) | 426/1.40 min |
| 62 | 4-ethoxy-tert-butylphenyl (b, c) | 423/1.81 min |
| 63 | 2-methoxy-tert-butylphenyl (a, d) | 399/1.65 min |
| 64 | 2-methyl-tert-butylphenyl (a, c) | 383/1.75 min | a) Used PdCl₂(dppf) (8 mg, 0.3 mmol)
b) Used PS-PPh₂-Pd (15 mg, 0.3 mmol)
c) Heated at 130° C. for 10 min
d) Heated at 140° C. for 20 min Example 65

5-[4-(Cyanomethyl)phenyl]-3-(1,1-dioxidotetrahydro-2H-thiopyran-4-yl)-1H-indole-7-carboxamide

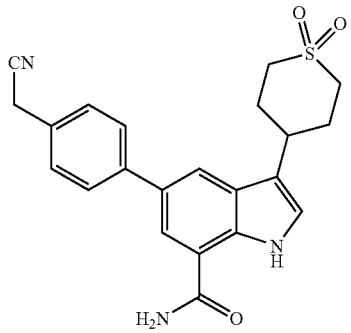

A mixture of 5-bromo-3-(1,1-dioxidotetrahydro-2H-thiopyran-4-yl)-1H-indole-7-carboxamide (60 mg, 0.162 mmol), [4-(cyanomethyl)phenyl]boronic acid (52.0 mg, 0.323 mmol) and K2CO3 (67.0 mg, 0.485 mmol) in 1,4-dioxane (0.18 mL) and water (0.08 mL) was degassed in a Biotage microwave vial for 10 min. PdCl2(dppf) (11.83 mg, 0.016 mmol) was added, the vial sealed, and the reaction heated at 100° C. for 5 min (microwave reaction). EtOAc (3 mL) and water (1 mL) were added, the layers were separated, and the aqueous layer was extracted with EtOAc (4×2 mL). The combined organic layers were washed with saturated NaCl (1×2 mL), dried (Na₂SO₄), and concentrated under a stream of nitrogen at 50° C. Recovered 27 mg (42%) of the title compound.

LC/MS: m/z 409.1 (M+H), Rt 1.61 min.

Intermediate 130

3-(1,1-Dioxidotetrahydro-2H-thiopyran-4-yl)-5-(5-{3-methyl-3-[(triethylsilyl)oxy]butyl}-2-thienyl)-1H-indole-7-carboxamide

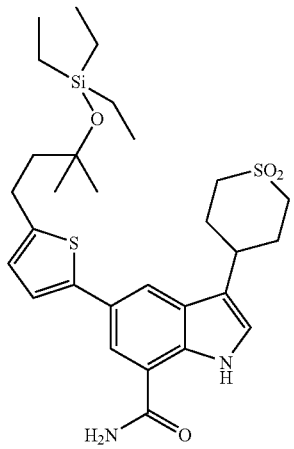

5-bromo-3-(1,1-dioxidotetrahydro-2H-thiopyran-4-yl)-1H-indole-7-carboxamide (90 mg, 0.24 mmol), ({1,1-dimethyl-3-[5-(4,4,5,5-tetramethyl-1,3,2-dioxaborolan-2-yl)-2-thienyl]propyl}oxy)(triethyl)silane (149 mg, 0.36 mmol, 1.5 eq), potassium carbonate (200 mg, 1.4 mmol, 6 eq), and palladium tetrakistriphenylphosphine (28 mg, 0.024 mmol, 0.1 eq) were diluted in dioxane (1.5 mL) and water (0.5 mL) in a 2-5 mL microwave vial. The mixture was degassed by bubbling argon through for 5 minutes, then heated in a microwave oven at 150° C. under high absorption for 40 minutes. The mixture was filtered through a thiol SPE cartridge, then concentrated to give the crude product as a brown oil. This material was purified by Isco Combiflash, 40 gram column, eluting with 0-15% methanol in dichloromethane. The desired product was obtained as a brownish tarry substance and was re-purified by ammonium hydroxide Gilson eluting with 20-95% acetonitrile in water. The product fractions were concentrated in a Genevac EZ2 evaporator to give the title compound as a light yellow solid (55 mg, 40%).

LC/MS: m/z 443.3 (M−131), Rt 1.49 min.

Example 66

3-(1,1-Dioxidotetrahydro-2H-thiopyran-4-yl)-5-[5-(3-hydroxy-3-methylbutyl)-2-thienyl]-1H-indole-7-carboxamide

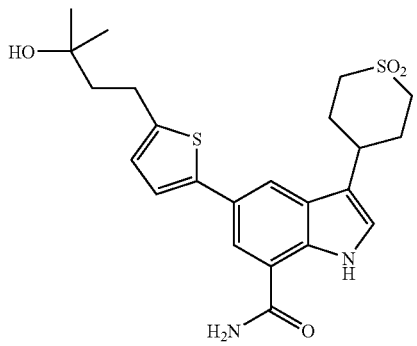

3-(1,1-Dioxidotetrahydro-2H-thiopyran-4-yl)-5-(5-{3-methyl-3-[(triethylsilyl)oxy]butyl}-2-thienyl)-1H-indole-7-carboxamide (55 mg, 0.1 mmol) was dissolved in tetrahydrofuran (3 mL). Tetrabutylammonium fluoride (1 M in THF, 0.3 mL, 0.3 mmol) was added and the mixture was stirred at rt for 2 h. Additional TBAF (1 M in THF, 0.7 mL, 0.7 mmol) was added, and the mixture was stirred at 45° C. overnight. The reaction mixture was concentrated, re-diluted in dichloromethane (20 mL), and washed with water (20 mL). The organic layer was dried over sodium sulfate and concentrated. The crude product was purified by flash chromatography, eluting with 0-15% methanol in dichloromethane. The residue was then repurified by Gilson HPLC (NH4OH buffer). The product fractions were combined and concentrated in an EZ2 Genevac evaporator, giving 17 mg (40%) of the title compound.

LC/MS: m/z 461.2 (M+H), Rt 0.84 min.

Example 67

5-[6-(Dimethylamino)-3-pyridinyl]-3-(1,1-dioxidotetrahydro-2H-thiopyran-4-yl)-1H-indole-7-carboxamide

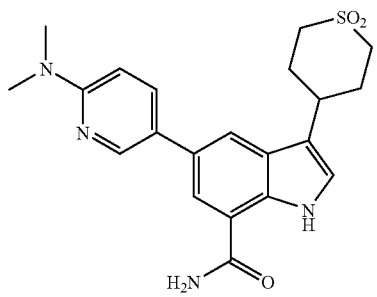

[6-(Dimethylamino)-3-pyridinyl]boronic acid (34 mg, 0.202 mmol), 5-bromo-3-(1,1-dioxidotetrahydro-2H-thiopyran-4-yl)-1H-indole-7-carboxamide (75 mg, 0.202 mmol) and potassium carbonate (84 mg, 0.606 mmol) were suspended in 4 mL of dioxane:water (3:1) and degassed for a few minutes with nitrogen gas. Pd(PPh3)4 (23 mg) was then added and the reaction mixture was heated in a microwave oven at 150° C. for 40 minutes on 'high' absorption setting. After heating, LCMS of all crude reaction mixtures showed the desired m/z with few impurities. The crude reaction mixtures were filtered through 500 mg Stratospheres SPE Thiol cartridges eluting with 10 mL methanol/DCM (1:1) and concentrated. The residues were dissolved in DMSO (~3 mL) and purified via RP-HPLC using an XBridge Prep C18 column with water/acetonitrile (0.1% NH4OH buffer). The desired fractions were concentrated, giving 0.029 g (34.8%) of the title compound.

LCMS: m/z 413.1 (M+H) Rt 0.55 min.

Example 68

5-(2-Chloro-4-pyridinyl)-3-(1,1-dioxidotetrahydro-2H-thiopyran-4-yl)-1H-indole-7-carboxamide To a mixture of (2-chloro-4-pyridinyl)boronic acid (0.095 g, 0.606 mmol), 5-bromo-3-(1,1-dioxidotetrahydro-2H-thiopyran-4-yl)-1H-indole-7-carboxamide (0.075 g, 0.202 mmol) and potassium carbonate (0.168 g, 1.212 mmol) was added 1,4-dioxane (0.898 mL)/water (0.449 mL). The mixture was degassed with nitrogen and PdCl2(dppf) (0.015 g, 0.020 mmol) was added. The reaction mixture was heated in a microwave oven at 100° C. for 5 minutes on 'high' absorption setting. LCMS of crude reaction mixture shows the desired m/z and some unreacted starting material (very close ret. times). The reaction mixture was filtered through a Thiol SPE cartridge (500 mg) eluting with 1:1 MeOH/DCM (10 mL). The filtrate was purified with RP-HPLC (XBridge Column, 0.1% NH4OH). The fractions containing the desired compound are combined and concentrated to give 5-(2-chloro-4-pyridinyl)-3-(1,1-dioxidotetrahydro-2H-thiopyran-4-yl)-1H-indole-7-carboxamide (0.016 g, 19.61%).

LCMS: m/z 404.0 (M+H)Rt 0.89 min.

Example 69

5-(2,3-Dihydro-1-benzofuran-5-yl)-3-(1,1-dioxidotetrahydro-2H-thiopyran-4-yl)-1H-indole-7-carboxamide

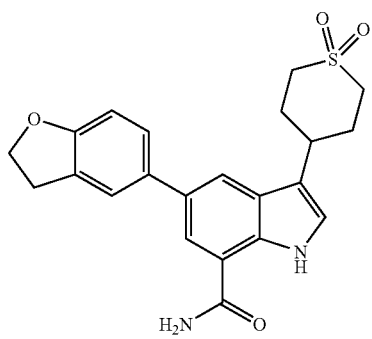

A mixture of 5-bromo-3-(1,1-dioxidotetrahydro-2H-thiopyran-4-yl)-1H-indole-7-carboxamide (30 mg, 0.081 mmol), 2,3-dihydro-1-benzofuran-5-ylboronic acid (26.5 mg, 0.162 mmol), and $K_2CO_3$ (33.7 mg, 0.242 mmol) in 1,4-dioxane (0.36 mL) and water (0.180 mL) was degassed in a Biotage microwave vial for 10 min. $PdCl_2(dppf)$ (5.91 mg, 8.08 μmol) was added, the vial was sealed, and the reaction was heated at 100° C. (bath temp) for 5 min in a Biotage microwave oven at high absorption. EtOAc (3 mL) and water (1 mL) were added, the layers were separated, and the aqueous layer was extracted with EtOAc (4×2 mL). The combined organic layers were washed with saturated NaCl (1×2 mL), dried ($Na_2SO_4$), and concentrated under a stream of nitrogen at 50° C. The crude product was dissolved in DMSO (1.2 mL), filtered through a 0.2 mm acrodisc, and purified on a Gilson HPLC (XBridge C18 5 mm OBD 19×100 mm preparatory column), eluting at 15 mL/min with a linear gradient running from 20% $CH_3CN/H_2O$ (0.1% $NH_4OH$) to 70% $CH_3CN/H_2O$ (0.1% $NH_4OH$) over 18 min. The desired fractions were concentrated under a stream of nitrogen at 50° C., giving 6.8 mg (20%) of the title compound.

LC/MS: m/z 410.9 (M+H), Rt 1.71 min.

Intermediate 131

4-(4,4,5,5-Tetramethyl-1,3,2-dioxaborolan-2-yl)-2-thiophenecarbaldehyde

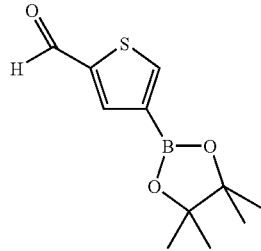

4-bromo-2-thiophenecarbaldehyde (25 g, 131 mmol), bispinacolatodiboron (30 g, 118 mmol, 0.9 eq), PdCl2(dppf)-CH2Cl2 adduct (1.7 g, 2.1 mmol, 0.02 eq), and potassium acetate (21 g, 214 mmol, 1.6 eq) were diluted in DME (200 mL). The mixture was degassed by evacuating the flask and back-filling with argon twice, then was heated at 80° C. overnight under argon. The crude reaction mixture was cooled to rt, filtered through a large plastic Buchner funnel pre-filled with celite, washing with ethyl acetate (1.5 L). The solvent was removed in vacuo to afford a brown oil which partially crystallized upon standing. The batch was divided into two portions and each was purified by Isco Combiflash (330 gram column, eluting with 0-30% ethyl acetate in hexanes). Mixed fractions were repurified by Combiflash as described above. The product fractions were combined and concentrated to give the desired as a fluffy white solid. Over time the color darkened a bit to light tan, even with storage in an amber jar, but the quality did not seem to be affected. 17.9 g (57%) of the title compound was obtained.

LCMS m/z 238.7 (M+H), Rt 0.98 min.

Intermediate 132

3-(1,1-Dioxidotetrahydro-2H-thiopyran-4-yl)-5-(5-formyl-3-thienyl)-1H-indole-7-carboxamide

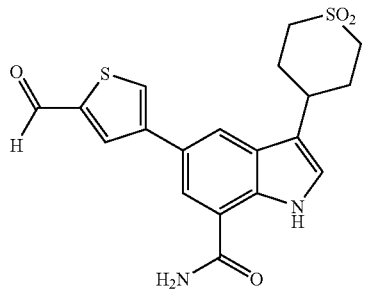

5-bromo-3-(1,1-dioxidotetrahydro-2H-thiopyran-4-yl)-1H-indole-7-carboxamide (150 mg, 0.4 mmol), 4-(4,4,5,5-tetramethyl-1,3,2-dioxaborolan-2-yl)-2-thiophenecarbaldehyde (115 mg, 0.48 mmol, 1.2 eq), PdCl2(dppf)-CH2Cl2 adduct (29 mg, 0.04 mmol, 0.09 eq), and potassium carbonate (170 mg, 1.2 mmol, 3 eq) were diluted in dioxane (3 mL) and water (1.5 mL) in a 2-5 mL microwave tube. The mixture was degassed by bubbling argon through for 5 minutes, then the reaction was heated in a microwave oven under regular absorption at 10° C. for 5 minutes. The reaction mixture was filtered through a thiol SPE cartridge, washing well with acetone, and the solvent was removed in vacuo. The crude residue was triturated from diethyl ether to give a pink solid. Minor impurities were present, but this material was suitable for use in the reductive amination step as is (210 mg, 0.52 mmol, 129%).

LCMS m/z 402.9 (M+H), Rt 0.75 min.

Example 70

5-[5-(1-Azetidinylmethyl)-3-thienyl]-3-(1,1-dioxi-dotetrahydro-2H-thiopyran-4-yl)-1H-indole-7-carboxamide

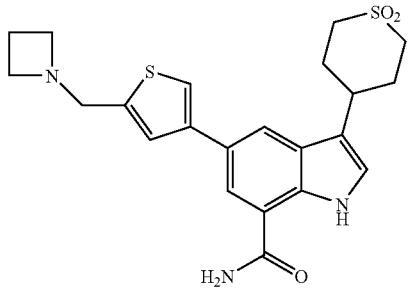

3-(1,1-dioxidotetrahydro-2H-thiopyran-4-yl)-5-(5-formyl-3-thienyl)-1H-indole-7-carboxamide (105 mg, 0.26 mmol) was diluted in dimethylsulfoxide (0.5 mL) and methanol (0.5 mL) in a 2 dram vial. Azetidine (75 mg, 5 eq) was added, followed by glacial acetic acid (0.3 mL). The mixture was stirred at rt for 1 h, then sodium cyanoborohydride (35 mg, 0.56 mmol, 2.1 eq) was added and the mixture was stirred at rt overnight. The mixture was filtered through a 1 g silica gel pad (commercial, in syringe tube), and the solvent was removed in vacuo. The crude product was re-diluted in a mixture of methanol and DMSO, and purified by ammonium hydroxide Gilson HPLC. The desired fractions were concentrated in an EZ2 Genevac evaporator, giving 10 mg (9%) of title compound.

LCMS m/z 444.3 (M+H), Rt 0.57 min.

Example 71

3-(1,1-Dioxidotetrahydro-2H-thiopyran-4-yl)-5-[5-({methyl[2-(methyloxy)ethyl]amino}methyl)-3-thienyl]-1H-indole-7-carboxamide

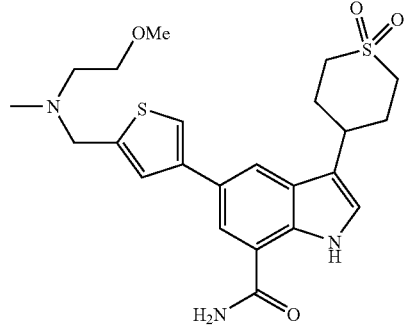

To 5-bromo-3-(1,1-dioxidotetrahydro-2H-thiopyran-4-yl)-1H-indole-7-carboxamide (100 mg, 0.27 mmol) in dioxane and water (3 mL/1 mL) were added 4-(4,4,5,5-tetramethyl-1,3,2-dioxaborolan-2-yl)-2-thiophenecarbaldehyde (116 mg), Pd(PPH$_3$)$_4$ (30 mg) and K$_2$CO$_3$ (112 mg). The reaction mixture was heated to 150° C. for 900 seconds in microwave. The organic phase was separated, concentrated, and redissolved in DMSO (3 mL). The resulting solution was split to two. NaBH$_3$CN (30 mg), ZnCl$_2$ (30 mg) and N-methyl-2-(methyloxy)ethanamine (50 mg) were added. The mixture was heated to 100° C. for 30 minutes in microwave which was then purified by HPLC with TFA to afford the title compound (9 mg).

LC/MS: m/z 476.0 (M+H), Rt 1.26 min.

Example 72

3-(1,1-Dioxidotetrahydro-2H-thiopyran-4-yl)-5-[5-(hexahydro-1H-azepin-1-ylmethyl)-3-thienyl]-1H-indole-7-carboxamide

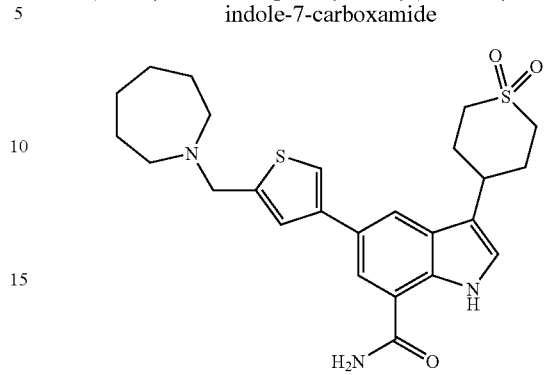

To 5-bromo-3-(1,1-dioxidotetrahydro-2H-thiopyran-4-yl)-1H-indole-7-carboxamide (100 mg, 0.27 mmol) in dioxane and water (3 mL/1 mL) was added 4-(4,4,5,5-tetramethyl-1,3,2-dioxaborolan-2-yl)-2-thiophenecarbaldehyde (116 mg), Pd(PPH$_3$)$_4$ (30 mg) and K$_2$CO$_3$ (112 mg). The reaction mixture was heated to 150° C. for 900 seconds by microwave irradiation. The organic phase was separated, concentrated, and redissolved in DMSO (3 mL). The resulting solution was split to two. NaBH$_3$CN (30 mg), ZnCl$_2$ (30 mg) and hexahydro-1H-azepine (50 mg) was added. The mixture was heated to 100° C. for 30 minutes which was then purified by HPLC with TFA to afford the title compound (13 mg).

LC/MS: m/z 486.1 (M+H), Rt 1.30 min.

The title compound could also be made according to the following procedure:

To 3-(1,1-dioxidotetrahydro-2H-thiopyran-4-yl)-5-(5-formyl-3-thienyl)-1H-indole-7-carboxamide (100 mg, 0.248 mmol) in Dimethyl Sulfoxide (DMSO) (3 mL), hexahydro-1H-azepine (246 mg, 2.485 mmol), AcOH (0.014 mL, 0.248 mmol), and sodium triacetoxyborohydride (527 mg, 2.485 mmol) were added. The reaction mixture was stirred at 25° C. for 16 hours. Then the solid was filtered. Purification by Gilson-HPLC (amine column) gave 20.7 mg (17.15%) of the title compound.

LC/MS: m/z 486.2 (M+H), Rt 0.77 min.

Example 73

5-{5-[(Dimethylamino)methyl]-3-thienyl}-3-(1,1-dioxidotetrahydro-2H-thiopyran-4-yl)-1H-indole-7-carboxamide

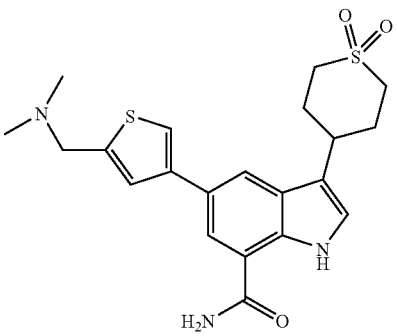

To 5-bromo-3-(1,1-dioxidotetrahydro-2H-thiopyran-4-yl)-1H-indole-7-carboxamide (400 mg, 1.08 mmol) in dioxane and water (4 mL/1 mL) was added 4-(4,4,5,5-tetramethyl-1,3,2-dioxaborolan-2-yl)-2-thiophenecarbaldehyde (462 mg, 1.94 mmol), Pd(PPH₃)₄ (100 mg) and K₂CO₃ (447 mg, 3.24 mmol). The reaction mixture was heated to 150° C. for 20 minutes by microwave irradiation. The organic phase was concentrated and redissolved in DMSO (10 mL). The resulting solution was split to eight. NaBH₃CN (30 mg), ZnCl₂ (30 mg) and dimethyl amine (2N in THF, 0.5 mL) were added. The mixture was heated to 100° C. for 30 minutes which was then filtered and purified by HPLC with TFA to afford the title compound (10 mg).

LC/MS: m/z 433.2 (M+H), Rt 1.12 min

Example 74

3-(1,1-Dioxidotetrahydro-2H-thiopyran-4-yl)-5-(5-{[methyl(1-methylethyl)amino]methyl}-3-thienyl)-1H-indole-7-carboxamide

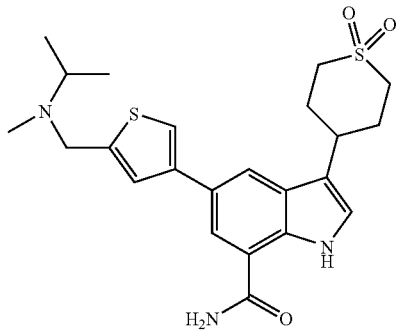

To 5-bromo-3-(1,1-dioxidotetrahydro-2H-thiopyran-4-yl)-1H-indole-7-carboxamide (400 mg, 1.08 mmol) in dioxane and water (4 mL/1 mL) was added 4-(4,4,5,5-tetramethyl-1,3,2-dioxaborolan-2-yl)-2-thiophenecarbaldehyde (462 mg), Pd(PPh₃)₄ (100 mg) and K₂CO₃ (447 mg). The reaction mixture was heated to 150° C. for 20 minutes in microwave. The organic phase was concentrated and redissolved in DMSO (10 mL). The resulting solution was split to eight. NaBH₃CN (30 mg), ZnCl₂ (30 mg) and N-methyl-2-propanamine (50 mg) were added. The mixture was heated at 100° C. for 30 minutes which was then filtered and purified by HPLC with TFA to afford the title compound (12 mg).

LC/MS: m/z 460.0 (M+H), Rt 1.20 min.

Example 75

3-(1,1-Dioxidotetrahydro-2H-thiopyran-4-yl)-5-(5-{[ethyl(methyl)amino]methyl}-3-thienyl)-1H-indole-7-carboxamide

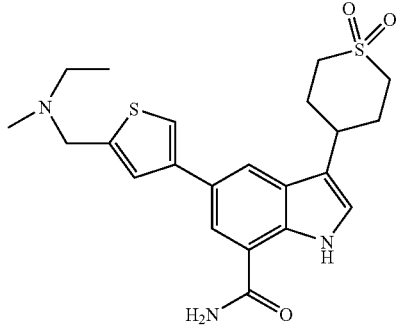

To 5-bromo-3-(1,1-dioxidotetrahydro-2H-thiopyran-4-yl)-1H-indole-7-carboxamide (400 mg, 1.08 mmol) in dioxane and water (4 mL/1 mL) was added 4-(4,4,5,5-tetramethyl-1,3,2-dioxaborolan-2-yl)-2-thiophenecarbaldehyde (462 mg, 1.94 mmol), Pd(PPh₃)₄ (100 mg) and K₂CO₃ (447 mg, 3.24 mmol). The reaction mixture was heated to 150° C. for 20 minutes by microwave irradiation. The organic phase was concentrated and redissolved in DMSO (10 mL). The resulting solution was split to eight. NaBH₃CN (30 mg), ZnCl₂ (30 mg) and methyl ethylamine (50 mg) were added. The mixture was heated at 100° C. for 30 minutes which was then filtered and purified by HPLC with TFA to afford the title compound (13 mg).

Example 76

5-{5-[(diethylamino)methyl]-3-thienyl}-3-(1,1-dioxidotetrahydro-2H-thiopyran-4-yl)-1H-indole-7-carboxamide

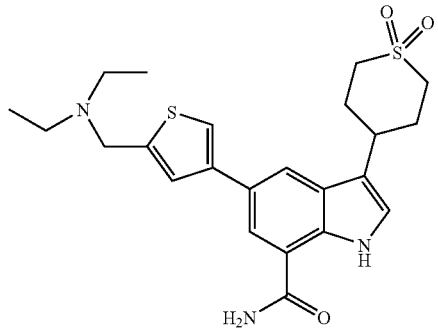

To 5-bromo-3-(1,1-dioxidotetrahydro-2H-thiopyran-4-yl)-1H-indole-7-carboxamide (400 mg, 1.08 mmol) in dioxane and water (4 mL/1 mL) was added 4-(4,4,5,5-tetramethyl-1,3,2-dioxaborolan-2-yl)-2-thiophenecarbaldehyde (462 mg, 1.94 mmol), Pd(PPh₃)₄ (100 mg) and K₂CO₃ (447 mg, 3.24 mmol). The reaction mixture was heated at 150° C. for 20 minutes by microwave irradiation. The organic phase was concentrated and redissolved in DMSO (10 mL). The resulting solution was split to eight. NaBH₃CN (30 mg), ZnCl₂ (30 mg) and N-ethylethanamine (50 mg) were added. The mixture was heated to 100° C. for 30 minutes which was then filtered and purified by HPLC with TFA to afford the title compound (16 mg).

LC/MS: m/z 460.1 (M+H), Rt 1.29 min

Example 77

5-(5-{[{2-[(1,1-Dimethylethyl)oxy]ethyl}(methyl)amino]methyl}-3-thienyl)-3-(1,1-dioxidotetrahydro-2H-thiopyran-4-yl)-1H-indole-7-carboxamide

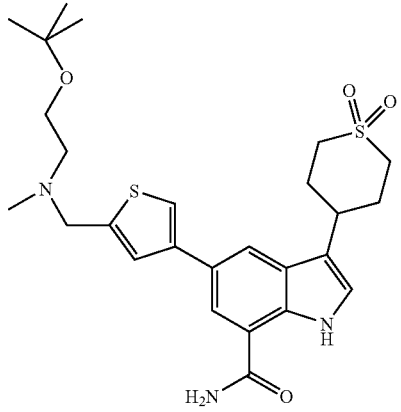

To 5-bromo-3-(1,1-dioxidotetrahydro-2H-thiopyran-4-yl)-1H-indole-7-carboxamide (400 mg, 1.08 mmol) in dioxane and water (4 mL/1 mL) was added 4-(4,4,5,5-tetramethyl-1,3,2-dioxaborolan-2-yl)-2-thiophenecarbaldehyde (462 mg, 1.94 mmol), Pd(PPh$_3$)$_4$ (100 mg) and K$_2$CO$_3$ (447 mg, 3.24 mmol). The reaction mixture was heated at 150° C. for 20 minutes by microwave irradiation. The organic phase was concentrated and redissolved in DMSO (10 mL). The resulting solution was split to eight. NaBH$_3$CN (30 mg), ZnCl$_2$ (30 mg) and -[(1,1-dimethylethyl)oxy]ethyl}methylamine (50 mg) were added. The mixture was heated at 100° C. for 30 minutes which was then filtered and purified by HPLC with TFA to afford the title compound (15 mg).

LC/MS: m/z 518.2 (M+H), Rt 1.48 min.

Intermediate 133

3-(1,1-Dioxidotetrahydro-2H-thiopyran-4-yl)-5-(3-formylphenyl)-1H-indole-7-carboxamide

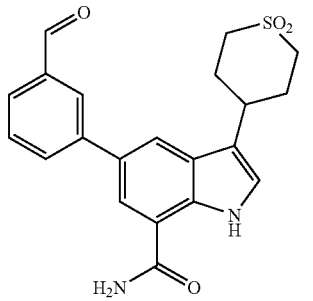

A mixture of (3-formylphenyl)boronic acid (0.121 g, 0.808 mmol), 5-bromo-3-(1,1-dioxidotetrahydro-2H-thiopyran-4-yl)-1H-indole-7-carboxamide (0.150 g, 0.404 mmol) and Potassium carbonate (0.168 g, 1.212 mmol) in 1,4-Dioxane (1.796 mL)/Water (0.898 mL) was degassed with nitrogen for several minutes and PdCl2(dppf) (0.030 g, 0.040 mmol) was added. The mixture was heated at 100° C. for 5 minutes in the microwave on 'high' absorption setting. The aqueous layer was removed via pipette and the reaction mixture was filtered through a 500 mg Stratospheres PL Thiol SPE cartridge, eluting with 10 mL of DCM/MeOH (1:1). Crude LCMS shows the desired compound as major peak. Concentrated under nitrogen to obtain 3-(1,1-dioxidotetrahydro-2H-thiopyran-4-yl)-5-(3-formylphenyl)-1H-indole-7-carboxamide (0.160 g, 0.404 mmol, 100% yield).

LCMS: m/z 398.2 (M+H) Rt 0.77 min.

Example 78

3-(1,1-Dioxidotetrahydro-2H-thiopyran-4-yl)-5-{3-[(methylamino)methyl]phenyl}-1H-indole-7-carboxamide

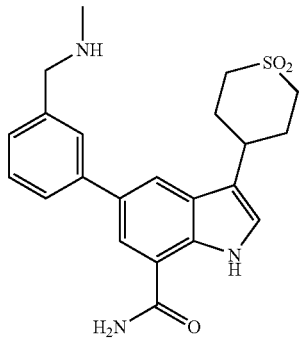

3-(1,1-Dioxidotetrahydro-2H-thiopyran-4-yl)-5-(3-formylphenyl)-1H-indole-7-carboxamide (0.160 g, 0.404 mmol) was taken up in MeOH (1.802 mL)/DMSO (1.802 mL). Methyl amine HCl (0.136 g, 2.018 mmol) was added followed by acetic acid (0.462 mL, 8.07 mmol). The reaction mixture was allowed to stir at room temperature for 1 hour. Sodium cyanoborohydride (0.051 g, 0.807 mmol) was added and the reaction mixture was allowed to stir for 45 minutes and LCMS then shows conversion to desired product. The reaction mixture was purified through a 500 mg SCX cartridge eluting with MeOH followed by ammonia in methanol. The fractions are concentrated under a stream of nitrogen. The residue was dissolved in DMSO (~3 mL) and purified via RP-HPLC using an XBridge Prep C18 column with water/acetonitrile (0.1% NH$_4$OH buffer). Obtained 0.023 g (13.85%) of the title compound.

LCMS: m/z 411.9 (M+H) Rt 0.57 min.

Example 79

3-(1,1-Dioxidotetrahydro-2H-thiopyran-4-yl)-5-{3-[(methylamino)methyl]phenyl}-1H-indole-7-carboxamide

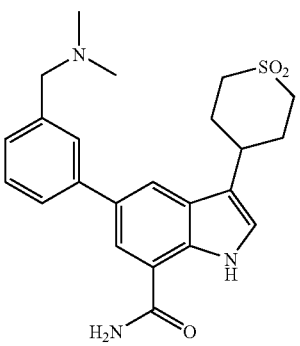

To 3-(1,1-dioxidotetrahydro-2H-thiopyran-4-yl)-5-(3-formylphenyl)-1H-indole-7-carboxamide (0.160 g, 0.404 mmol) in DMSO (1.8 ml) and MeOH (1.8 ml) was added 2M dimethyl amine in methanol (1.0 ml, 2.0 mmol) and HOAc (0.46 ml, 8.1 mmol). The mixture was allowed to stir for 1 hour, and then NaCNBH$_3$ (0.051 g, 0.808 mmol) was added. After 1 hour, the reaction mixture was concentrated and purified via RP-HPLC (0.1% NH$_4$OH in water/acetonitrile). The fractions containing product were combined and concentrated, giving 0.027 g (15%) of the title compound.

LCMS: m/z 426.1 (M+H) Rt 0.63 min.

Example 80

5-[3-({[(1S)-1,2-Dimethylpropyl]amino}methyl)phenyl]-3-(1,1-dioxidotetrahydro-2H-thiopyran-4-yl)-1H-indole-7-carboxamide

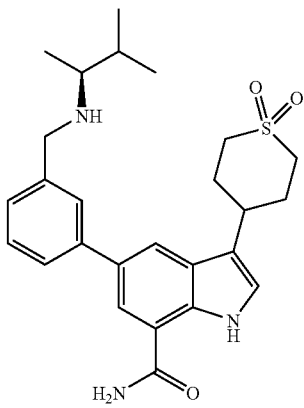

To 5-bromo-3-(1,1-dioxidotetrahydro-2H-thiopyran-4-yl)-1H-indole-7-carboxamide (80 mg, 0.216 mmol) in dioxane and water (4 mL/1 mL) was added (3-formylphenyl)boronic acid (45 mg), Pd(PPh₃)₄ (25 mg) and K₂CO₃ (104 mg). The reaction mixture was redissolved in DMSO (2 mL). To the resultant mixture zinc chloride (30 mg), NaCNBH₃ (30 mg) and (2s)-3-methyl-2-butanamine (50 mg) were added. The mixture was heated to 100° C. for 30 minutes by microwave irradiation and purified by HPLC with TFA to afford the title compound (16 mg).

LC/MS: m/z 468.3 (M+H), Rt 1.78 min

Intermediate 134

1-[(5-Bromo-2-thienyl)sulfonyl]azetidine

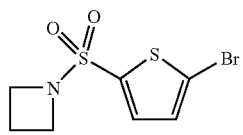

Azetidine (0.258 mL, 3.82 mmol) was added to a solution of 5-bromo-2-thiophenesulfonyl chloride (500 mg, 1.912 mmol) in DCM (4.8 mL) in a 4 dram vial. The reaction was stirred at room temperature for 5 min. The reaction mixture was concentrated under a stream of nitrogen at 50° C. and dried under high vacuum. The residue was taken up in EtOAc (10 mL) and extracted with saturated NaHCO₃ (2×2 mL). The organic layer was dried (Na₂SO₄), concentrated under a stream of nitrogen at 50° C., and dried under high vacuum, giving 501 mg of the title compound.

LC/MS: m/z 281.9.0 (M), Rt 0.88 min.

Example 81

5-[5-(1-Azetidinylsulfonyl)-2-thienyl]-3-(1,1-dioxidotetrahydro-2H-thiopyran-4-yl)-1H-indole-7-carboxamide

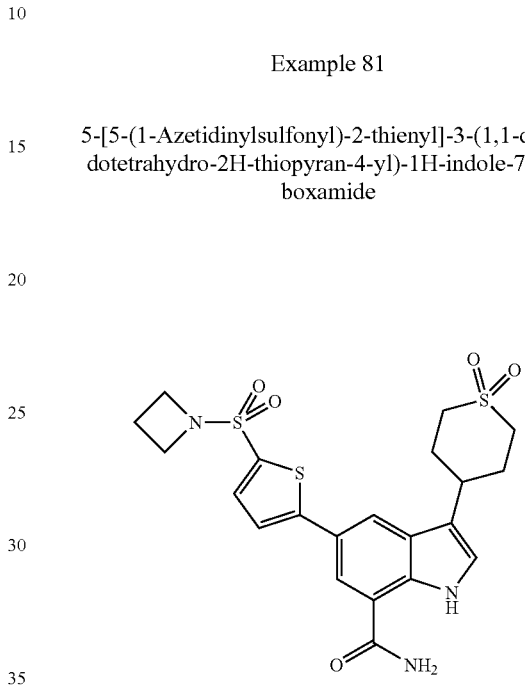

A mixture of 3-(1,1-dioxidotetrahydro-2H-thiopyran-4-yl)-5-(4,4,5,5-tetramethyl-1,3,2-dioxaborolan-2-yl)-1H-indole-7-carboxamide (21 mg, 0.050 mmol), 1-[(5-bromo-2-thienyl)sulfonyl]azetidine (28.3 mg, 0.100 mmol), and K₂CO₃ (20.81 mg, 0.151 mmol) in 1,4-dioxane (0.22 mL) and water (0.110 mL) was degassed with argon in a Biotage microwave vial for 10 min. PdCl₂(dppf) (3.67 mg, 5.02 μmol) was added, the vial was sealed, and the reaction was heated at 100° C. for 5 min in a Biotage microwave at high absorption. Additional PdCl2(dppf) (3.67 mg, 5.02 μmol) was added, and the reaction was heated at 130° C. in a Biotage microwave for 30 min on high absorption. The aqueous layer was removed via pipette, and the reaction mixture was filtered through a Stratosphere PL-Thio MP SPE cartridge (0.5 g), eluting with 1:1 DCM/MeOH (10 mL). The crude product was dissolved in DMSO (1.2 mL) and purified on a Gilson HPLC (XBridge C18 5 mm OBD 19×100 mm preparatory column), eluting at 15 mL/min with a linear gradient running from 20% CH₃CN/H₂O (0.1% NH₄OH) to 70% CH₃CN/H₂O (0.1% NH₄OH) over 18 min. The desired fractions were concentrated under a stream of nitrogen at 50° C., giving 11.9 mg of impure product. The impure product was dissolved in DMSO (1.2 mL) and purified on a Gilson HPLC (YMC C18 S-5 mm/12 nm 50×20 mm preparatory column), eluting at 20 mL/min with a linear gradient running from 20% CH₃CN/H₂O (0.1% TFA) to 70% CH₃CN/H₂O (0.1% TFA) over 10 min. The desired fractions were concentrated under a stream of nitrogen at 50° C., giving 6.1 mg (25%) of the title compound.

LC/MS: m/z 494.4 (M+H), Rt 1.37 min.

Example 82

3-(1,1-Dioxidotetrahydro-2H-thiopyran-4-yl)-5-(1H-indazol-5-yl)-1H-indole-7-carboxamide

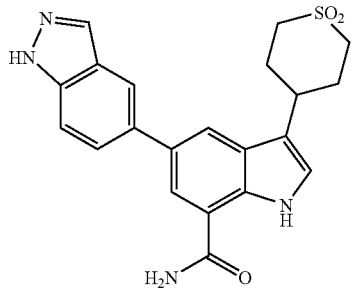

3-(1,1-dioxidotetrahydro-2H-thiopyran-4-yl)-5-(4,4,5,5-tetramethyl-1,3,2-dioxaborolan-2-yl)-1H-indole-7-carboxamide (0.085 g, 0.203 mmol) and 5-bromo-1H-indazole (0.048 g, 0.244 mmol, 1.2 eq) was dissolved in a 6:1 solution of 1,4 dioxane/water in a 20 mL microwave reaction vessel. Potassium carbonate (0.128, 0.929 mmol, 4.6 eq) was added and the solution was degassed with Argon. $PdCl_2(dppf)$ (0.023 g, 0.032 mmol, 0.16 eq) was added and the reaction was heated in a microwave at 100° C. for 20 min. Solution was passed through a StratoSphere SPE PL-Thiol MP SPE column to remove palladium and purified on Gilson preparative HPLC using Acetonitrile/Water with 0.1% TFA. 0.020 g (24%) product obtained.

LCMS m/z 409 (M+H), Rt 0.65 min.

Example 83

5-(4-Bromo-1,3-thiazol-2-yl)-3-(1,1-dioxidotetrahydro-2H-thiopyran-4-yl)-1H-indole-7-carboxamide

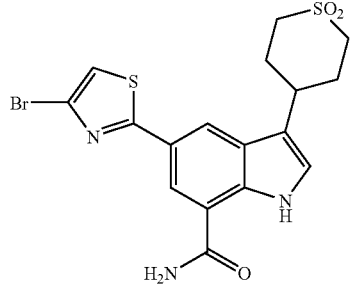

To a microwave vial was added 2,4-dibromo-1,3-thiazole (0.035 g, 0.143 mmol), 3-(1,1-dioxidotetrahydro-2H-thiopyran-4-yl)-5-(4,4,5,5-tetramethyl-1,3,2-dioxaborolan-2-yl)-1H-indole-7-carboxamide (0.060 g, 0.143 mmol) and potassium carbonate (0.059 g, 0.429 mmol) along with 1,4-dioxane (1.073 mL)/water (0.358 mL). The mixture was degassed with nitrogen and $Pd(PPh_3)_4$ (0.017 g, 0.014 mmol) was added. The reaction mixture was heated in the microwave under 'high' absorption setting for 40 minutes at 150° C. The reaction mixture was filtered through a Thiol SPE cartridge (500 mg) eluting with 1:1 MeOH/DCM (10 mL). The eluent was concentrated under nitrogen and purified by RP-HPLC on an X-Bridge C18 column with Acetonitrile/Water (0.1% $NH_4OH$), giving 3 mg (4.6%) of the title compound.

LCMS: m/z 455.8 (M+H) Rt 0.82 min.

Example 84

3-(1,1-Dioxidotetrahydro-2H-thiopyran-4-yl)-5-[5-(3-hydroxypropyl)-3-thienyl]-1H-indole-7-carboxamide

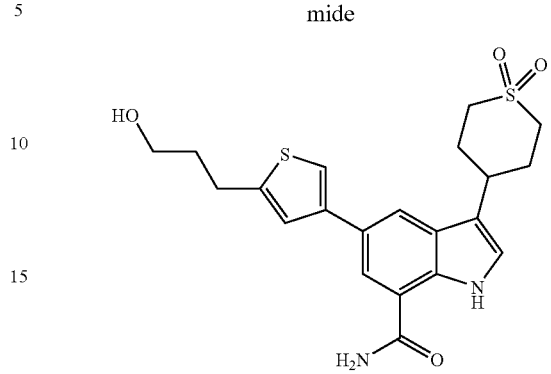

In a 5 mL microwave vial was added 3-(1,1-dioxidotetrahydro-2H-thiopyran-4-yl)-5-(4,4,5,5-tetramethyl-1,3,2-dioxaborolan-2-yl)-1H-indole-7-carboxamide (55 mg, 0.131 mmol), PdCl2(dppf)-CH2Cl2 adduct (17.18 mg, 0.021 mmol), and $K_2CO_3$ (83 mg, 0.601 mmol). Then 3-(4-bromo-2-thienyl)-1-propanol (37.8 mg, 0.171 mmol) in 1,4-dioxane (3 mL) was added to give an orange solution. Water (1.5 mL) was added and the solution was heated to 100° C. at high power in the microwave for 5 min, cooled. The reaction was filtered through a thiol paladium extraction column. The column was washed with $CH_2Cl_2$ and the combined filtrates were concentrated and purified on a Gilson HPLC ($NH_4OH$ buffer), giving 23 mg (41%) of the title compound.

LCMS m/z 433 (M+H), Rt 1.53 min.

Example 85

3-(1,1-Dioxidotetrahydro-2H-thiopyran-4-yl)-5-(1,3-thiazol-2-yl)-1H-indole-7-carboxamide

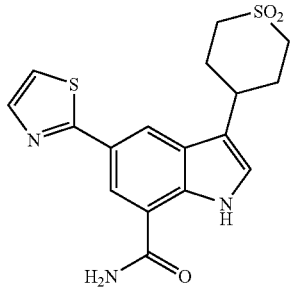

3-(1,1-dioxidotetrahydro-2H-thiopyran-4-yl)-5-(4,4,5,5-tetramethyl-1,3,2-dioxaborolan-2-yl)-1H-indole-7-carboxamide (60 mg, 0.14 mmol), 2-bromo-1,3-thiazole (29 mg, 1.2 eq), PdCl2(dppf)-CH2Cl2 adduct (19 mg, 0.02 mmol, 0.16 eq), potassium carbonate (90 mg, 4.6 eq) were diluted in a mixture of dioxane (3 mL) and water (1.5 mL) in a 2-5 mL biotage microwave reaction tube. After the mixture was degassed by bubbling argon through for 5 minutes, it was heated in a biotage microwave at normal absorption for 5 minutes at 10° C. The reaction mixture was filtered through a thiol SPE cartridge (polymer labs), then was concentrated and purified by ammonium hydroxide gilson hplc. The desired fractions were combined and concentrated in an EZ2 Genevac evaporator, giving the title compound (12 mg, 25%).

LC/MS: m/z 375.8 (M+H), Rt 1.65 min.

Following the procedure described above for 3-(1,1-dioxidotetrahydro-2H-thiopyran-4-yl)-5-(1,3-thiazol-2-yl)-1H-indole-7-carboxamide, 3-(1,1-dioxidotetrahydro-2H-thiopyran-4-yl)-5-(4,4,5,5-tetramethyl-1,3,2-dioxaborolan-2-yl)-1H-indole-7-carboxamide was reacted with an appropriate heteroaromatic bromide to give the compounds listed in Table 4.

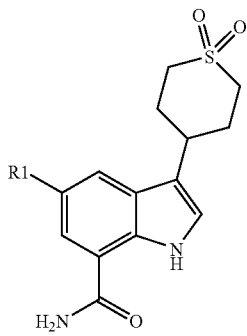

TABLE 4

| Example | R1 | MS [M]+/RT (min) Or NMR |
|---|---|---|
| 86 | [thiazolyl] | 375.8/1.46 |
| 87 | [methylthienyl] | 389.1/1.80 |
| 88 | [methylthienyl] | 389.1/1.81 |
| 89 | [methylthienyl] | 389.1/1.76 |
| 90 | [dimethylpyrazolyl] | 400.9/1.27 |
| 91 | [chlorothienyl] | 409.0/1.91 |
| 92 | [cyanothienyl] | 399.9/1.72 |
| 93 | [methylthienyl] | 389.0/1.74 |
| 94 | [thiazolyl] | 1H NMR (400 MHz, d6-DMSO) δ 11.00 (s, 1H), 9.25 (s, 1H), 8.45 (s, 1H), 8.30 (s, 1H), 8.21 (bs, 1H), 8.05 (s, 1H), 7.45 (bs, 1H), 7.22 (s, 1H), 3.48 (tr, 2H), 3.30 (s, 1H), 3.15 (d, 2H), 2.35 (d, 2H), 2.20 (dd, 2H). |
| 95 | [methylthiazolyl] | 390.1/1.49 |
| 96 | [cyanothienyl] | 399.9/1.56 |

Intermediates

Thiophene Ethers

Intermediate 135

(5-Bromo-2-thienyl)methanol

Bromothiophene carboxaldehyde (4.8 g, 25.1 mmol) was dissolved in ethanol (30 mL) and cooled to 0° C. A suspension of sodium borohydride (0.5 g, 13.2 mmol) in ethanol (15 mL) was added to the aldehyde solution over 15 minutes, and the mixture was stirred at room temperature for 5 h. Glacial acetic acid was added dropwise until effervescence ceased, and the resultant solution was evaporated. The residue was dissolved in diethyl ether, washed with water, and the aqueous layer extracted twice with ether. The combined organics were dried over sodium sulfate, filtered, and concentrated. The crude product was purified by flash chromatography eluting with EtOAc/hexanes, giving 4.1 g (84%) of the title compound.

Alkylation of (4-bromo-2-thienyl)methanol and (5-bromo-2-thienyl)methanol

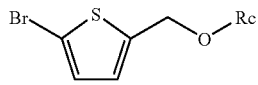

The alcohol (prepared as shown above or using the commercially available (4-Bromo-2-thienyl)methanol, 150 mg, 0.78 mmol) was dissolved in dry tetrahydrofuran (0.15-0.2 M solution), and sodium hydride (95%, 1.1-1.5 equiv) was added. The mixture was stirred for approximately 5 minutes until gas evolution ceased, and the appropriate alkyl iodide (1.1-1.5 equiv) was added. The mixture was stirred at rt overnight, then was carefully quenched by the addition of water. The mixture was then extracted with dichloromethane and the combined organics were concentrated. The crude oil was purified by Isco Combiflash, eluting with ethyl acetate in hexanes. Fractions containing the desired were concentrated to afford the products as oils.

Proceeding in the similar procedure as described above, the compounds listed in Table 5 were prepared.

TABLE 5

| Intermediate | Structure | NMR |
|---|---|---|
| 136 | Br-thienyl-CH₂-O-CH₃ | $^1$H NMR (400 MHz, $d_6$-DMSO) δ 6.94 (d, 1H), 6.78 (d, 1H), 4.55 (s, 2H), 3.39 (s, 3H). |
| 137 | Br-thienyl-CH₂-O-Et | $^1$H NMR (400 MHz, $d_6$-DMSO) δ 6.93 (d, 1H), 6.77 (d, 1H), 4.59 (s, 2H), 3.55 (q, 2H), 1.25 (t, 3H). |
| 138 | 4-Br-thienyl-CH₂-O-Et | $^1$H NMR (400 MHz, $d_6$-DMSO) δ 7.10 (s, 1H), 6.84 (s, 1H), 4.53 (s, 2H), 3.48 (q, 2H), 1.16 (t, 3H). |
| 139 | Br-thienyl-CH₂-O-Pr | $^1$H NMR (400 MHz, $d_6$-DMSO) δ 6.93 (d, 1H), 6.75 (d, 1H), 4.59 (s, 2H), 3.45 (q, 2H), 1.63 (m, 2H), 0.95 (t, 3H). |
| 140 | 4-Br-thienyl-CH₂-O-Pr | $^1$H NMR (400 MHz, $d_6$-DMSO) δ 7.19 (s, 1H), 6.93 (s, 1H), 4.63 (s, 2H), 3.46 (t, 2H), 1.64 (m, 2H), 0.96 (t, 3H). |

Intermediates 2-(5-bromo-2-thienyl)ethyl alkyl ethers

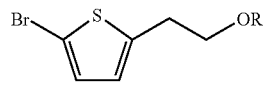

Intermediate 141

2-(5-Bromo-2-thienyl)ethanol

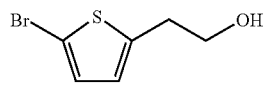

2-(2-thienyl)ethanol (Aldrich, 5.0 g, 39 mmol) was diluted in toluene (50 mL) and cooled to −20° C. using an ice/NaCl bath. NBS (6.95 g, 39 mmol, 1 eq) was added portionwise over 15 minutes and the mixture was stirred at rt overnight. After quenching with 10% aq potassium hydroxide (20 mL), the layers were separated and the aqueous layer was extracted twice with dichloromethane (50 mL). The combined organic layers were dried over sodium sulfate, filtered, and concentrated. Purification by Isco Combiflash, eluting with 0-80% ethyl acetate in hexanes (120 g column), afforded the desired as a slightly yellow oil (6.72 g, 83%).

2-Bromo-Thiophene Ethers

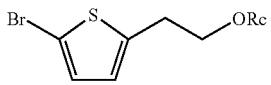

2-(5-bromo-2-thienyl)ethanol (250 mg, 1.2 mmol) was diluted in dry tetrahydrofuran (5 mL). Sodium hydride (95%, 46 mg, 1.8 mmol, 1.5 eq) was added, and the mixture was stirred at rt for 5 minutes. The appropriate alkyl iodide (1.8 mmol, 1.5 eq) was added, and the mixture was stirred at rt over the weekend. The reaction mixtures were quenched by the careful addition of water, then extracted with ethyl acetate (20 mL), followed by dichloromethane (20 mL). The combined organics were dried over sodium sulfate, filtered, and concentrated. The residue was purified by Isco Combiflash, 12 or 40 g column (depending on crude reaction purity), eluting with 0-25% ethyl acetate in hexanes. The product fractions were combined and concentrated to afford the title compound s as clear colorless oils.

Proceeding in the similar procedure as described above, the compounds listed in Table 6 were prepared.

TABLE 6

| Intermediate | Structure | NMR |
|---|---|---|
| 142 | Br-thienyl-CH₂CH₂-O-CH₃ | $^1$H NMR (400 MHz, CDCl₃) δ 6.90 (d, 1H), 6.67 (d, 1H), 3.64 (t, 2H), 3.40 (s, 3H), 3.05 (t, 2H) |

TABLE 6-continued

| Intermediate | Structure | NMR |
|---|---|---|
| 143 | Br-[thiophene]-CH2CH2-O-CH2CH3 | ¹H NMR (400 MHz, CDCl₃) δ 6.91 (d, 1H), 6.63 (d, 1H), 6.63 (d, 1H), 3.68 (t, 3H), 3.52 (q, 2H), 3.05 (t, 2H), 1.27 (t, 2H) |

Intermediate 144

2-Bromo-5-(methyloxy)thiophene

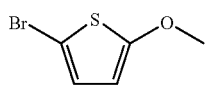

2-methoxythiophene (1 mL, 9.9 mmol, 1.8 eq) was diluted in carbon tetrachloride (2 mL) and cooled to 0° C. NBS (1.0 g, 5.6 mmol) was added in a single portion, resulting in an exotherm. The mixture was heated at reflux for 10 minutes, then was cooled to rt and treated with saturated aq. sodium bicarbonate. Following extraction with dichloromethane, the combined organics were dried over sodium sulfate, filtered, and concentrated to give the crude product as yellowish brown oil. The oil was further purified by Isco Combiflash, 40 gram column, eluting with 0-20% ethyl acetate in hexanes. The desired was obtained as clear colorless oil.

Intermediates

Bromothienylmethyl Alkyl Amines and Bromofuranylmethyl Alkyl Amines

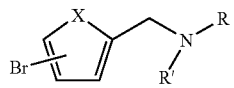

Aldehyde (1 mmol) was diluted in dichloromethane (6 mL) and N,N-dimethylformamide (2 mL). The appropriate amine (1.5 mmol, 1.5 eq) was added at 0° C., followed by sodium triacetoxyborohydride (1.0 g, 4.9 mmol, 4.9 eq) and glacial acetic acid (2 drops). The mixture was stirred at rt for 3 h, then was carefully quenched by the addition of saturated aqueous sodium bicarbonate. The mixture was extracted with ethyl acetate, and the combined organics were dried over sodium sulfate, filtered, and concentrated. The crude products were purified by isco combiflash, 12 or 40 g column (depending on cleanliness of crude tlc), eluting with 0-70% ethyl acetate in hexanes. Desired reductive amination products were obtained as oils.

Proceeding in the similar procedure as described above, the compounds listed in Table 7 were prepared.

TABLE 7

| Intermediate | Structure | NMR |
|---|---|---|
| 145 | 4-bromo-thiophen-2-ylmethyl morpholine | ¹H NMR (400 MHz, CDCl₃) δ 7.15 (s, 1H), 6.85 (s, 1H), 3.75 (m, 4H), 3.68 (s, 2H), 2.55 (bs, 4H), |
| 146 | 5-bromo-thiophen-2-ylmethyl morpholine | ¹H NMR (400 MHz, CDCl₃) δ 6.92 (d, 1H), 6.71 (d, 1H), 3.75 (m, 4H), 3.68 (s, 2H), 2.54 (bs, 4H). |
| 147 | 5-bromo-furan-2-ylmethyl morpholine | ¹H NMR (400 MHz, CDCl₃) δ 6.27 (d, 1H), 6.21 (d, 1H), 3.77 (m, 4H), 3.51 (s, 2H), 2.51 (m, 4H), |
| 148 | 5-bromo-thiophen-2-ylmethyl azepane | ¹H NMR (400 MHz, CDCl₃) δ 6.89 (d, 1H), 6.63 (d, 1H), 3.75 (s, 2H), 2.68 (m, 4H), 1.65 (m, 8H), |
| 149 | 5-bromo-furan-2-ylmethyl azepane | ¹H NMR (400 MHz, CDCl₃) δ 6.17 (d, 1H), 6.10 (d, 1H), 3.55 (s, 2H), 2.60 (m, 4H), 1.65 (m, 8H), |
| 150 | 4-bromo-furan-2-ylmethyl morpholine | ¹H NMR (400 MHz, CDCl₃) δ 7.19 (s, 1H), 6.21 (s, 1H), 3.68 (m, 4H), 3.43 (s, 2H), 2.42 (bs, 4H), |
| 151 | 4-bromo-furan-2-ylmethyl azepane | ¹H NMR (400 MHz, CDCl₃) δ 7.20 (s, 1H), 6.20 (s, 1H), 3.58 (s, 2H), 2.60 (m, 4H), 1.65 (m, 8H), |
| 152 | 5-bromo-furan-2-ylmethyl N-methylpiperazine | ¹H NMR (400 MHz, CDCl₃) δ 6.24 (d, 1H), 6.20 (d, 1H), 3.54 (s, 2H), 2.46 (m, 8H), 2.30 (s, 3H) |
| 153 | 5-bromo-furan-2-ylmethyl 1,4-oxazepane | ¹H NMR (400 MHz, CDCl₃) δ 6.24 (d, 1H), 6.20 (d, 1H), 3.81 (t, 2H), 3.76 (t, 2H), 3.74 (s, 2H), 2.76 (m, 4H), 1.84 (m, 2H) |

TABLE 7-continued

| Intermediate | Structure | NMR |
|---|---|---|
| 154 | 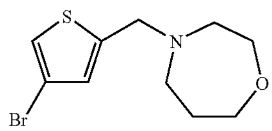 | ¹H NMR (400 MHz, CDCl₃) δ 7.15 (s, 1H), 6.85 (s, 1H), 3.83 (s, 2H), 3.82 (t, 2H), 3.75 (t, 2H), 2.77 (m, 4H), 1.94 (m, 2H) |
| 155 | 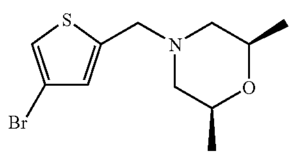 | ¹H NMR (400 MHz, CDCl₃) δ 7.16 (s, 1H), 6.86 (s, 1H), 3.70 (m, 2H), 3.68 (s, 2H), 2.78 (d, 2H), 1.81 (t, 2H), 1.18 (d, 6H) |

Intermediates (Bromo-alkylthio)methyl thiophenes

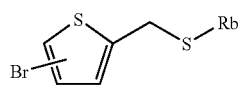

An alcohol (1 mmol) was diluted in 1,2-dichloroethane (2 mL). Zinc iodide (319 mg, 1 mmol) was added, followed by the appropriate thiol (2 mmol, 2 eq) and the mixture was stirred at rt overnight. The reaction was quenched with 0.5 M aqueous sodium hydroxide, then was extracted with dichloromethane using a phase separator device. The combined organic extracts were dried over sodium sulfate, filtered, and concentrated to afford the desired thioethers.

Proceeding in the similar procedure as described above, the compounds listed in Table 8 were prepared.

TABLE 8

| Intermediate | Structure | NMR |
|---|---|---|
| 156 | 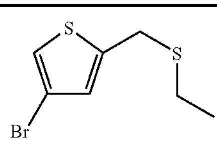 | ¹H NMR (400 MHz, CDCl₃) δ 7.05 (s, 1H), 6.77 (s, 1H), 3.78 (s, 2H), 2.41 (q, 2H), 1.15 (t, 3H), |
| 157 | 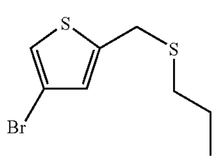 | |
| 158 | 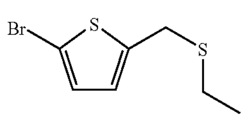 | |
| 159 | 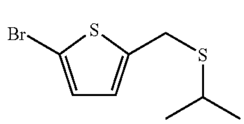 | ¹H NMR (400 MHz, CDCl₃) δ 6.75 (d, 1H), 6.58 (d, 1H), 3.78 (s, 2H), 2.80 (m, 1H), 1.19 (d, 6H), |

TABLE 8-continued

| Intermediate | Structure | NMR |
|---|---|---|
| 160 | 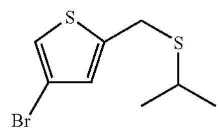 | ¹H NMR (400 MHz, CDCl₃) δ 7.05 (s, 1H), 6.71 (s, 1H), 2.75 (d, 2H), 1.90 (m, 1H), 0.97 (d, 6H), |
| 161 | 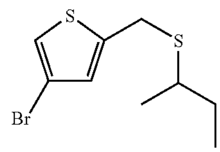 | |

Intermediate 162

2-Methyl-1-(2-thienyl)-1-propanone

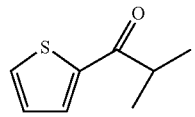

Aluminum chloride (4.75 g, 35.7 mmol, 3 eq) was diluted in ice cold dichloromethane (30 mL). Isobutyryl chloride (4 mL, 38 mmol, 3.2 eq) in dichloromethane (30 mL) was added to the aluminum chloride suspension at 0° C., and the mixture was stirred at 0° C. for 30 minutes. Thiophene (1 g, 11.9 mmol) was added as a solution in dichloromethane (30 mL) over 10 minutes. The reaction was stirred at 0° C. for 30 minutes, then at rt for 1 h. Bromine (0.65 mL, 12.6 mmol, 1.1 eq) was added dropwise at 0° C., and the reaction mixture was slowly warmed to rt overnight. The mixture was cooled to 0° C., and was carefully quenched by the dropwise addition of water. The reaction mixture was extracted with dichloromethane, and the combined organics washed with saturated aqueous sodium bicarbonate. The combined organics were then dried over sodium sulfate, filtered, and concentrated. The crude product was purified by isco combiflash, eluting with 0-10% ethyl acetate in hexanes to afford a slightly yellow oil (2.3 g, >100%).

Intermediate 163

1-(4-Bromo-2-thienyl)-2-methyl-1-propanone

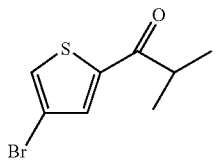

2-methyl-1-(2-thienyl)-1-propanone (2.3 g, 15 mmol) was diluted in chloroform (10 mL), and aluminum chloride (4.5 g, 34 mmol, 2.3 eq) was added. Bromine (0.82 mL, 16 mmol, 1.1 eq) was added as a solution in chloroform (15 mL), and the mixture was stirred at rt over the weekend. The crude reaction mixture was carefully poured onto ice water, then extracted with chloroform. The combined organics were dried over sodium sulfate, filtered, and concentrated to afford brown oil.

The crude was purified by isco combiflash to give the title compound as brown oil (1.28 g, 40%).

Intermediate 164

4-Bromo-2-(2-methylpropyl)thiophene

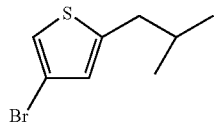

1-(4-bromo-2-thienyl)-2-methyl-1-propanone (816 mg, 3.52 mmol) was diluted in ethylene glycol (3 mL). Hydrazine monohydrate (0.46 mL, 9.5 mmol, 2.7 eq) was added, and the mixture was heated to 160° C. for 1.5 h behind a blast shield. The mixture was cooled to rt, and diluted with water. 6 M aqueous HCl was added until pH was acidic (pH paper), and the mixture was extracted three times with hexanes. The combined organics were dried over sodium sulfate, filtered, and concentrated. The crude product was purified by biotage, 25M+ column, eluting with 5% ethyl acetate in hexanes. Fractions containing the desired product were concentrated in vacuo to afford the title compound as light yellow oil (192 mg, 25%).

Intermediate 165

(4-Bromo-2-thienyl)(cyclopropyl)methanone

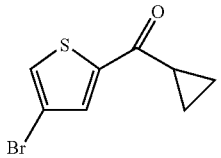

Cyclopropyl(2-thienyl)methanone (Aldrich, 1.5 g, 9.9 mmol) was diluted in chloroform (10 mL). Aluminum chloride (2.96 g, 22.2 mmol, 2.3 eq) was added, followed by the dropwise addition of bromine (0.56 mL, 11 mmol, 1.1 eq) in chloroform (10 mL). The mixture was stirred at rt overnight, then poured onto ice water (100 mL). The whole was extracted with dichloromethane, and the combined organic layers were dried over sodium sulfate, filtered, and concentrated to give brown oil. The crude product was purified by isco combiflash, 120 g column, eluting with 0-15% ethyl acetate in hexanes. Yellow oil was obtained.

Intermediate 166

4-Bromo-2-(cyclopropylmethyl)thiophene

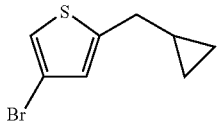

(4-bromo-2-thienyl)(cyclopropyl)methanone (1.02 g, 4.4 mmol) was diluted in ethylene glycol (3.75 mL). Potassium hydroxide (809 mg, 14.4 mmol, 3.3 eq) and hydrazine hydrate (0.58 mL, 18 mmol, 4.2 eq) were added, and the reaction mixture was heated at 160° C. for 45 minutes behind a blast shield. The reaction was cooled to room temperature, water was added, and the pH adjusted to acidic (by pH paper) with 6M aqueous HCl. The mixture was extracted with dichloromethane, the combined organics dried over sodium sulfate, filtered, and concentrated. The crude product was purified by isco combiflash, eluting with 0-10% ethyl acetate in hexanes. The title compound was obtained as clear colorless oil (50 mg, 5%).

Example 97

5-[5-(Cyclopropylmethyl)-3-thienyl]-3-(1,1-dioxidotetrahydro-2H-thiopyran-4-yl)-1H-indole-7-carboxamide

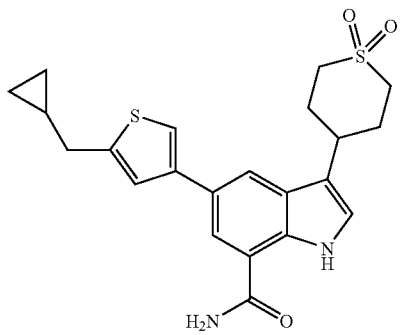

4-Bromo-2-(cyclopropylmethyl)thiophene (50 mg, 0.23 mmol), 3-(1,1-dioxidotetrahydro-2H-thiopyran-4-yl)-5-(4,4,5,5-tetramethyl-1,3,2-dioxaborolan-2-yl)-1H-indole-7-carboxamide (80 mg, 0.19 mmol) and $K_2CO_3$ (105 mg, 0.76 mmol) was taken up in 1,4-dioxane (3 mL) and water (1.5 mL) in a microwave vial. The mixture was degassed by bubbling argon through it for 5 min. $PdCl_2(dppf).DCM$ adduct (25 mg, 0.031 mmol) was added, and the reaction was heated in a microwave for 5 min at 100° C. The reaction mixture was concentrated, diluted in DMSO, and purified on a Gilson HPLC ($NH_4OH$ buffer). The desired fractions were concentrated, giving 18 mg (22%) of the title compound.

LCMS: m/z 428.9 (M−32) Rt 0.99 min.

Intermediate 167

(5-Bromo-2-furanyl)methanol

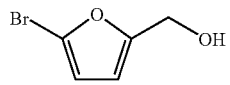

5-bromo-2-furancarbaldehyde (1 g, 0.23 mmol) was dissolved in ethanol (7.5 mL) and cooled to 0° C. Sodium borohydride (114 mg) in ethanol (2.5 mL) was added to the aldehyde solution over 15 minutes, and the mixture was stirred at room temperature for 20 mins. Glacial acetic acid was added dropwise until effervescence ceased, and the resultant solution was evaporated. The residue was dissolved in diethyl ether, washed with water, and the aqueous layer extracted twice with ether. The combined organics were dried over sodium sulfate, filtered, and concentrated to give the title compound as an oil which was used in the next step directly without purification.

$^1$H NMR (400 MHz, $CDCl_3$) δ 6.30 (dd, 2H), 2.11 (s, 2H).

Intermediate 168

2-Bromo-5-[(methyloxy)methyl]furan

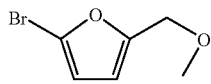

Sodium hydride (95%, 28 mg, 1.12 mmol) was diluted in dry DMF (1 mL) and cooled to 0° C. (5-bromo-2-furanyl)methanol (177 mg, 1 mmol) in DMF (2 mL) was added, and the mixture was stirred for 5 minutes. Methyl iodide (0.07 mL, 1.12 mmol) was added, and the mixture was stirred at room temperature overnight. The reaction mixture was quenched by the careful addition of water, then extracted with ethyl acetate (20 mL), followed by dichloromethane (20 mL). The combined organics were dried over sodium sulfate, filtered, and concentrated. The residue was purified by flash chromatography, eluting with EtOAc/hexanes. The desired fractions were combined and concentrated, giving 40 mg (21%) of the title compound.

$^1$H NMR (400 MHz, CDCl$_3$) δ 6.32 (d, 1H), 6.27 (d, 1H), 4.36 (s, 2h), 3.38 (s, 1H).

Intermediate 169

2-Bromo-5-[(ethyloxy)methyl]furan

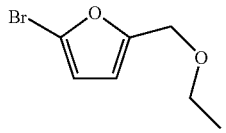

Sodium hydride (95%, 19 mg, 0.75 mmol) was diluted in dry DMF (0.5 mL) and cooled to 0° C. A solution of (5-bromo-2-furanyl)methanol (120 mg, 0.68 mmol) was added, and the mixture was stirred for 5 minutes. Ethyl iodide (117 mg, 0.75 mmol) was added, and the mixture was stirred at rt overnight. The reaction mixtures were quenched by the careful addition of water, then extracted with diethyl ether. The combined organics were dried and concentrated. The residue was purified by flash chromatography, eluting with 10% EtOAc/hexanes. The desired fractions were combined and concentrated to afford the title compound.

$^1$H NMR (400 MHz, CDCl$_3$) δ 6.30 (dd, 2H), 4.40 (s, 2h), 3.56 (q, 2H), 1.26 (t, 3H).

Intermediate 170

2-Bromo-5-[(ethylthio)methyl]furan

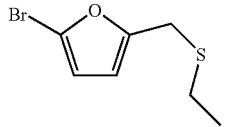

(5-bromo-2-furanyl)methanol (177 mg, 1 mmol) was diluted in 1,2-dichloroethane (2 mL). Zinc iodide (319 mg, 1 mmol) was added, followed by the appropriate ethyl thiol (2 mmol, 0.15 mL) and the mixture was stirred at room temperature overnight. The reaction was quenched with 1 M aqueous sodium hydroxide, then was extracted with dichloromethane using a phase separator device. The combined organic extracts were dried over sodium sulfate, filtered, and concentrated to afford the desired thioethers (78.7 mg).

$^1$H NMR (400 MHz, CDCl$_3$) δ 6.23 (d, 1H), 6.16 (d, 1H), 3.70 (s, 2h), 2.55 (q, 2H), 1.28 (t, 3H).

Intermediates

1-[(5-Bromo-2-thienyl)sulfonyl]amines

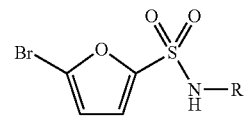

5-bromo-2-thiophenesulfonyl chloride (523 mg, 2 mmol) was dissolved in dichloromethane (20 mL). Pyrrolidine (3 mmol, 1.5 eq) and potassium carbonate (829 mg, 6 mmol, 3 eq) are added, and the mixture was stirred at rt for 1 h. After tlc (30% ethyl acetate in hexanes) indicated that the reaction had gone to completion, brine was added and the mixture was extracted with dichloromethane. The combined organic layers were dried over sodium sulfate, filtered, and concentrated. The crude product was purified by isco combiflash, eluting with 0-50% ethyl acetate in hexanes (40 g column).

Proceeding in the similar procedure as described above, the compounds listed in Table 9 were prepared.

TABLE 9

| Intermediate | Structure | NMR |
|---|---|---|
| 171 | ![structure] | $^1$H NMR (400 MHz, CDCl$_3$) δ 7.36 (d, 1H), 7.14 (d, 1H), 3.31 (t, 4H), 1.84 (t, 4H). |
| 172 | ![structure] | $^1$H NMR (400 MHz, CDCl$_3$) δ 7.38 (d, 1H), 7.07 (d, 1H), 4.44 (br m, 1H), 3.29 (m, 1H), 1.72 (m, 1H), 1.07 (d, 3H), 0.88 (d, 6H) |

Example 98

3-(1,1-Dioxidotetrahydro-2H-thiopyran-4-yl)-5-{5-[(methyloxy)methyl]-2-thienyl}-1H-indole-7-carboxamide

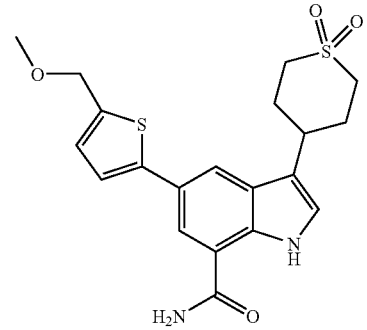

2-Bromo-5-[(methyloxy)methyl]thiophene (35 mg, 0.16 mmol), 3-(1,1-dioxidotetrahydro-2H-thiopyran-4-yl)-5-(4,4,5,5-tetramethyl-1,3,2-dioxaborolan-2-yl)-1H-indole-7-carboxamide (55 mg, 0.13 mmol) and K₂CO₃ (83 mg, 0.14 mmol) was taken up in 1,4-dioxane (3 mL) and water (1.5 mL) in a microwave vial. The mixture was degassed by bubbling argon through it for 5 min. PdCl₂(dppf) (17 mg, 0.023 mmol) was added, and the reaction was heated in a microwave for 5 min at 100° C. The reaction mixture was concentrated, diluted in DMSO, and purified on a Gilson HPLC (NH₄OH buffer), giving 18.2 mg (43%) of the title compound.

LCMS: m/z 386.9 (M−32) Rt 1.76 min.

Following the procedure described above for the preparation of 3-(1,1-dioxidotetrahydro-2H-thiopyran-4-yl)-5-{5-[(methyloxy)methyl]-2-thienyl}-1H-indole-7-carboxamide, 3-(1,1-dioxidotetrahydro-2H-thiopyran-4-yl)-5-(4,4,5,5-tetramethyl-1,3,2-dioxaborolan-2-yl)-1H-indole-7-carboxamide was reacted with an appropriate heteroaromatic bromide, giving the compounds listed in Table 10. Note: Examples with a "*" were prepared using PdCl₂(dppf).DCM adduct in place of PdCl₂(dppf).

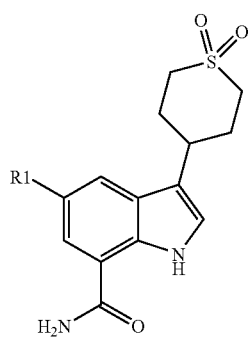

TABLE 10

| Example | R1 | MS [M]⁺/RT (min) Or NMR |
|---|---|---|
| 99 | | 431.1/1.76 |
| 100 | | 433.1/1.76 |
| 101 | | 446.4/1.91 |
| 102 | | 447.3/1.91 |
| 103 | | 474.3/1.42 |
| 104 | | 433.2/2.04 |
| 105 | | 447.3/2.07 |
| 106 | | 405.1/1.97 |
| 107 | | 474.3/1/42 |
| 108 | | 458.1/1.38 |

TABLE 10-continued
| Example | R1 | MS [M]⁺/RT (min) Or NMR |
|---|---|---|
| 109 | 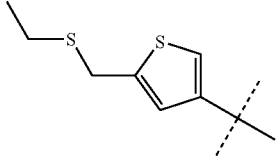 | 448.8/1.59 |
| 110 | 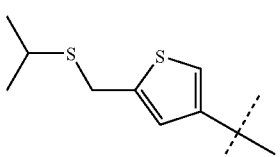 | 463.0/1.69 |
| 111 | 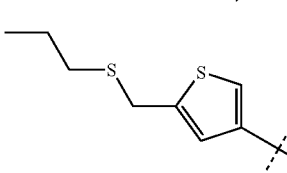 | 463.0/1.70 |
| 112 | 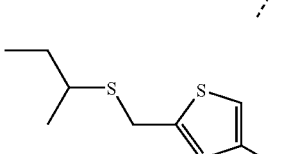 | 476.8/1.82 |
| 113 | 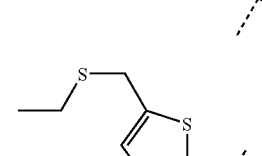 | 386.8/1.58 [M − 48]⁺ |
| 114 | 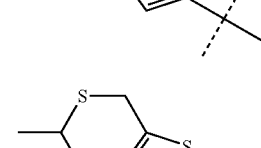 | 462.1/2.34 |
| 115 | 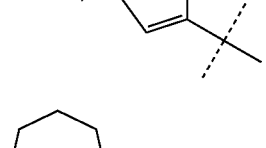 | 470.3/1.60 |
| 116 | 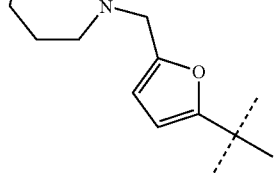 | 486.2/1.64 |
| 117 | 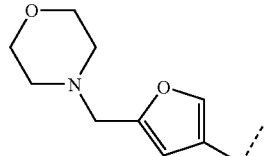 | 458.1/1.44 |
| 118 | 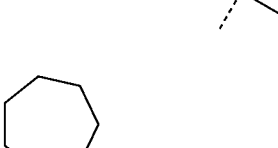 | 470.3/1.58 |
| 119 | 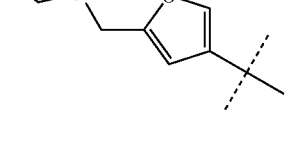 | 431.0/2.41 |
| 120 | 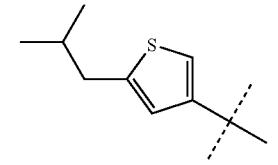 | 416.2/0.79 |
| 121 | 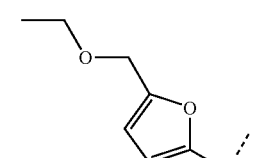 | 405.1/0.66 |
| 122 | 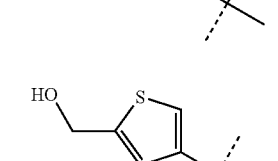 | 488.3/0.56 |
| 123 |  | 472.5/0.53 |

TABLE 10-continued

| Example | R1 | MS [M]+/RT (min) Or NMR |
|---|---|---|
| 124 | (2,6-dimethylmorpholin-4-yl)methyl-thiophene-tBu | 502.3/0.62 |
| 125 | (4-methylpiperazin-1-yl)methyl-furan-tBu | 471.4/0.53 |
| 126 | ethylthiomethyl-furan-tBu | 433.1/0.88 |
| 127 | methoxymethyl-furan-tBu | 401.9/0.73 |
| 128* | pyrrolidin-1-ylsulfonyl-thiophene-tBu | 508.1/0.83 |
| 129* | N-(3-methylbutan-2-yl)sulfamoyl-thiophene-tBu | 524.3/0.90 |
| 130* | HO-CH2CH2-SO2-CH2-thiophene-tBu | 387.0/0.66 [M − 109]+ |
| 131* | HO-CH2CH2-thiophene-tBu | 419.3/0.71 |
| 132* | HO-CH2-thiophene-tBu | 387.0/0.67 [M − 17]+ |
| 133* | 1-methylimidazol-2-yl-tBu | 372.9/0.45 |
| 134* | 1-methylimidazol-2-yl-thiophene-tBu | 454.9/0.56 |
| 135* | 1H-imidazol-2-yl-thiophene-tBu | 441.2/0.55 |
| 136* | 1-methylimidazol-2-yl-thiophene-tBu | 454.9/0.56 |
| 137* | imidazol-1-yl-phenyl-tBu | 435.2/0.81 |
| 138* | isoxazol-5-yl-thiophene-tBu | 442.2/0.81 |

TABLE 10-continued

| Example | R1 | MS [M]+/RT (min) Or NMR |
|---|---|---|
| 139* | 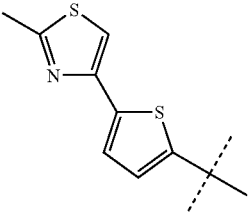 | 472.4/0.86 |

Example 140

5-(3,5-Dimethyl-1H-pyrazol-4-yl)-3-(1,1-dioxidotetrahydro-2H-thiopyran-4-yl)-1H-indole-7-carboxamide

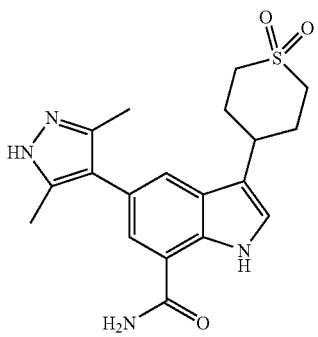

4-Bromo-3,5-dimethyl-1H-pyrazole (35 mg, 0.2 mmol), 3-(1,1-dioxidotetrahydro-2H-thiopyran-4-yl)-5-(4,4,5,5-tetramethyl-1,3,2-dioxaborolan-2-yl)-1H-indole-7-carboxamide (30 mg, 0.072 mmol) and $K_2CO_3$ (50 mg, 0.36 mmol) was taken up in a 3:1 mixture of 1,4-dioxane/water (2 mL) in a microwave vial. The mixture was degassed by bubbling argon through it for 5 min. $PdCl_2$(dppf) (8 mg, 0.011 mmol) was added, and the reaction was heated in a microwave for 10 min at 120° C. The reaction mixture was concentrated, diluted in DMSO, and purified on a Gilson HPLC ($NH_4OH$ buffer), giving 3 mg (11%) of the title compound.

LCMS: m/z 387 (M−32) Rt 1.06 min.

Proceeding in the similar procedure as described above for the preparation of 5-(3,5-dimethyl-1H-pyrazol-4-yl)-3-(1,1-dioxidotetrahydro-2H-thiopyran-4-yl)-1H-indole-7-carboxamide, 3-(1,1-dioxidotetrahydro-2H-thiopyran-4-yl)-5-(4,4,5,5-tetramethyl-1,3,2-dioxaborolan-2-yl)-1H-indole-7-carboxamide was reacted with an appropriate aromatic or heteroaromatic bromide, giving the compounds listed in Table 11.

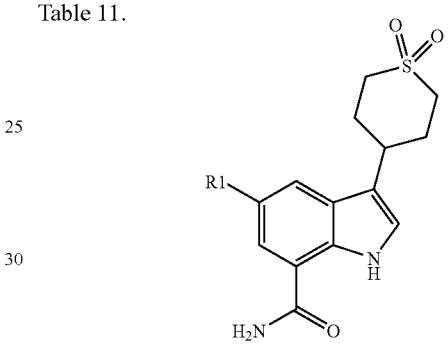

TABLE 11

| Example | R1 | MS [M]+/RT |
|---|---|---|
| 141 | 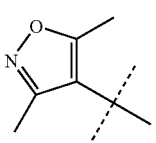 | 388/1.40 min |
| 142 | 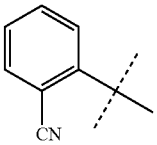 | 394/1.53 min |
| 143 | 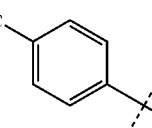 | 394/1.66 min |
| 144 | 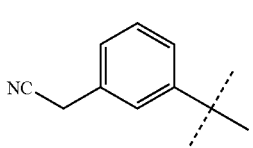 | 408/1.61 min |

TABLE 11-continued

| Example | R1 | MS [M]+/RT |
|---|---|---|
| 145 | (5-tert-butyl-2,3-dihydro-1H-indole) | 410/1.06 min |
| 146 | (2-cyano-5-tert-butyl-3-fluorophenyl) | 412/1.76 min |
| 147 | (2-tert-butylbenzamide) | 412/1.22 min |
| 148 | (3-tert-butyl-N,N-dimethylaniline) | 412/1.18 min |
| 149 | (2-(3-tert-butylphenyl)ethanol) | 413/1.54 min |
| 150 | (2-(2-tert-butylphenyl)ethanol) | 413/1.47 min |
| 151 | (5-fluoro-2-methoxy-tert-butylphenyl) | 417/1.70 min |
| 152 | (3-chloro-4-methyl-tert-butylphenyl) | 417/1.97 min |
| 153 | (4-cyano-2-tert-butyl-anisole) | 424/1.62 min |

TABLE 11-continued

| Example | R1 | MS [M]+/RT |
|---|---|---|
| 154 | 2-MeO, 5-position, with CN (3-cyano-4-methoxyphenyl) | 424/1.72 min |
| 155 | 2-MeO, 3-(hydroxymethyl)phenyl | 429/1.41 min |
| 156 | 4-(2-hydroxyethoxy)phenyl | 430/1.40 min |
| 157 | 2-MeO, 3-(cyanomethyl)phenyl | 439/1.68 min |
| 158 | 4-(diethylamino)phenyl | 441/1.21 min |
| 159 | 4-(2-oxopyrrolidin-1-yl)phenyl | 453/1.55 min |
| 160 | 5-[2-(N-(1-hydroxybutan-2-yl)sulfamoyl)ethyl]thiophen-2-yl | 555/1.53 min |
| 161 | 4-[2-(N-(4-hydroxycyclohexyl)sulfamoyl)ethyl]thiophen-2-yl | 580/1.51 min |

TABLE 11-continued

| Example | R1 | MS [M]+/RT |
|---|---|---|
| 162 | ![structure with HO-CH2CH2-NH-SO2-CH2CH2-thiophene-tBu] | 527/1.41 min |
| 163 | ![structure with CHF2-thiophene-tBu] | 425/1.80 min |
| 164 | ![structure with Cl-thiophene-tBu] | 409/1.75 min |
| 165 | ![structure with N-methyl, CF3 pyrazole-tBu] | 441/1.49 min |
| 166 | ![structure with dimethylthiazole-tBu] | 404/1.23 min |
| 167 | ![structure with methylthiazole-tBu] | 390/1.43 min |

Example 168

3-(1,1-Dioxidotetrahydro-2H-thiopyran-4-yl)-6-fluoro-5-phenyl-1H-indole-7-carboxamide

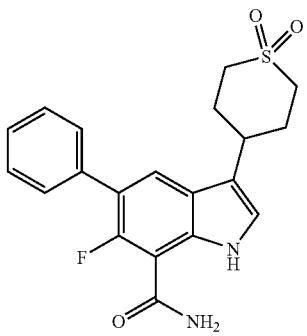

A mixture of 5-bromo-3-(1,1-dioxidotetrahydro-2H-thiopyran-4-yl)-6-fluoro-5,6-dihydro-1H-indole-7-carboxamide (9.2 mg, 0.024 mmol), phenylboronic acid (5.73 mg, 0.047 mmol), and K$_2$CO$_3$ (9.75 mg, 0.071 mmol) was taken up in 1,4-dioxane (0.3 mL) and water (0.150 mL). The mixture was degassed with argon for 10 min, and PdCl$_2$(dppf) (1.721 mg, 2.351 μmol) was added. The vial was sealed, and the reaction was heated in a Biotage microwave for 5 min at 100° C. on high absorption. The aqueous layer was removed via pipette, and the reaction mixture was filtered through a Stratosphere PL-Thio MP SPE cartridge (0.5 g), eluting with 1:1 DCM/MeOH (10 mL). The eluent was concentrated under a stream of nitrogen at 50° C., and the crude product was dissolved in DMSO (1.2 mL) and purified on a Gilson HPLC (XBridge C18 5 μm OBD 19×100 mm preparatory column), eluting at 15 mL/min with a linear gradient running from 20% CH$_3$CN/H$_2$O (0.1% NH$_4$OH) to 70% CH$_3$CN/H$_2$O (0.1% NH$_4$OH) over 18 min. The desired fractions were concentrated under a stream of nitrogen at 50° C. and dried under high vacuum, giving 3.9 mg (43%) of the title compound.

LC/MS: m/z 386.9 (M+H), Rt 1.74 min.

Example 169

3-(1,1-Dioxidotetrahydro-2H-thiopyran-4-yl)-4-fluoro-5-phenyl-1H-indole-7-carboxamide

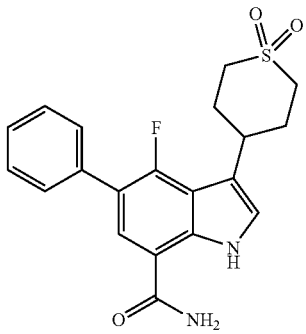

A mixture of 5-bromo-3-(1,1-dioxidotetrahydro-2H-thiopyran-4-yl)-4-fluoro-1H-indole-7-carboxamide (15 mg, 0.039 mmol), phenylboronic acid (9.40 mg, 0.077 mmol), and $K_2CO_3$ (15.98 mg, 0.116 mmol) was taken up in 1,4-dioxane (0.2 mL) and water (0.100 mL). The mixture was degassed with argon for 10 min, and $PdCl_2$(dppf) (2.82 mg, 3.85 µmol) was added. The vial was sealed, and the reaction was heated in a Biotage microwave for 30 min at 130° C. on high absorption. The aqueous layer was removed via pipette, and the reaction mixture was filtered through a Stratosphere PL-Thio MP SPE cartridge (0.5 g), eluting with 1:1 DCM/MeOH (10 mL). The eluent was concentrated under a stream of nitrogen at 50° C., and the crude product was dissolved in DMSO (1.2 mL) and purified on a Gilson HPLC (XBridge C18 5 mm OBD 19×100 mm preparatory column), eluting at 15 mL/min with a linear gradient running from 20% $CH_3CN$/$H_2O$ (0.1% $NH_4OH$) to 70% $CH_3CN$/$H_2O$ (0.1% $NH_4OH$) over 18 min. The desired fractions were concentrated under a stream of nitrogen at 50° C. and dried under high vacuum, giving 10.4 mg (70%) of the title compound.

LC/MS: m/z 386.9 (M+H), Rt 0.83 min.

Example 170

3-(1,1-Dioxidotetrahydro-2H-thiopyran-4-yl)-4-fluoro-5-(3-thienyl)-1H-indole-7-carboxamide

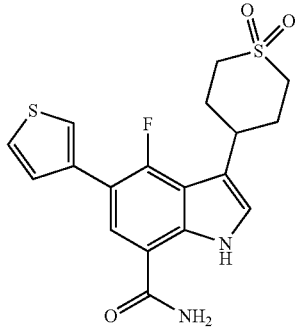

A mixture of 5-bromo-3-(1,1-dioxidotetrahydro-2H-thiopyran-4-yl)-4-fluoro-1H-indole-7-carboxamide (15 mg, 0.039 mmol), 3-thiopheneboronic acid (9.86 mg, 0.077 mmol), and $K_2CO_3$ (15.98 mg, 0.116 mmol) was taken up in 1,4-dioxane (0.2 mL) and water (0.100 mL). The mixture was degassed with argon for 10 min, and $PdCl_2$(dppf) (2.82 mg, 3.85 µmol) was added. The vial was sealed, and the reaction was heated in a Biotage microwave for 30 min at 130° C. on high absorption. The aqueous layer was removed via pipette, and the reaction mixture was filtered through a Stratosphere PL-Thio MP SPE cartridge (0.5 g), eluting with 1:1 DCM/MeOH (10 mL). The eluent was concentrated under a stream of nitrogen at 50° C., and the crude product was dissolved in DMSO (1.2 mL) and purified on a Gilson HPLC (XBridge C18 5 mm OBD 19×100 mm preparatory column), eluting at 15 mL/min with a linear gradient running from 20% $CH_3CN$/$H_2O$ (0.1% $NH_4OH$) to 70% $CH_3CN$/$H_2O$ (0.1% $NH_4OH$) over 18 min. The desired fractions were concentrated under a stream of nitrogen at 50° C. and dried under high vacuum, giving 9.2 mg (61%) of the title compound.

LC/MS: m/z 393.1 (M+H), Rt 0.82 min.

Intermediate 173

5-(4,4,5,5-Tetramethyl-1,3,2-dioxaborolan-2-yl)-1H-indole-7-carboxamide

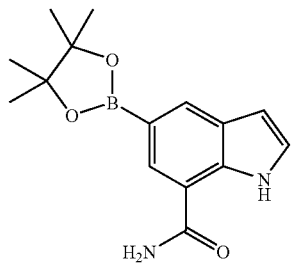

5-bromo-1H-indole-7-carboxamide (1 g, 4.17 mmol), bispinacolatodiboron (3.06 g, 12.05 mmol), potassium acetate (2.81 g, 28.75 mmol), and $PdCl_2$ (dppf)-$CH_2Cl_2$ adduct (300 mg) in DME (20 mL) were degassed by evacuating the vial with argon, then was heated at 140 degree for 3000 seconds by microwave. The reaction mixture was concentrated and workup with water and ethyl acetate (100 mL/25 mL), dried over $MgSO_4$ and concentrated to give 670 mg title compound.

LC/MS: m/z 287.0 (M+H), Rt 1.87 min.

Intermediate 174

5-(5-{[(1,1-Dimethylethyl)amino]sulfonyl}-2-thienyl)-1H-indole-7-carboxamide

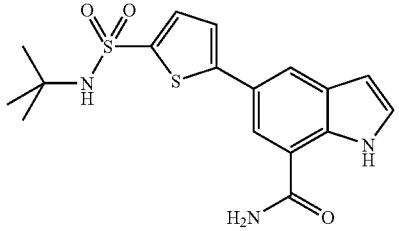

5-bromo-N-(1,1-dimethylethyl)-2-thiophenesulfonamide (828 mg, 2.78 mmol) and 5-(4,4,5,5-tetramethyl-1,3,2-dioxaborolan-2-yl)-1H-indole-7-carboxamide (4.17 mmol, 1.5 eq), potassium carbonate (1.524 g) and Pd(PPh$_3$)$_4$ (50 mg) were heated in Microwave at 150 degree for 15 mins after degassing for 5 mins with argon. The reaction solution was filtered off palladium with PL-thiol MP SPE cartridge, concentrated and purified by HPLC with CH₃CN/H₂O/0.1% TFA to give 620 mg title compound.

Example 171

(rac)-3-(1,1-Dioxidotetrahydro-3-thienyl)-5-(4-fluorophenyl)-1H-indole-7-carboxamide

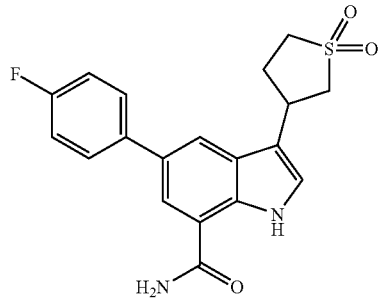

5-Bromo-3-(1,1-dioxidotetrahydro-3-thienyl)-1H-indole-7-carboxamide (100 mg, 0.28 mmol), and dioxane water (3:1, 2 mL) were dissolved together. 4-fluorophenyl boronic acid (59 mg, 0.42 mmol), potassium carbonate (116 mg, 0.84 mmol) were added and a stream of Ar was passed through the solution for 5 min and then Pd(PPh₃)₄ was added (32 mg, 0.028 mmol). Argon was passed through the solution for 5 min and then the mixture was heated on the microwave at 150° C. for 20 min. The reaction mixture was concentrated and purified by HPLC to afforded 17 mg of the title compound.

LC/MS: m/z 372.9 (M+H), Rt 1.84 min.

Enantiomer Separation

Example 172 and 173

Amides Methyl 5-(4-fluorophenyl)-3-[(3S)-tetrahydro-3-thienyl]-1H-indole-7-carboxylate and methyl 5-(4-fluorophenyl)-3-[(3R)-tetrahydro-3-thienyl]-1H-indole-7-carboxylate

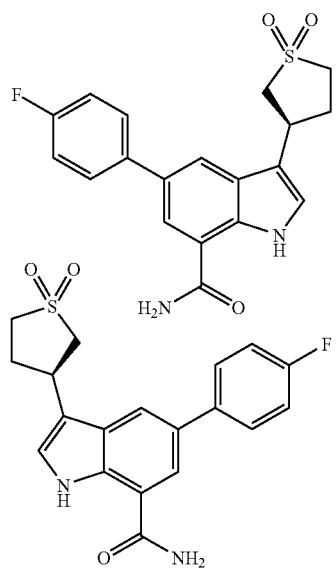

Method found using 30% MeOH with 0.5% DEA on an AS column with SFC. (74 mg) were Methyl 5-(4-fluorophenyl)-3-[(3S)-tetrahydro-3-thienyl]1Hindole-7-carboxylate (97 mg) and methyl 5-(4-fluorophenyl)-3-[(3R)-tetrahydro-3-thienyl]1Hindole-7-carboxylate separated. The absolute configuration of this enantiomer was assigned by ab initio VCD analysis.

Following the procedure for the preparation of (rac)-3-(1,1-dioxidotetrahydro-3-thienyl)-5-(4-fluorophenyl)-1H-indole-7-carboxamide, 5-bromo-3-(1,1-dioxidotetrahydro-3-thienyl)-1H-indole-7-carboxamide was reacted with the required boronic acid or boronate ester, giving the compounds shown in Table 12 in racemic form.

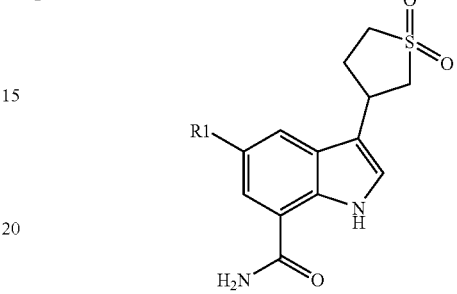

TABLE 12

| Example | R | MS [M]⁺/RT |
|---|---|---|
| 174 | phenyl | 354.7/1.71 min |
| 175 | 3-thiophene | 361.3/1.67 min |
| 176 | 4-CN-phenyl | 380.0/1.65 min |
| 177 | 4-fluoro-3-methyl-phenyl | 387.0/1.83 min |
| 178 | 3,4-dimethoxy-phenyl | 415.0/1.55 min |
| 179 | 3,4-difluoro-phenyl | 390.9/1.77 min |
| 180 | 4-CF₃O-phenyl | 438.9/2.02 min |
| 181 | 3-CN-phenyl | 379.8/1.72 min |
| 182 | 3-CF₃O-phenyl | 438.9/1.70 min |
| 183 | 3-methyl-phenyl | 368.9/1.89 min |
| 184 | 2,4-difluoro-phenyl | 391.2/1.82 min |

Intermediate 175

1-{[4-(4,4,5,5-Tetramethyl-1,3,2-dioxaborolan-2-yl)-2-thienyl]methyl}azetidine

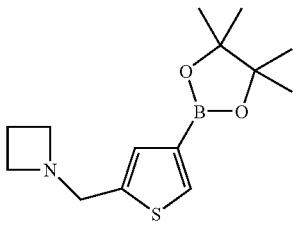

A solution of azetidine (0.014 g, 0.252 mmol) in THF (1 mL) was added to a solution of 4-(4,4,5,5-tetramethyl-1,3,2-dioxaborolan-2-yl)-2-thiophenecarbaldehyde (0.05 g, 0.210 mmol) in THF (1 mL) in 1-Dram vial and let stir for 30 minutes. Sodium Cyanoborohydride Resin (0.128 g, 0.583 mol, 2.33 mmol/g)) was then added to the mixture and let stir 3 days. The mixture was then agitated for 3 hrs with MP-Isocyanate Resin (0.135 g, 0.230 mmol, 1.7 mmol/g) and THF (2 mL). The reaction was resubjected to the same amounts of Sodium Cyanoborohydride Resin and amine as above and stirred for 2 days. The resins were then filtered and solvent concentrated to give 0.035 g of the title compound.

LC/MS m/z 280 (M+H), Rt 1.33 min.

Intermediate 176

1-{[4-(4,4,5,5-Tetramethyl-1,3,2-dioxaborolan-2-yl)-2-thienyl]methyl}hexahydro-1H-azepine

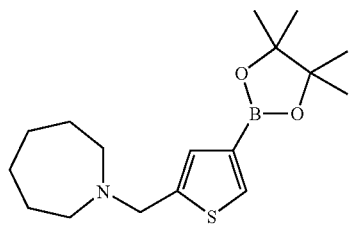

A solution of hexahydro-1H-azepine (0.025 g, 0.252 mmol) in THF (1 mL) was added to a solution of 4-(4,4,5,5-tetramethyl-1,3,2-dioxaborolan-2-yl)-2-thiophenecarbaldehyde (0.05 g, 0.210 mmol) in THF (1 mL) in 1-Dram vial and let stir for 30 minutes. Sodium triacetoxyborohydride (0.225 g, 0.582 mmol) was then added to the mixture and let stir 18 h. The mixture was then agitated for 1 hour with MP-Isocyanate Resin (0.135 g, 0.230 mmol, 1.7 mmol/g) and THF (2 mL). The solution was filtered and the resin was washed with THF (4 mL×2). The combined solution was concentrated, giving 0.055 g (82%) of the title compound.

LC/MS m/z 321 (M+H), Rt 0.8 min.

Example 185

5-[5-(1-Azetidinylmethyl)-3-thienyl]-3-(1,1-dioxidotetrahydro-3-thienyl)-1H-indole-7-carboxamide

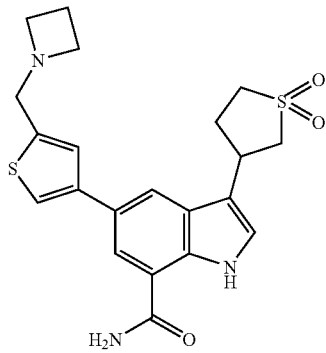

5-bromo-3-(1,1-dioxidotetrahydro-3-thienyl)-1H-indole-7-carboxamide (0.040 g, 0.112 mmol) and 1-{[4-(4,4,5,5-tetramethyl-1,3,2-dioxaborolan-2-yl)-2-thienyl]methyl}azetidine (0.035 g, 0.126 mmol, 1.1 eq) was dissolved in a 6:1 solution of 1,4 dioxane/water in a 20 mL microwave reaction vessel. Potassium carbonate (0.077 g, 0.560 mmol, 5 eq) was added and the solution was degassed with Argon. PdCl$_2$(dppf) (0.014 g, 0.019 mmol) was added and the reaction was heated in a microwave at 100° C. for 20 min. Solution was passed through a StratoSphere SPE PL-Thiol MP SPE column to remove palladium and purified on Gilson preparative HPLC using Acetonitrile/Water with 0.1% TFA. The desired fractions were concentrated, giving 0.011 g (23%) of the title compound.

LC/MS m/z 430 (M+H), Rt 0.56 min.

Example 186

3-(1,1-Dioxidotetrahydro-3-thienyl)-5-[5-(hexahydro-1H-azepin-1-ylmethyl)-3-thienyl]-1H-indole-7-carboxamide

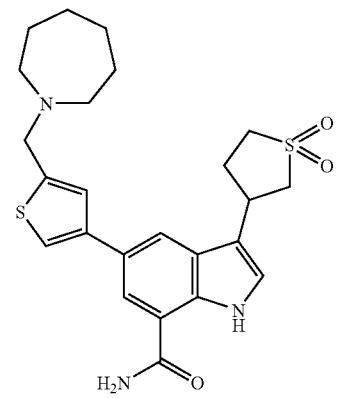

5-bromo-3-(1,1-dioxidotetrahydro-3-thienyl)-1H-indole-7-carboxamide (0.040 g, 0.112 mmol) and 1-{[4-(4,4,5,5-tetramethyl-1,3,2-dioxaborolan-2-yl)-2-thienyl]methyl}hexahydro-1H-azepine (0.055 g, 0.172 mmol) was dissolved in a 6:1 solution of 1,4 dioxane/water in a 20 mL microwave reaction vessel. Potassium carbonate (0.077 g, 0.560 mmol) was added and the solution was degassed with Argon. PdCl$_2$(dppf) (0.014 g, 0.019 mmol) was added and the reaction was heated in a microwave at 100° C. for 20 min. The solution was passed through a StratoSphere SPE PL-Thiol MP SPE column to remove palladium and purified on Gilson preparative HPLC using Acetonitrile/Water with 0.1% TFA. The desired fractions were concentrated, giving 0.015 g (28%) of the title compound.

LC/MS m/z 472 (M+H), Rt 0.62 min.

Example 187

3-(1,1-Dioxidotetrahydro-3-thienyl)-5-[5-(1-pyrrolidinylmethyl)-3-thienyl]-1H-indole-7-carboxamide

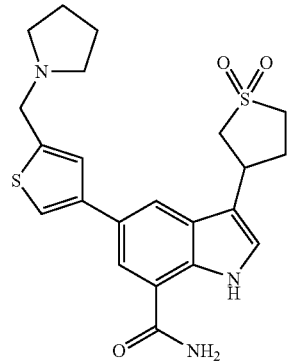

5-bromo-3-(1,1-dioxidotetrahydro-3-thienyl)-1H-indole-7-carboxamide (0.035 g, 0.098 mmol) and 1-{[4-(4,4,5,5-tetramethyl-1,3,2-dioxaborolan-2-yl)-2-thienyl]methyl}hexahydro-1H-azepine (0.038 g, 0.130 mmol, 1.3 eq) was dissolved in a 6:1 solution of 1,4 dioxane/water in a 20 mL microwave reaction vessel. Potassium carbonate (0.068, 0.490 mmol, 5 eq) was added and the solution was degassed with Argon. PdCl$_2$(dppf) (0.012 g, 0.017 mmol, 0.17 eq) was added and the reaction was heated in a microwave at 100° C.

for 20 min. The solution was passed through a StratoSphere SPE PL-Thiol MP SPE column to remove palladium and purified on Gilson preparative HPLC using Acetonitrile/Water with 0.1% TFA. The desired fractions were concentrated, giving 0.0052 g (12%) of the title compound.
LC/MS m/z 444.3 (M+H), Rt 0.58 min.

Example 188

3-(1,1-Dioxidotetrahydro-3-thienyl)-5-(2-furanyl)-1H-indole-7-carboxamide

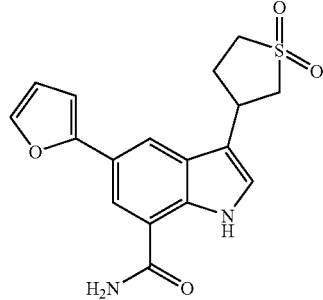

5-bromo-3-(1,1-dioxidotetrahydro-3-thienyl)-1H-indole-7-carboxamide (0.050 g, 0.140 mmol) and 2-furanylboronic acid (0.020 g, 0.182 mmol) was dissolved in a 6:1 solution of 1,4 dioxane/water in a 20 mL microwave reaction vessel. Potassium carbonate (0.097, 0.70 mmol) was added and the solution was degassed with Argon. PdCl$_2$(dppf) (0.017 g, 0.024 mmol) was added and the reaction was heated in a microwave at 100° C. for 10 min. The solution was passed through a StratoSphere SPE PL-Thiol MP SPE column to remove palladium and purified on Gilson preparative HPLC using Acetonitrile/0.1% NH4OH/H20. The desired fractions were concentrated, giving 0.017 g (36%) of the title compound.
LC/MS m/z 344 (M+H), Rt 0.74 min.

Example 189

3-(1,1-Dioxidotetrahydro-3-thienyl)-5-(3-furanyl)-1H-indole-7-carboxamide

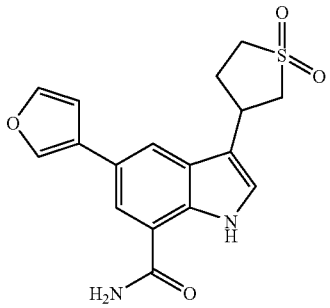

5-bromo-3-(1,1-dioxidotetrahydro-3-thienyl)-1H-indole-7-carboxamide (0.050 g, 0.140 mmol) and 3-furanylboronic acid (0.020 g, 0.182 mmol) was dissolved in a 6:1 solution of 1,4 dioxane/water in a 20 mL microwave reaction vessel. Potassium carbonate (0.097 g, 0.70 mmol) was added and the solution was degassed with Argon. PdCl$_2$(dppf) (0.017 g, 0.024 mmol) was added and the reaction was heated in a microwave at 100° C. for 10 min. The solution was passed through a StratoSphere SPE PL-Thiol MP SPE column to remove palladium and purified on Gilson preparative HPLC using Acetonitrile/0.1% NH4OH/H20. The desired fractions were concentrated, giving 0.017 g (36%) of the title compound.
LC/MS m/z 344 (M+H), Rt 0.75 min.

Example 190

3-(1,1-Dioxidotetrahydro-3-thienyl)-5-(2-thienyl)-1H-indole-7-carboxamide

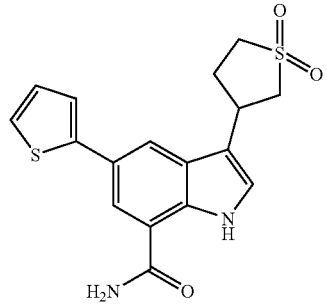

5-bromo-3-(1,1-dioxidotetrahydro-3-thienyl)-1H-indole-7-carboxamide (0.050 g, 0.140 mmol) and 2-thienylboronic acid (0.018 g, 0.140 mmol) was dissolved in a 6:1 solution of 1,4 dioxane/water in a 20 mL microwave reaction vessel. Potassium carbonate (0.097 g, 0.70 mmol) was added and the solution was degassed with Argon. PdCl$_2$(dppf) (0.017 g, 0.024 mmol) was added and the reaction was heated in a microwave at 100° C. for 10 min. The solution was passed through a StratoSpheres SPE PL-Thiol MP SPE column to remove palladium and purified on Gilson preparative HPLC using Acetonitrile/0.1% NH4OH/H20. The desired fractions were concentrated, giving 0.017 g (36%) of the title compound.
LC/MS m/z 361 (M+H), Rt 0.79 min.

Example 191

5-(1-Benzothien-5-yl)-3-(1,1-dioxidotetrahydro-3-thienyl)-1H-indole-7-carboxamide

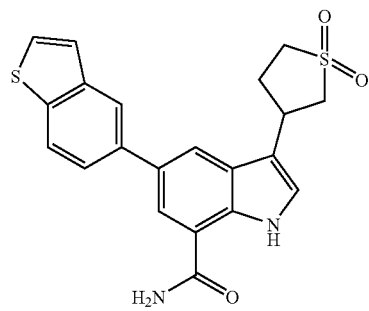

5-Bromo-3-(1,1-dioxidotetrahydro-3-thienyl)-1H-indole-7-carboxamide (0.06 g, 0.168 mmol) and 1-benzothien-5-ylboronic acid (0.036 g, 0.202 mmol) was dissolved in a 6:1 solution of 1,4 dioxane/water in a 20 mL microwave reaction vessel. Potassium carbonate (0.113 g, 0.816 mmol) was added and the solution was degassed with Argon. PdCl$_2$(dppf) (0.025 g, 0.034 mmol) was added and the reaction was heated in a microwave at 100° C. for 20 min. The solution was passed through a StratoSphere SPE PL-Thiol MP SPE column to remove palladium and purified on Gilson preparative HPLC using Acetonitrile/Water with 0.1% TFA. The desired fractions were concentrated, giving 0.044 g (67%) of the title compound.
LC/MS m/z 411 (M+H), Rt 0.88 min.

Example 192

3-[(3-endo)-8,8-Dioxido-8-thiabicyclo[3.2.1]oct-3-yl]-5-phenyl-1H-indole-7-carboxamide

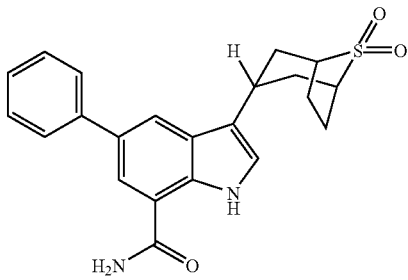

5-Bromo-3-[(3-endo)-8,8-dioxido-8-thiabicyclo[3.2.1]oct-3-yl]-1H-indole-7-carboxamide (45 mg, 0.11 mmol), phenylboronic acid (17 mg, 0.14 mmol), PdCl2(dppf)-CH2Cl2 adduct (17 mg, 0.02 mmol), and potassium carbonate (83 mg, 0.6 mmol) were diluted in dioxane (3 mL) and water (1.5 mL) in a 2-5 mL biotage microwave reaction tube. The mixture was degassed by bubbling argon through for 5 minutes, then the reaction was heated in the microwave at 100° C. for 5 minutes under normal absorption. The crude reaction mixture was filtered through a thiol SPE cartridge (polymer labs) to remove palladium, then was concentrated. The residue was diluted in ~3 mL of dmso, filtered through a syringe filter, and purified by ammonium hydroxide Gilson hplc. The product fractions were combined and concentrated in a genevac EZ2 evaporator, to afford 23.6 mg (53%) of the title compound.

LC/MS: m/z 395.0 (M+H), Rt 0.92 min.

Following the procedure for the preparation of 3-[(3-endo)-8,8-dioxido-8-thiabicyclo[3.2.1]oct-3-yl]-5-phenyl-1H-indole-7-carboxamide, 5-bromo-3-[(3-endo)-8,8-dioxido-8-thiabicyclo[3.2.1]oct-3-yl]-1H-indole-7-carboxamide was reacted with the required boronic acid, giving the compounds shown in Table 13.

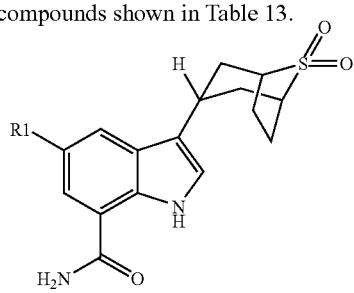

TABLE 13

| Example | R1 | MS [M]+/RT |
|---|---|---|
| 193 | (2-furyl) | 384.9/0.81 min |
| 194 | (3-furyl) | 384.9/0.80 min |
| 195 | (3-thienyl) | 400.9/0.84 min |
| 196 | (2-thienyl) | 400.9/0.84 min |
| 197 | (4-fluorophenyl) | 413.1/0.89 min |

Following the procedure shown for the preparation of 3-[(3-endo)-8,8-dioxido-8-thiabicyclo[3.2.1]oct-3-yl]-5-phenyl-1H-indole-7-carboxamide, 5-bromo-3-[(3-exo)-8,8-dioxido-8-thiabicyclo[3.2.1]oct-3-yl]-1H-indole-7-carboxamide was reacted with an appropriate boronic acid or boronate ester, giving the compounds shown in Table 14.

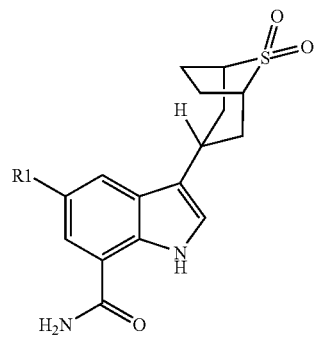

TABLE 14

| Example | R1 | MS [M]+/RT |
|---|---|---|
| 198 | (phenyl) | 395.0/0.88 min |
| 199 | (2-furyl) | 385.1/0.83 min |
| 200 | (3-thienyl) | 400.9/0.85 min |

TABLE 14-continued

| Example | R1 | MS [M]+/RT |
|---|---|---|
| 201 | | 400.9/0.84 min |
| 202 | | 413.1/0.91 min |

Example 203

3-[(3-endo)-8,8-Dioxido-8-thiabicyclo[3.2.1]oct-3-yl]-5-[5-(hexahydro-1H-azepin-1-ylmethyl)-3-thienyl]-1H-indole-7-carboxamide

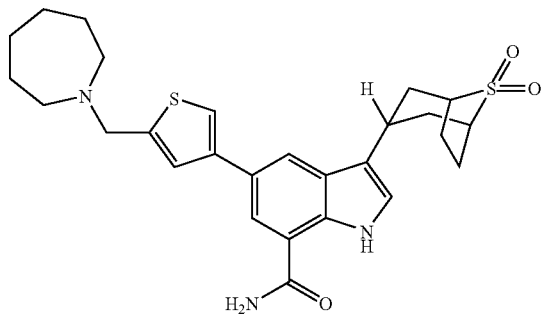

3-[(3-endo)-8,8-Dioxido-8-thiabicyclo[3.2.1]oct-3-yl]-5-(5-formyl-3-thienyl)-1H-indole-7-carboxamide (42 mg, 0.097 mmol) was diluted in dimethyl sulfoxide (0.3 mL) and methanol (0.3 mL) in a 2 dram vial. Hexahydro-1H-azepine (48 mg, 0.49 mmol) was added, followed by glacial acetic acid (0.11 mL, 1.94 mmol). The reaction mixture was stirred at 23° C. for 1 h. Sodium cyanoborohydride (13 mg, 0.21 mmol) was added. The mixture was stirred at 23° C. for 3 h, then was filtered through a 2 g SCX cartridge eluting with methanol (2 mL). The methanol wash was discarded, and the product was eluted from the cartridge with methanolic ammonia (2 M, 9 mL). The latter fraction was concentrated, re-diluted in methanol/dmso, and purified by ammonium hydroxide Gilson HPLC. The desired fractions were concentrated, giving 16.7 mg (34%) of the title compound.

LC/MS: m/z 512.3 (M+H), Rt 0.70 min.

Example 204

3-[(3-endo)-8,8-Dioxido-8-thiabicyclo[3.2.1]oct-3-yl]-5-[5-(1-azetidinylmethyl)-3-thienyl]-1H-indole-7-carboxamide

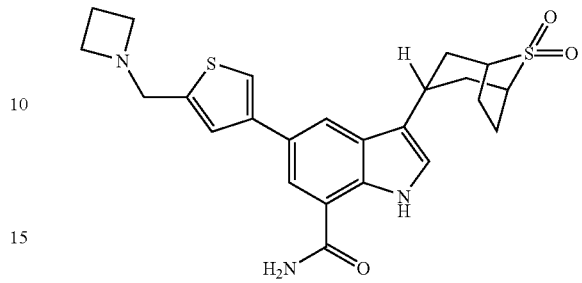

3-[(3-endo)-8,8-Dioxido-8-thiabicyclo[3.2.1]oct-3-yl]-5-(5-formyl-3-thienyl)-1H-indole-7-carboxamide (81 mg, 0.19 mmol) was diluted in dimethyl sulfoxide (0.4 mL) and methanol (0.4 mL) in a 2 dram vial. Azetidine (54 mg, 0.95 mmol) was added, followed by glacial acetic acid (210 mg, 3.49 mmol). The reaction mixture was stirred at 23° C. for 1 h. Sodium cyanoborohydride (25 mg, 0.40 mmol) was added. The mixture was stirred at 23° C. overnight, then was filtered through a 2 g SCX cartridge eluting with methanol (2 mL). The methanol wash was discarded, and the product was eluted from the cartridge with methanolic ammonia (2 M, 9 mL). The latter fraction was concentrated, re-diluted in methanol/dmso, and purified by ammonium hydroxide Gilson HPLC. The desired fractions were concentrated, giving 26.9 mg (29%) of the title compound.

LC/MS: m/z 470.3 (M+H), Rt 0.66 min.

Example 205

3-[(3-endo)-8,8-Dioxido-8-thiabicyclo[3.2.1]oct-3-yl]-5-[5-(1-pyrrolidinylmethyl)-3-thienyl]-1H-indole-7-carboxamide

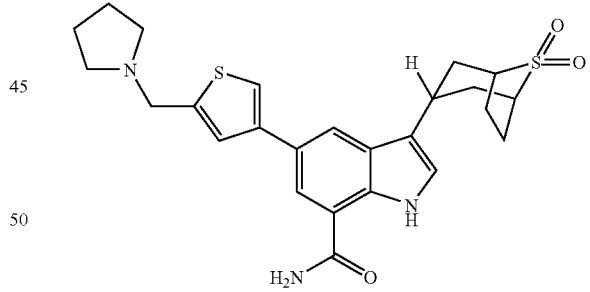

3-[(3-endo)-8,8-Dioxido-8-thiabicyclo[3.2.1]oct-3-yl]-5-(5-formyl-3-thienyl)-1H-indole-7-carboxamide (50 mg, 0.12 mmol) was diluted in dimethyl sulfoxide (0.3 mL) and methanol (0.3 mL) in a 2 dram vial. Pyrrolidine (42 mg, 0.58 mmol, 5 eq) was added, followed by glacial acetic acid (0.13 mL, 2.33 mmol, 20 eq). The reaction mixture was stirred at 23° C. for 1 h. Sodium cyanoborohydride (16 mg, 0.255 mmol) was added. The mixture was stirred at 23° C. for 3 h, then was filtered through a 2 g SCX cartridge eluting with methanol (2 mL). The methanol wash was discarded, and the product was eluted from the cartridge with methanolic ammonia (2M, Aldrich, 9 mL). The latter fraction was concentrated, re-diluted in methanol/dmso, and purified by ammonium hydroxide Gilson. The desired fractions were concentrated, giving 7.4 mg (13%) of the title compound.

LC/MS: m/z 484.1 (M+H), Rt 0.65 min.

Following the procedure for the preparation of 3-[(3-endo)-8,8-dioxido-8-thiabicyclo[3.2.1]oct-3-yl]-5-[5-(1-pyrrolidinylmethyl)-3-thienyl]-1H-indole-7-carboxamide, 3-[(3-endo)-8,8-dioxido-8-thiabicyclo[3.2.1]oct-3-yl]-5-(5-formyl-3-thienyl)-1H-indole-7-carboxamide was reacted with the required amine, giving the compounds shown in Table 15.

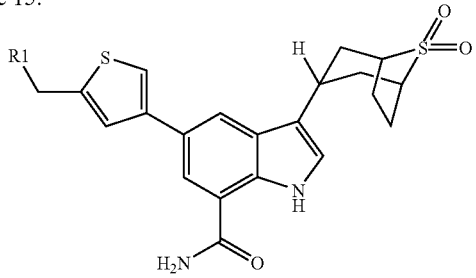

TABLE 15

| Example | R | MS [M]+/RT |
|---|---|---|
| 206 | | 458.1/0.61 min |
| 207 | | 484.1/0.68 min |

Example 208

3-[(3-exo)-8,8-Dioxido-8-thiabicyclo[3.2.1]oct-3-yl]-5-[5-(hexahydro-1H-azepin-1-ylmethyl)-3-thienyl]-1H-indole-7-carboxamide

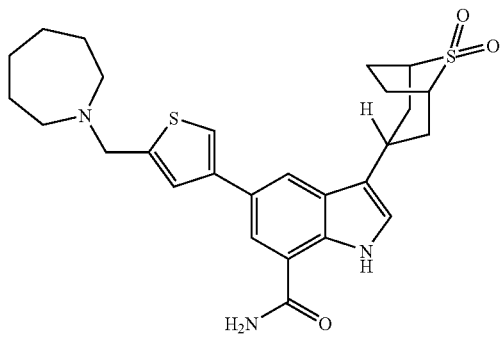

3-[(3-endo)-8,8-Dioxido-8-thiabicyclo[3.2.1]oct-3-yl]-5-(5-formyl-3-thienyl)-1H-indole-7-carboxamide (75 mg, 0.18 mmol) was diluted in dimethyl sulfoxide (0.3 mL) and methanol (0.3 mL) in a 2 dram vial. Hexahydro-1H-azepine (87 mg, 0.49 mmol) was added, followed by glacial acetic acid (157 mg, 2.6 mmol). The reaction mixture was stirred at 23° C. for 1 h. Sodium cyanoborohydride (17 mg, 0.27 mmol) was added. The mixture was stirred at 23° C. for 2 h, then was filtered through a 2 g SCX cartridge eluting with methanol (2 mL). The methanol wash was discarded, and the product was eluted from the cartridge with methanolic ammonia (2 M, 9 mL). The latter fraction was concentrated, re-diluted in methanol/dmso, and purified by ammonium hydroxide Gilson HPLC. The desired fractions were concentrated, giving 24 mg (25%) of the title compound.

LC/MS: m/z 512.3 (M+H), Rt 0.72 min.

Following the procedure for the preparation of 3-[(3-exo)-8,8-dioxido-8-thiabicyclo[3.2.1]oct-3-yl]-5-[5-(hexahydro-1H-azepin-1-ylmethyl)-3-thienyl]-1H-indole-7-carboxamide, 3-[(3-endo)-8,8-dioxido-8-thiabicyclo[3.2.1]oct-3-yl]-5-(5-formyl-3-thienyl)-1H-indole-7-carboxamide was reacted with an appropriate amine, giving the compounds shown in Table 16.

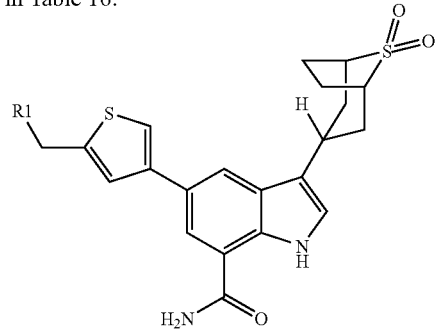

TABLE 16

| Example | R | MS [M]+/RT |
|---|---|---|
| 209 | | 458.1/0.65 min |
| 210 | | 484.1/0.69 min |
| 211 | | 470.3/0.66 min |

Example 212

3-(1,1-Dioxido-4-thiepanyl)-5-phenyl-1H-indole-7-carboxamide

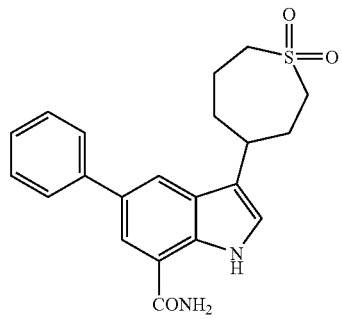

3-(1,1-Dioxido-4-thiepanyl)-5-phenyl-1H-indole-7-carboxylic acid (0.076 mmol), HOBT (10 mg, 0.074 mmol), EDC (15 mg, 0.078 mmol) were mixed together. A solution of 0.5 M NH₃ in dioxane (1.5 mL) was added in, and the reaction was heated in a microwave at 120° C. for 10 minutes, then allowed to sit at room temperature overnight. The solvent was evaporated and the crude product was dissolved in DMSO and purified by Gilson HPLC (0.1% TFA, 10%-90% CH₃CN, 10 minutes). The desired fractions were concentrated, giving 4 mg of the title compound.

LC/MS: m/z 383.0 (M+H), Rt 1.81 min.

The compounds in Table 17 were prepared according to the following procedure:

5-bromo-3-(1,1-dioxido-4-thiepanyl)-1H-indole-7-carboxamide (20.0 mg, 0.052 mmol) in Dioxane:H₂O (2.0 mL, 3:1) was suspended into a microwave tube with fitted magnetic stir bar containing K₂CO₃ (40 mg), Aryl boronic acid (0.2 mmol), Catalyst (Pd(dppf)₂, 5 mg). The reaction mixture was heated by microwave to 120 degrees for 10 min. The reaction mixture was concentrated and purified with HPLC to give the compounds listed in Table 17.

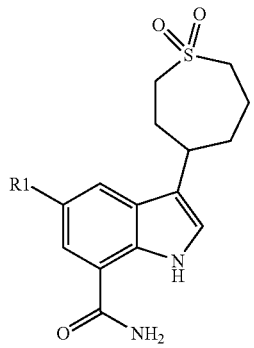

TABLE 17

| Example | R1 | MS [M]⁺/RT |
|---|---|---|
| 213 | 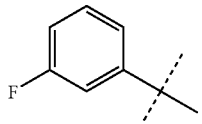 | 401/1.86 min |
| 214 | 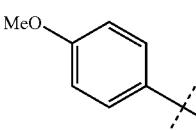 | 413/1.77 min |
| 215 | 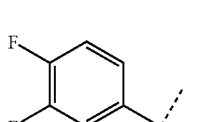 | 419/1.88 min |
| 216 | 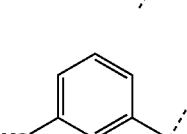 | 408/1.74 min |

Example 217

3-(1,1-Dioxidotetrahydro-2H-thiopyran-3-yl)-5-(3-furanyl)-1H-indole-7-carboxamide

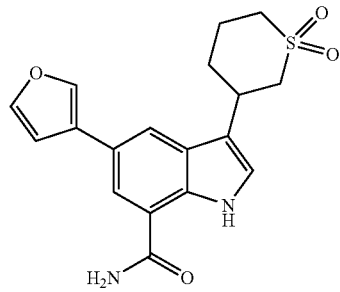

5-Bromo-3-(1,1-dioxidotetrahydro-2H-thiopyran-3-yl)-1H-indole-7-carboxamide (0.050 g, 0.135 mmol) and 3-furanylboronic acid (0.020 g, 0.175 mmol, 1.3 eq) was dissolved in a 6:1 solution of 1,4 dioxane (3 mL)/water (0.5 mL) in a 20 mL microwave reaction vessel. Potassium carbonate (0.093 g, 0.673 mmol, 5 eq) was added and the solution was degassed with Nitrogen. PdCl₂(dppf)₂ (0.017 g, 0.023 mmol) was added and the reaction was heated in a microwave at 100° C. for 20 min. The solution was passed through a StratoSphere SPE PL-Thiol MP SPE column to remove palladium and purified on Gilson preparative HPLC using Acetonitrile/Water with 0.1% NH₄OH. The desired fractions were concentrated, giving 0.022 g (45%) of the title compound.

LC/MS: m/z 359 (M+H), Rt 0.76 min.

Example 218

3-(1,1-Dioxidotetrahydro-2H-thiopyran-3-yl)-5-(2-furanyl)-1H-indole-7-carboxamide

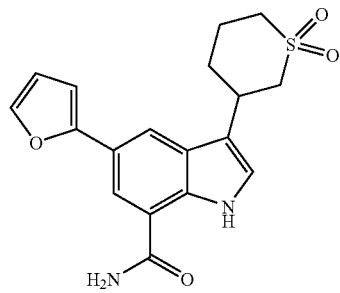

5-Bromo-3-(1,1-dioxidotetrahydro-2H-thiopyran-3-yl)-1H-indole-7-carboxamide (0.050, 0.135 mol) and 2-furanylboronic acid (0.020, 0.175 mol) was dissolved in a 6:1 solution of 1,4 dioxane (3 L)/water (0.5 L) in a 20 L microwave reaction vessel. potassium carbonate (0.093, 0.673 mol) was added and the solution was degassed with Nitrogen. PdCl₂(dppf)₂ (0.017, 0.023 mol) was added and the reaction was heated in a microwave at 100° C. for 20 min. The solution was passed through a StratoSphere SPE PL-Thiol MP SPE column to remove palladium and purified on Gilson preparative HPLC using Acetonitrile/Water with 0.1% NH4OH. The desired fractions were concentrated, giving 0.018 g (37%) of the title compound.

LC/MS: m/z 359 (M+H), Rt 0.76 min.

Example 219

3-(1,1-Dioxidotetrahydro-2H-thiopyran-3-yl)-5-(3-thienyl)-1H-indole-7-carboxamide

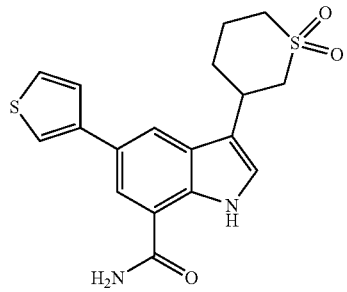

5-Bromo-3-(1,1-dioxidotetrahydro-2H-thiopyran-3-yl)-1H-indole-7-carboxamide (0.069 g, 0.187 mmol) and 3-thienylboronic acid (0.031 g, 0.242 mmol) was dissolved in a 6:1 solution of 1,4 dioxane (3 mL)/water (0.5 mL) in a 20 mL microwave reaction vessel. Potassium carbonate (0.129 g, 0.933 mmol) was added and the solution was degassed with Nitrogen. $PdCl_2(dppf)_2$ (0.023 g, 0.032 mmol) was added and the reaction was heated in a microwave at 100° C. for 20 min. The solution was passed through a StratoSphere SPE PL-Thiol MP SPE column to remove palladium and purified on Gilson preparative HPLC using Acetonitrile/Water with 0.1% NH4OH. The desired fractions were concentrated, giving 0.038 g (54%) of the title compound.

LC/MS: m/z 375 (M+H), Rt 0.85 min.

Example 220

3-(1,1-Dioxidotetrahydro-2H-thiopyran-3-yl)-5-(4-fluorophenyl)-1H-indole-7-carboxamide

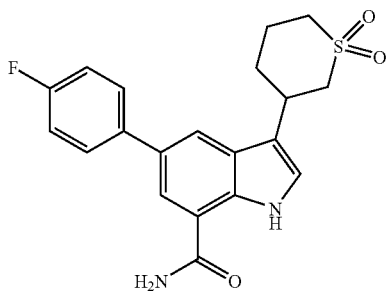

5-Bromo-3-(1,1-dioxidotetrahydro-2H-thiopyran-3-yl)-1H-indole-7-carboxamide (0.050 g, 0.134 mmol) and (4-fluorophenyl)boronic acid (0.024 g, 0.174 mmol) was dissolved in a 6:1 solution of 1,4 dioxane (3 mL)/water (0.5 mL) in a 20 mL microwave reaction vessel. Potassium carbonate (0.093 g, 0.670 mmol) was added and the solution was degassed with Nitrogen. $PdCl_2(dppf)_2$ (0.017 g, 0.023 mmol) was added and the reaction was heated in a microwave at 100° C. for 20 min. The solution was passed through a StratoSphere SPE PL-Thiol MP SPE column to remove palladium and purified on Gilson preparative HPLC using Acetonitrile/Water with 0.1% TFA. The desired fractions were concentrated, giving 0.016 g (30%) of the title compound.

LC/MS: m/z 387 (M+H), Rt 0.85 min.

Example 221

3-(1,1-Dioxidotetrahydro-2H-thiopyran-3-yl)-5-phenyl-1H-indole-7-carboxamide

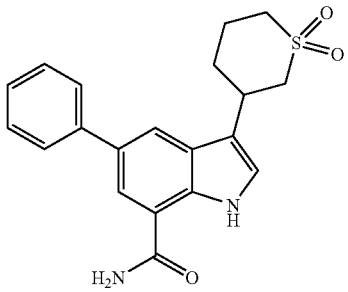

5-Bromo-3-(1,1-dioxidotetrahydro-2H-thiopyran-3-yl)-1H-indole-7-carboxamide (0.050 g, 0.134 mmol) and (4-fluorophenyl)boronic acid (0.021 g, 0.174 mmol) was dissolved in a 6:1 solution of 1,4 dioxane (3 mL)/water (0.5 mL) in a 20 mL microwave reaction vessel. Potassium carbonate (0.093, 0.670 mmol) was added and the solution was degassed with Nitrogen. $PdCl_2(dppf)_2$ (0.017 g, 0.023 mmol) was added and the reaction was heated in a microwave at 100° C. for 20 min. The solution was passed through a StratoSphere SPE PL-Thiol MP SPE column to remove palladium and purified on Gilson preparative HPLC using Acetonitrile/Water with 0.1% TFA. The desired fractions were concentrated, giving 0.016 g (30%) of the title compound.

LC/MS: m/z 369 (M+H), Rt 0.83 min.

Example 222

3-(1,1-Dioxidotetrahydro-2H-thiopyran-3-yl)-5-(2-thienyl)-1H-indole-7-carboxamide

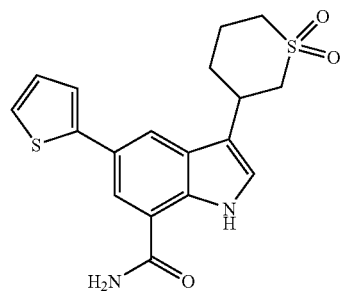

5-Bromo-3-(1,1-dioxidotetrahydro-2H-thiopyran-3-yl)-1H-indole-7-carboxamide (0.050 g, 0.134 mmol) and 2-thienylboronic acid (0.022 g, 0.174 mmol) was dissolved in a 6:1 solution of 1,4 dioxane (3 mL)/water (0.5 mL) in a 20 mL microwave reaction vessel. Potassium carbonate (0.093 g, 0.670 mmol) was added and the solution was degassed with Nitrogen. $PdCl_2(dppf)_2$ (0.017 g, 0.023 mmol) was added and the reaction was heated in a microwave at 100° C. for 20 min. The solution was passed through a StratoSphere SPE PL-Thiol MP SPE column to remove palladium and purified on Gilson preparative HPLC using Acetonitrile/Water. The desired fractions were concentrated, giving 0.014 g (28%) of the title compound.

LC/MS: m/z 375 (M+H), Rt 0.79 min.

Example 223

3-(2,6-Dimethyl-1,1-dioxidotetrahydro-2H-thiopyran-4-yl)-5-(3-thienyl)-1H-indole-7-carboxamide

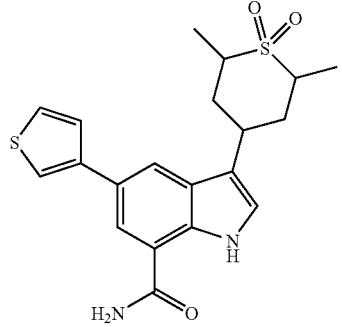

5-bromo-3-(2,6-dimethyl-1,1-dioxidotetrahydro-2H-thiopyran-4-yl)-1H-indole-7-carboxamide (0.050 g, 0.125 mmol) and 3-thienylboronic acid (0.016 g, 0.125 mmol) was dissolved in a 6:1 solution of 1,4 dioxane (3 mL)/water (0.5 mL) in a 20 mL microwave reaction vessel. Potassium carbonate (0.087 g, 0.626 mmol, 5 eq) was added and the solution was degassed with Nitrogen. PdCl$_2$(dppf)$_2$ (0.016 g, 0.021 mmol, 0.17 eq) was added and the reaction was heated in a microwave at 100° C. for 20 min. The solution was passed through a StratoSphere SPE PL-Thiol MP SPE column to remove palladium and purified on Gilson preparative HPLC using Acetonitrile/Water with 0.1% TFA. The desired fractions were concentrated, giving 0.051 g of a mixture of diasteriomers and their respective enantiomers.

LC/MS: m/z 403 (M+H), Rt 0.90 and 0.93 min.

Example 224 and 225

3-[(4S)-2,2-Dimethyl-1,1-dioxidotetrahydro-2H-thiopyran-4-yl]-5-(4-fluorophenyl)-1H-indole-7-carboxamide and 3-[(4R)-2,2-dimethyl-1,1-dioxidotetrahydro-2H-thiopyran-4-yl]-5-(4-fluorophenyl)-1H-indole-7-carboxamide

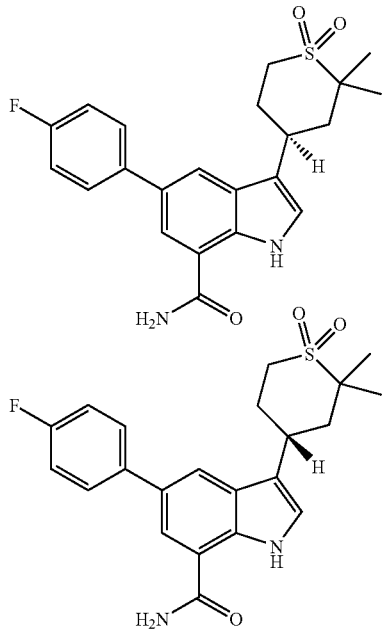

(racemic)-5-Bromo-3-(1,1-dioxido-2,2-dimethylthian-4-yl)-1H-indole-7-carboxamide (500 mg, 1.252 mmol) was placed in a microwave vial and dissolved with 1,4-dioxane (12 mL) and water (6.00 mL). (4-fluorophenyl)boronic acid (350 mg, 2.504 mmol) and K2CO3 (519 mg, 3.76 mmol) were added. Argon was bubbled in the mixture for 10 min with stirring. PdCl$_2$(dppf) (48.3 mg, 0.100 mmol) was added, and argon was bubbled another 10 mins. The vial was sealed and put under microwave 5 min at 100° C. with high absorption parameter. Crude material was run through a thiol-SPE cartridge eluting with 2 mL of methanol and the residue evaporated. The residue was sonicated in 10 mL of water. Water was then removed (centrifugation) and the new residue was sonicated in first DCM (2 mL), removed by centrifugation, and then methanol (5 mL) removed as well by centrifugation to afford 300 mg of a pale brown powder. This process was repeated a second time and then these samples are combined to afford 550 mg of (racemic) 3-(2,2-dimethyl-1,1-dioxidotetrahydro-2H-thiopyran-4-yl)-5-(4-fluorophenyl)-1H-indole-7-carboxamide of suitable purity for enantiomer separation.

Enantiomer Separation

The combined sample of (racemic) 3-(2,2-dimethyl-1,1-dioxidotetrahydro-2H-thiopyran-4-yl)-5-(4-fluorophenyl)-1H-indole-7-carboxamide was then purified using the OJ 10 um 10×250 mm column, 50% MeOH, 140 bar, 40° C. Compound needs more than 50% of DMSO to dissolve. Run time was ~8 minutes. Multiple runs afford each enantiomer as 200 mg of 3-[(4S)-2,2-dimethyl-1,1-dioxidotetrahydro-2H-thiopyran-4-yl]-5-(4-fluorophenyl)-1H-indole-7-carboxamide and 233 mg of 3-[(4R)-2,2-dimethyl-1,1-dioxidotetrahydro-2H-thiopyran-4-yl]-5-(4-fluorophenyl)-1H-indole-7-carboxamide. The absolute configurations of these enantiomers were determined using ab initio VCD analysis.

Example 226

3-(2,2-Dimethyl-1,1-dioxidotetrahydro-2H-thiopyran-4-yl)-5-phenyl-1H-indole-7-carboxamide

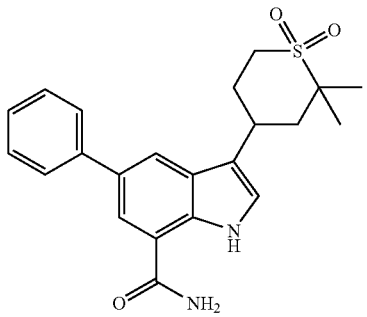

5-Bromo-3-(2,2-dimethyl-1,1-dioxidotetrahydro-2H-thiopyran-4-yl)-1H-indole-7-carboxamide (104 mg, 0.26 mmol) was placed in a microwave vial and dissolved with 1,4-dioxane (6 mL) and water (3 mL). 3-Phenylboronic acid (64 mg, 0.52 mmol) and K2CO3 (108 mg, 0.78 mmol) were added. Argon was bubbled in the mixture for 10 min with stirring. PdCl2(dppf) (10 mg, 0.02 mmol) was added, and argon was bubbled another 10 min. The vial is sealed and heated in a microwave for 5 min at 100° C. on high absorption. The reaction was evaporated to remove most of the dioxane. The residue was partitioned between ethyl acetate and water. The layers were separated, the organic layer was dried (MgSO$_4$), and the solvent was removed under vacuum. The residue was dissolved in DMSO (3 mL), and was purified on a Gilson HPLC. The desired fractions were concentrated, giving 20 mg (18%) of the title compound.

LC/MS: m/z 396.9 (M+H), Rt 0.90 min.

Example 227

3-(2,2-Dimethyl-1,1-dioxidotetrahydro-2H-thiopyran-4-yl)-5-(3-thienyl)-1H-indole-7-carboxamide

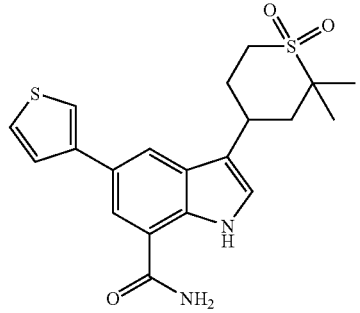

5-Bromo-3-(2,2-dimethyl-1,1-dioxidotetrahydro-2H-thiopyran-4-yl)-1H-indole-7-carboxamide (144 mg, 0.36 mmol) was placed in a microwave vial and dissolved with 1,4-dioxane (6 mL) and water (3 mL). 3-Thiopheneboronic acid (92 mg, 0.72 mmol) and K2CO3 (150 mg, 1.1 mmol) were added. Argon was bubbled in the mixture for 10 min with stirring. PdCl2(dppf) (21 mg, 0.29 mmol) was added, and argon was bubbled another 10 min. The vial is sealed and heated in a microwave for 5 min at 100° C. on high absorption. The reaction was evaporated to remove most of the dioxane. The residue was partitioned between ethyl acetate and water. The layers were separated, the organic layer was dried (MgSO$_4$), and the solvent was removed under vacuum. The residue was dissolved in DMSO (3 mL), and was purified on a Gilson HPLC. The desired fractions were concentrated, giving 28 mg (19%) of the title compound.

LC/MS: m/z 403.0 (M+H), Rt 2.08 min.

Example 228

3-(2,2-Dimethyl-1,1-dioxidotetrahydro-2H-thiopyran-4-yl)-5-(3-furanyl)-1H-indole-7-carboxamide

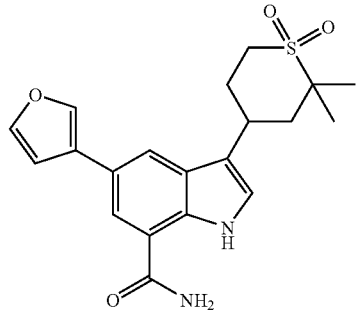

5-Bromo-3-(2,2-dimethyl-1,1-dioxidotetrahydro-2H-thiopyran-4-yl)-1H-indole-7-carboxamide (80 mg, 0.20 mmol) was placed in a microwave vial and dissolved with 1,4-dioxane (2 mL) and water (1 ml). 3-Furanylboronic acid (44.8 mg, 0.401 mmol) and K2CO3 (83 mg, 0.60 mmol) were added. Argon was bubbled in the mixture for 10 min with stirring. PdCl2(dppf) (4.83 mg, 0.01 mmol) was added, and argon was bubbled another 10 min. The vial is sealed and heated in a microwave for 5 min at 100° C. on high absorption. The reaction was evaporated to remove most of the dioxane. The residue was partitioned between ethyl acetate and water. The layers were separated, the organic layer was dried (MgSO$_4$), and the solvent was removed under vacuum. The residue was dissolved in the minimum amount of MeOH and EtOAc, and was run through a thiol-SPE cartridge eluting with 2 mL of MeOH. The solvent was removed under vacuum, and the residue was dissolved in 1-2 mL of DMSO, and purified on a Gilson HPLC. The desired fractions were concentrated, giving 22 mg (26%) of the title compound.

LC/MS: m/z 387.1 (M+H), Rt 0.83 min.

Following the procedure for the preparation of 3-(2,2-dimethyl-1,1-dioxidotetrahydro-2H-thiopyran-4-yl)-5-(3-furanyl)-1H-indole-7-carboxamide, 5-Bromo-3-(2,2-dimethyl-1,1-dioxidotetrahydro-2H-thiopyran-4-yl)-1H-indole-7-carboxamide as reacted with the appropriate boronic acid or ester, giving the compounds shown in Table 18.

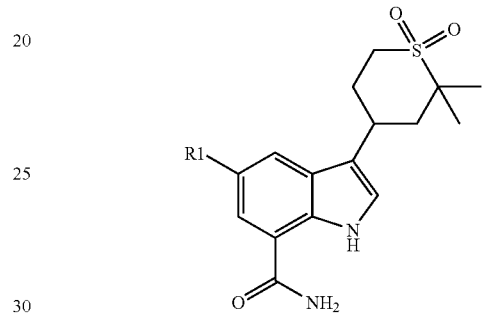

TABLE 18

| Example | R1 | MS [M]$^+$/RT |
|---|---|---|
| 229 | ![thienyl] | 403.0/0.78 min |
| 230 | ![furanyl] | 387.3/0.84 min |

Intermediate 177

3-(2,2-Dimethyl-1,1-dioxidotetrahydro-2H-thiopyran-4-yl)-5-(5-formyl-3-thienyl)-1H-indole-7-carboxamide

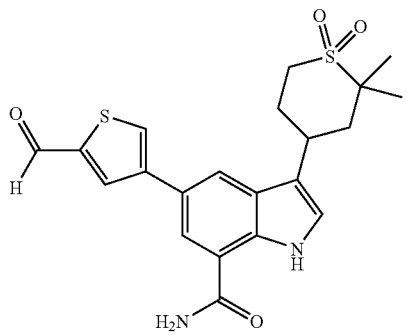

(racemic)-5-Bromo-3-(2,2-dimethyl-1,1-dioxidotetrahydro-2H-thiopyran-4-yl)-1H-indole-7-carboxamide (170 mg, 0.426 mmol) was placed in a microwave vial and dissolved in 1,4-dioxane (10 mL) and water (5 mL). 4-(4,4,5,5-tetramethyl-1,3,2-dioxaborolan-2-yl)-2-thiophenecarbaldehyde (203 mg, 0.851 mmol) and $K_2CO_3$ (177 mg, 1.277 mmol) was added. Argon was bubbled through the mixture for 10 min. $PdCl_2$(dppf) (16.43 mg, 0.034 mmol) was added, and argon was bubbled another 10 mins. The vial was sealed and put under microwave 5 mins at 100° C. with high absorption parameter. The mixture was run through a thiol-SPE column eluting with MeOH. The fraction containing product (lcms) are combined and solvent was evaporated. One fraction of the residue was purified by Preparative HPLC. Conditions: aqueous phase contains 0.1% $NH_4OH$ (Ammonium Gilson) starting with 20% acetonitrile to finish with 80% acetonitrile in 60 min. The product stays around 17-18 mins in the column. The title product (10 mg) was obtained. The other fraction was purified by FlashChromatography (DCM 100% to DCM 30%/-DCM 90/MeOH 7/NH4OH aq 3-70% in 30 mins) to give 90 mg of the title compound.

LC/MS: m/z 431.1 (M+H), Rt 0.81 min.

Example 231

3-(2,2-Dimethyl-1,1-dioxidotetrahydro-2H-thiopyran-4-yl)-5-[5-(hexahydro-1H-azepin-1-ylmethyl)-3-thienyl]-1H-indole-7-carboxamide

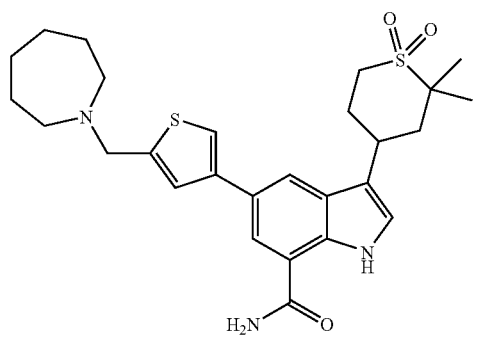

3-(2,2-Dimethyl-1,1-dioxidotetrahydro-2H-thiopyran-4-yl)-5-(5-formyl-3-thienyl)-1H-indole-7-carboxamide (40 mg, 0.093 mmol) was dissolved in dimethyl sulfoxide (1.5 mL) and put in a microwave vial. The mixture was stirred and acetic acid (0.056 mg, 0.929 µmol) was added, hexahydro-1H-azepine (0.453 mL, 4.02 mmol) was added. The mixture was left stirring 30 minutes at 23° C., before adding sodium triacetoxyborohydride polymer bound (399 mg, 0.929 mmol). The vial was sealed and the mixture heated in a microwave 10 minutes at 100° C. The sodium triacetoxyborohydride polymer bound was removed by filtration, and the mixture was run through prep HPLC from 10% acetonitrile containing 0.1% TFA to 50% acetonitrile containing 0.1% TFA in 25 minutes. The desired fractions were concentrated, giving 12 mg of the title compound.

LC/MS: m/z 514.4 (M+H), Rt 0.71 min.

Intermediate 178

3-(2,2-Dimethyl-1,1-dioxidotetrahydro-2H-thiopyran-4-yl)-5-(4,4,5,5-tetramethyl-1,3,2-dioxaborolan-2-yl)-1H-indole-7-carboxamide

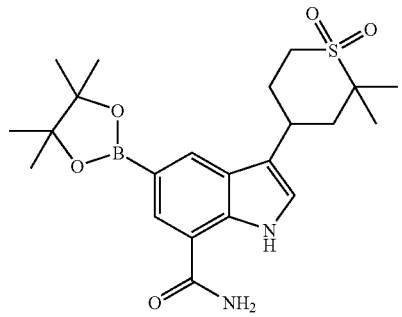

5-Bromo-3-(2,2-dimethyl-1,1-dioxidotetrahydro-2H-thiopyran-4-yl)-1H-indole-7-carboxamide (500 mg, 1.25 mmol), bis-pinacolatodiboron (1.06 g, 4.17 mmol, 3.3 eq), potassium acetate (745 mg, 7.59 mmol, 6.1 eq) and $PdCl_2$(dppf)-$CH_2Cl_2$ adduct (128 mg, 0.16 mmol, 0.13 eq) were diluted in dry dioxane (25 mL). The mixture was degassed twice by evacuating the flask and backfilling with argon, then was heated overnight at 100° C. The mixture was cooled to 23° C., filtered through a thin pad of celite washing well with dichloromethane, and concentrated to afford the crude product as brown oil. The crude material was re-diluted in dichloromethane and washed twice with water. The combined organic extracts were dried ($Na_2SO_4$), filtered, and concentrated. The resultant brown oil was diluted in dichloromethane (10 mL). Hexanes (40 mL) was slowly added with stirring to crash out the product. The solid was isolated by vacuum filtration, re-dissolved in dichloromethane (5 mL), and crashed out again by the slow addition of hexanes (30 mL) with stirring, giving 480 mg (86%) of the title compound, which was of sufficient purity to carry on for the next reaction.

LC/MS: m/z 447.4 (M+H), Rt 0.95 min.

Intermediate 179

1-(5-Bromo-2-thienyl)-N,N-dimethylmethanamine

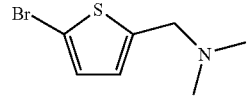

The above procedure to make 1-[(5-bromo-2-thienyl)methyl]pyrrolidine was repeated except using 2 M dimethylamine in methanol (0.75 mL, 1.5 mmol) to afford 204 mg (93%) of the title compound.

$^1$H NMR (400 MHz, $CDCl_3$) δ 6.90 (d, 1H), 6.68 (d, 1H), 3.59 (s, 2H), 2.29 (s, 6H).

Intermediate 180

1-[(5-Bromo-2-thienyl)methyl]pyrrolidine

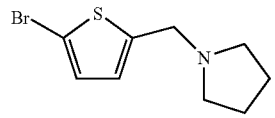

5-Bromo-2-thiophenecarbaldehyde (191 mg, 1.0 mmol) was diluted in a mixture of dichloromethane (6 mL) and N,N-dimethylformamide (2 mL), and cooled to 0° C. Pyrrolidine (107 mg, 1.5 mmol)) was added, followed by sodium triacetoxyborohydride (1.04 g, 4.9 mmol, 4.9 eq) and glacial acetic acid (2 drops). The reaction mixture was stirred at 23° C. for 2 h, then carefully quenched with saturated aq sodium bicarbonate (fizzing!). The reaction mixture was extracted with dichloromethane (2×10 mL), then the combined organic layers were filtered through a SCX cartridge (5 grams), eluting with methanol (10 mL). The first fraction was discarded if no product was present by tlc, and the desired product was eluted from the resin with methanol in ammonia (2M, Aldrich, 25 mL). The latter fraction was concentrated to afford 349 mg (>100%) of the title compound.

$^1$H NMR (400 MHz, CDCl$_3$) δ 6.88 (d, 1H), 6.69 (d, 1H), 3.77 (s, 2H), 2.57 (m, 4H), 1.81 (m, 4H).

Intermediate 181

1-[(5-Bromo-2-thienyl)methyl]azetidine

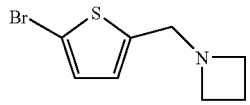

The above procedure to make 1-[(5-bromo-2-thienyl)methyl]pyrrolidine was repeated except using azetidine (86 mg, 1.5 mmol) as the amine. Following the purification with the SCX column as described -[(5-bromo-2-thienyl)methyl]pyrrolidine an additional purification step on a 40 g ISCO silica column was necessary to afford the title compound (166 mg) of acceptable purity for use in the next reaction.

$^1$H NMR (400 MHz, CDCl$_3$) δ 6.88 (d, 1H), 6.64 (d, 1H), 3.66 (s, 2H), 3.24 (t, 4H), 2.09 (m, 2H).

Intermediate 182

1-[(5-Bromo-2-thienyl)sulfonyl]pyrrolidine

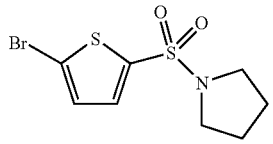

5-Bromo-2-thiophenesulfonyl chloride (523 mg, 2 mmol) was dissolved in dichloromethane (20 mL). Pyrrolidine (213 mg, 3 mmol) and potassium carbonate (829 mg, 6 mmol,) are added, and the mixture was stirred at 23° C. for 1 h. After tlc (30% ethyl acetate in hexanes) indicated that the reaction had gone to completion, brine was added and the mixture was extracted with dichloromethane. The combined organic layers were dried (Na$_2$SO$_4$), filtered, and concentrated. The crude product was purified by isco combiflash, eluting with 0-50% ethyl acetate in hexanes (40 g column), giving the title compound.

$^1$H NMR (400 MHz, CDCl$_3$) δ 7.35 (d, 1H), 7.13 (d, 1H), 3.30 (m, 4H), 1.83 (m, 4H)

Intermediate 183

1-[(5-Bromo-2-thienyl)methyl]hexahydro-1H-azepine

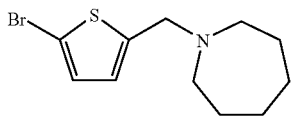

5-Bromo-2-thiophenecarbaldehyde (191 mg, 1 mmol) was diluted in a mixture of dichloromethane (6 mL) and N,N-dimethylformamide (2 mL), and cooled to 0° C. Hexahydro-1H-azepine (0.17 mL, 1.5 mmol, 1.5 eq) was added, followed by sodium triacetoxyborohydride (1.04 g, 4.9 mmol, 4.9 eq) and glacial acetic acid (2 drops). The mixture was stirred at 23° C. for 3 h. The reaction mixture was carefully quenched with saturated aqueous sodium bicarbonate. The reaction mixture was extracted with ethyl acetate, dried over sodium sulfate, filtered, and concentrated. The crude product was purified by isco combiflash, 40 g column, using a 0-70% ethyl acetate in hexanes gradient. The product fractions were concentrated to give the title compound as clear colorless oil (200 mg, 73%).

$^1$H NMR (400 MHz, CDCl$_3$) δ: 6.88 (d, 1H), 6.64 (d, 1H), 3.77 (s, 2H), 2.66 (m, 4H), 1.63 (m, 8H)

Example 232

5-{5-[(Dimethylamino)methyl]-3-thienyl}-3-(2,2-dimethyl-1,1-dioxidotetrahydro-2H-thiopyran-4-yl)-1H-indole-7-carboxamide

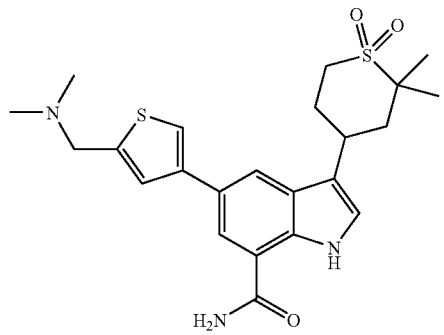

3-(2,2-Dimethyl-1,1-dioxidotetrahydro-2H-thiopyran-4-yl)-5-(5-formyl-3-thienyl)-1H-indole-7-carboxamide (30 mg, 0.070 mmol) was dissolved in dimethyl sulfoxide (1.5 mL) and put in a microwave vial. The mixture was stirred and 1-2 drops of acetic acid was added, dimethylamine (0.348 mL, 0.697 mmol) was added. The mixture was stirred 2 hours at 23° C., before adding sodium triacetoxyborohydride polymer bound (299 mg, 0.697 mmol). The vial was sealed using a silicon septum, and the mixture left stirring overnight at 23° C. The sodium triacetoxyborohydride polymer bound was removed by filtration (syringe filter 45 um). The product was purified by preparative HPLC (NH$_4$OH buffer). The desired fractions were concentrated, giving 12 mg of the title compound.

LC/MS: m/z 460.2 (M+H), Rt 0.64 min.

Example 233

3-(2,2-Dimethyl-1,1-dioxidotetrahydro-2H-thiopyran-4-yl)-5-[5-(1-pyrrolidinylmethyl)-3-thienyl]-1H-indole-7-carboxamide

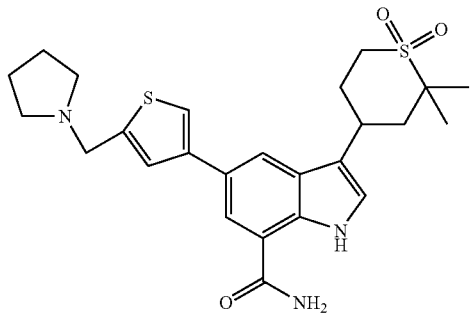

3-(2,2-Dimethyl-1,1-dioxidotetrahydro-2H-thiopyran-4-yl)-5-(5-formyl-3-thienyl)-1H-indole-7-carboxamide (30 mg, 0.070 mmol) was dissolved in dimethyl sulfoxide (1.5 mL) and put in a microwave vial. The mixture was stirred and 1-2 drops of acetic acid, and pyrrolidine (0.058 mL, 0.697 mmol) was added. Stirred for 30 minutes at 23° C., before adding sodium triacetoxyborohydride polymer bound (299 mg, 0.697 mmol). The vial was sealed using a silicon septum, and the mixture left stirring overnight at 23° C. The mixture was quenched with water, extracted with DCM, the DCM solution was evaporated to dryness, and the resulting mixture was rerun through the same process: 1.5 mL of DMSO, 1 drop of glacial acetic acid, and 0.577 mL of pyrrolidine. Left stirring 30 min and then 299 mg of polymer bound sodium triacetoxyborohydride was added and the mixture was left stirring 16 h. The sodium triacetoxyborohydride polymer bound was removed by filtration. The mixture was dissolved in 1 mL of DMSO, and the product was purified by preparative HPLC (NH$_4$OH buffer). The desired fractions were concentrated, giving 6 mg of the title compound.

LC/MS: m/z 486.2 (M+H), Rt 0.67 min.

Example 234

5-[5-(1-Azetidinylmethyl)-3-thienyl]-3-(2,2-dimethyl-1,1-dioxidotetrahydro-2H-thiopyran-4-yl)-1H-indole-7-carboxamide

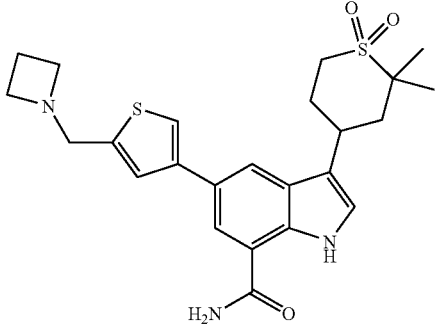

3-(2,2-Dimethyl-1,1-dioxidotetrahydro-2H-thiopyran-4-yl)-5-(5-formyl-3-thienyl)-1H-indole-7-carboxamide (30 mg, 0.070 mmol) was dissolved in dimethyl sulfoxide (1.5 mL) and put in a microwave vial. The mixture was stirred and 1-2 drops of acetic acid and azetidine (0.047 mL, 0.697 mmol) was added. The mixture was left stirring 30 minutes at 23° C., before adding sodium triacetoxyborohydride polymer bound (299 mg, 0.697 mmol). The vial was sealed using a silicon septum, and the mixture left stirring 16 h at 23° C. Based on LCMS only 60-70% of conversion was observed. The sodium triacetoxyborohydride polymer bound was removed by filtration. The crude product was purified by preparative HPLC (NH$_4$OH buffer). The desired fractions were concentrated, giving 12 mg of the title compound.

LC/MS: m/z 472.5 (M+H), Rt 0.66 min.

Example 235

3-(2,2-Dimethyl-1,1-dioxidotetrahydro-2H-thiopyran-4-yl)-5-[5-(1-pyrrolidinylmethyl)-2-thienyl]-1H-indole-7-carboxamide

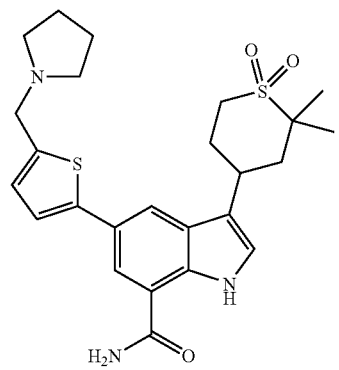

3-(2,2-Dimethyl-1,1-dioxidotetrahydro-2H-thiopyran-4-yl)-5-(4,4,5,5-tetramethyl-1,3,2-dioxaborolan-2-yl)-1H-indole-7-carboxamide (75 mg, 0.17 mmol), 1-[(5-bromo-2-thienyl)methyl]pyrrolidine (50 mg, 0.17 mmol), PdCl$_2$ (dppf)-CH$_2$Cl$_2$ adduct (20 mg, 0.024 mmol), and potassium carbonate (100 mg, 0.72 mmol) were diluted in a mixture of 1,4-dioxane (3 mL) and water (1.5 mL) in a 2-5 mL microwave tube. The mixture was degassed by bubbling argon through for 5 minutes, then heated in a biotage microwave at 100° C. for 5 minutes. The crude reaction mixture was filtered through a thiol SPE cartridge (polymer labs) to remove palladium, and concentrated. The residue was dissolved in ~3 mL of dmso, and filtered through a syringe filter. The crude product was purified by ammonium hydroxide Gilson HPLC, and the desired fractions were concentrated. The product was further purified by trituration from diethyl ether to afford 18.6 mg of the title compound.

LC/MS: m/z 415.2 (M+H), Rt 0.69 min.

Following the procedure for the preparation of 3-(2,2-dimethyl-1,1-dioxidotetrahydro-2H-thiopyran-4-yl)-5-[5-(1-pyrrolidinylmethyl)-2-thienyl]-1H-indole-7-carboxamide, 3-(2,2-dimethyl-1,1-dioxidotetrahydro-2H-thiopyran-4-yl)-5-(4,4,5,5-tetramethyl-1,3,2-dioxaborolan-2-yl)-1H-indole-7-carboxamide was reacted with an appropriate heteroaromatic bromide to give the compounds shown in Table 19.

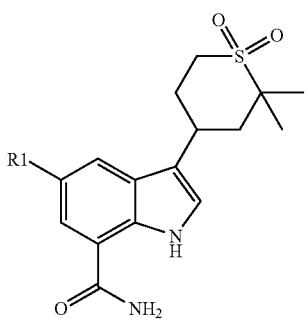

TABLE 19

| Example | R1 | MS [M]+/RT |
|---|---|---|
| 236 | (dimethylaminomethyl-thienyl-t-butyl) | 460.2/0.67 min |
| 237 | (azetidinylmethyl-thienyl-t-butyl) | 472.5/0.68 min |
| 238 | (azepanylmethyl-thienyl-t-butyl) | 514.6/0.75 min |

Example 239

3-(2,2-Dimethyl-1,1-dioxidotetrahydro-2H-thiopyran-4-yl)-5-[5-(1-pyrrolidinylsulfonyl)-2-thienyl]-1H-indole-7-carboxamide

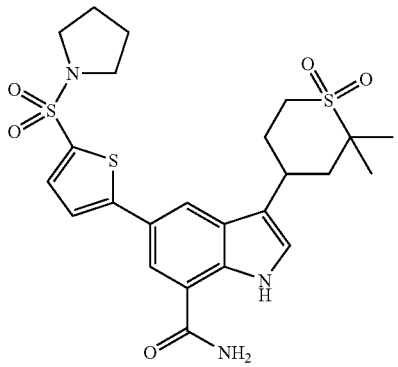

3-(2,2-Dimethyl-1,1-dioxidotetrahydro-2H-thiopyran-4-yl)-5-(4,4,5,5-tetramethyl-1,3,2-dioxaborolan-2-yl)-1H-indole-7-carboxamide (75 mg, 0.17 mmol), 1-[(5-bromo-2-thienyl)sulfonyl]pyrrolidine (60 mg, 0.17 mmol, 1 eq), PdCl₂(dppf)-CH₂Cl₂ adduct (20 mg, 0.024 mmol, 0.15 eq), and potassium carbonate (100 mg, 0.72 mmol, 4.3 eq) were diluted in a mixture of 1,4-dioxane (3 mL) and water (1.5 mL) in a 2-5 mL microwave tube. The mixture was degassed by bubbling argon through for 5 minutes, then heated in a biotage microwave at 100° C. for 5 minutes. The crude reaction mixture was filtered through a thiol SPE cartridge (polymer labs) to remove palladium, and concentrated. The residue was dissolved in ~3 mL of dmso, and filtered. The crude product was purified by ammonium hydroxide Gilson hplc, and the desired fractions were evaporated. The product was further purified by trituration from diethyl ether to afford 19.5 mg (21%) of the title compound.

LC/MS: m/z 536.0 (M+H), Rt 0.92 min.

Example 240

5-[5-(Cyclopentylsulfonyl)-2-thienyl]-3-(2,2-dimethyl-1,1-dioxidotetrahydro-2H-thiopyran-4-yl)-1H-indole-7-carboxamide

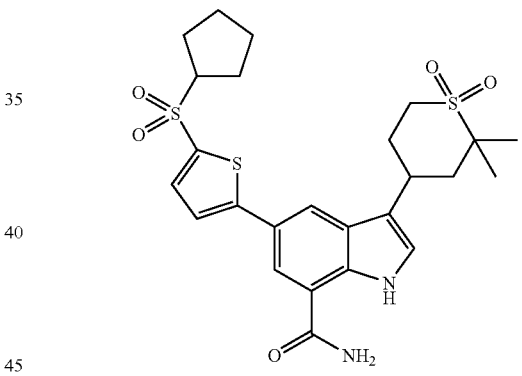

3-(2,2-Dimethyl-1,1-dioxidotetrahydro-2H-thiopyran-4-yl)-5-(4,4,5,5-tetramethyl-1,3,2-dioxaborolan-2-yl)-1H-indole-7-carboxamide (75 mg, 0.17 mmol), 5-bromo-2-thienyl cyclopentyl sulfone (60 mg, 0.20 mmol), PdCl₂(dppf)-CH₂Cl₂ adduct (20 mg, 0.024 mmol, 0.15 eq), and potassium carbonate (100 mg, 0.72 mmol, 4.3 eq) were diluted in a mixture of 1,4-dioxane (3 mL) and water (1.5 mL) in a 2-5 mL microwave tube. The mixture was degassed by bubbling argon through for 5 minutes, then was heated in a biotage microwave at 100° C. for 5 minutes. The crude reaction mixture was filtered through a thiol SPE cartridge (polymer labs) to remove palladium, and was concentrated. The residue was re-diluted in ~3 mL of dmso, and filtered through a syringe filter. The crude product was purified by ammonium hydroxide Gilson HPLC, and the desired fractions were evaporated to afford 5-[5-(cyclopentylsulfonyl)-2-thienyl]-3-(2,2-dimethyl-1,1-dioxidotetrahydro-2H-thiopyran-4-yl)-1H-indole-7-carboxamide as an off white solid (22.4 mg, 24%).

LC/MS: m/z 535.1 (M+H), Rt 0.96 min.

Example 241

(racemic)-3-[trans-2-(1-Methylethyl)-1,1-dioxidotetrahydro-2H-thiopyran-4-yl]-5-(3-thienyl)-1H-indole-7-carboxamide

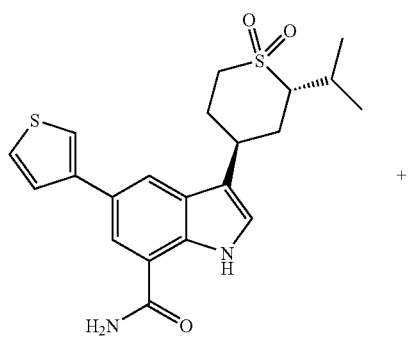

+

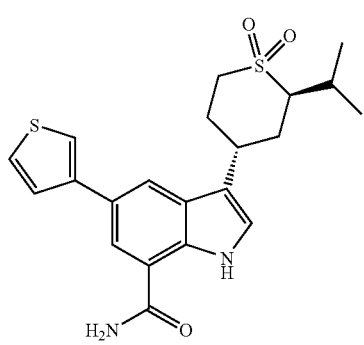

(racemic)-5-Bromo-3-[trans-2-(1-methylethyl)-1,1-dioxidotetrahydro-2H-thiopyran-4-yl]-1H-indole-7-carboxamide (65 mg, 0.157 mmol) was placed in a microwave vial and dissolved in 1,4-Dioxane (2 mL) and Water (1.000 mL). Thiophene 3-boronic acid (40.2 mg, 0.315 mmol) and $K_2CO_3$ (65.2 mg, 0.472 mmol) was added. Argon was bubbled in the mixture for 10 min, and then $PdCl_2(dppf)_2$ (6.07 mg, 0.013 mmol) was added, and argon was bubbled another 10 min. The vial was sealed and put under microwave 5 mins at 100° C. with high absorption parameter. The crude was run through a thiol-SPE cartridge eluting with methanol (2 mL) and the treated solution was evaporated to remove most the dioxane and methanol. The resulting mixture was partitioned between ethyl acetate and water. The organic layer was dried ($MgSO_4$) and solvent removed in vacuo to give a gummy brown crude material which was dissolved in 2-3 mL of DMSO, and run through the ammonium Gilson eluting with 35% to 90% organic in 15 min. The product was isolated to afford 16 mg. Stereochemistry of the product was assigned as the trans isomer based on the NMR analysis of the starting material.

LC/MS: m/z 416.9 (M+H), Rt 1.97 min.

Example 242 racemic-3-[(trans)-2-(1-Methylethyl)-1,1-dioxidotetrahydro-2H-thiopyran-4-yl]-5-phenyl-1H-indole-7-carboxamide

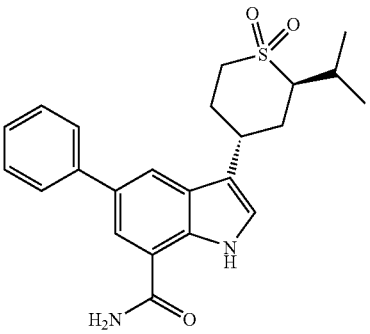

(racemic)-5-Bromo-3-[trans-2-(1-methylethyl)-1,1-dioxidotetrahydro-2H-thiopyran-4-yl]-1H-indole-7-carboxamide (65 mg, 0.157 mmol) was placed in a microwave vial and dissolved in 1,4-dioxane (2 mL) and water (1.000 mL). Phenylboronic acid (19.17 mg, 0.157 mmol) and $K_2CO_3$ (65.2 mg, 0.472 mmol) were added. Argon was bubbled in the mixture for 10 min, and then $PdCl_2(dppf)$ (6.07 mg, 0.013 mmol) was added, and argon was bubbled another 10 min. The vial was sealed and put under microwave 5 mins at 100° C. with high absorption parameter. The crude was run through a thiol-SPE cartridge eluting with methanol (2 mL) and the treated solution was evaporated to remove the biggest part of dioxane and methanol. The resulting mixture was partitioned between ethyl acetate and water. The organic layer was dried ($MgSO_4$) and solvent removed in vacuo to give crude material which was dissolved in 1-2 mL of DMSO filtered through a syringe filter (Acrodisc CR 13 mm; 45 um PTFE filter), and run through the ammonium Gilson eluting with 35% to 90% organic in 15 min. The product was isolated to afford 17 mg of the title compound.

LC/MS: m/z 411.2 (M+H), Rt 1.01 min.

Example 243

(racemic)-5-(3-Furanyl)-3-[trans-2-(1-methylethyl)-1,1-dioxidotetrahydro-2H-thiopyran-4-yl]-1H-indole-7-carboxamide

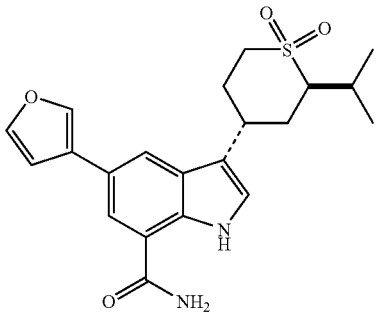

(racemic)-5-Bromo-3-[trans-2-(1-methylethyl)-1,1-dioxidotetrahydro-2H-thiopyran-4-yl]-1H-indole-7-carboxamide (60 mg, 0.145 mmol) was placed in a microwave vial and dissolved in 1,4-Dioxane (2 mL) and Water (1 mL). 3-Furanylboronic acid (16.24 mg, 0.145 mmol) and K2CO3 (60.2 mg, 0.435 mmol) were added. Argon was bubbled in the mixture for 10 mins, stirring. $PdCl_2(dppf)$ (5.60 mg, 0.012 mmol) was added, and argon was bubbled another 10 mins.

The vial was sealed and put under microwave 5 mins at 100° C. with high absorption parameter. The crude was run through a thiol-SPE cartridge eluting with 2 mL of methanol and the eluted solvents are evaporated. The residue was dissolved in 2-3 mL of DMSO, filtered through a syringe filter (Acrodisc CR 13 mm; 45 um PTFE filter), and purified on a Gilson HPLC. The desired fractions were concentrated, giving 22 mg of the title compound.

LC/MS: m/z 400.7 (M+H), Rt 0.90 min.

Example 244

(racemic)-5-(2-Furanyl)-3-[trans-2-(1-methylethyl)-1,1-dioxidotetrahydro-2H-thiopyran-4-yl]-1H-indole-7-carboxamide

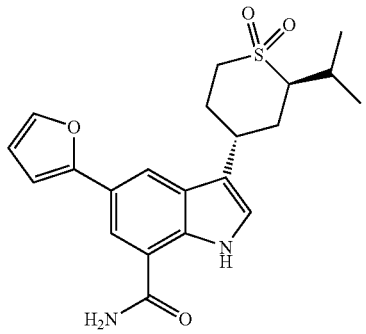

(racemic)-5-Bromo-3-[trans-2-(1-methylethyl)-1,1-dioxidotetrahydro-2H-thiopyran-4-yl]-1H-indole-7-carboxamide (60 mg, 0.145 mmol) was placed in a microwave vial and dissolved with 1,4-Dioxane (2 mL) and Water (1 mL). 2-Furanylboronic acid (33 mg, 0.29 mmol) and K2CO3 (60 mg, 0.44 mmol) were added. Argon was bubbled into the mixture for 10 mins, stirring. PdCl$_2$(dppf) (5.60 mg, 0.012 mmol) was added, and argon was bubbled another 10 mins. The vial was sealed and put under microwave 5 mins at 100° C. with high absorption parameter. The crude was run through a thiol-SPE cartridge eluting with 2 mL of methanol and the eluted solvents are evaporated. The brown oil was dissolved in 2-3 mL of DMSO, and on a Gilson HPLC. The desired fractions were concentrated, giving 32 mg of the title compound.

LC/MS: m/z 400.9 (M+H), Rt 0.92 min.

Example 245

(racemic)-3-[trans-2-(1-Methylethyl)-1,1-dioxidotetrahydro-2H-thiopyran-4-yl]-5-(2-thienyl)-1H-indole-7-carboxamide

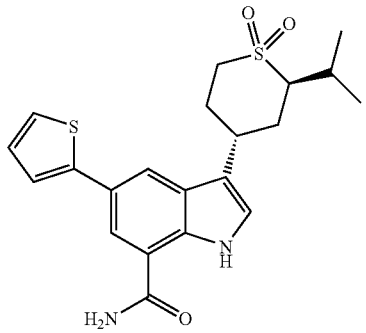

(racemic)-5-Bromo-3-[trans-2-(1-methylethyl)-1,1-dioxidotetrahydro-2H-thiopyran-4-yl]-1H-indole-7-carboxamide (60 mg, 0.145 mmol) was placed in a microwave vial and dissolved with 1,4-Dioxane (2 mL) and Water (1.000 mL). 2-Thienylboronic acid (37.1 mg, 0.290 mmol) and K2CO3 (60.2 mg, 0.435 mmol) were added. Argon was bubbled in the mixture for 10 min with stirring, PdCl$_2$(dppf) (5.60 mg, 0.012 mmol) was added, and argon was bubbled another 10 mins. The vial was sealed and put under microwave 5 mins at 100° C. with high absorption parameter. The reaction was complete after the microwave treatment. The crude was run through a thiol-SPE cartridge eluting with 2 mL of methanol and the eluted solvents are evaporated. The brown oil was dissolved in 2-3 mL of DMSO, and purified on a Gilson HPLC. The desired fractions were concentrated, giving 13 mg of the title compound.

LC/MS: m/z 417.3 (M+H), Rt 0.97 min.

Example 246

(racemic)-3-[cis-2-(1-Methylethyl)-1,1-dioxidotetrahydro-2H-thiopyran-4-yl]-5-(3-thienyl)-1H-indole-7-carboxamide

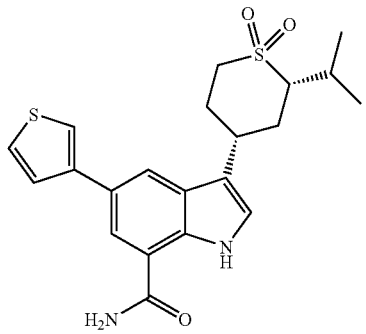

5-Bromo-3-[cis-2-(1-methylethyl)-1,1-dioxidotetrahydro-2H-thiopyran-4-yl]-1H-indole-7-carboxamide (37 mg, 0.090 mmol) was placed in a microwave vial and dissolved with 1,4-Dioxane (1 mL) and Water (0.500 mL). Thiophene 3-boronic acid (22.91 mg, 0.179 mmol) and K2CO3 (37.1 mg, 0.269 mmol) were added. Argon was bubbled in the mixture for 10 mins, stirring. PdCl$_2$(dppf) (3.45 mg, 7.16 μmol) was added, and argon was bubbled another 10 mins. The vial was sealed and put under microwave 5 mins at 100° C. with high absorption parameter. The mixture was run through a thiol-SPE column, eluting with methanol. The collected solution was concentrated in vacuo. The brown solid was dissolved in 2-3 mL of DMSO, and run through the ammonium Gilson, in 3 injections to afford 10 mg of the title compound. The cis stereochemistry of the product was confirmed by a $^1$H NMR NOE study.

LC/MS: m/z 417.3 (M+H), Rt 0.97 min.

Example 247 and 248

(racemic)-3-[1,1-Dioxido-2-cis-phenyltetrahydro-2H-thiopyran-4-yl]-5-(3-thienyl)-1H-indole-7-carboxamide

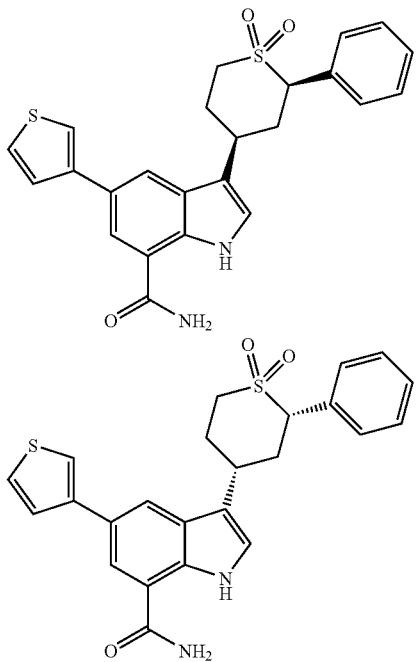

5-Bromo-3-(1,1-dioxido-2-phenyltetrahydro-2H-thiopyran-4-yl)-1H-indole-7-carboxamide (400 mg, 0.894 mmol) was placed in a microwave vial and combined with 1,4-Dioxane (12 mL) and Water (6 mL) and thiophene 3-boronic acid (229 mg, 1.788 mmol) Argon was bubbled in the mixture for 10 min, with stirring. $PdCl_2(dppf)$ (21 mg, 0.045 mmol) was added, and argon was bubbled another 10 mins. The vial was sealed and put under microwave 5 mins at 100° C. with high absorption parameter. The crude was concentrated in vacuo and partitioned between ethyl acetate (3×50 mL) and water (25 mL). Organic layer was dried $(MgSO_4)$ and solvent was removed in vacuo to give a brown oil which was dissolved in 2-3 mL of DMSO, and run through the ammonium Gilson. The major isomer was isolated affording 120 mg (28.3%). An NOE study confirms the cis stereochemistry of (racemic)-cis-3-(1,1-dioxido-2-phenyltetrahydro-2H-thiopyran-4-yl)-5-(3-thienyl)-1H-indole-7-carboxamide.

Enantiomer Separation:

About 105 mg of the sample of (racemic)-cis-3-(1,1-dioxido-2-phenyltetrahydro-2H-thiopyran-4-yl)-5-(3-thienyl)-1H-indole-7-carboxamide was then separated into pure enantiomers by SFC chromatography using the Prep conditions: Sample diluted in DMSO to about 30 mg/mL. 40% MeOH (0.5% DEA), 140 bar, 40° C., 10 mL/min total flow on an ASH 10×250 mm column. Both enantiomers are >98% pure. 3-[(2S,4R)1,1-dioxido-2-phenyltetrahydro-2H-thiopyran-4-yl]-5-(3-thienyl)-1H-indole-7-carboxamide (55 mg) and 3-[(2R,4S)1,1-dioxido-2-phenyltetrahydro-2H-thiopyran-4-yl]-5-(3-thienyl)-1H-indole-7-carboxamide (47 mg).

LC/MS: m/z 452.0 (M+H), Rt 0.93 min.

Example 249

3-(1,1-Dioxido-2-cis-phenyltetrahydro-2H-thiopyran-4-yl)-5-(2-thienyl)-1H-indole-7-carboxamide

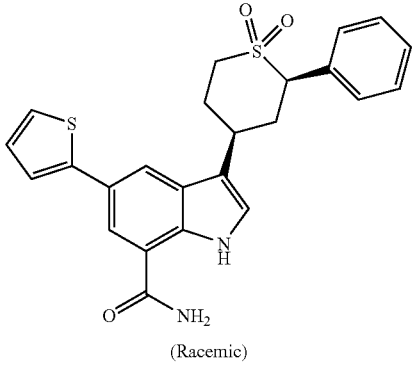

5-Bromo-3-(1,1-dioxido-2-phenyltetrahydro-2H-thiopyran-4-yl)-1H-indole-7-carboxamide (80 mg, 0.179 mmol) was placed in a microwave vial and combined with 1,4-Dioxane (2 mL) and Water (1 mL), 2-thienylboronic acid (45.8 mg, 0.358 mmol), and $K_2CO_3$ (74.1 mg, 0.536 mmol) and argon was bubbled through the mixture for 10 mins, stirring, then $PdCl_2(dppf)_2$ (6.90 mg, 0.014 mmol) was added, and argon was bubbled another 10 mins. The vial was sealed and put under microwave 5 mins at 100° C. with high absorption parameter. The crude was run through a thiol-SPE cartridge eluting with methanol (2 mL) and the residue was evaporated. The residue was dissolved in 1-2 mL of DMSO, filtered through a syringe filter (Acrodisc CR 13 mm; 45 um PTFE filter), and run through the ammonium Gilson to isolate 27 mg of the major product which was assigned the cis stereochemistry, 3-(1,1-dioxido-2-cis-phenyltetrahydro-2H-thiopyran-4-yl)-5-(2-thienyl)-1H-indole-7-carboxamide, based on assignments for the products of (racemic)-3-[1,1-dioxido-2-cis-phenyltetrahydro-2H-thiopyran-4-yl]-5-(3-thienyl)-1H-indole-7-carboxamide.

LC/MS: m/z 452.0 (M+H), Rt 0.98 min.

Example 250

3-(1,1-Dioxido-2-cis-phenyltetrahydro-2H-thiopyran-4-yl)-5-(3-furanyl)-1H-indole-7-carboxamide

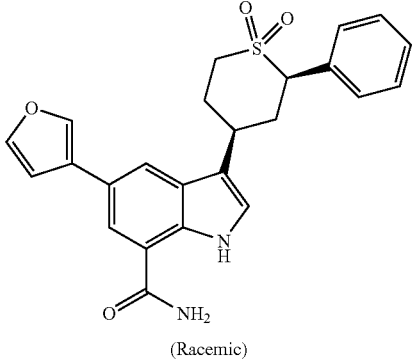

The above procedure was repeated except that 3-furanylboronic acid (40.0 mg, 0.358 mmol) was used as the boronic acid to afford 27.5 mg of (racemic)-3-(1,1-dioxido-2-cis-phenyltetrahydro-2H-thiopyran-4-yl)-5-(3-furanyl)-1H-indole-7-carboxamide.

LC/MS: m/z 435.2 (M+H), Rt 0.90 min.

Example 251

3-(1,1-Dioxido-2-phenyltetrahydro-2H-thiopyran-4-yl)-5-(2-furanyl)-1H-indole-7-carboxamide

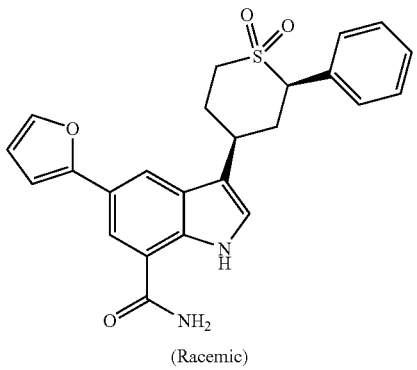
(Racemic)

The above procedure was repeated except that 2-furanylboronic acid (40.0 mg, 0.358 mmol) was used as the boronic acid to afford 15 mg of (racemic)-3-(1,1-dioxido-2-cis-phenyltetrahydro-2H-thiopyran-4-yl)-5-(2-furanyl)-1H-indole-7-carboxamide.

LC/MS: m/z 435.1 (M+H), Rt 0.92 min.

Example 252

3-(1,1-Dioxido-2-phenyltetrahydro-2H-thiopyran-4-yl)-5-phenyl-1H-indole-7-carboxamide

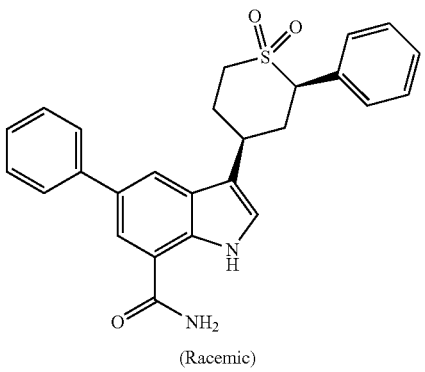
(Racemic)

5-Bromo-3-(1,1-dioxido-2-phenyltetrahydro-2H-thiopyran-4-yl)-1H-indole-7-carboxamide (100 mg, 0.224 mmol) was placed in a microwave vial and combined with 1,4-Dioxane (3 mL) and Water (1.5 mL). Argon was bubbled through the mixture for 10 mins, stirring and then PdCl$_2$(dppf) (8.18 mg, 0.011 mmol) was added, and argon was bubbled another 10 mins. The vial was sealed and put under microwave 5 mins at 100° C. with high absorption parameter. The crude was evaporated to remove the most of the dioxane. Then it was partitioned between EtOAc and water. Organic layer was dried over magnesium sulfate and solvent removed under vacuum to afford 155 mg of crude material as a gummy brown oil which was dissolved in 1-2 mL of DMSO, and run through the ammonium Gilson to afford 17 mg of (racemic)-3-(1,1-dioxido-2-phenyltetrahydro-2H-thiopyran-4-yl)-5-phenyl-1H-indole-7-carboxamide.

LC/MS: m/z 445.4 (M+H), Rt 0.97 min.

Example 253

3-[(1,1-dioxidotetrahydro-2H-thiopyran-4-yl)methyl]-5-(3-furanyl)-1H-indole-7-carboxamide

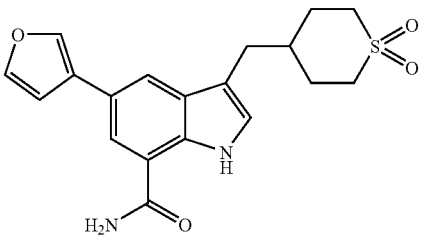

5-bromo-3-[(1,1-dioxidotetrahydro-2H-thiopyran-4-yl)methyl]-1H-indole-7-carboxamide (30 mg, 0.078 mmol), 3-furanylboronic acid (24.05 mg, 0.215 mmol, 2.76 eq), potassium carbonate (64.6 mg, 6 eq), PdCl$_2$(dppf) (4.56 mg, 0.006 mmol, 0.08 eq), were dissolved in a mixture of 1,4-dioxane (2 mL) and water (1 mL) in a 2-5 mL biotage microwave reaction tube. The mixture was heated in a Biotage microwave at high absorption for 10 minutes at 120° C. The reaction mixture was filtered through a polypropylene cartridge (10 mL tube) on a Bohdan Miniblock in a reaction tube and was then concentrated and purified by Gilson HPLC with a water-acetonitrile with 0.1% TFA buffer. The desired product fractions were combined and concentrated in an EZ2 Genevac evaporator, giving 14.4 mg (44.7%) of the title compound.

LC/MS: m/z 372.9 (M+H), Rt 0.79 min.

Following the procedure as described above in the preparation of 3-[(1,1-dioxidotetrahydro-2H-thiopyran-4-yl)methyl]-5-(3-furanyl)-1H-indole-7-carboxamide, 5-bromo-3-[(1,1-dioxidotetrahydro-2H-thiopyran-4-yl)methyl]-1H-indole-7-carboxamide was reacted with an appropriate heterocyclic boronic acid to give the compounds listed in Table 20.

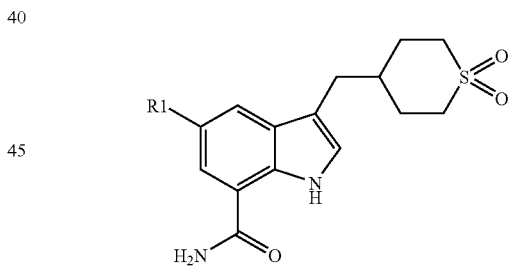

TABLE 20

| Example | R1 | MS [M]+/RT (min) |
|---|---|---|
| 254 | phenyl | 383.1/0.86 |
| 255 | 2-thienyl | 389.1/0.83 |

TABLE 20-continued

| Example | R1 | MS [M]+/RT (min) |
|---------|----|--------------------|
| 256 | 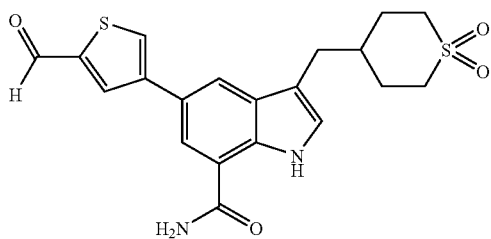 | 400.9/0.92 |
| 257 | | 389.1/0.87 |

Intermediate 184

3-[(1,1-Dioxidotetrahydro-2H-thiopyran-4-yl)methyl]-5-(5-formyl-3-thienyl)-1H-indole-7-carboxamide The title compound was made in two batches. The first batch was made as follows:

In a 0.5-2 mL microwave vial, 5-bromo-3-[(1,1-dioxidotetrahydro-2H-thiopyran-4-yl)methyl]-1H-indole-7-carboxamide (30 mg, 0.078 mmol), 4-(4,4,5,5-tetramethyl-1,3,2-dioxaborolan-2-yl)-2-thiophenecarbaldehyde (37.1 mg, 0.156 mmol), $K_2CO_3$ (32.3 mg, 0.234 mmol) and $PdCl_2$(dppf) (4.56 mg, 6.23 µmol) were dissolved in 1,4-dioxane (2 ml) and water (1 ml). The reaction was heated for 20 min at 100° C. in a Biotage Intiator Microwave (high absorption). The reaction mixture was filtered through a Bohdan Miniblock reaction tube, and the solvents were removed by concentration under a stream of nitrogen. The crude product was combined with the batch shown below for further work-up.

The second batch was made as follows:

In a 0.5-2 mL microwave vial, 5-bromo-3-[(1,1-dioxidotetrahydro-2H-thiopyran-4-yl)methyl]-1H-indole-7-carboxamide (60 mg, 0.156 mmol), 4-(4,4,5,5-tetramethyl-1,3,2-dioxaborolan-2-yl)-2-thiophenecarbaldehyde (74.2 mg, 0.311 mmol), $K_2CO_3$ (64.6 mg, 0.467 mmol) and $PdCl_2$(dppf) (9.12 mg, 0.012 mmol) were dissolved in 1,4-dioxane (3 ml) and water (1.5 ml). The reaction was heated for 20 min at 100° C. in a Biotage Intiator Microwave (high absorption). The reaction mixture was filtered through a Bohdan Miniblock reaction tube. The crude product from the previous batch was combined with this material. The combined batches were washed with $H_2O$ then with DCM. The organic layer was concentrated under a stream of nitrogen, giving 40 mg of the crude product.

LCMS m/z=417.2 (M+H); Rt=0.79 min.

Example 258

3-[(1,1-dioxidotetrahydro-2H-thiopyran-4-yl)methyl]-5-[5-(hexahydro-1H-azepin-1-ylmethyl)-3-thienyl]-1H-indole-7-carboxamide

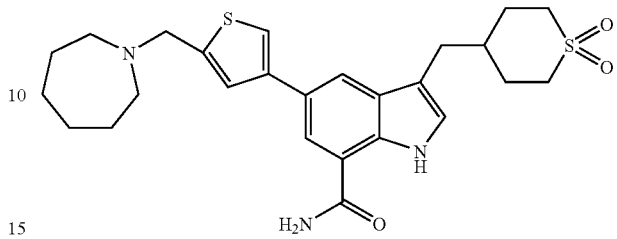

3-[(1,1-dioxidotetrahydro-2H-thiopyran-4-yl)methyl]-5-(5-formyl-3-thienyl)-1H-indole-7-carboxamide (30 mg, 0.072 mmol), hexahydro-1H-azepine (71.4 mg, 0.720 mmol, 10 eq), acetic acid (0.4 µL, 0.007 mmol, 0.1 eq) were dissolved in DMSO (2 mL) in a 5 mL A-vial reaction tube. The mixture was stirred in VX-2500 Multi-Tube Vortexer for overnight at room temperature. MP-triacetoxyborohydride (309 mg, 0.72 mmol, 10 eq) was then added and the mixture was stirred again in VX-2500 Multi-Tube Vortexer for overnight at room temperature. The reaction mixture was filtered through a polypropylene cartridge (10 mL tube) on Bohdan Miniblock in a reaction tube and was then concentrated and purified by Gilson HPLC with a water-acetonitrile with 0.1% TFA buffer. The desired product fractions were combined and concentrated in a Glas-Col evaporator, giving 3.8 mg (9.5%) of the title compound.

LC/MS: m/z 500.2 (M+H), Rt 0.73 min.

Example 259

3-[(1,1-Dioxidotetrahydro-3-thienyl)methyl]-5-phenyl-1H-indole-7-carboxamide

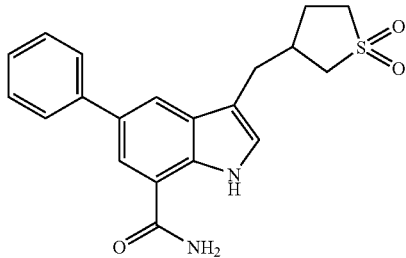

5-bromo-3-[(1,1-dioxidotetrahydro-3-thienyl)methyl]-1H-indole-7-carboxamide (40 mg, 0.108 mmol), phenylboronic acid (19.71 mg, 0.162 mmol, 1.5 eq), $PdCl_2$(dppf) (7.88 mg, 10.77 µmol, 0.1 eq), potassium carbonate (44.7 mg, 0.323 mmol, 3 eq) were diluted in a mixture of 1,4-dioxane (3 mL) and water (1 mL), in a 2-5 mL biotage microwave reaction tube. The mixture was degassed by bubbling nitrogen through for 5 minutes and was then heated in a microwave at high absorption for 15 minutes at 120° C. The reaction was filtered through a thiol SPE cartridge (polymer labs) and was concentrated and purified by Gilson HPLC with trifluoroacetic acid buffer. The desired product fractions were combined and concentrated in an EZ2 Genevac evaporator, giving 35.3 mg (84%) of the title compound.

LC/MS: m/z 368.8 (M+H), Rt 0.89 min.

Example 260

3-[(1,1-Dioxidotetrahydro-3-thienyl)methyl]-5-(3-thienyl)-1H-indole-7-carboxamide

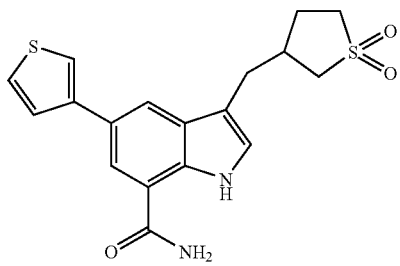

5-bromo-3-[(1,1-dioxidotetrahydro-3-thienyl)methyl]-1H-indole-7-carboxamide (40 mg, 0.108 mmol), 2-thienylboronic acid (20.68 mg, 0.162 mmol, 1.5 eq), PdCl$_2$(dppf) (7.88 mg, 10.77 μmol, 0.1 eq), potassium carbonate (44.7 mg, 0.323 mmol, 3 eq) were diluted in a mixture of 1,4-dioxane (3 mL) and water (1 mL), in a 2-5 mL biotage microwave reaction tube. The mixture was degassed by bubbling nitrogen through for 5 minutes and was then heated in a microwave at high absorption for 15 minutes at 120° C. The reaction was filtered through a thiol SPE cartridge (polymer labs) and was concentrated and purified by Gilson HPLC with trifluoroacetic acid buffer. The desired product fractions were combined and concentrated in an EZ2 Genevac evaporator, giving 35.3 mg (82%) of the title compound.

LC/MS: m/z 374.7 (M+H), Rt 0.86 min.

Example 261

5-{5-[(Dimethylamino)methyl]-3-thienyl}-3-[(1,1-dioxidotetrahydro-3-thienyl)methyl]-1H-indole-7-carboxamide

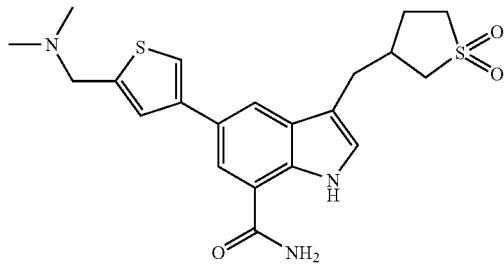

5-bromo-3-[(1,1-dioxidotetrahydro-3-thienyl)methyl]-1H-indole-7-carboxamide (120 mg, 0.323 mmol), (5-formyl-3-thienyl)boronic acid (76 mg, 0.485 mmol, 1.5 eq), PdCl$_2$(dppf) (23.65 mg, 0.032 mmol, 0.1 eq), potassium carbonate (134 mg, 0.970 mmol, 3 eq) were diluted in a mixture of 1,4-dioxane (3 mL) and water (1 mL), in a 2-5 mL biotage microwave reaction tube. The mixture was degassed by bubbling nitrogen through for 5 minutes and was then heated in a microwave at high absorption for 15 minutes at 120° C. The reaction was filtered through a thiol SPE cartridge (polymer labs) and was concentrated. Then a solution of 2 M dimethylamine in THF (553 mg, 1.242 mmol, 10 eq), HOAc (1 mL), NaBH(OAc)$_3$ (263 mg, 1.242 mmol, 10 eq) were added in DMSO) (2 mL, and the reaction mixture was stirred at room temperature overnight. Then the solvent was evaporated, EtOAc and water were added, the layers were separated, and the aqueous layer extracted with EtOAc. The combined layers were washed with satured NaCl, dried, concentrated and purified by Gilson HPLC with trifluoroacetic acid buffer. The desired product fractions were combined and concentrated in an EZ2 Genevac evaporator, giving 35.3 mg (82.3%) of the title compound.

LC/MS: m/z 431.9 (M+H), Rt 0.57 min.

Example 262

3-[(1,1-Dioxidotetrahydro-2H-thiopyran-3-yl)methyl]-5-(3-thienyl)-1H-indole-7-carboxamide

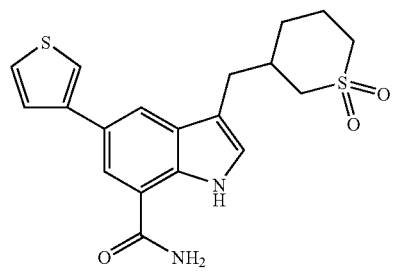

5-bromo-3-[(1,1-dioxidotetrahydro-2H-thiopyran-4-yl)methyl]-1H-indole-7-carboxamide (40 mg, 0.104 mmol) 3-thienylboronic acid (19.93 mg, 0.156 mmol, 1.5 eq), PdCl$_2$(dppf) (7.60 mg, 10.38 μmol, 0.1 eq), potassium carbonate (43.0 mg, 0.311 mmol, 3 eq) were diluted in a mixture of 1,4-dioxane (3 mL) and water (1 mL), in a 2-5 mL biotage microwave reaction tube. The mixture was degassed by bubbling nitrogen through for 5 minutes and was then heated in a microwave at high absorption for 20 minutes at 120° C. The reaction was filtered through a thiol SPE cartridge (polymer labs) and was concentrated and purified by Gilson HPLC with trifluoroacetic acid buffer. The desired product fractions were combined and concentrated in an EZ2 Genevac evaporator, giving 26.9 mg (63.4%) of the title compound.

LC/MS: m/z 388.9 (M+H), Rt 0.91 min.

Example 263

3-[(1,1-Dioxidotetrahydro-2H-thiopyran-3-yl)methyl]-5-(4-fluorophenyl)-1H-indole-7-carboxamide

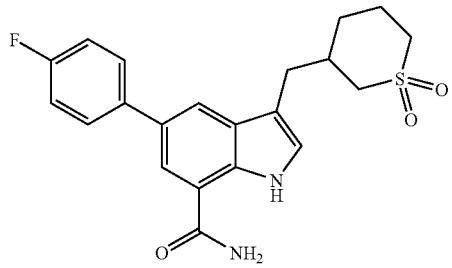

5-bromo-3-[(1,1-dioxidotetrahydro-2H-thiopyran-4-yl)methyl]-1H-indole-7-carboxamide (40 mg, 0.104 mmol) (4-fluorophenyl)boronic acid (21.79 mg, 0.156 mmol, 1.5 eq), PdCl$_2$(dppf) (7.60 mg, 10.38 μmol, 0.1 eq), potassium carbonate (43.0 mg, 0.311 mmol, 3 eq) were diluted in a mixture of 1,4-dioxane (3 mL) and water (1 mL), in a 2-5 mL biotage microwave reaction tube. The mixture was degassed by bubbling nitrogen through for 5 minutes and was then heated in a microwave at high absorption for 20 minutes at 120° C. The reaction was filtered through a thiol SPE cartridge (polymer labs) and was concentrated and purified by Gilson HPLC with trifluoroacetic acid buffer. The desired product fractions were combined and concentrated in an EZ2 Genevac evaporator, giving 21.7 mg (49.6%) of the title compound.

LC/MS: m/z 400.8 (M+H), Rt 0.97 min.

Biological Data

IKK2 Assay

Recombinant human IKK6 (residues 5-746) was expressed in baculovirus as a C-terminal GST-tagged fusion protein, and its activity was assessed using a time-resolved fluorescence resonance energy transfer (TR-FRET) assay. Briefly, IKK2 (0.5 nM-5 nM final) diluted in assay buffer (50 mM HEPES, 10 mM $MgCl_2$, 1 mM CHAPS pH 7.4 with 1 mM DTT and 0.01% w/v BSA) was added to wells containing various concentrations of compound or DMSO vehicle (1.7% final). The reaction was initiated by the addition of GST-IkappaB substrate (25 nM final)/ATP (1 µM final), in a total volume of 6 µl. The reaction was incubated for 15 minutes at room temperature, then terminated by the addition of 3 µl of detection reagent in buffer containing 50 mM EDTA (100 mM HEPES pH 7.4, 150 mM NaCl, 50 mM EDTA and 0.01% w/v BSA) containing antiphosphoserine-IB-32/36 monoclonal antibody 12C2 (Cell Signalling Technology, Beverly Mass., USA) labelled with W-1024 europium chelate (Wallac OY, Turku, Finland), and an APC-labelled anti-GST antibody (Prozyme, San Leandro, Calif., USA) was added and the reaction was further incubated for 60 minutes at room temperature. The degree of phosphorylation of GST-IB was measured using a BMG Rubystar plate reader (BMG Labtech, Aylesbury, UK) as a ratio of specific 665 nm energy transfer signal to reference europium 620 nm signal.

Results

Examples 11, 14-16, 18-19, 25, 54, 80, 143, 212, 223, 226, and 253-258 were not tested for activity against IKK2. The remaining Examples were tested for activity against IKK2 and these Examples were found to be inhibitors of IKK2. These compounds had a $pIC_{50}$ of about 5.0 to about 8.5 in the IKK2 assay.

Monocyte Assay

Effect of IKK-β inhibition on human monocyte stimulated cytokine production was assessed as follows: Monocytes were isolated from heparinized whole blood by Ficoll gradient, followed by purification of CD14+ cells using MACS magnetic cell separation beads. Isolated monocytes were then adhered to 96-well culture plates at $1\times10^6$ cells/mL in RPMI 1640 10% FBS (JRH Biosciences, Lenexa Kans.) for 2 h. Test compounds are added to the wells 30 minutes prior to stimulation with a final vehicle concentration of 0.1% DMSO. Monocytes were activated by the addition of 200 ng/mL endotoxin (LPS; *E. coli* serotype 026:B6) (Sigma, St. Louis, Mo.) and incubated for 24 hrs at 37 C. Cell-free supernates were analyzed by Alphascreen™ (Perkin Elmer, Waltham, Mass.) for TNF-α using R&D Systems matched pair Abs. Viability of the cells was determined by 10% trypan blue exclusion.

Results

Certain Examples of this invention were tested in the monocyte assay. Examples 1-19, 23-26, 28-29, 32-35, 38, 47, 53, 56-57, 59-60, 65-69, 71-76, 78-82, 84-89, 91-92, 94-95, 97-111, 113-116, 118-123, 126-129, 131-132, 136-139, 143-144, 148, 152, 154, 157, 160, 163-164, 166, 168-175, 181, 183-185, 187-188, 190-191, 196, 203, 205-207, 212-214, 218-219, 225-230, 232, 234-241, 244-247, and 249-261 were found to have a $pIC_{50}$ of about 6.0 to about 8.3 in the monocyte assay.

Examples 83, 130, 140, 189, 194, 197, 224, and 248 were found to have a $pIC_{50}$ less than 6.0 in the monocyte assay.

Examples 20-22, 27, 30-31, 36-37, 39-46, 48-52, 54-55, 61-64, 70, 77, 93, 96, 112, 117, 124-125, 141-142, 145-147, 149-151, 153, 155-156, 158-159, 161-162, 165, 167, 176-180, 182, 186, 192-193, 195, 198-202, 204, 208-211, 215-217, 220-222, 231, and 242-243 showed 0-100% inhibition at 300 nM in the monocyte assay.

Certain Examples of the invention were tested in the following in vivo assays.

Induction and Assessment of Streptococcal Cell Wall-Induced Arthritis

SCW-induced arthritis was induced in 6 to 8 week-old male Lewis rats (120-140 g) (Charles River, UK) following a similar method to that previously described by Esser et al. (Arthritis and Rheumatism, 1985, 28(12):1402-1411). A SCW preparation (100 p fraction) was suspended in phosphate-buffered saline (PBS) and 10 µl of the suspension containing 5 µg Peptidoglycan-polysaccharide from *Streptococcus pyrogenes* (PG-PS) was injected into the right ankle joint.

Reactivation of the arthritic inflammation was induced 18 days (+/−3 days) after intra-articular injection, (designated day 0), by intravenous injection of 200 µg of PG-PS. This results in monoarticular arthritis involving the joint originally injected with PG-PS. Ankle swelling was measured using a caliper at different time points. The inflammatory response was expressed as change in ankle diameter relative to the starting diameter. Treatments were administered from Day 0 to Day 2 by a route, frequency and dose predicted to achieve efficacious circulating compound levels based on in vitro data and DMPK properties. On Day 3, a final dose is given after the last ankle diameter measurement was made in order to collect blood for PK and/or biomarkers.

Endotoxin-Induced TNFα Production in Mice and Rats

Male Balb/c mice or Lewis rats from Charles River Breeding Laboratories were pretreated with compound or vehicle. After a determined pretreatment time, the mice were given LPS (lipopolysaccharide from *Escherichia coli* Serotype 055-B5, Sigma Chemical Co., St Louis, Mo.) 7 ug/mouse or 30 ug/rat in saline, intraperitoneally. Ninety minutes later, the mice or rats were euthanized by $CO_2$ inhalation and blood samples were collected by exanquination into heparinized blood collection tubes and stored on ice. The blood samples were centrifuged and the plasma collected for analysis by ELISA for TNFα levels.

Samples were assayed for TNFα according to manufactures specifications. Elisa kit purchased from R&D Systems Inc. (Mouse TNFα Quantikine Kit Catalog #MTA00 and Rat TNFα Quantikine Kit catalog #RTA00). Plate reader and software by Molecular Devices.

Inhaled LPS-Induced Lung Neutrophilia in the Rat

Rats were dosed orally 30 min prior to LPS administration. Rats were placed into a modified Rubbermaid box that contained an inflow and outflow. A nebulizer containing 100 ug/ml LPS (lipopolysaccharide, serotype 026:B6 from Sigma Chemical Co.) was connected to the inflow port and LPS was driven into the box at a rate of 4.5 ml/min for 20 min. After LPS challenge, the rats were returned to their cages. 4 hours later, rats were euthanized with Fatal Plus (1 ml/rat, i.p.). Terminal bleeds were taken via the carotid artery for DMPK compound analysis. A 14 gauge metal cannula was placed into the trachea and the lungs were lavaged 5 times with 5 ml Dulbecco's PBS (without calcium and magnesium).

The bronchioalveolar lavage (BAL) fluid was centrifuged for 10 min at 3000 rpm. The supernatant was discarded and the cell pellet resuspended in 5 ml PBS. Slides were made on a cytospin (Shandon) at 300 rpm for 5 min for differential cell counts, then stained with Diff-Quick solution. Total cell counts were performed using a hemocytometer and Tuerkes solution for staining.

Total number of mononuclear cells, neutrophils and eosinophils were determined by multiplying the differential percentage and the total cell type. Each compound was reported as percent inhibition of neutrophilia.

What is claimed is:
1. A compound according to formula (I):

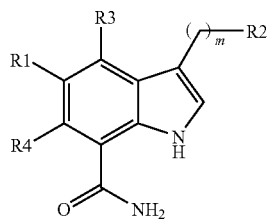

wherein:
R1 is the group —YZ;
Y is a bond, $C_1$-$C_6$ alkylene, $C_2$-$C_6$ alkenylene, or $C_2$-$C_6$ alkynylene;
Z is optionally substituted aryl or optionally substituted heteroaryl,
where said aryl and heteroaryl are optionally substituted with one to three substituents each independently selected from the group consisting of: halo, —CN, optionally substituted $C_1$-$C_6$ alkyl, optionally substituted $C_1$-$C_6$ haloalkyl, heteroaryl optionally substituted with one to three $C_1$-$C_6$ alkyl groups; —N(Rb)SO$_2$Re, N(Rb)C(O)Ra, —C(O)NRaRb, —C(O)NRfRg, —C(O)H, —SO$_2$Ri, —NRaRb, —SO$_2$NRaRb, SO$_2$NRfRg, —ORc, —SRb, —N(Rb)C(O)NRaRb, —N(Rb)C(O)NRfRg, and N(Rb)C(O)ORd, where said $C_1$-$C_6$ alkyl and $C_1$-$C_6$ haloalkyl are optionally substituted with one to three substituents each independently selected from the group consisting of: —CN, —NRaRb—N(Rb)SO$_2$Re, —C(O)Ra, —C(O)NRaRb, —SO$_2$Ri, SO$_2$NRaRb, $C_3$-$C_6$ cycloalkyl, —ORc, —SRb, phenyl, and heterocycloalkyl optionally substituted with one or two $C_1$-$C_6$ alkyl groups;
R2 is an optionally substituted 4-10 member heterocycloalkyl containing S, S=O, or S(O)$_2$ as member atom(s) and the remaining member atoms are carbon, said 4-10 member heterocycloalkyl being optionally substituted with one to three substituents each independently selected from the group consisting of OH, $C_1$-$C_6$ alkyl, and phenyl; or
R2 is the bicyclo group of formula (II):

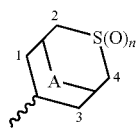

wherein A is a bridging group selected from: —CH$_2$—CH$_2$— or —CH$_2$—X—CH$_2$ and connects carbon atoms 1 or 2 to carbon atoms 3 or 4; X is O, NR5, or S(O)$_n$; R5 is H, $C_1$-$C_6$ alkyl, or —SO$_2$NRaRb; and each n is independently 0, 1, or 2;

R3 and R4 are each independently H or fluoro;
m is 0 or 1;
each Ra is independently selected from the group consisting of: H, $C_2$-$C_6$ alkenyl, $C_1$-$C_6$ alkyl, $C_1$-$C_6$ alkyl substituted with one to three substituents independently selected from the group consisting of: halo, CN, C(O)NH$_2$, N(CH$_3$)$_2$, SO$_2$Ri, —C(O)ORb, —N(Rb)C(O)Rb, —ORc, —SRc, $C_3$-$C_7$ cycloalkyl, $C_1$-$C_6$ haloalkyl, heterocycloalkyl, phenyl, and heteroaryl; phenyl, phenyl substituted with one to three substituents independently selected from the group consisting of: halo, $C_1$-$C_6$ alkyl, $C_1$-$C_6$ haloalkyl, NH$_2$, heteroaryl, —ORc, and —NRfRg; heteroaryl, heteroaryl substituted with one to three substituents independently selected from the group consisting of: halo, $C_1$-$C_6$ alkyl, $C_1$-$C_6$ haloalkyl, NH$_2$, heteroaryl, —ORc, and —NRfRg; $C_3$-$C_7$ cycloalkyl, $C_3$-$C_7$ cycloalkyl substituted with one to three substituents independently selected from the group consisting of: halo, $C_1$-$C_6$ alkyl, $C_1$-$C_6$ haloalkyl, NH$_2$, heteroaryl, —ORc, and —NRfRg; heterocycloalkyl, and heterocycloalkyl substituted with one to three substituents independently selected from the group consisting of: halo, $C_1$-$C_6$ alkyl, $C_1$-$C_6$ haloalkyl, NH$_2$, heteroaryl, —ORc, and —NRfRg;
each Rb is independently selected from the group consisting of: H, $C_1$-$C_6$ alkyl, and $C_3$-$C_7$ cycloalkyl;
each Rc is independently selected from the group consisting of: H, $C_1$-$C_6$ alkyl, $C_1$-$C_6$ alkyl substituted with one to three substituents independently selected from the group consisting of: OH, $C_3$-$C_6$ cycloalkyl, phenyl, heterocycloalkyl, and heteroaryl; $C_1$-$C_6$ haloalkyl, $C_1$-$C_6$ haloalkyl substituted with one to three substituents independently selected from the group consisting of: OH, $C_3$-$C_6$ cycloalkyl, phenyl, heterocycloalkyl, and heteroaryl; $C_3$-$C_7$ cycloalkyl, $C_3$-$C_7$ cycloalkyl substituted with one to three $C_1$-$C_3$ alkyl groups; heterocycloalkyl, heterocycloalkyl substituted with one to three $C_1$-$C_3$ alkyl groups; aryl, aryl substituted with one to three substituents independently selected from the group consisting of: halo, $C_1$-$C_3$ alkyl, $C_1$-$C_3$ haloalkyl, and OH; heteroaryl, and heteroaryl substituted with one to three substituents independently selected from the group consisting of: halo, $C_1$-$C_3$ alkyl, $C_1$-$C_3$ haloalkyl, and OH;
each Rd is independently an optionally substituted $C_1$-$C_3$ alkyl, where said $C_1$-$C_3$ alkyl is optionally substituted with one to three substituents selected from the group consisting of: $C_3$-$C_6$ cycloalkyl, optionally substituted phenyl, and optionally substituted heteroaryl; and where said phenyl and heteroaryl are optionally substituted with one to three substituents selected from the group consisting of: halo, $C_1$-$C_6$ alkyl, and $C_3$-$C_6$ cycloalkyl;
each Re is independently selected from the group consisting of: $C_1$-$C_6$ alkyl, $C_1$-$C_6$ alkyl substituted with one substituent selected from the group consisting of: phenyl, heteroaryl, heterocycloalkyl, and NRaRb; phenyl, phenyl substituted with one to three substituents selected from the group consisting of: halo, CN, $C_1$-$C_6$ alkyl, $C_1$-$C_6$ haloalkyl, and ORh; heteroaryl, heteroaryl substituted with one to three substituents selected from the group consisting of: halo, CN, $C_1$-$C_6$ alkyl, $C_1$-$C_6$ haloalkyl, and, ORh; $C_5$-$C_7$ cycloalkyl, $C_5$-$C_7$ cycloalkyl substituted with one to three substituents selected from the group consisting of: halo, $C_1$-$C_6$ alkyl, and $C_3$-$C_6$ cycloalkyl; heterocycloalkyl, and heterocycloalkyl substituted with one to three substituents selected from the group consisting of: halo, $C_1$-$C_6$ alkyl, and $C_3$-$C_6$ cycloalkyl;

each Rf and Rg is independently taken together with the nitrogen atom to which they are attached forming a ring having from 4 to 7 member atoms wherein said ring optionally contains one additional heteroatom as a member atom, said ring being saturated or unsaturated but not aromatic, and said ring being optionally substituted with one or two $C_1$-$C_3$ alkyl substituents;

each Rh is independently selected from the group consisting of: H, $C_1$-$C_6$ alkyl, and $C_1$-$C_6$ haloalkyl; and each Ri is independently selected from the group consisting of: $C_3$-$C_7$ cycloalkyl, OH, and $C_1$-$C_3$ alkyl optionally substituted with one OH; or a pharmaceutically acceptable salt thereof.

2. A compound according to claim 1 wherein Y is a bond; or a pharmaceutically acceptable salt thereof.

3. A compound according to claim 1 wherein m is 0; or a pharmaceutically acceptable salt thereof.

4. A compound according to claim 1 wherein R3 and R4 are both H; or a pharmaceutically acceptable salt thereof.

5. A compound according to claim 1 wherein R2 is the group of formula (III):

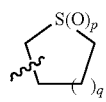

(III)

optionally substituted with one to three substituents each independently selected from the group consisting of OH, $C_1$-$C_6$ alkyl, and phenyl; and wherein p is 0, 1, or 2 and q is 1, 2, or 3; or a pharmaceutically acceptable salt thereof.

6. A compound according to claim 1 wherein R2 is

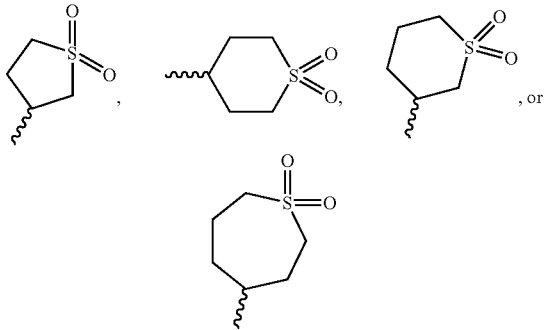

optionally substituted with one to three substituents each independently selected from the group consisting of OH, $C_1$-$C_3$ alkyl, and phenyl; or R2 is the bicyclo group

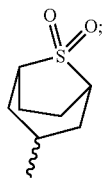

or a pharmaceutically acceptable salt thereof.

7. A compound according to claim 1 wherein R2 is

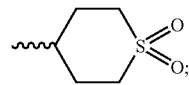

or a pharmaceutically acceptable salt thereof.

8. A compound according to claim 1 wherein Z is optionally substituted phenyl; or a pharmaceutically acceptable salt thereof.

9. A compound according to claim 1 wherein Z is phenyl optionally substituted with one to three substituents each independently selected from the group consisting of halo, —CN, optionally substituted $C_1$-$C_6$ alkyl, optionally substituted $C_1$-$C_6$ haloalkyl, optionally substituted heteroaryl, —N(Rb)SO$_2$Re, —NRbC(O)Ra, —C(O)NRaRb, —C(O)H, —NRaRb, and —ORc; wherein said $C_1$-$C_6$ alkyl and $C_1$-$C_6$ haloalkyl are optionally substituted with one to three substituents each independently selected from the group consisting of: —CN, —NRaRb, and —ORc;

each Ra, Rb, and Rc is independently selected from the group consisting of H and $C_1$-$C_6$ alkyl; and each Re is $C_1$-$C_6$ alkyl; or a pharmaceutically acceptable salt thereof.

10. A compound according to claim 1 wherein Z is optionally substituted heteroaryl; or a pharmaceutically acceptable salt thereof.

11. A compound according to claim 10 wherein Z is an optionally substituted heteroaryl selected from the group consisting of thienyl, furanyl, thiazolyl, pyrazolyl, isoxazolyl, pyridinyl, indazolyl, 2,3-dihydrobenzofuranyl, and benzothienyl; or a pharmaceutically acceptable salt thereof.

12. A compound according to claim 10 wherein Z is optionally substituted with one to three substituents each independently selected from the group consisting of halo, —CN, optionally substituted $C_1$-$C_6$ alkyl, optionally substituted $C_1$-$C_6$ haloalkyl, —NRaRb, —SO$_2$NRaRb, —SO$_2$NRfRg, —ORc, and heteroaryl optionally substituted with one to three $C_1$-$C_6$ alkyl groups; where said $C_1$-$C_6$ alkyl and $C_1$-$C_6$ haloalkyl are optionally substituted with one to three substituents each independently selected from the group consisting of —CN, —NRaRb, —SO$_2$Ri, —SO$_2$NRaRb, $C_3$-$C_6$ cycloalkyl, —ORc, —SRb, and heterocycloalkyl optionally substituted with one or two $C_1$-$C_6$ alkyl groups;

each Ra is independently selected from the group consisting of $C_1$-$C_6$ alkyl and $C_1$-$C_6$ alkyl substituted with one to three —ORc groups;

each Rb and Rc is independently selected from the group consisting of H and $C_1$-$C_6$ alkyl;

each Rf and Rg is independently taken together with the nitrogen atom to which they are attached forming a ring having from 4 to 7 member atoms wherein said ring optionally contains one additional heteroatom as a member atom, said ring being saturated or unsaturated but not aromatic, and said ring being optionally substituted with one or two $C_1$-$C_3$ alkyl substituents; and each Ri is independently selected from the group consisting of $C_3$-$C_7$ cycloalkyl and $C_1$-$C_3$ alkyl optionally substituted with one OH; or a pharmaceutically acceptable salt thereof.

13. A pharmaceutical composition comprising a compound according to claim 1, or a pharmaceutically acceptable salt thereof, and one or more pharmaceutically acceptable excipients.

14. A method of treating a disorder mediated by inappropriate IKK2 activity wherein the disorder is rheumatoid arthritis, asthma, rhinitis, or chronic obstructive pulmonary disease comprising administering an effective amount of a compound according to claim 1, or a pharmaceutically acceptable salt thereof, to a patient in need thereof.

15. A compound which is 5-{5-[(Dimethylamino)methyl]-3-thienyl}-3-(1,1-dioxidotetrahydro-2H-thiopyran-4-yl)-1H-indole-7-carboxamide; or a pharmaceutically acceptable salt thereof.

16. A pharmaceutical composition comprising a compound according to claim 15, or a pharmaceutically acceptable salt thereof, and one or more pharmaceutically acceptable excipients.

17. A compound which is 3-(2,2-Dimethyl-1,1-dioxidotetrahydro-2H-thiopyran-4-yl)-5-[5-(1-pyrrolidinylmethyl)-3-thienyl]-1H-indole-7-carboxamide; or a pharmaceutically acceptable salt thereof.

18. A pharmaceutical composition comprising a compound according to claim 17, or a pharmaceutically acceptable salt thereof, and one or more pharmaceutically acceptable excipients.

19. A compound according to claim 10 wherein Z is a thienyl group.

20. A pharmaceutical composition comprising a compound according to claim 19, or a pharmaceutically acceptable salt thereof, and one or more pharmaceutically acceptable excipients.

21. A compound selected from:
5-{5-[(Dimethylamino)methyl]-3-thienyl}-3-(1,1-dioxidotetrahydro-2H-thiopyran-4-yl)-1H-indole-7-carboxamide;
3-(1,1-Dioxidotetrahydro-2H-thiopyran-4-yl)-5-(5-{[methyl(1-methylethyl)amino]methyl}-3-thienyl)-1H-indole-7-carboxamide;
3-(1,1-Dioxidotetrahydro-2H-thiopyran-4-yl)-5-(5-{[ethyl(methyl) amino]methyl}-3-thienyl)-1 H-indole-7-carboxamide;
5-{5-[(diethylamino)methyl]-3-thienyl}-3-(1,1-dioxidotetrahydro-2H-thiopyran-4-yl)-1H-indole-7-carboxamide;
or a pharmaceutically acceptable salt thereof.

22. A pharmaceutical composition comprising a compound according to claim 21, or a pharmaceutically acceptable salt thereof, and one or more pharmaceutically acceptable excipients.

23. A compound selected from:
3-(2,2-Dimethyl-1,1-dioxidotetrahydro-2H-thiopyran-4-yl)-5-[5-(1-pyrrolidinylmethyl)-3-thienyl]-1H-indole-7-carboxamide;
3-(2,2-Dimethyl-1,1-dioxidotetrahydro-2H-thiopyran-4-yl)-5-[5-(1-pyrrolidinylmethyl)-2-thienyl]-1H-indole-7-carboxamide;
or a pharmaceutically acceptable salt thereof.

24. A pharmaceutical composition comprising a compound according to claim 23, or a pharmaceutically acceptable salt thereof, and one or more pharmaceutically acceptable excipients.

\* \* \* \* \*